US010781428B2

(12) United States Patent
Held et al.

(10) Patent No.: US 10,781,428 B2
(45) Date of Patent: Sep. 22, 2020

(54) LACCASE VARIANTS AND POLYNUCLEOTIDES ENCODING SAME

(71) Applicant: NOVOZYMES A/S, Bagsvaerd (DK)

(72) Inventors: Daniel Held, Camas, WA (US); Sheryl Luttringer, Loomis, CA (US); Tammy Doty, Sacramento, CA (US)

(73) Assignee: NOVOZYMES A/S, Bagsvaerd (DK)

( * ) Notice: Subject to any disclaimer, the term of this patent is extended or adjusted under 35 U.S.C. 154(b) by 170 days.

(21) Appl. No.: 15/531,835

(22) PCT Filed: Dec. 2, 2015

(86) PCT No.: PCT/US2015/063550
§ 371 (c)(1),
(2) Date: May 31, 2017

(87) PCT Pub. No.: WO2016/090059
PCT Pub. Date: Jun. 9, 2016

(65) Prior Publication Data
US 2018/0282708 A1 Oct. 4, 2018

Related U.S. Application Data

(60) Provisional application No. 62/086,454, filed on Dec. 2, 2014.

(51) Int. Cl.
*C12N 9/00* (2006.01)
*C12N 9/02* (2006.01)

(52) U.S. Cl.
CPC .... *C12N 9/0061* (2013.01); *C12Y 110/03002* (2013.01)

(58) Field of Classification Search
CPC ................ C12N 9/0061; C12Y 110/03002
See application file for complete search history.

(56) References Cited

U.S. PATENT DOCUMENTS 7,169,965 B2 * 1/2007 Iimura ............... C12N 9/0061
435/468

FOREIGN PATENT DOCUMENTS

| WO | 98/027197 A1 | 6/1998 |
| WO | 98/027198 A1 | 6/1998 |
| WO | 98/038286 A1 | 9/1998 |
| WO | 01/83761 A1 | 11/2001 |
| WO | 2009/127702 A2 | 10/2009 |
| WO | 2012/138474 A1 | 10/2012 |
| WO | 2013/038062 A1 | 3/2013 |

OTHER PUBLICATIONS

Liu et al. 2003; Molecular cloning and characterization of a laccase gene from the basidiomycete Fome lignosus and expression in Pichia pastoris. Applied Microbiology and Biotechnology. 63: 174-181, with sequence alignment attached.*
Kojima et al. 1990; Cloning, sequence analysis, and expression of ligninolytic phenoloxidase genes of the white-rot basidiomycete Coriolus hirsutus. J. Biol. Chem. 265(25): 15224-15230, with sequence alignment attached.*
Gonzalez et al. 2003; Identification of a new laccase gene and confirmation of genomic predictions by cDNA sequences of Trametes sp.I-62 laccase family. Mycological Research. 107(6); 727-735, with sequence alignment attached.*
Jolivalt et al. 2005; Expression of laccase IIIb from the white-rot fungus Trametes versicolor in the yeast Yarrowia lipolytica for environmental applications. Applied Mircrobiology and Biotechnology. 66: 450-456.*
Mikuni, 1992; Untitled, EMBL D13372; Sequence alignment only.*
Schuren et al. 2002; Laccase production by genetic transformation of the basidiomycete Trametes versicolor. EMBL AY081188; Sequence alignment only.*
Jonsson et al. 1999; Untitled, EMBL Y18012; Sequence alignment only.*
USP 7,169,965, 2007; Sequence Alignment Only.*
Kojima et al. 1990; Cloning, sequence analysis, and expression of ligninolytic phenoloxidase genes of the white-rot basidiomycete Coriolus hirsutus. J. Biol. Chem. 265(25): 15224-15230).*
Xiao et al. 2006; Cloning of novel laccase isozyme genes from Trametes sp. AH28-2 and analysis of their differential expression. Appl Microbiol Biotechnol 71:493-501.*
Hoshida et al. 2001; Isolation of five laccase gene sequences from the white-rot fungus Trametes sanguinea by PCR, and cloning, characterization, and expression of the laccase cDNA in yeasts. Journal of Bioscience and Bioengineering. 92(4): 372-380.*
Wahleithner et al. 1996; The identification and characterization of four laccases from the plant pathogenic fungus Rhizoctonia solini. Curr Genet 29: 395-403.*

* cited by examiner

*Primary Examiner* — Karen Cochrane Carlson
(74) *Attorney, Agent, or Firm* — Adam Rucker

(57) ABSTRACT

The present invention relates to laccase variants comprising a substitution at one or more positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. The present invention also relates to polynucleotides encoding the variants; nucleic acid constructs, vectors, and host cells comprising the polynucleotides; and methods of using the variants.

20 Claims, 11 Drawing Sheets
Specification includes a Sequence Listing.

LACCASE VARIANTS AND POLYNUCLEOTIDES ENCODING SAME

CROSS-REFERENCE TO RELATED APPLICATIONS

This application is a 35 U.S.C. 371 national application of PCT/US2015/063550, filed Dec. 2, 2015, which claims priority under 35 U.S.C. 119 to U.S. Provisional Patent Application No. 62/086,454, filed Dec. 2, 2014, the contents of each of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to laccase variants, polynucleotides encoding the variants, methods of obtaining the variants, methods of producing the variants, and methods of using the variants.

Description of the Related Art

Laccase is a polyphenol oxidase (EC 1.10.3.2) catalyzing the oxidation of a variety of inorganic and aromatic compounds, particularly phenols, with the concomitant reduction of molecular oxygen to water.

Since laccases are able to catalyze the oxidation of a variety of inorganic and aromatic compounds, they have many potential industrial applications such as lignin modification, paper strengthening, dye transfer inhibition in detergents, phenol polymerization, hair coloring, and waste water treatment. However, the industrial use of laccases has been limited due to low expression in microbial host cells. Consequently, there is a need in the art to improve recombinant expression of laccases in industrially important microbial host cells.

WO 98/27197, WO 98/27198, WO 98/38286, WO 01/83761, WO 2012/138474, and WO 2013/038062 disclose variants of laccases with improved properties.

The present invention provides laccase variants with increased expression yield compared to its parent.

SUMMARY OF THE INVENTION

The present invention relates to isolated laccase variants, comprising a substitution at one or more (e.g., several) positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2, wherein the variants have laccase activity.

The present invention also relates to isolated polynucleotides encoding the variants; nucleic acid constructs, vectors, and host cells comprising the polynucleotides; methods of producing the variants, and methods for obtaining the variants.

The present invention also relates to compositions comprising the variants.

The present invention also relates to use of the variants.

DEFINITIONS

Figure 1:
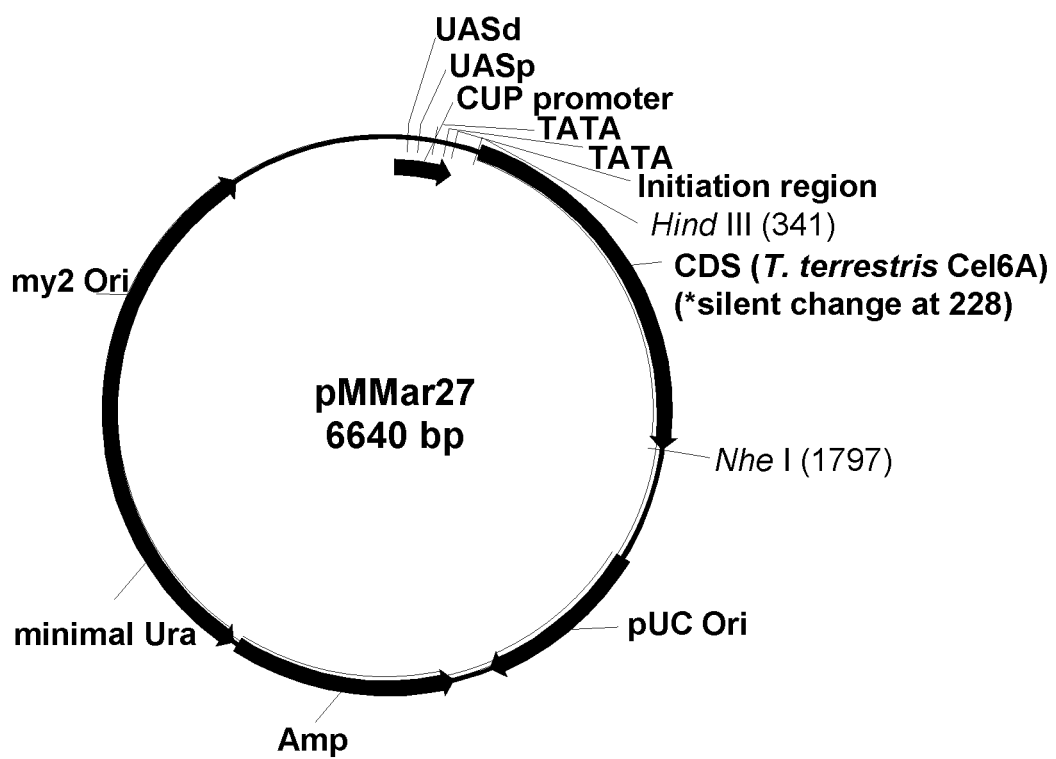
FIG. 1 shows a restriction map of pMMar27.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide, wherein the fragment has laccase activity. In one aspect, a fragment contains at least 85%, at least 90%, or at least 95% of the amino acid residues of the mature polypeptide.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, catalytic efficiency, catalytic rate, chemical stability, dye bleaching activity, expression yield, oxidation stability, pH activity, pH stability, specific activity, stability under storage conditions, substrate binding, substrate cleavage, substrate specificity, substrate stability, surface properties, thermal activity, thermostability, and volumetric laccase activity.

In one aspect, the improved property is increased expression yield of a variant compared to the parent. In another aspect, the improved property is increased specific activity of a variant compared to the parent. In another aspect, the improved property is increased expression yield and increased specific activity of a variant compared to the parent. In another aspect, the improved property is increased dye bleaching. For example, dye bleaching is employed in various industrial applications such as lignin modification, paper strengthening, dye transfer inhibition in detergents, phenol polymerization, hair dyeing, bleaching of textiles (in particular bleaching of denim as described in WO 96/12845 and WO 96/12846), and waste water treatment.

Increased dye bleaching activity: The term "increased dye bleaching activity" means a higher ability of a variant compared to the parent to decolorize any dye that can be decolorized using a laccase enzyme. Examples of such dyes include, but are not limited to, azo, monoazo, disazo, nitro, xanthene, quinoline, anthroquinone, triarylmethane, paraazoanyline, azineoxazine, stilbene, aniline, and phtalocyanine dyes, or mixtures thereof. In some embodiments, the dye is an azo dye (e.g., Reactive Black 5 (2,7-naphthalenedisulfonic acid, 4-amino-5-hydroxy-3,6-bis((4-((2-(sulfooxy)ethyl)sulfonyl)phenyl)azo)-tetrasodium salt), Reactive Violet 5, methyl yellow, congo red). In some embodiments, the dye is an anthraquinone dye (e.g., remazol blue), indigo (indigo carmine), or a triarylmethane/paraazoanyline dye (e.g., crystal violet, malachite green). In various embodiments, the dye is a reactive, direct, disperse, or pigment dye. In another embodiment, the dye is contained within an ink. In another embodiment, the dye is contained within a textile. In another embodiment, the dye is indigo and/or a sulfur-based dye. In some embodiments, the textile is denim dyed with indigo and/or a sulfur-based dye. In a particular embodiment, the textile is dyed with indigo, and a laccase variant is used to oxidize the indigo to isatin.

In one aspect, the dye bleaching activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the dye bleaching activity of the parent.

Increased expression yield: The term "increased expression yield" means a higher amount (g) of secreted active enzyme per liter of culture medium from cultivation of a host cell expressing the variant gene compared to the amount (g) of secreted active enzyme per liter produced under the same cultivation conditions by the same host cell expressing the parent gene.

In one aspect, the expression yield of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, or at least 40-fold compared to the expression yield of the parent.

Increased specific activity: The term "increased specific activity" means a higher enzyme activity per molecule or µmole of a variant compared to the enzyme activity per molecule or µmole of the parent of the variant. The enzyme activity is measured in units per gram, wherein one unit is defined as the amount of laccase activity required to oxidize 1 nmole of substrate (e.g., 4,4'-[azinobis(methanylylidene)] bis(2,6-dimethoxyphenol) (syringaldazine); 2,2'-azinobis(3-ethylbenzthiazoline-6-sulfonate [ABTS]; 10-(2-hydroxyethyl)-phenoxazine (HEPO); 2,2,6,6-tetramethylpiperidin-1-yloxy [TEMPO], indigo carmine, Reactive Black 5) per second under conditions of an assay based on the ability of laccase enzyme to oxidize the substrate, e.g., ABTS, into its corresponding stable cation radical, e.g., ABTS+. For example, unlike the initial form of ABTS, the radical form is dark green in color with increased absorbance at 420 nm. The amount of green color formation is proportional to the amount of laccase activity, and can be compared to a laccase standard curve to determine the absolute amount of laccase activity.

The increased specific activity of the variant compared to the parent can be assessed, for example, under specific conditions of pH and/or temperature. For example, the pH can be any pH in the range of 3 to 7, e.g., 3.0, 3.5, 4.0, 4.5, 5.0, 5.5, 6.0, 6.5, or 7.0 (or in between). Any suitable buffer for achieving the desired pH can be used. For example, the temperature can be any temperature in the range of 25° C. to 90° C., e.g., 25, 30, 35, 40, 45, 50, 55, 60, 65, 70, 75, 80, 85, or 90° C. (or in between). In another aspect, a combination of two or more (e.g., several) of the above conditions are used to determine the increased specific activity of the variant compared to the parent, such as any temperature in the range of 25° C. to 90° C., e.g., 25, 30, 35, 40, 45, 50, 55, 60, 65, 70, 75, 80, 85, or 90° C. (or in between) at a pH in the range of 3 to 7, e.g., 3.0, 3.5, 4.0, 4.5, 5.0, 5.5, 6.0, 6.5, or 7.0 (or in between).

In one aspect, the specific activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the specific activity of the parent.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laccase: The term "laccase" means a benzenediol:oxygen oxidoreductase (E.C. 1.10.3.2) that catalyzes the following reaction: 1,2- or 1,4-benzenediol+$O_2$=1,2- or 1,4-benzosemiquinone+2$H_2O$.

Laccase activity can be determined by measuring the oxidation of syringaldazine (4,4'-[azinobis(methanylylidene)]bis(2,6-dimethoxyphenol)) to the corresponding quinone 4,4'-[azobis(methanylylidene])bis(2,6-dimethoxycyclohexa-2,5-dien-1-one). The reaction (shown below) is detected by an increase in absorbance at 530 nm.

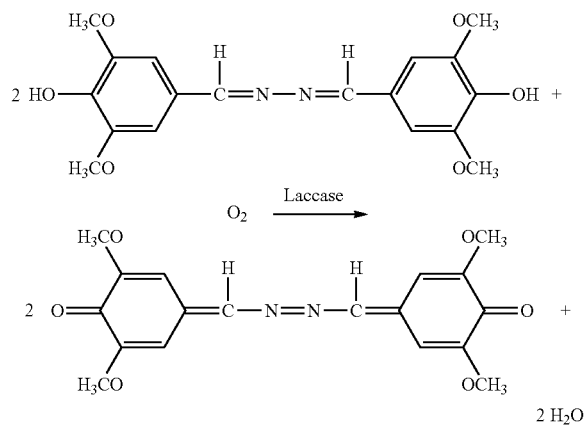

The reaction is conducted in 23 mM 2-(N-morpholino)ethanesulfonic acid (MES) pH 5.5 at 30° C. with 19 µM substrate (syringaldazine) and 1 g/L polyethylene glycol (PEG) 6000. The sample is placed in a spectrophotometer and the change in absorbance is measured at 530 nm every 15 seconds up to 90 seconds. One laccase unit is the amount of enzyme that catalyzes the conversion of 1 µmole syringaldazine per minute under the specified analytical conditions.

Laccase activity can also be determined from the oxidation of syringaldazine under aerobic conditions. The violet color produced is photometered at 530 nm. The assay conditions are 19 mM syringaldazine, 23 mM Tris/maleate buffer, pH 7.5, 30° C., and 1 minute reaction time. One laccase unit (LAMU) is the amount of enzyme that catalyzes the conversion of 1.0 µmole syringaldazine per minute under these conditions.

Laccase activity can also be measured using 10-(2-hydroxyethyl)-phenoxazine (HEPO) as substrate. HEPO is synthesized using the same procedure as described for 10-(2-hydroxyethyl)-phenothiazine, (Cauquil, 1960, *Bulletin de la Society Chemique de France* p. 1049). In the presence of oxygen, laccase oxidizea HEPO to a HEPO radical that can be monitored photometrically at 528 nm.

Laccase activity can also be measured using 2,2'-azino-bis (3-ethylbenzothiazoline-6-sulfonic acid) diammonium salt (ABTS, CAS number: 30931-67-0) as substrate in 100 mM sodium acetate pH 4 and measuring the absorbance at 405 nm.

Laccase activity can also be measured using other substrates such as indigo carmine or Reactive Black 5 using methods known in the art.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 520 of SEQ ID NO: 2 based on the SignalP 3.0 program (Bendtsen et al., 2004, *J. Mol. Biol.* 340: 783-795) that predicts amino acids 1 to 21 of SEQ ID NO: 2 are a signal peptide. In another aspect, the mature polypeptide is amino acids 22 to 520 of SEQ ID NO: 4 based on the SignalP 3.0 program that predicts amino acids 1 to 21 of SEQ ID NO: 4 are a signal peptide. In another aspect, the mature polypeptide is amino acids 22 to 520 of SEQ ID NO: 6 based on the SignalP 3.0 program that predicts amino acids 1 to 21 of SEQ ID NO: 6 are a signal peptide. In another aspect, the mature polypeptide is amino acids 22 to 520 of SEQ ID NO: 8 based on the SignalP 3.0 program that predicts amino acids 1 to 21 of SEQ ID NO: 8 are a signal peptide. In another aspect, the mature polypeptide is amino acids 22 to 520 of SEQ ID NO: 10 based on the SignalP 3.0 program that predicts amino acids 1 to 21 of SEQ ID NO: 10 are a signal peptide. In another aspect, the mature polypeptide is amino acids 22 to 520 of SEQ ID NO: 12 based on the SignalP 3.0 program that predicts amino acids 1 to 21 of SEQ ID NO: 12 are a signal peptide. In another aspect, the mature polypeptide is amino acids 22 to 520 of SEQ ID NO: 14 based on the SignalP 3.0 program that predicts amino acids 1 to 21 of SEQ ID NO: 14 are a signal peptide. In another aspect, the mature polypeptide is amino acids 22 to 520 of SEQ ID NO: 16 based on the SignalP 3.0 program that predicts amino acids 1 to 21 of SEQ ID NO: 16 are a signal peptide. In another aspect, the mature polypeptide is amino acids 22 to 520 of SEQ ID NO: 18 based on the SignalP 3.0 program that predicts amino acids 1 to 21 of SEQ ID NO: 18 are a signal peptide. In another aspect, the mature polypeptide is amino acids 22 to 520 of SEQ ID NO: 20 based on the SignalP 3.0 program that predicts amino acids 1 to 21 of SEQ ID NO: 20 are a signal peptide. In another aspect, the mature polypeptide is amino acids 22 to 520 of SEQ ID NO: 22 based on the SignalP 3.0 program that predicts amino acids 1 to 21 of SEQ ID NO: 22 are a signal peptide. In another aspect, the mature polypeptide is amino acids 22 to 519 of SEQ ID NO: 24 based on the SignalP 3.0 program that predicts amino acids 1 to 21 of SEQ ID NO: 24 are a signal peptide. In another aspect, the mature polypeptide is amino acids 22 to 520 of SEQ ID NO: 26 based on the SignalP 3.0 program that predicts amino acids 1 to 21 of SEQ ID NO: 26 are a signal peptide. In another aspect, the mature polypeptide is amino acids 22 to 520 of SEQ ID NO: 28 based on the SignalP 3.0 program that predicts amino acids 1 to 21 of SEQ ID NO: 28 are a signal peptide. In another aspect, the mature polypeptide is amino acids 22 to 520 of SEQ ID NO: 30 based on the SignalP 3.0 program that predicts amino acids 1 to 21 of SEQ ID NO: 30 are a signal peptide. In another aspect, the mature polypeptide is amino acids 22 to 520 of SEQ ID NO: 32 based on the SignalP 3.0 program that predicts amino acids 1 to 21 of SEQ ID NO: 32 are a signal peptide. In another aspect, the mature polypeptide is amino acids 22 to 520 of SEQ ID NO: 34 based on the SignalP 3.0 program that predicts amino acids 1 to 21 of SEQ ID NO: 34 are a signal peptide. In another aspect, the mature polypeptide is amino acids 22 to 518 of SEQ ID NO: 36 based on the SignalP 3.0 program that predicts amino acids 1 to 21 of SEQ ID NO: 36 are a signal peptide. In another aspect, the mature polypeptide is amino acids 22 to 518 of SEQ ID NO: 38 based on the SignalP 3.0 program that predicts amino acids 1 to 21 of SEQ ID NO: 38 are a signal peptide. In another aspect, the mature polypeptide is amino acids 22 to 515 of SEQ ID NO: 40 based on the SignalP 3.0 program that predicts amino acids 1 to 21 of SEQ ID NO: 40 are a signal peptide. In another aspect, the mature polypeptide is amino acids 22 to 520 of SEQ ID NO: 42 based on the SignalP 3.0 program that predicts amino acids 1 to 21 of SEQ ID NO: 42 are a signal peptide. In another aspect, the mature polypeptide is amino acids 64 to 518 of SEQ ID NO: 44 based on the SignalP 3.0 program that predicts amino acids 1 to 63 of SEQ ID NO: 44 are a signal peptide. In another aspect, the mature polypeptide is amino acids 22 to 518 of SEQ ID NO: 46 based on the SignalP 3.0 program that predicts amino acids 1 to 21 of SEQ ID NO: 46 are a signal peptide. In another aspect, the mature polypeptide is amino acids 22 to 518 of SEQ ID NO: 48 based on the SignalP 3.0 program that predicts amino acids 1 to 21 of SEQ ID NO: 48 are a signal peptide. In another aspect, the mature polypeptide is amino acids 22 to 518 of SEQ ID NO: 50 based on the SignalP 3.0 program that predicts amino acids 1 to 21 of SEQ ID NO: 50 are a signal peptide. In another aspect, the mature polypeptide is amino acids 22 to 518 of SEQ ID NO: 52 based on the SignalP 3.0 program that predicts amino acids 1 to 21 of SEQ ID NO: 52 are a signal peptide. In another aspect, the mature polypeptide is amino acids 26 to 524 of SEQ ID NO: 54 based on the SignalP 3.0 program that predicts amino acids 1 to 25 of SEQ ID NO: 54 are a signal peptide. In another aspect, the mature polypeptide is amino acids 26 to 524 of SEQ ID NO: 56 based on the SignalP 3.0 program that predicts amino acids 1 to 25 of SEQ ID NO: 56 are a signal peptide. In another aspect, the mature polypeptide is amino acids 22 to 521 of SEQ ID NO: 58 based on the SignalP 3.0 program that predicts amino acids 1 to 21 of SEQ ID NO: 58 are a signal peptide. In another aspect, the mature polypeptide is amino acids 24 to 524 of SEQ ID NO: 60 based on the SignalP 3.0 program that predicts amino acids 1 to 23 of SEQ ID NO: 60 are a signal peptide. In another aspect, the mature polypeptide is amino acids 22 to 517 of SEQ ID NO: 62 based on the SignalP 3.0 program that predicts amino acids 1 to 21 of SEQ ID NO: 62 are a signal peptide. In another aspect, the mature polypeptide is amino acids 19 to 539 of SEQ ID NO: 64 based on the SignalP 3.0 program that predicts amino acids 1 to 18 of SEQ ID NO: 64 are a signal peptide. In another aspect, the mature polypeptide is amino acids 24 to 533 of SEQ ID NO: 66 based on the SignalP 3.0 program that predicts amino acids 1 to 23 of SEQ ID NO: 66 are a signal peptide. In another aspect, the mature polypeptide is amino acids 21 to 531 of SEQ ID NO: 68 based on the SignalP 3.0 program that predicts amino acids 1 to 20 of SEQ ID NO: 68 are a signal peptide. In another aspect, the mature polypeptide is amino acids 25 to 518 of SEQ ID NO: 70 based on the SignalP 3.0 program that predicts amino acids 1 to 24 of SEQ ID NO: 70 are a signal peptide. In another aspect, the mature polypeptide is amino acids 22 to 518 of SEQ ID NO: 93 based on the SignalP 3.0 program that predicts amino acids 1 to 21 of SEQ ID NO: 93 are a signal peptide. In another aspect, the mature polypeptide is amino acids 22 to 620 of SEQ ID NO: 95 based on the SignalP 3.0 program that predicts amino acids 1 to 21 of SEQ ID NO: 95 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having laccase activity. In one aspect, the mature polypeptide coding sequence is nucleotides 64 to 1560 of SEQ ID NO: 1 based on the SignalP 3.0 program that predicts nucleotides 1 to 63 of SEQ ID NO: 1 encode a signal peptide. In another aspect, the mature polypeptide coding sequence is nucleotides 64 to 1560 of SEQ ID NO: 3 based on the SignalP 3.0 program that predicts nucleotides 1 to 63 of SEQ ID NO: 3 encode a signal peptide. In another aspect, the mature polypeptide coding sequence is nucleotides 64 to 1560 of SEQ ID NO: 5 based on the SignalP 3.0 program that predicts nucleotides 1 to 63 of SEQ ID NO: 5 encode a signal peptide. In another aspect, the mature polypeptide coding sequence is nucleotides 64 to 1560 of SEQ ID NO: 7 based on the SignalP 3.0 program that predicts nucleotides 1 to 63 of SEQ ID NO: 7 encode a signal peptide. In another aspect, the mature polypeptide coding sequence is nucleotides 64 to 1560 of SEQ ID NO: 9 based on the SignalP 3.0 program that predicts nucleotides 1 to 63 of SEQ ID NO: 9 encode a signal peptide. In another aspect, the mature polypeptide coding sequence is nucleotides 64 to 1560 of SEQ ID NO: 11 based on the SignalP 3.0 program that predicts nucleotides 1 to 63 of SEQ ID NO: 11 encode a signal peptide. In another aspect, the mature polypeptide coding sequence is nucleotides 64 to 1560 of SEQ ID NO: 13 based on the SignalP 3.0 program that predicts nucleotides 1 to 63 of SEQ ID NO: 13 encode a signal peptide. In another aspect, the mature polypeptide coding sequence is nucleotides 64 to 1560 of SEQ ID NO: 15 based on the SignalP 3.0 program that predicts nucleotides 1 to 63 of SEQ ID NO: 15 encode a signal peptide. In another aspect, the mature polypeptide coding sequence is nucleotides 64 to 1560 of SEQ ID NO: 17 based on the SignalP 3.0 program that predicts nucleotides 1 to 63 of SEQ ID NO: 17 encode a signal peptide. In another aspect, the mature polypeptide coding sequence is nucleotides 64 to 1560 of SEQ ID NO: 19 based on the SignalP 3.0 program that predicts nucleotides 1 to 63 of SEQ ID NO: 19 encode a signal peptide. In another aspect, the mature polypeptide coding sequence is nucleotides 64 to 1560 of SEQ ID NO: 21 based on the SignalP 3.0 program that predicts nucleotides 1 to 63 of SEQ ID NO: 21 encode a signal peptide. In another aspect, the mature polypeptide coding sequence is nucleotides 64 to 1557 of SEQ ID NO: 23 based on the SignalP 3.0 program that predicts nucleotides 1 to 63 of SEQ ID NO: 23 encode a signal peptide. In another aspect, the mature polypeptide coding sequence is nucleotides 64 to 1560 of SEQ ID NO: 25 based on the SignalP 3.0 program that predicts nucleotides 1 to 63 of SEQ ID NO: 25 encode a signal peptide. In another aspect, the mature polypeptide coding sequence is nucleotides 64 to 1560 of SEQ ID NO: 27 based on the SignalP 3.0 program that predicts nucleotides 1 to 63 of SEQ ID NO: 27 encode a signal peptide. In another aspect, the mature polypeptide coding sequence is nucleotides 64 to 1560 of SEQ ID NO: 29 based on the SignalP 3.0 program that predicts nucleotides 1 to 63 of SEQ ID NO: 29 encode a signal peptide. In another aspect, the mature polypeptide coding sequence is nucleotides 64 to 1560 of SEQ ID NO: 31 based on the SignalP 3.0 program that predicts nucleotides 1 to 63 of SEQ ID NO: 31 encode a signal peptide. In another aspect, the mature polypeptide coding sequence is nucleotides 64 to 1560 of SEQ ID NO: 33 based on the SignalP 3.0 program that predicts nucleotides 1 to 63 of SEQ ID NO: 33 encode a signal peptide. In another aspect, the mature polypeptide coding sequence is nucleotides 64 to 1554 of SEQ ID NO: 35 based on the SignalP 3.0 program that predicts nucleotides 1 to 63 of SEQ ID NO: 35 encode a signal peptide. In another aspect, the mature polypeptide coding sequence is nucleotides 64 to 1554 of SEQ ID NO: 37 based on the SignalP 3.0 program that predicts nucleotides 1 to 63 of SEQ ID NO: 37 encode a signal peptide. In another aspect, the mature polypeptide coding sequence is nucleotides 64 to 1545 of SEQ ID NO: 39 based on the SignalP 3.0 program that predicts nucleotides 1 to 63 of SEQ ID NO: 39 encode a signal peptide. In another aspect, the mature polypeptide coding sequence is nucleotides 64 to 1560 of SEQ ID NO: 41 based on the SignalP 3.0 program that predicts nucleotides 1 to 63 of SEQ ID NO: 41 encode a signal peptide. In another aspect, the mature polypeptide coding sequence is nucleotides 64 to 1554 of SEQ ID NO: 43 based on the SignalP 3.0 program that predicts nucleotides 1 to 63 of SEQ ID NO: 43 encode a signal peptide. In another aspect, the mature polypeptide coding sequence is nucleotides 64 to 1554 of SEQ ID NO: 45 based on the SignalP 3.0 program that predicts nucleotides 1 to 63 of SEQ ID NO: 45 encode a signal peptide. In another aspect, the mature polypeptide coding sequence is nucleotides 64 to 1554 of SEQ ID NO: 47 based on the SignalP 3.0 program that predicts nucleotides 1 to 63 of SEQ ID NO: 47 encode a signal peptide. In another aspect, the mature polypeptide coding sequence is nucleotides 64 to 1554 of SEQ ID NO: 49 based on the SignalP 3.0 program that predicts nucleotides 1 to 63 of SEQ ID NO: 49 encode a signal peptide. In another aspect, the mature polypeptide coding sequence is nucleotides 64 to 1554 of SEQ ID NO: 51 based on the SignalP 3.0 program that predicts nucleotides 1 to 63 of SEQ ID NO: 51 encode a signal peptide. In another aspect, the mature polypeptide coding sequence is nucleotides 76 to 1572 of SEQ ID NO: 53 based on the SignalP 3.0 program that predicts nucleotides 1 to 75 of SEQ ID NO: 53 encode a signal peptide. In another aspect, the mature polypeptide coding sequence is nucleotides 76 to 1572 of SEQ ID NO: 55 based on the SignalP 3.0 program that predicts nucleotides 1 to 75 of SEQ ID NO: 55 encode a signal peptide. In another aspect, the mature polypeptide coding sequence is nucleotides 64 to 1563 of SEQ ID NO: 57 based on the SignalP 3.0 program that predicts nucleotides 1 to 63 of SEQ ID NO: 57 encode a signal peptide. In another aspect, the mature polypeptide coding sequence is nucleotides 70 to 1572 of SEQ ID NO: 59 based on the SignalP 3.0 program that predicts nucleotides 1 to 69 of SEQ ID NO: 59 encode a signal peptide. In another aspect, the mature polypeptide coding sequence is nucleotides 64 to 1551 of SEQ ID NO: 61 based on the SignalP 3.0 program that predicts nucleotides 1 to 63 of SEQ ID NO: 61 encode a signal peptide. In another aspect, the mature polypeptide coding sequence is nucleotides 55 to 1617 of SEQ ID NO: 63 based on the SignalP 3.0 program that predicts nucleotides 1 to 54 of SEQ ID NO: 63 encode a signal peptide. In another aspect, the mature polypeptide coding sequence is nucleotides 70 to 1599 of SEQ ID NO: 65 based on the SignalP 3.0 program that predicts nucleotides 1 to 69 of SEQ ID NO: 65 encode a signal peptide. In another aspect, the mature polypeptide coding sequence is nucleotides 61 to 1593 of SEQ ID NO: 67 based on the SignalP 3.0 program that predicts nucleotides 1 to 60 of SEQ ID NO: 67 encode a signal peptide. In another aspect, the mature polypeptide coding sequence is nucleotides 73 to 1554 of SEQ ID NO: 69 based on the SignalP 3.0 program that predicts nucleotides 1 to 72 of SEQ ID NO: 69 encode a signal peptide. In another aspect, the mature polypeptide coding sequence is nucleotides 64 to 1554 of SEQ ID NO: 92 based on the SignalP 3.0 program that predicts nucleotides 1 to 63 of SEQ ID NO: 92 encode a signal peptide. In another aspect, the mature polypeptide coding sequence is nucleotides 64 to 1860 of SEQ ID NO: 94 based on the SignalP 3.0 program that predicts nucleotides 1 to 63 of SEQ ID NO: 94 encode a signal peptide.

In each of the aspects above, the term "mature polypeptide coding sequence" shall be understood to include the cDNA sequence of the genomic DNA sequence or the genomic DNA sequence of the cDNA sequence.

Mediator: The term "mediator" (or "chemical mediator" may be used interchangeably herein) is defined herein as a chemical compound which acts as a redox mediator to effectively shuttle electrons between a laccase and a substrate. Chemical mediators are also known as enhancers and accelerators in the art.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent laccase: The term "parent" or "parent laccase" means a laccase to which an alteration, i.e., a substitution, insertion, and/or deletion, at one or more (e.g., several) positions, is made to produce the laccase variants of the present invention. The parent may be a naturally occurring (wild-type) polypeptide or a variant thereof, or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having laccase activity. In one aspect, a subsequence contains at least 85%, at least 90%, or at least 95% of the nucleotides of the mature polypeptide coding sequence.

Variant: The term "variant" means a polypeptide having laccase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the laccase activity of the parent.

Volumetric activity: The term "volumetric activity" is the level of laccase activity produced per unit volume (e.g., ml or liter) of a culture broth. Laccase activity is determined as described herein.

Wild-type laccase: The term "wild-type" laccase means a laccase expressed by a naturally occurring microorganism, such as a bacterium, yeast, or filamentous fungus found in nature.

Conventions for Designation of Variants

For purposes of the present invention, the full-length polypeptide disclosed in SEQ ID NO: 2 is used for numbering to determine the corresponding amino acid residue in another laccase. The amino acid sequence of another laccase is aligned with the full-length polypeptide disclosed as SEQ ID NO: 2, and based on the alignment, the amino acid position number corresponding to any amino acid residue in the full-length polypeptide of SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 2 wherein position 1 is the first amino acid of the signal peptide (i.e., Met) and position 22 (i.e., Gly) is the first position of the mature polypeptide of SEQ ID NO: 2.

Identification of the corresponding amino acid residue in another laccase can be determined by alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another laccase has diverged from the full-length polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Different alterations. Where different alterations can be introduced at a position, the different alterations are separated by a comma, e.g., "Arg170Tyr,Glu" or "R170Y,E" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated laccase variants, comprising a substitution at one or more (e.g., several) positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2, wherein the variants have laccase activity.

Variants

In an embodiment, the variants have a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the full-length polypeptide of the parent or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 2 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 4 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 6 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 8 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 10 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 12 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 14 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 16 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 18 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 20 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 22 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 24 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 26 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 28 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 30 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 32 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 34 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 36 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 38 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 40 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 42 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 44 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 46 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 48 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 50 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 52 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 54 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 56 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 58 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 60 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 62 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 64 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 66 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 68 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 70 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 93 or the mature polypeptide thereof.

In another embodiment, the variants have at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 95 or the mature polypeptide thereof.

In one aspect, the number of substitutions in the variants of the present invention is 1-24, e.g., 1, 2, 3, 4, 5, 6, 7, 8, 9, 10, 11, 12, 13, 14, 15, 16, 17, 18, 19, 20, 21, 22, 23, or 24 substitutions.

In another aspect, a variant comprises a substitution at one or more (e.g., several) positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at two positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at three positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at four positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at five positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at six positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at seven positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at eight positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at nine positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at ten positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at eleven positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at twelve positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at thirteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at fourteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at fifteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at sixteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at seventeen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at eighteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at nineteen positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at twenty positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at twenty-one positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at twenty-two positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at twenty-three positions corresponding to any of positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2. In another aspect, a variant comprises a substitution at each position corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2.

In another aspect, the variant comprises or consists of a substitution at a position corresponding to position 9. In another aspect, the amino acid at a position corresponding to position 9 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution A9R of the full-length polypeptide of SEQ ID NO: 2.

In another aspect, the variant comprises or consists of a substitution at a position corresponding to position 21. In another aspect, the amino acid at a position corresponding to position 21 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant comprises or consists of the substitution A21C of the full-length polypeptide of SEQ ID NO: 2.

In another aspect, the variant comprises or consists of a substitution at a position corresponding to position 37. In another aspect, the amino acid at a position corresponding to position 37 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant comprises or consists of the substitution S37C of the full-length polypeptide of SEQ ID NO: 2 or the mature polypeptide thereof.

In another aspect, the variant comprises or consists of a substitution at a position corresponding to position 79. In another aspect, the amino acid at a position corresponding to position 79 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Glu, Phe, Gly, Ile, Met, Asn, Gln, Ser. In another aspect, the variant comprises or consists of the substitution L79A,D,E,F,G,I,M,N,Q,S of the full-length polypeptide of SEQ ID NO: 2 or the mature polypeptide thereof.

In another aspect, the variant comprises or consists of a substitution at a position corresponding to position 102. In another aspect, the amino acid at a position corresponding to position 102 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution F102A of the full-length polypeptide of SEQ ID NO: 2 or the mature polypeptide thereof.

In another aspect, the variant comprises or consists of a substitution at a position corresponding to position 170. In another aspect, the amino acid at a position corresponding to position 170 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Met, Gln, Ser, or Thr. In another aspect, the variant comprises or consists of the substitution V170A,M,Q,S,T of the full-length polypeptide of SEQ ID NO: 2 or the mature polypeptide thereof.

In another aspect, the variant comprises or consists of a substitution at a position corresponding to position 175. In another aspect, the amino acid at a position corresponding to position 175 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser or Thr. In another aspect, the variant comprises or consists of the substitution V175S,T of the full-length polypeptide of SEQ ID NO: 2 or the mature polypeptide thereof.

In another aspect, the variant comprises or consists of a substitution at a position corresponding to position 178. In another aspect, the amino acid at a position corresponding to position 178 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution K178S of the full-length polypeptide of SEQ ID NO: 2 or the mature polypeptide thereof.

In another aspect, the variant comprises or consists of a substitution at a position corresponding to position 179. In another aspect, the amino acid at a position corresponding to position 179 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution L179N of the full-length polypeptide of SEQ ID NO: 2 or the mature polypeptide thereof.

In another aspect, the variant comprises or consists of a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution S200D of the full-length polypeptide of SEQ ID NO: 2 or the mature polypeptide thereof.

In another aspect, the variant comprises or consists of a substitution at a position corresponding to position 262. In another aspect, the amino acid at a position corresponding to position 262 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another aspect, the variant comprises or consists of the substitution A262G of the full-length polypeptide of SEQ ID NO: 2 or the mature polypeptide thereof.

In another aspect, the variant comprises or consists of a substitution at a position corresponding to position 275. In another aspect, the amino acid at a position corresponding to position 275 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution V275I of the full-length polypeptide of SEQ ID NO: 2 or the mature polypeptide thereof.

In another aspect, the variant comprises or consists of a substitution at a position corresponding to position 276. In another aspect, the amino acid at a position corresponding to position 276 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another aspect, the variant comprises or consists of the substitution D276G of the full-length polypeptide of SEQ ID NO: 2 or the mature polypeptide thereof.

In another aspect, the variant comprises or consists of a substitution at a position corresponding to position 289. In another aspect, the amino acid at a position corresponding to position 289 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Lys, Gln, Arg, or Thr. In another aspect, the variant comprises or consists of the substitution V289I,K,Q,R,T of the full-length polypeptide of SEQ ID NO: 2 or the mature polypeptide thereof.

In another aspect, the variant comprises or consists of a substitution at a position corresponding to position 292. In another aspect, the amino acid at a position corresponding to position 292 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Phe, Gly, His, or Lys. In another aspect, the variant comprises or consists of the substitution T292D,F,G,H,K of the full-length polypeptide of SEQ ID NO: 2 or the mature polypeptide thereof.

In another aspect, the variant comprises or consists of a substitution at a position corresponding to position 333. In another aspect, the amino acid at a position corresponding to position 333 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser, Glu, Lys, or Arg. In another aspect, the variant comprises or consists of the substitution A333S,E,K,R of the full-length polypeptide of SEQ ID NO: 2 or the mature polypeptide thereof.

In another aspect, the variant comprises or consists of a substitution at a position corresponding to position 357. In another aspect, the amino acid at a position corresponding to position 357 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Ala, Glu, Phe, Gly, Met, Gln, Ser, Thr, Val, or Tyr. In another aspect, the variant comprises or consists of the substitution N357D,A,E,F,G, M,Q,S,T,V,Y of the full-length polypeptide of SEQ ID NO: 2 or the mature polypeptide thereof.

In another aspect, the variant comprises or consists of a substitution at a position corresponding to position 360. In another aspect, the amino acid at a position corresponding to position 360 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Ala, His, or Met. In another aspect, the variant comprises or consists of the substitution I360V,A,H,M of the full-length polypeptide of SEQ ID NO: 2 or the mature polypeptide thereof.

In another aspect, the variant comprises or consists of a substitution at a position corresponding to position 393. In another aspect, the amino acid at a position corresponding to position 393 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution Y393I of the full-length polypeptide of SEQ ID NO: 2 or the mature polypeptide thereof.

In another aspect, the variant comprises or consists of a substitution at a position corresponding to position 397. In another aspect, the amino acid at a position corresponding to position 397 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution S397A of the full-length polypeptide of SEQ ID NO: 2 or the mature polypeptide thereof.

In another aspect, the variant comprises or consists of a substitution at a position corresponding to position 418. In another aspect, the amino acid at a position corresponding to position 418 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Val, Leu, or Met. In another aspect, the variant comprises or consists of the substitution F418I,V,L,M of the full-length polypeptide of SEQ ID NO: 2 or the mature polypeptide thereof.

In another aspect, the variant comprises or consists of a substitution at a position corresponding to position 485. In another aspect, the amino acid at a position corresponding to position 485 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution A485S of the full-length polypeptide of SEQ ID NO: 2 or the mature polypeptide thereof.

In another aspect, the variant comprises or consists of a substitution at a position corresponding to position 506. In another aspect, the amino acid at a position corresponding to position 506 is substituted with Ala, Arg, Asn, Asp, Cys, Gln, Glu, Gly, His, Ile, Leu, Lys, Met, Phe, Pro, Ser, Thr, Trp, Tyr, or Val, preferably with His. In another aspect, the variant comprises or consists of the substitution S506H of the full-length polypeptide of SEQ ID NO: 2 or the mature polypeptide thereof.

In another aspect, the variant comprises or consists of a substitution at a position corresponding to position 518. In another aspect, the amino acid at a position corresponding to position 518 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution S518A of the full-length polypeptide of SEQ ID NO: 2 or the mature polypeptide thereof.

In each of the aspects above, the variant comprises or consists of one or more substitutions described above at positions corresponding to the full-length polypeptide of SEQ ID NO: 2 in other laccases as parents.

In each of the aspects below, the variant comprises or consists of one or more substitutions described below at positions corresponding to the full-length polypeptide of SEQ ID NO: 2 in other laccases or at positions of the full-length polypeptide of SEQ ID NO: 2 or the mature polypeptide thereof.

In another aspect, the variant comprises or consists of one or more (e.g., several) substitutions selected from the group consisting of A9R; A21C; S37C; L79A,D,E,F,G,I,M,N,Q,S; F102A; V170A,M,Q,S,T; V175S,T; K178S; L179N; S200D; A262G; V275I; D276G; V289I,K,Q,R,T; T292D,F, G,H,K; A333S,E,K,R; N357D,A,E,F,G,M,Q,S,T,V,Y; I360V,A,H,M; Y393I; S397A; F418I,V,L,M; A485S; S506H; and S518A.

In another aspect, the variant comprises or consists of the substitutions A262G+I360V of the full-length polypeptide of SEQ ID NO: 2 or the mature polypeptide thereof. In another aspect, the variant comprises or consists of the substitutions F418I+S506H of the full-length polypeptide of SEQ ID NO: 2 or the mature polypeptide thereof. In another aspect, the variant comprises or consists of the substitutions A9R+L79D+L179N of the full-length polypeptide of SEQ ID NO: 2. In another aspect, the variant comprises or consists of the substitutions A21C+K178S+F418V+S518A of the full-length polypeptide of SEQ ID NO: 2. In another aspect, the variant comprises or consists of the substitutions A262G+V289I+T292D+N357D of the full-length polypeptide of SEQ ID NO: 2 or the mature polypeptide thereof. In another aspect, the variant comprises or consists of the substitutions S37C+A262G+Y393I+A485S of the full-length polypeptide of SEQ ID NO: 2 or the mature polypeptide thereof. In another aspect, the variant comprises or consists of the substitutions F102A+V175S+A262G+ I360V+S397A of the full-length polypeptide of SEQ ID NO: 2 or the mature polypeptide thereof. In another aspect, the variant comprises or consists of the substitutions V175T+ S200D+A262G+I360V+Y393I of the full-length polypeptide of SEQ ID NO: 2 or the mature polypeptide thereof. In another aspect, the variant comprises or consists of the substitutions F102A+V175T+S200D+A262G+N357D+ S397A of the full-length polypeptide of SEQ ID NO: 2 or the mature polypeptide thereof. In another aspect, the variant comprises or consists of the substitutions V175T+S200D+ A262G+D276G+I360V+Y393I+F418I+S506H of the full-length polypeptide of SEQ ID NO: 2 or the mature polypeptide thereof. In another aspect, the variant comprises or consists of the substitutions V175T+S200D+A262G+ V275I+D276G+A333S+I360V+Y393I+F418I+S506H of the full-length polypeptide of SEQ ID NO: 2 or the mature polypeptide thereof.

In another aspect, the variant comprises or consists of the substitutions S37C+L79D+F102A+V175S,T+K178S+L179N+S200D+A262G+V275I+D276G+V289I+T292D+A333S+N357D+I360V+Y393I+S397A+F418I,V+A485S+S506H+ and S518A of the full-length polypeptide of SEQ ID NO: 2 or the mature polypeptide thereof.

In another aspect, the variant comprises or consists of the substitutions F418I+S506H of the full-length polypeptide of SEQ ID NO: 2 or the mature polypeptide thereof. In another aspect, the variant comprises or consists of the substitutions A9R+L79D+L179N of the full-length polypeptide of SEQ ID NO: 2. In another aspect, the variant comprises or consists of the substitutions A21C+K178S+F418V+S518A of the full-length polypeptide of SEQ ID NO: 2. In another aspect, the variant comprises or consists of the substitutions S37C+A262G+Y393I+A485S of the full-length polypeptide of SEQ ID NO: 2 or the mature polypeptide thereof. In another aspect, the variant comprises or consists of the substitutions A262G+V289I+T292D+N357D of the full-length polypeptide of SEQ ID NO: 2 or the mature polypeptide thereof. In another aspect, the variant comprises or consists of the substitutions F102A+V175S+A262G+I360V+S397A of the full-length polypeptide of SEQ ID NO: 2 or the mature polypeptide thereof. In another aspect, the variant comprises or consists of the substitutions V175T+S200D+A262G+I360V+Y393I of the full-length polypeptide of SEQ ID NO: 2 or the mature polypeptide thereof. In another aspect, the variant comprises or consists of the substitutions F102A+V175T+S200D+A262G+N357D+S397A of the full-length polypeptide of SEQ ID NO: 2 or the mature polypeptide thereof. In another aspect, the variant comprises or consists of the substitutions V175T+S200D+A262G+D276G+I360V+Y393I+F418I+S506H of the full-length polypeptide of SEQ ID NO: 2 or the mature polypeptide thereof. In another aspect, the variant comprises or consists of the substitutions V175T+S200D+A262G+V275I+D276G+A333S+I360V+Y393I+F418I+S506H of the full-length polypeptide of SEQ ID NO: 2 or the mature polypeptide thereof.

The variants may further comprise one or more additional alterations, e.g., substitutions, insertions, and/or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

For example, the variants may further comprise substitutions at one or more (e.g., several) positions corresponding to positions 89, 151, 286, 307, 313, 339, and 355 of SEQ ID NO: 2, which are described in WO 2012/138474.

In one aspect, the variant further comprises a substitution at a position corresponding to position 89. In another aspect, the amino acid at a position corresponding to position 89 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Val, Leu, or Ile. In another aspect, the variant further comprises the substitution F89A,V,L,I of the full-length polypeptide of SEQ ID NO: 2 or the mature polypeptide thereof.

In another aspect, the variant further comprises a substitution at a position corresponding to position 151. In another aspect, the amino acid at a position corresponding to position 151 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Glu, Arg, or Lys. In another aspect, the variant further comprises the substitution N151D,E,R,K of the full-length polypeptide of SEQ ID NO: 2 or the mature polypeptide thereof.

In another aspect, the variant further comprises a substitution at a position corresponding to position 286. In another aspect, the amino acid at a position corresponding to position 286 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, His, or Val. In another aspect, the variant further comprises the substitution F286R,H,V of the full-length polypeptide of SEQ ID NO: 2 or the mature polypeptide thereof.

In another aspect, the variant further comprises a substitution at a position corresponding to position 307. In another aspect, the amino acid at a position corresponding to position 307 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro, His, or Gly. In another aspect, the variant further comprises the substitution A307P,H,G of the full-length polypeptide of SEQ ID NO: 2 or the mature polypeptide thereof.

In another aspect, the variant further comprises a substitution at a position corresponding to position 313. In another aspect, the amino acid at a position corresponding to position 313 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Thr, or Ser. In another aspect, the variant further comprises the substitution T313N,T,S of the full-length polypeptide of SEQ ID NO: 2 or the mature polypeptide thereof.

In another aspect, the variant further comprises a substitution at a position corresponding to position 339. In another aspect, the amino acid at a position corresponding to position 339 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Thr, or Ser. In another aspect, the variant further comprises the substitution V339W,T,S of the full-length polypeptide of SEQ ID NO: 2 or the mature polypeptide thereof.

In another aspect, the variant further comprises a substitution at a position corresponding to position 355. In another aspect, the amino acid at a position corresponding to position 355 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant further comprises the substitution G355R of the full-length polypeptide of SEQ ID NO: 2 or the mature polypeptide thereof.

In each of the aspects above, the variant further comprises one or more substitutions described above at positions corresponding to the full-length polypeptide of SEQ ID NO: 2 in other laccases as parents.

In another aspect, the variant further comprises one or more (e.g., several) substitutions selected from the group consisting of F89A,V,L,I; N151D,E,R,K; F286R,H,V; A307P,H,G; T313N,T,S; V339W,T,S; and G355R.

The variants may further comprise or even further comprise substitutions at one or more (e.g., several) positions as described in WO 98/27197, WO 98/27198, WO 98/27198, WO 98/38286, WO 01/83761, and WO 2013/038062, which are incorporated herein by reference in their entireties.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for laccase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential copper binding site amino acids (active site) are located at positions corresponding to positions H85, H87, H130, H132, H416, H419, H421, H473, C474, H475, I476, H479, and F484 of SEQ ID NO: 2.

In an embodiment, the variant has one or more improved properties selected from the group consisting of increased expression yield, increased specific activity, and increased dye bleaching activity compared to the parent enzyme.

In an embodiment, the expression yield of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, or at least 40-fold compared to the expression yield of the parent.

In another embodiment, the specific activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the specific activity of the parent.

In another embodiment, the dye bleaching activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the dye bleaching activity of the parent.

In another embodiment, a combination of mutations increasing expression yield and specific activity increases the volumetric activity of the laccase at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, or at least 40-fold compared to the parent.

Parent Laccases

The parent laccase can be any laccase. The parent laccase may be (a) a polypeptide having at least 60% sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95; or the mature polypeptide thereof; (b) a polypeptide encoded by a polynucleotide that hybridizes under at least low stringency conditions with (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or the mature polypeptide coding sequence thereof, or (ii) the full-length complement of (i); (c) a polypeptide encoded by a polynucleotide having at least 60% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94; or the mature polypeptide coding sequence thereof; and (d) a fragment of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof, which has laccase activity.

In one embodiment, the parent has a sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof, of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have laccase activity. In one aspect, the amino acid sequence of the parent differs by up to 10 amino acids, e.g., 1, 2, 3, 4, 5, 6, 7, 8, 9, or 10, from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof.

In another embodiment, the parent comprises or consists of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95. In another aspect, the parent comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95.

In another embodiment, the parent is a fragment of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof, containing at least 85%, e.g., at least 90% and at least 95% of the amino acid residues of the parent.

In another embodiment, the parent is an allelic variant of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof.

In another embodiment, the parent is encoded by a polynucleotide that hybridizes under very low stringency conditions, low stringency conditions, medium stringency conditions, medium-high stringency conditions, high stringency conditions, or very high stringency conditions with (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or the mature polypeptide coding sequence thereof; or (ii) the full-length complement of (i) (Sambrook et al., 1989, *Molecular Cloning, A Laboratory Manual,* 2d edition, Cold Spring Harbor, N.Y.).

The polynucleotide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or a subsequence thereof, as well as the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or a fragment thereof (e.g., mature polypeptide), may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94; or the mature polypeptide coding sequence thereof; (ii) the full-length complement of (i); or (iii) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94. In another aspect, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95; the mature polypeptide thereof; or a fragment thereof. In another aspect, the nucleic acid probe is SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94.

In another embodiment, the parent is encoded by a polynucleotide having a sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or the mature polypeptide coding sequence thereof, of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide (chimera) in which a region of the parent is replaced with a region of another polypeptide.

The parent may be a fusion polypeptide or cleavable fusion polypeptide in which another polypeptide is fused at the N-terminus or the C-terminus of the parent. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

In one aspect, the parent is an *Agaricus* laccase. In another aspect, the parent is an *Agaricus bisporus* laccase.

In another aspect, the parent is a *Ceriporiopsis* laccase. In another aspect, the parent is a *Ceriporiopsis subvermispora* laccase.

In another aspect, the parent is a *Cerrena* laccase. In another aspect, the parent is a *Cerrena unicolor* laccase.

In another aspect, the parent is a *Cinnabarina* laccase. In another aspect, the parent is a *Cinnabarina coccineus* laccase.

In another aspect, the parent is a *Coprinellus* laccase. In another aspect, the parent is a *Coprinellus congregatus* laccase.

In another aspect, the parent is a *Coprinopsis* laccase. In another aspect, the parent is a *Coprinopsis cinerea* laccase.

In another aspect, the parent is a *Coprinus* laccase. In another aspect, the parent is a *Coprinus comatus* laccase.

In another aspect, the parent is a *Coriolopsis* laccase. In another aspect, the parent is a *Coriolopsis gallica* laccase. In another aspect, the parent is a *Coriolopsis rigida* laccase. In another aspect, the parent is a *Coriolopsis trogii* laccase.

In another aspect, the parent is a *Cyathus* laccase. In another aspect, the parent is a *Cyathus bulleri* laccase. In another aspect, the parent is a *Flammulina* laccase. In another aspect, the parent is a *Flammulina velutipes* laccase.

In another aspect, the parent is a *Ganoderma* laccase. In another aspect, the parent is a *Ganoderma lucidum* laccase. In another aspect, the parent is a *Ganoderma tsugae* laccase. In another aspect, the parent is a *Ganoderma tsunodae* laccase.

In another aspect, the parent is a *Halocyphina* laccase. In another aspect, the parent is a *Halocyphina villosa* laccase.

In another aspect, the parent is a *Laccaria* laccase. In another aspect, the parent is a *Laccaria bicolor* laccase.

In another aspect, the parent is a *Lentinula* laccase. In another aspect, the parent is a *Lentinula edodes* laccase.

In another aspect, the parent is a *Lentinus* laccase. In another aspect, the parent is a *Lentinus sajor-caju* laccase. In another aspect, the parent is a *Lentinus similis* laccase. In another aspect, the parent is a *Lentinus tigrinus* laccase.

In another aspect, the parent is a *Lenzites* laccase. In another aspect, the parent is a *Lenzites gibbosa* laccase.

In another aspect, the parent is a *Meripilus* laccase. In another aspect, the parent is a *Meripilus giganteus* laccase.

In another aspect, the parent is a *Myceliophthora* laccase. In another aspect, the parent is a *Myceliophthora thermophila* laccase.

In another aspect, the parent is a *Moniliophthora* laccase. In another aspect, the parent is a *Moniliophthora perniciosa* laccase.

In another aspect, the parent is a *Panus* laccase. In another aspect, the parent is a *Panus rudis* laccase.

In another aspect, the parent is a *Phlebia* laccase. In another aspect, the parent is a *Phlebia radiata* laccase. In another aspect, the parent is a *Phlebia tremellosa* laccase.

In another aspect, the parent is a *Pholiota nameko* laccase. In another aspect, the parent is a *Pholiota nameko* laccase.

In another aspect, the parent is a *Pleurotus* laccase. In another aspect, the parent is a *Pleurotus ertngii* laccase. In another aspect, the parent is a *Pleurotus ostreatus* laccase. In another aspect, the parent is a *Pleurotus pulmonarius* laccase. In another aspect, the parent is a *Pleurotus salmoneostramineus* laccase. In another aspect, the parent is a *Pleurotus sapidus* laccase.

In another aspect, the parent is a *Polyporus* laccase. In another aspect, the parent is a *Polyporus brumalis* laccase. In another aspect, the parent is a *Polyporus ciliates* laccase. In another aspect, the parent is a *Polyporus grammocephalus* laccase. In another aspect, the parent is a *Polyporus pinsitus* laccase.

In another aspect, the parent is a *Postia* laccase. In another aspect, the parent is a *Postia placenta* laccase.

In another aspect, the parent is a *Pycnoporus* laccase. In another aspect, the parent is a *Pycnoporus coccineus* laccase. In another aspect, the parent is a *Pycnoporus cinnabarinus* laccase.

In another aspect, the parent is a *Rigidoporus* laccase. In another aspect, the parent is a *Rigidoporus microporus* laccase.

In another aspect, the parent is a *Schizophyllum* laccase. In another aspect, the parent is a *Schizophyllum commune* laccase.

In another aspect, the parent is a *Serpula* laccase. In another aspect, the parent is a *Serpula lacrymans* laccase.

In another aspect, the parent is a *Spongipellis* laccase. In another aspect, the parent is a *Spongipellis ochraceum* laccase.

In another aspect, the parent is a *Stropharia* laccase. In another aspect, the parent is a *Stropharia aeruginosa* laccase.

In another aspect, the parent is a *Thanatephorus* laccase. In another aspect, the parent is a *Thanatephorus cucumeris* laccase.

In another aspect, the parent is a *Trametes* laccase. In another aspect, the parent is a *Trametes cinnabarina* laccase. In another aspect, the parent is a *Trametes gibbosa* laccase. In another aspect, the parent is a *Trametes hirsuta* laccase. In another aspect, the parent is a *Trametes maxima* laccase. In another aspect, the parent is a *Trametes ochracea* laccase. In another aspect, the parent is a *Trametes pubescens* laccase. In another aspect, the parent is a *Trametes sanguinea* laccase. In another aspect, the parent is a *Trametes trogii* laccase. In another aspect, the parent is a *Trametes velutina* laccase. In another aspect, the parent is a *Trametes versicolor* laccase. In another aspect, the parent is a *Trametes villosa* (*Polyporus pinsitus*) laccase. In another aspect, the parent is a *Trametes* sp. 420 laccase. In another aspect, the parent is a *Trametes* sp. 48424 laccase. In another aspect, the parent is a *Trametes* sp. AH28-2 laccase. In another aspect, the parent is a *Trametes* sp. C30 laccase. In another aspect, the parent is a *Trametes* sp. Ha1 laccase. In another aspect, the parent is a *Trametes* sp. I-62 laccase.

In another aspect, the parent is a *Volvariella* laccase. In another aspect, the parent is a *Volvariella volvacea* laccase.

In another aspect, the parent is a *Yarrowia* laccase. In another aspect, the parent is a *Yarrowia lipolytica* laccase.

In another aspect, the parent is a basidiomycete PM1 laccase.

Other parent laccases useful in the present invention are described in the Laccase and Multicopper Oxidase Engineering Database, which are incorporated herein by reference.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having laccase activity, comprising: (a) introducing into a parent laccase a substitution at one or more (e.g., several) positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2, wherein the variant has laccase activity; and optionally (b) recovering the variant. In one embodiment, the methods further comprise introducing into a parent laccase a substitution at one or more (e.g., several) positions corresponding to positions 89, 151, 286, 307, 313, 339, and 355 of the full-length polypeptide of SEQ ID NO: 2, as described herein.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases).

A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant of the present invention.

The host cell may be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising (a) cultivating a recombinant host cell of the present invention under conditions conducive for production of the variant; and optionally (b) recovering the variant.

The host cells are cultivated in a nutrient medium suitable for production of the variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for laccases. These detection methods include, but are not limited to, use of specific antibodies, formation of an enzyme product, or disappearance of an enzyme substrate. For example, an enzyme assay may be used to determine the activity of the variant, as described herein.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth comprising a variant of the present invention is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant which are used to produce the variant of interest), cell debris, biomass, fermentation media and/or fermentation products. In some embodiments, the composition is a cell-killed whole broths containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell composition comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulation or cell composition may further comprise a preservative and/or anti-microbial (e.g., bacteriostatic) agent, including, but not limited to, sorbitol, sodium chloride, potassium sorbate, and others known in the art.

The fermentation broth formulation or cell composition may further comprise multiple enzymatic activities, such as one or more (e.g., several) enzymes selected from the group consisting of a hydrolase, an isomerase, a ligase, a lyase, an oxidoreductase, and a transferase, e.g., an AA9 polypeptide, alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, expansin, glucoamylase, invertase, laccase, ligninolytic enzyme, lipase, mannosidase, mutanase, oxidase, pectinolytic enzyme, peroxidase, phytase, polyphenoloxidase, proteolytic enzyme, ribonuclease, swollenin, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulation and cell composition of the present invention may be produced by a method described in WO 90/15861 or WO 2010/096673.

Enzyme Compositions

The present invention also relates to a composition comprising a variant of the present invention. Preferably, the composition is enriched in such a variant. The term "enriched" indicates that the laccase activity of the composition has been increased, e.g., with an enrichment factor of at least 1.1.

The composition may comprise a variant of the present invention as the major enzymatic component, e.g., a mono-component composition. Alternatively, the composition may comprise multiple enzymatic activities, such as one or more (e.g., several) enzymes selected from the group consisting of a hydrolase, an isomerase, a ligase, a lyase, an oxidoreductase, and a transferase, e.g., an AA9 polypeptide, alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, expansin, glucoamylase, invertase, laccase, ligninolytic enzyme, lipase, mannosidase, mutanase, oxidase, pectinolytic enzyme, peroxidase, phytase, polyphenoloxidase, proteolytic enzyme, ribonuclease, swollenin, transglutaminase, or xylanase.

The composition may be prepared in accordance with methods known in the art and may be in the form of a liquid or a dry composition. The composition may be stabilized in accordance with methods known in the art.

Examples are given below of preferred uses of the composition of the present invention. The dosage of the composition and other conditions under which the composition is used may be determined on the basis of methods known in the art.

Uses

The variants of the present invention can be used in various industrial applications, including, but not limited to, cellulose conversion (WO 2013/087027), lignin modification (WO 1995/033836 and WO 1996/000290), paper strengthening, dye transfer inhibition in detergents, phenol polymerization, hair dyeing, bleaching of textiles (in particular bleaching of denim as described in WO 1996/12845 and WO 1996/12846), textile dyeing (WO 2001/044563, WO 2000/031333, WO 1997/023684, WO 1997/023685), fabric abrasion (WO 1997/025468), waste water treatment, and detoxification of pretreated cellulosic material (WO 2008/134259), which are incorporated herein in their entireties. Any detergent composition normally used for enzymes may be used, e.g., the detergent compositions disclosed in WO 95/01426, which is incorporated herein in its entirety.

In one aspect, the present invention relates to a method of decolorizing a dye, comprising treating the dye with a laccase variant of the present invention. In an embodiment, the dye can be any dye that is a substrate for a laccase. For example the dye may be indigo carmine or Reactive Black 5.

The present invention is further described by the following examples that should not be construed as limiting the scope of the invention.

EXAMPLES

Media and Solutions

Cellulase Inducing Medium (CIM) was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of Trichoderma trace metals solution, 1-2 drops of antifoam, and deionized water to 1 liter; pH adjusted to 6.0.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2+10 mM Uridine plates were composed of 30 g of sucrose, 20 ml of COVE salt solution, 10 ml of 1 M acetamide, 10 ml of 1 M uridine, 25 g of Noble agar (Difco), and deionized water to 1 liter.

COVE-N-JP top agarose was composed of 342.3 g of sucrose, 3 g of $NaNO_3$, 0.52 g of KCl, 0.52 g of $MgSO_4.7H_2O$, 6 g of $NaNO_3$, 1.52 g of $KH_2PO_4$, 0.04 mg of $Na_2B_4O_7.10H_2O$, 0.4 mg of $CuSO_4.5H_2O$, 1.2 mg of $FeSO_4.7H_2O$, 0.7 mg of $MnSO_4.2H_2O$, 0.8 mg of $Na_2MoO_4.2H_2O$, 10 mg of $ZnSO_4.7H_2O$, 15 g of low melt agarose, and deionized water to 1 liter.

COVE-N-gly agar plates were composed of 218 g of sorbitol, 10 g of glycerol, 2.02 g of $KNO_3$, 1.3 g of KCl, 1.3 g of $MgSO_4.7H_2O$, 6 g of $NaNO_3$, 3.8 g of $KH_2PO_4$, 0.1 mg of $Na_2B_4O_7.10H_2O$, 1 mg of $CuSO_4.5H_2O$, 3 mg of $FeSO_4.7H_2O$, 1.75 mg of $MnSO_4.2H_2O$, 2 mg of $Na_2MoO_4.2H_2O$, 25 mg of $ZnSO_4.7H_2O$, 25 g of Noble agar, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

LB plates were composed of 10 g of tryptone, 5 g of yeast extract, 5 g of NaCl, 15 g of bacteriological agar, and deionized water to 1 liter.

LB medium was composed of 10 g of tryptone, 5 g of yeast extract, 5 g of NaCl, and deionized water to 1 liter.

M410 medium was composed of 50 g of maltose, 50 g of glucose, 2 g of $MgSO_4.7H_2O$, 2 g of $KH_2PO_4$, 4 g of citric acid anhydrous powder, 8 g of yeast extract, 2 g of urea, 0.5 g of $CaCl_2$, 17 mg of $MnSO_4.H_2O$, 0.1 mg of $NiCl_2.6H_2O$, 5 mg of $CuSO_4.5H_2O$, 27.6 mg of $FeSO_4.7H_2O$, 28.6 mg of $ZnSO_4.7H_2O$, and deionized water to 1 liter; the medium was pH-adjusted to 6.0 with 10-20 ml of 10 N NaOH. The final solution was filter-sterilized through a 0.22 μm membrane.

Minimal medium agar plates were composed of 342.3 g of sucrose, 10 g of glucose, 4 g of $MgSO_4.7H_2O$, 6 g of $NaNO_3$, 0.52 g of KCl, 1.52 g of $KH_2PO_4$, 0.04 mg of $Na_2B_4O_7.10H_2O$, 0.4 mg of $CuSO_4.5H_2O$, 1.2 mg of $FeSO_4.7H_2O$, 0.7 mg of $MnSO_4.2H_2O$, 0.8 mg of $Na_2MoO_4.2H_2O$, 10 mg of $ZnSO_4.7H_2O$, 500 mg of citric acid, 4 mg of d-biotin, 20 g of Noble agar, and deionized water to 1 liter.

PEG buffer was composed of 500 g of polyethylene glycol 4000 (PEG 4000), 10 mM $CaCl_2$, 10 mM Tris-HCl pH 7.5, and deionized water to 1 liter; filter sterilized.

STC was composed of 1 M sorbitol, 10 mM $CaCl_2$, and 10 mM Tris-HCl, pH 7.5; filter sterilized.

Synthetic Defined medium lacking uridine was composed of 18 mg of adenine hemisulfate, 76 mg of alanine, 76 mg of arginine hydrochloride, 76 mg of asparagine monohydrate, 76 mg of aspartic acid, 76 mg of cysteine hydrochloride monohydrate, 76 mg of glutamic acid monosodium salt, 76 mg of glutamine, 76 mg of glycine, 76 mg of histidine, 76 mg of myo-inositol, 76 mg of isoleucine, 380 mg of leucine, 76 mg of lysine monohydrochloride, 76 mg of methionine, 8 mg of p-aminobenzoic acid potassium salt, 76 mg of phenylalanine, 76 mg of proline, 76 mg of serine, 76 mg of threonine, 76 mg of tryptophan, 76 mg of tyrosine disodium salt, 76 mg of valine, and deionized water to 1 liter.

TAE buffer was composed of 4.84 g of Tris Base, 1.14 ml of Glacial acetic acid, 2 ml of 0.5 M EDTA pH 8.0, and deionized water to 1 liter.

TBE buffer was composed of 10.8 g of Tris Base, 5.5 g boric acid, 4 ml of 0.5 M EDTA pH 8.0, and deionized water to 1 liter.

Trichoderma trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

YP medium was composed of 10 g of yeast extract, 20 g of Bacto peptone, and deionized water to 1 liter.

2× YT+ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was tempered to 55° C.

TABLE 1

Primers used in the Examples below.

| Identifier | SEQ ID No. | Sequence (5'-3') |
|---|---|---|
| 1204672 | 71 | TCCTCTATATACACAACTGGGGATCCACCATGTCGAGGTTTCACTCTCTTCTCGCTTTC |
| 1204673 | 72 | TCTAGATCTCGAGCTCGCTAGAGTCGACCTACTGGTCGCTCGGGTCGAG |
| 1204564 | 73 | CATGGTGGATCCCCAGTTGTGTATATAGAGG |
| 614604 | 74 | TAGGTCGACTCTAGCGAGCTCGAGATC |
| 999551 | 75 | ACATGTCTTTGATAAgCTAGcGGGCCGCATCATGTA |
| 999552 | 76 | TACATGATGCGGCCCgCTAGcTTATCAAAGACATGT |
| 613017 | 77 | ttaatcgccttgcagcacaCCGCTTCCTCGCTCACTGACTC |
| 613018 | 78 | acaataaccctgataaatgcGGAACAACACTCAACCCTATCTCGGTC |
| 613019 | 79 | agatagggttgagtgttgttccGCATTTATCAGGGTTATTGTCTCATGAGCGG |
| 613020 | 80 | ttctacacgaaggaaagagGAGGAGAGAGTTGAACCTGGACG |
| 613022 | 81 | aggttcaactctctcctcCTCTTTCCTTCGTGTAGAAGACCAGACAG |
| 613021 | 82 | tcagtgagcgaggaagcggTGTGCTGCAAGGCGATTAAGTTGG |
| 1209071 | 83 | TCAACCGCGGACTGCGCACCATGTCGAGGTTTCACTCTCT |
| 1209072 | 84 | GGCTTTCGCCACGGAGCTTACTACTGGTCGCTCGGGTCGA |
| 1206637 | 85 | CTGGCCGTAGAGCTTAAAGTATGTCCC |
| 1206638 | 86 | CGGTCGATTACAATCACATGACTTGGCTTC |
| 1217524 | 88 | TCCTCTATATACACAACTGGGGATCCACCATGTCGAGGTTCCAGTCTCTTTTCTTCTTCG |
| 1217525 | 89 | TCTAGATCTCGAGCTCGCTAGAGTCGACCTAGAGGTCGCTCGGGTCGAGCGCG |
| 1217528 | 90 | TCCTCTATATACACAACTGGGGATCCACCATGAGGTCCTTCATCAGCGCCGCGAC |

TABLE 1-continued

Primers used in the Examples below.

| Identifier | SEQ ID No. | Sequence (5'-3') |
|---|---|---|
| 1217529 | 91 | TCTAGATCTCGAGCTCGCTAGAGTCGACCTACGCCTTGACCAGCCACTCGCCC |

Example 1

ABTS Agar Halo Screen for Laccase Activity in Primary Transformants

Primary transformants were screened for the production of laccase activity on Minimal medium agar plates overlayed with COVE-N-JP top agarose containing 1 mM 2,2'-azinobis-(3-ethybenzthiazoline-6-sulfonic acid) (ABTS). Transformants producing green halos on the ABTS plates were picked to COVE-N-gly agar plates before further analysis.

Example 2

ABTS Liquid Assay for Laccase Activity

The assay was performed using a Beckman Coulter Biomek 3000 (Beckman Coulter, Inc.). Culture supernatants were diluted appropriately in 0.1 M sodium acetate, 0.01% TRITON® X-100 pH 5.0 buffer (sample buffer) followed with a series dilution from 0-fold to ⅓-fold to ⅑-fold of the diluted sample. A laccase standard was diluted using 2-fold steps starting with a 0.06 LAMU/ml concentration and ending with a 0.0075 LAMU/ml concentration in the sample buffer. A total of 20 µl of each dilution including the laccase standard was transferred to a 96-well flat bottom plate. Two hundred micro-liters of an ABTS (2,2'-azino-bis(3-ethylbenzthiazoline-6-sulfonic acid)) substrate solution (0.1 M sodium acetate pH 5.0+0.275 mg/ml ABTS+0.01% TRITON® X-100) were added to each well and then incubated at ambient temperature for 30 minutes. During the incubation the rate of the reaction was measured at an optical density of 405 nm in a SPECTRAMAX® M5 spectrophotometer (Molecular Devices). Sample concentrations were determined by extrapolation from the generated standard curve.

Example 3

Syringaldazine Liquid Assay for Laccase Activity

The assay was performed using a Beckman Coulter Biomek 3000. Culture supernatants were diluted appropriately in 0.1 M sodium acetate, 0.01% TRITON® X-100 pH 5.0 buffer (sample buffer) followed by a series of dilutions from 0-fold to ⅓-fold to ⅑-fold of the diluted sample. A laccase standard was diluted using 2-fold steps starting with a 1.16 LAMU/ml concentration and ending with a 0.145 LAMU/ml concentration in the sample buffer. A total of 20 µl of each dilution including the laccase standard was transferred to a 96-well flat bottom plate. Two hundred microliters of a 0.22 mM syringaldazine substrate solution (0.56 mM syringaldazine in 96% ethanol (Stock) diluted to 0.22 mM in sample buffer) was added to each well and then incubated at ambient temperature for 6 minutes. During the incubation the rate of the reaction was measured at an optical density of 540 nm in a SPECTRAMAX® M5 spectrophotometer. Sample concentrations were determined by extrapolation from the generated standard curve.

Example 4

HOBT-Indigo Carmine Liquid Assay for Laccase Activity

An additional laccase activity assay is employed to monitor the dye-bleaching (indigo carmine) activity of laccase variants relative to the parent laccase through oxidation by molecular oxygen, catalyzed by laccase in the presence of a mediator (hydroxybenzotriazole). For each reaction, 12 μl of hydroxybenzotriazole (HOBT) mediator solution (Sigma-Aldrich) (37.5 mM in 10% DMSO) were combined with 12 μl of indigo carmine solution (Sigma-Aldrich) (1.0 g/ml in water), 60 μl of 100 mM sodium acetate pH 5.0, 1 mM $CuSO_4$, and 60 μl of water, and dispensed into 96 well plates. Reactions were initiated by the addition of 10 μl of liquid culture broth to each well, and the plates were sealed with a PCR plate seal and incubated at 60° C. for 30 minutes. Dye-bleaching was assessed by measuring the absorbance at 610 nm in a SPECTRAMAX® M5 spectrophotometer.

Example 5

Construction of Plasmid pMMar27 as a Yeast Expression Vector

Plasmid pMMar27 was constructed for expression of the *Thielavia terrestris* Cel6A cellobiohydrolase II in yeast. The plasmid was generated from a lineage of yeast expression vectors: plasmid pMMar27 was constructed from plasmid pBM175b; plasmid pBM175b was constructed from plasmid pBM143b (WO 2008/008950) and plasmid pJLin201; and plasmid pJLin201 was constructed from pBM143b.

Plasmid pJLin201 is identical to pBM143b except an Xba I site immediately downstream of a *Thermomyces lanuginosus* lipase variant gene in pBM143b was mutated to a unique Nhe I site. A QUIKCHANGE® II XL Site-Directed Mutagenesis Kit (Stratagene) was used to change the Xba I sequence (TCTAGA) to a Nhe I sequence (gCTAGc) in pBM143b. The PCR was composed of 125 ng of primers 999551 and 999552, 20 ng of pBM143b, 1× QUIKCHANGE® Reaction Buffer (Stratagene), 3 μl of QUIKSOLUTION® (Stratagene), 1 μl of dNTP mix, and 1 μl of a 2.5 units/ml Pfu Ultra HF DNA polymerase (Stratagene) in a final volume of 50 μl. The PCR was performed using an EPPENDORF® MASTERCYCLER® thermocycler (Eppendorf AG) programmed for 1 cycle at 95° C. for 1 minute; 18 cycles each at 95° C. for 50 seconds, 60° C. for 50 seconds, and 68° C. for 6 minutes and 6 seconds; and 1 cycle at 68° C. for 7 minutes. After the PCR, the tube was placed on ice for 2 minutes. One microliter of Dpn I (Promega) was then directly added to the reaction mixture and incubated at 37° C. for 1 hour. A 2 μl volume of the Dpn I digested reaction was used to transform *E. coli* XL10 GOLD® Ultracompetent Cells (Stratagene) according to the manufacturer's instructions. *E. coli* transformants were selected on 2× YT plus ampicillin plates. Plasmid DNA was isolated from several of the transformants using a BIOROBOT® 9600 (QIAGEN Inc.). One plasmid with the desired Nhe I change was confirmed by restriction digestion and sequencing analysis using a 3130XL Genetic Analyzer (Applied Biosystems) and designated plasmid pJLin201. To eliminate possible PCR errors introduced by site-directed-mutagenesis, plasmid pBM175b was constructed by cloning the Nhe I site containing fragment back into plasmid pBM143b. Briefly, plasmid pJLin201 was digested with Nde I and Mlu I and the resulting fragment was cloned into pBM143b, previously digested with the same enzymes, using a Rapid Ligation Kit (Roche Diagnostics Corp.). Briefly, 7 μl of the Nde I/Mlu I digested pJLin201 fragment and 1 μl of the digested pBM143b were mixed with 2 μl of 5× DNA dilution buffer (Roche Diagnostics Corp.), 10 μl of 2× T4 DNA Ligation buffer (Roche Diagnostics Corp.), and 1 μl of T4 DNA ligase (Roche Diagnostics Corp.) and incubated for 15 minutes at room temperature. Two microliters of the ligation were transformed into XL1-Blue Subcloning-Grade Competent Cells (Stratagene) cells and spread onto 2× YT plus ampicillin plates. Plasmid DNA was purified from several transformants using a BIOROBOT® 9600 and analyzed by DNA sequencing using a 3130XL Genetic Analyzer to identify a plasmid containing the desired *A. nidulans* pyrG insert. One plasmid with the expected DNA sequence was designated pBM175b.

Plasmid pMMar27 was constructed from pBM175b and an amplified gene of the *T. terrestris* Cel6A cellobiohydrolase II with overhangs designed for insertion into digested pBM175b. Plasmid pBM175b containing the *Thermomyces lanuginosus* lipase variant gene under control of the CUP I promoter contains unique Hind III and Nhe I sites to remove the lipase gene. Plasmid pBM175b was digested with these restriction enzymes to remove the lipase gene. After digestion, the empty vector was isolated by 1.0% agarose gel electrophoresis using TBE buffer where an approximately 5,215 bp fragment was excised from the gel and extracted using a QIAQUICK® Gel Extraction Kit (QIAGEN Inc.). The ligation reaction (20 μl) was composed of 1× IN-FUSION® Buffer (BD Biosciences), 1× BSA (BD Biosciences), 1 μl of IN-FUSION® enzyme (diluted 1:10) (BD Biosciences), 99 ng of pBM175b digested with Hind III and Nhe I, and 36 ng of the purified *T. terrestris* Cel6A cellobiohydrolase II PCR product. The reaction was incubated at room temperature for 30 minutes. A 2 μl volume of the IN-FUSION® reaction was transformed into *E. coli* XL10-GOLD® Ultracompetent Cells (Stratagene). Transformants were selected on LB plates supplemented with 100 μg of ampicillin per ml. A colony was picked that contained the *T. terrestris* Cel6A inserted into the pBM175b vector in place of the lipase gene, resulting in pMMar27 (FIG. 1). The plasmid chosen contained a PCR error at position 228 from the start codon, TCT instead of TCC, but resulted in a silent change in the *T. terrestris* Cel6A cellobiohydrolase II.

Example 6

Construction of pEvFz1 Expression Vector

Expression vector pEvFz1 was constructed by modifying pBM120a (U.S. Pat. No. 8,263,824) to comprise the NA2/NA2-tpi promoter, *Aspergillus niger* amyloglucosidase terminator sequence (AMG terminator), and *Aspergillus nidulans* orotidine-5'-phosphate decarboxylase gene (pyrG) as a selectable marker.

Plasmid pEvFz1 was generated by cloning the *A. nidulans* pyrG gene from pAILo2 (WO 2004/099228) into pBM120a. Plasmids pBM120a and pAILo2 were digested with Nsi I overnight at 37° C. The resulting 4176 bp linearized pBM120a vector fragment and the 1479 bp pyrG gene insert from pAILo2 were each purified by 0.7% agarose gel electrophoresis using TAE buffer, excised from the gel, and extracted using a QIAQUICK® Gel Extraction Kit.

The 1479 bp pyrG gene insert was ligated to the Nsi I digested pBM120a fragment using a QUICK LIGATION™ Kit (New England Biolabs). The ligation reaction was composed of 1× QUICK LIGATION™ Reaction Buffer (New England Biolabs), 50 ng of Nsi I digested pBM120a vector, 54 ng of the 1479 bp Nsi I digested pyrG gene insert, and 1 μl of T4 DNA ligase in a total volume of 20 μl. The ligation mixture was incubated at 37° C. for 15 minutes followed at 50° C. for 15 minutes and then placed on ice.

Figure 2:
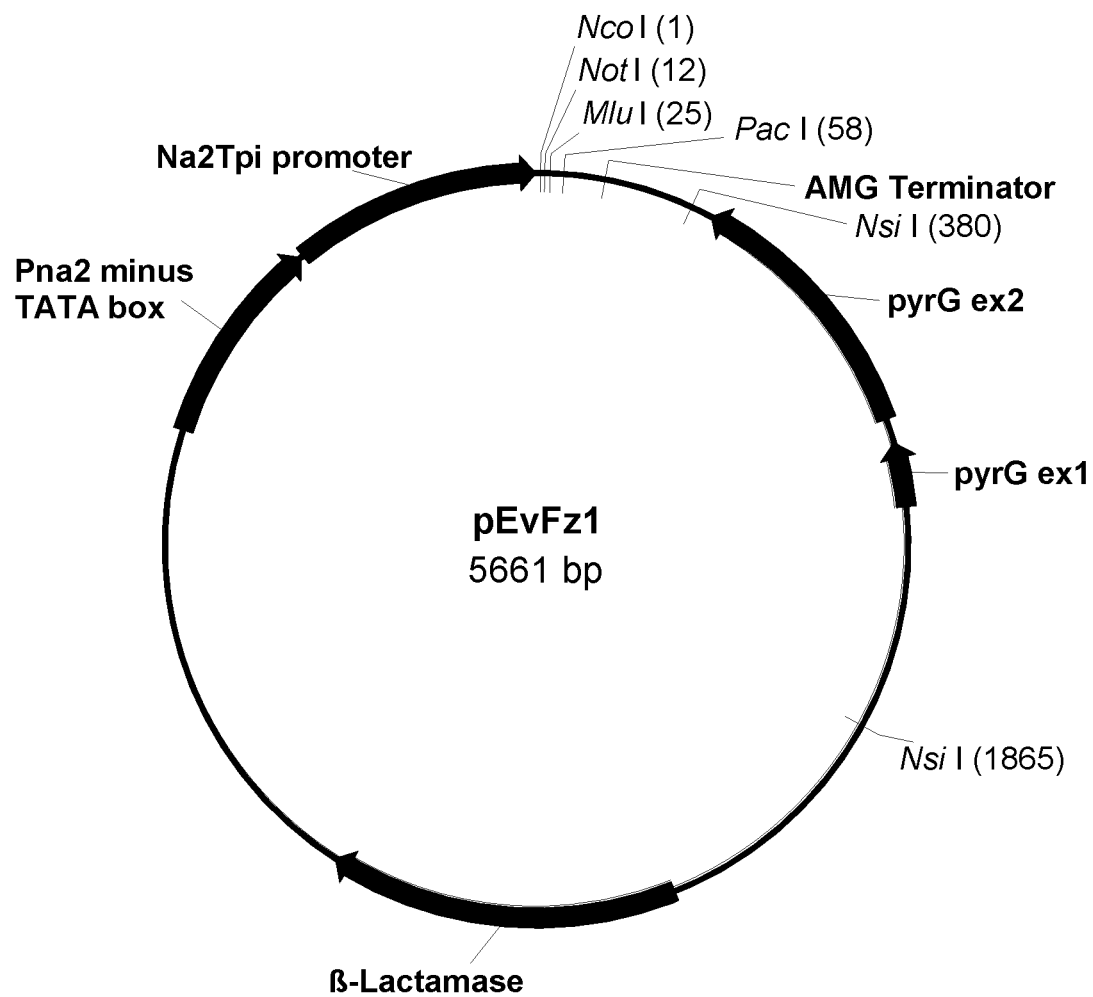
FIG. 2 shows a restriction map of pEvFz1.

One μl of the ligation mixture was transformed into ONE SHOT® TOP10 chemically competent *Escherichia coli* cells (Invitrogen). Transformants were selected on 2× YT plus ampicillin plates. Plasmid DNA was purified from several transformants using a BIOROBOT® 9600 and analyzed by DNA sequencing using a 3130XL Genetic Analyzer to identify a plasmid containing the desired *A. nidulans* pyrG insert. One plasmid with the expected DNA sequence was designated pEvFz1 (FIG. 2).

Example 7

Construction of the Plasmid pDLHD0006 as a Yeast/*E. coli*/*A. oryzae* Shuttle Vector Plasmid pDLHD0006 was constructed as a base vector to enable *Aspergillus oryzae* expression cassette library building using yeast recombinational cloning. Plasmid pDLHD0006 was constructed by combining three DNA fragments using yeast recombinational cloning: Fragment 1 containing the *E. coli* pUC origin of replication, *E. coli* beta-lactamase (ampR) selectable marker, URA3 yeast selectable marker, and yeast 2 micron origin of replication from pMMar27 (Example 5); Fragment 2 containing the NA2-tpi promoter (a hybrid of the promoters from the genes encoding *Aspergillus niger* neutral alpha-amylase and *Aspergillus oryzae* triose phosphate isomerase, *Thermomyces lanuginosus* lipase open reading frame (ORF), and *Aspergillus niger* glucoamylase terminator from pJaL1262 (WO 2013/178674); and Fragment 3 containing the *Aspergillus nidulans* pyrG selection marker from pEvFz1 (Example 5).

TABLE II

| pDLHD0006 | PCR Contents | PCR Template |
|---|---|---|
| Fragment 1 | E. coli ori/AmpR/URA/2 micron (4.1 kb) | pMMar27 |
| Fragment 2 | NA2-tpi PR/lipase/Tamg (4.5 kb) | pJaL1262 |
| Fragment 3 | pyrG gene from pEvFz1 (1.7 kb) | pEvFz1 |

Fragment 1 was amplified using primers 613017 (sense) and 613018 (antisense) shown below. Primer 613017 was designed to contain a flanking region with sequence homology to Fragment 3 (lower case) and primer 613018 was designed to contain a flanking region with sequence homology to Fragment 2 (lower case) to enable yeast recombinational cloning between the three PCR fragments.

Fragment 1 was amplified by PCR in a reaction composed of 10 ng of plasmid pMMar27, 0.5 μl of PHUSION® DNA Polymerase (New England Biolabs, Inc.), 20 pmol of primer 613017, 20 pmol of primer 613018, 1 μl of 10 mM dNTPs, 10 μl of 5× PHUSION® HF buffer (New England Biolabs, Inc.), and 35.5 μl of water. The reaction was incubated in an EPPENDORF® MASTERCYCLER® thermocycler programmed for 1 cycle at 98° C. for 30 seconds; and 30 cycles each at 98° C. for 10 seconds, 60° C. for 10 seconds, and 72° C. for 1.5 minutes. The resulting 4.1 kb PCR product (Fragment 1) was used directly for yeast recombination with Fragments 2 and 3 below.

Fragment 2 was amplified using primers 613019 (sense) and 613020 (antisense). Primer 613019 was designed to contain a flanking region of sequence homology to Fragment 1 (lower case) and primer 613020 was designed to contain a flanking region of sequence homology to Fragment 3 (lower case) to enable yeast recombinational cloning between the three PCR fragments.

Fragment 2 was amplified by PCR in a reaction composed of 10 ng of plasmid pJaL1262, 0.5 μl of PHUSION® DNA Polymerase, 20 pmol of primer 613019, 20 pmol of primer 613020, 1 μl of 10 mM dNTPs, 10 μl of 5× PHUSION® HF buffer, and 35.5 μl of water. The reaction was incubated in an EPPENDORF® MASTERCYCLER® thermocycler programmed for 1 cycle at 98° C. for 30 seconds; 30 cycles each at 98° C. for 10 seconds, 60° C. for 10 seconds, and 72° C. for 2 minutes; and a 20° C. hold. The resulting 4.5 kb PCR product (Fragment 2) was used directly for yeast recombination with Fragment 1 above and Fragment 3 below.

Fragment 3 was amplified using primers 613022 (sense) and 613021 (antisense). Primer 613021 was designed to contain a flanking region of sequence homology to Fragment 2 (lower case) and primer 613022 was designed to contain a flanking region of sequence homology to Fragment 1 (lower case) to enable yeast recombinational cloning between the three PCR fragments.

Fragment 3 was amplified by PCR in a reaction composed of 10 ng of plasmid pEvFz1 (Example 5), 0.5 μl of PHUSION® DNA Polymerase, 20 pmol of primer 613021, 20 pmol of primer 613022, 1 μl of 10 mM dNTPs, 10 μl of 5× PHUSION® HF buffer, and 35.5 μl of water. The reaction was incubated in an EPPENDORF® MASTERCYCLER® thermocycler programmed for 1 cycle at 98° C. for 30 seconds; 30 cycles each at 98° C. for 10 seconds, 60° C. for 10 seconds, and 72° C. for 2 minutes; and a 20° C. hold. The resulting 1.7 kb PCR product (Fragment 3) was used directly for yeast recombination with Fragments 1 and 2 above.

Figure 3:
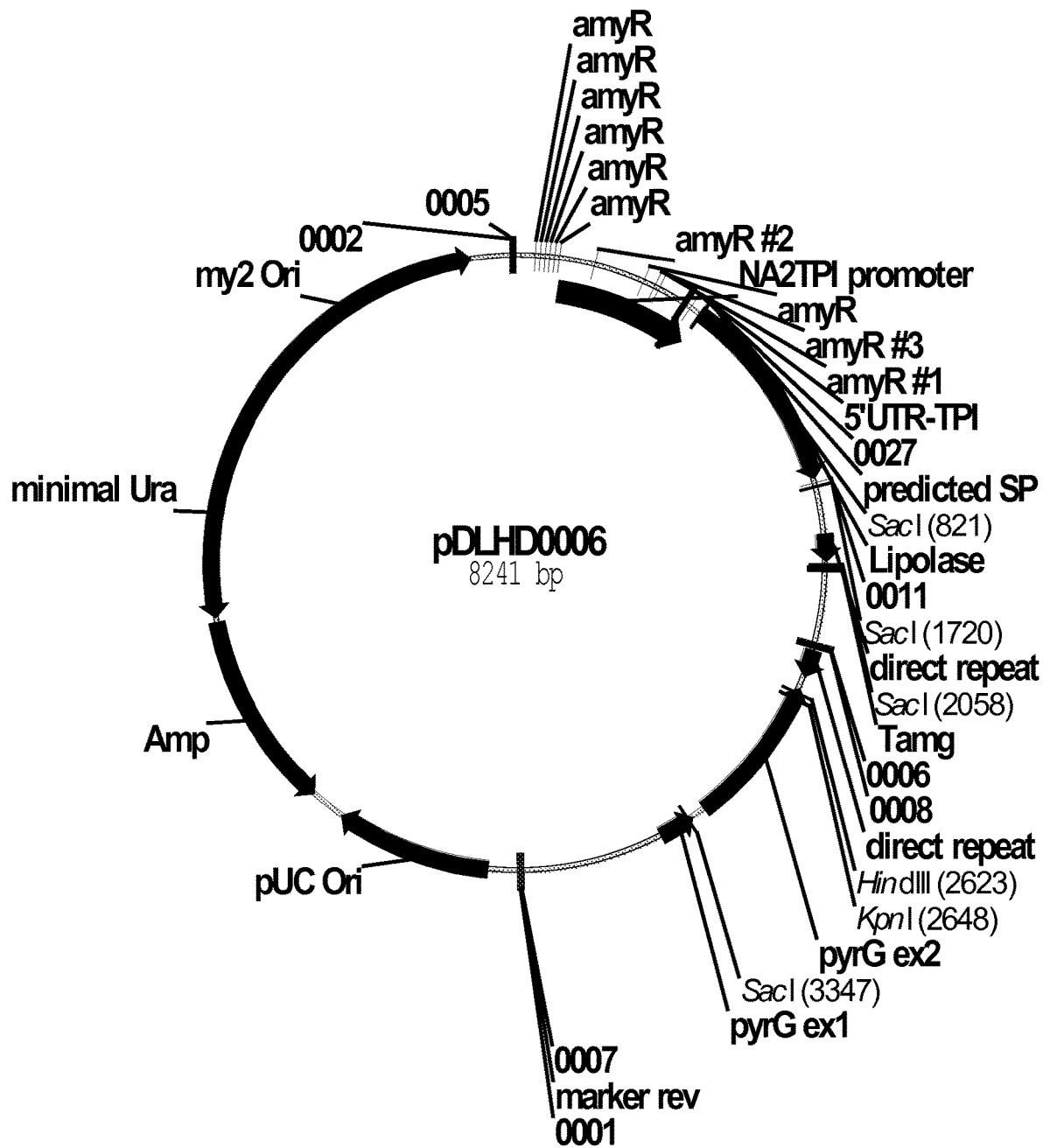
FIG. 3 shows a restriction map of pDLHD0006.

The following procedure was used to combine the three PCR fragments using yeast homology-based recombinational cloning. A 20 μl aliquot of each of the three PCR fragments was combined with 100 μg of single-stranded deoxyribonucleic acid from salmon testes (Sigma-Aldrich), 100 μl of competent yeast cells of strain YNG318 (*Saccharomyces cerevisiae* ATCC 208973), and 600 μl of PLATE Buffer (Sigma-Aldrich), and mixed. The reaction was incubated at 30° C. for 30 minutes with shaking at 200 rpm. The reaction was then continued at 42° C. for 15 minutes with no shaking. The cells were pelleted by centrifugation at 5,000×g for 1 minute and the supernatant was discarded. The cell pellet was suspended in 200 μl of autoclaved water and split over two agar plates containing Synthetic Defined medium lacking uridine and incubated at 30° C. for three days. The yeast colonies were isolated from the plate using 1 ml of autoclaved water. The cells were pelleted by centrifugation at 13,000×g for 30 seconds and a 100 μl aliquot of glass beads were added to the tube. The cell and bead mixture was suspended in 250 μl of P1 buffer (QIAGEN Inc.) and then vortexed for 1 minute to lyse the cells. The plasmid DNA was purified using a QIAPREP® Spin Miniprep Kit (QIAGEN Inc.). A 3 μl aliquot of the plasmid DNA was then transformed into *E. coli* ONE SHOT® TOP10 electrocompetent cells (Invitrogen) according to the manufacturer's instructions. Fifty μl of transformed cells were spread onto LB plates supplemented with 100 μg of ampicillin per ml and incubated at 37° C. overnight. Transformants were each picked into 3 ml of LB medium supplemented with 100 µg of ampicillin per ml and grown overnight at 37° C. with shaking at 250 rpm. The plasmid DNA was purified from colonies using a QIAPREP® Spin Miniprep Kit. DNA sequencing with a 3130XL Genetic Analyzer confirmed the presence of each of the three fragments in a final plasmid designated pDLHD0006 (FIG. 3).

Example 8

Figure 4:
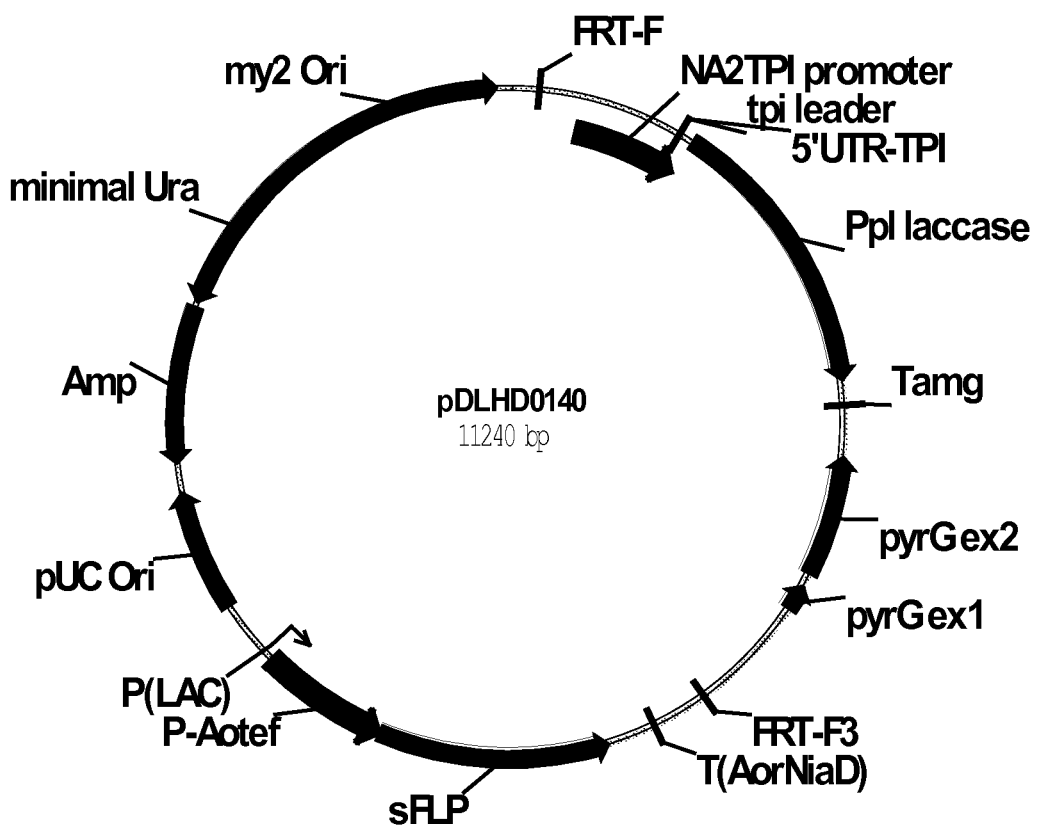
FIG. 4 shows a restriction map of pDLHD0140.

Cloning of the Wild-Type *Trametes villosa* Laccase for Expression in an *Aspergillus oryzae* Screening Strain The wild-type *Trametes villosa* laccase cDNA (SEQ ID NO; 1 for the cDNA sequence and SEQ ID NO: 2 for the deduced amino acid sequence) was cloned into a *Saccharomyces cerevisiae*/*A. oryzae* Flp/FRT shuttle vector by yeast recombinational cloning, resulting in vector pDLHD0140 (FIG. 4).

Expression vector pDLHD0140 was constructed to contain the *E. coli* pUC origin of replication, *E. coli* beta-lactamase (ampR) selectable marker, URA3 yeast selectable marker, yeast 2 micron origin of replication, NA2-tpi promoter, *T. villosa* laccase open reading frame, *Aspergillus niger* glucoamylase terminator, *Aspergillus nidulans* pyrG selection marker, *Saccharomyces cerevisiae* 2 µm flippase ORF between the *Aspergillus oryzae* TEF1 promoter and *Aspergillus oryzae* NiaD terminator, and *Saccharomyces cerevisiae* 2 µm flippase recognition targets FRT-F and FRT-F3.

Plasmid pDLHD0140 was constructed by combining two DNA fragments using yeast recombinational cloning: Fragment 1 contained the *E. coli* pUC origin of replication, *E. coli* beta-lactamase (ampR) selectable marker, URA3 yeast selectable marker, yeast 2 micron origin of replication, NA2-tpi promoter, *Aspergillus niger* glucoamylase terminator, *Aspergillus nidulans* pyrG selection marker, *Saccharomyces cerevisiae* 2 µm flippase ORF between the *Aspergillus oryzae* TEF1 promoter and *Aspergillus oryzae* NiaD terminator, and *Saccharomyces cerevisiae* 2 µm flippase recognition targets FRT-F and FRT-F3, and flanking sequences with homology to fragment 2. Fragment 2 contained the *T. villosa* laccase open reading frame, and flanking sequences with homology to fragment 1.

Figure 5:
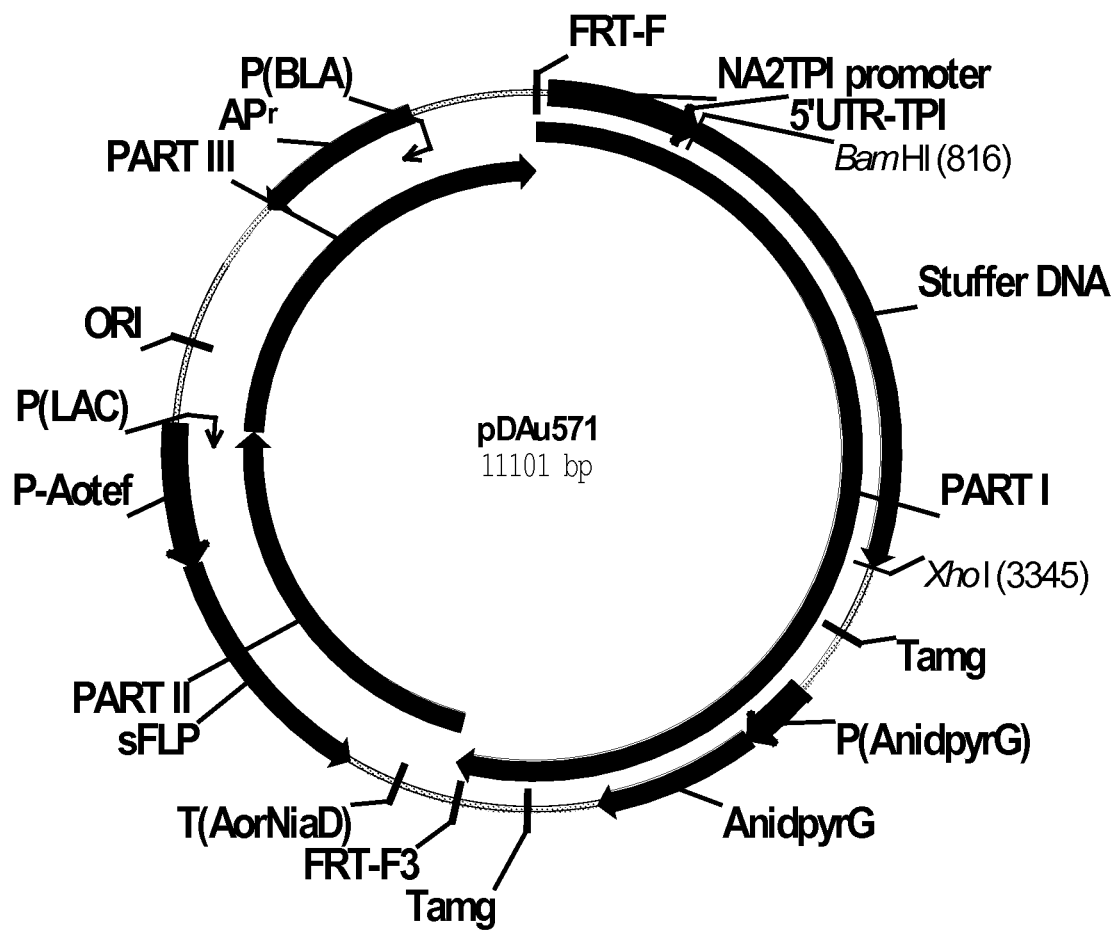
FIG. 5 shows a restriction map of pDAu571.

Fragment 1 was amplified using primer 614604 (sense) and primer 1204564 (antisense). These primers were designed to contain flanking regions of sequence homology to fragment 2 for ligation-free cloning between the PCR fragments. Fragment 1 was amplified by PCR in a reaction composed of 10 ng of pDAu571 (FIG. 5; SEQ ID NO: 87), 0.5 µl of PHUSION® DNA Polymerase, 20 pmol of primer 614604, 20 pmol of primer 1204564, 1 µl of 10 mM dNTPs, 10 µl of 5× PHUSION® HF buffer, and 35.5 µl of water. The reaction was incubated in an EPPENDORF® MASTERCYCLER® thermocycler programmed for 1 cycle at 98° C. for 30 seconds; and 30 cycles each at 98° C. for 10 seconds, 60° C. for 10 seconds, and 72° C. for 120 seconds. The resulting 9.7 kb PCR product (fragment 1) was treated with 1 µl of Dpn I to remove plasmid template DNA. The Dpn I was added directly to the PCR tube, mixed well, and incubated at 37° C. for 60 minutes.

Figure 6:
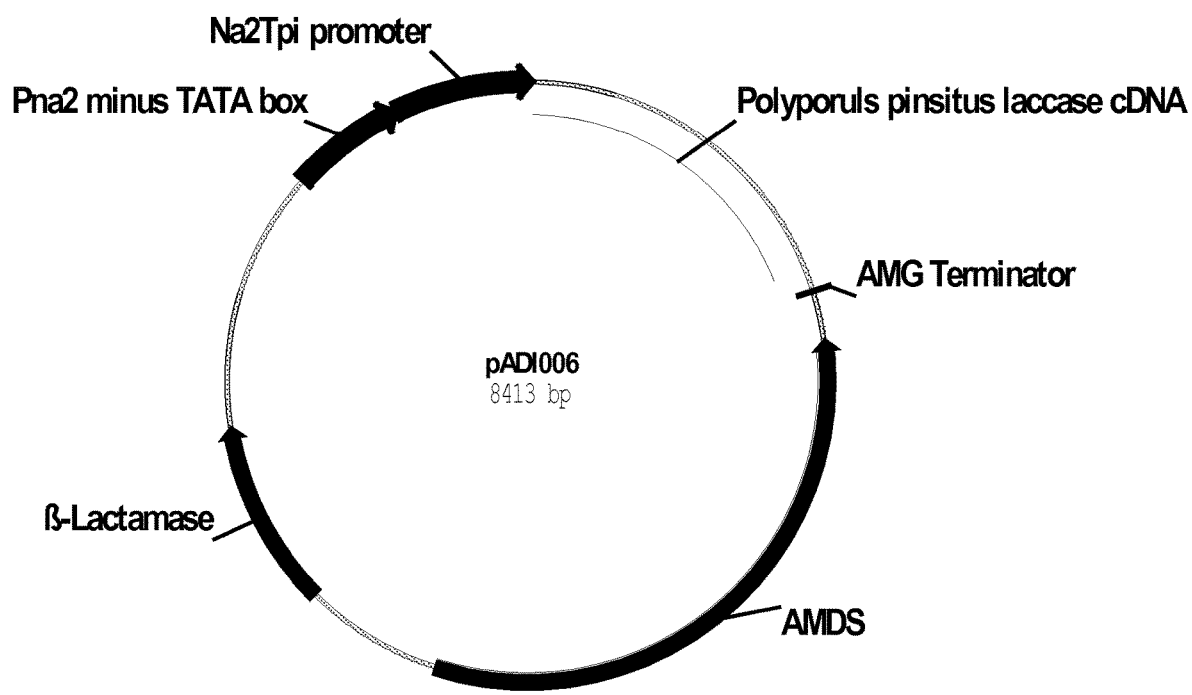
FIG. 6 shows a restriction map of pAD1006.

Fragment 2 was amplified using primer 1204672 (sense) and primer 1204673 (antisense). These primers were designed to contain flanking regions of sequence homology to fragment 1 for ligation-free cloning between the PCR fragments. Fragment 2 was amplified by PCR in a reaction composed of 10 ng of pADI006 (FIG. 6), 0.5 µl of PHUSION® DNA Polymerase, 20 pmol of primer 1204672, 20 pmol of primer 1204673, 1 µl of 10 mM dNTPs, 10 µl of 5× PHUSION® HF buffer, and 35.5 µl of water. The reaction was incubated in an EPPENDORF® MASTERCYCLER® thermocycler programmed for 1 cycle at 98° C. for 30 seconds; and 30 cycles each at 98° C. for 10 seconds, 60° C. for 10 seconds, and 72° C. for 120 seconds. The resulting 1.6 kb PCR product (fragment 2) was treated with 1 µl of Dpn I to remove plasmid template DNA. The Dpn I was added directly to the PCR tube, mixed well, and incubated at 37° C. for 60 minutes.

The following procedure was used to combine the two PCR fragments using yeast homology-based recombinational cloning. A 10 µl aliquot of each of the PCR fragments was combined with 100 µg of single-stranded deoxyribonucleic acid from salmon testes (Sigma-Aldrich), 100 µl of competent yeast cells of *Saccharomyces cerevisiae* strain YNG318 (ATCC 208973), and 600 µl of PLATE Buffer (Sigma-Aldrich), and mixed. The reaction was incubated at 30° C. for 30 minutes with shaking at 200 rpm. The reaction was then continued at 42° C. for 15 minutes with no shaking. The cells were pelleted by centrifugation at 5,000×g for 1 minute and the supernatant was discarded. The cell pellet was suspended in 200 µl of autoclaved water and split over two agar plates containing Synthetic Defined medium lacking uridine and incubated at 30° C. for three days. The yeast colonies were isolated from the plate using 1 ml of autoclaved water. The cells were pelleted by centrifugation at 13,000×g for 30 seconds and a 100 µl aliquot of glass beads were added to the tube. The cell and bead mixture was suspended in 250 µl of P1 buffer (QIAGEN Inc.) and then vortexed for 1 minute to lyse the cells. The plasmid DNA was purified using a QIAPREP® Spin Miniprep Kit. A 3 µl aliquot of the plasmid DNA was then transformed into *E. coli* ONE SHOT® TOP10 electrocompetent cells according the manufacturer's instructions. Fifty µl of transformed cells were spread onto 2× YT plates supplemented with 100 µg of ampicillin per ml and incubated at 37° C. overnight. Transformants were each picked into 3 ml of LB medium supplemented with 100 µg of ampicillin per ml and grown overnight at 37° C. with shaking at 250 rpm. The plasmid DNA was purified using a QIAPREP® Spin Miniprep Kit. DNA sequencing with a 3130XL Genetic Analyzer confirmed the presence of both of the three fragments in a final plasmid designated plasmid pDLHD0140 (FIG. 4).

Example 9

Confirmation of Wild-Type *Trametes villosa* Laccase Expression in Single-Copy in *Aspergillus oryzae* Screening Strain JaL1394

*Aspergillus oryzae* strain JaL1394 (WO 2012/160093) utilizing the *Saccharomyces cerevisiae* 2 µm plasmid flippase recognition target (FRT) and recombinase (Flp) system to generate a high efficiency single-copy, targeted transformation system was used for screening gene variant libraries. The Flp-FRT system of *Saccharomyces cerevisiae* is a site-specific recombination system which can be used to insert a DNA of interest into a known location in the genome of a host organism of interest. The *Aspergillus oryzae* strain JaL1394 had been previously engineered to possess FRT-F and FRT-F3 flippase recognition target sequences in the amyB locus, where the AmyB ORF had been deleted.

*Aspergillus oryzae* JaL1394 was transformed with plasmid pDLHD0140 comprising the wild-type *T. villosa* laccase gene. Approximately 10⁷ spores from *A. oryzae* JaL1394 were inoculated into 100 ml of YP+2% glucose medium supplemented with 10 mM uridine in a 500 ml shake flask and incubated at 28° C. and 110 rpm overnight. Ten ml of the overnight culture were filtered in a 125 ml sterile vacuum filter, and the mycelia were washed twice with 50 ml of 0.7 M KCl-20 mM CaCl$_2$. The remaining liquid was removed by vacuum filtration, leaving the mat on the filter. The mycelia were resuspended in 10 ml of 0.7 M KCl-20 mM CaCl$_2$ and transferred to a sterile 125 ml shake flask containing 20 mg of GLUCANEX® 200 G (Novozymes Switzerland AG) per ml and 0.2 mg of chitinase (Sigma-Aldrich) per ml in 10 ml of 0.7 M KCl-20 mM CaCl$_2$. The mixture was incubated at 37° C. and 100 rpm for 30-90 minutes until protoplasts were generated from the mycelia. The protoplast mixture was filtered through a sterile funnel lined with MIRACLOTH® (Calbiochem) into a sterile 50 ml plastic centrifuge tube to remove mycelial debris. The debris on the MIRACLOTH® was washed thoroughly with 10 ml of 0.7 M KCl-20 mM CaCl$_2$, and centrifuged at 2500 rpm for 10 minutes at 20-23° C. The supernatant was removed and the protoplast pellet was resuspended in 20 ml of 1 M sorbitol-10 mM CaCl$_2$-10 mM Tris-HCl (pH 6.5). This step was repeated twice, and the final protoplast pellet was resuspended in 1 M sorbitol-10 mM CaCl$_2$-10 mM Tris-HCl (pH 6.5) to obtain a final protoplast concentration of 2×10⁷/ml.

Protoplasts were transformed by the addition of two μg of pDLHD0140 to the bottom of a sterile 50 ml plastic centrifuge tube. One hundred μl of protoplasts were added to the tube followed by 300 μl of 60% PEG-4000 in 10 mM CaCl$_2$-10 mM Tris-HCl (pH 6.5). The tube was mixed gently by hand and incubated at 37° C. for 30 minutes. Thirty ml of COVE-N-JP top agarose containing 1 mM ABTS were added to the transformation and the mixture was transferred onto two 150 mm Minimal medium agar plates. Transformation plates were incubated at 34° C. until transformants appeared and green ABTS color was observed around each colony. The conversion of ABTS to a visible green color demonstrated that the transformants produced active *T. villosa* laccase.

Single transformants were picked to new COVE-N-gly agar plates and cultivated at 34° C. for four days until the transformants sporulated. Fresh spores were transferred to 48-well deep-well plates containing 2 ml of M410 medium containing 0.25 mM CuSO$_4$, covered with a breathable seal, and grown for 4 days at 34° C. with no shaking. After 4 days growth the culture medium for each transformant was assayed for laccase activity according to Examples 2, 3, and 4, and for laccase expression by SDS-PAGE.

SDS-PAGE was performed using a 8-16% CRITERION® Stain Free SDS-PAGE gel (Bio-Rad Laboratories, Inc.), and imaging the gel with a Stain Free Imager (Bio-Rad Laboratories, Inc.) using the following settings: 5-minute activation, automatic imaging exposure (intense bands), highlight saturated pixels=ON, color=Coomassie, and band detection, molecular weight analysis and reporting disabled. SDS-PAGE revealed a protein band migrating at approximately 70 kDa for the wild-type *T. villosa* laccase.

Example 10

Construction and Identification of Increased Expression and Increased Specific Activity Variants of *Trametes villosa* Laccase

*Trametes villosa* laccase gene mutant libraries were constructed by site-saturation mutagenesis of the gene encoding the wild-type laccase as parent. The mutant libraries of the *T. villosa* laccase gene (each fragment of the library comprises a mutant *T. villosa* laccase gene plus *Aspergillus nidulans* orotidine 5'-phosphate decarboxylase pyrG selection marker and the FRT-F and FRT-F3 flippase recognition target sequences) were transformed into protoplasts of *Aspergillus oryzae* JaL1394 as described in Example 9 along with one μg of vector pDLHD0095 encoding the *Saccharomyces cerevisiae* 2 μm flippase ORF between the *Aspergillus oryzae* TEF1 promoter and *Aspergillus oryzae* niaD gene terminator. After 4 days of protoplast recovery at 34° C. on Minimal medium agar plates overlayed with COVE-N-JP top agarose containing 1 mM ABTS, single colonies with green halos were picked into individual wells of 48-well deep-well plates containing 2 ml of M410 medium containing 0.25 mM CuSO$_4$, covered with a breathable seal, and grown for 4 days at 34° C. with no shaking. After 4 days growth the liquid culture medium was assayed for laccase activity as described in Examples 2, 3, and 4, and higher activity variants were scored as expression hits.

Individual mutant strains were spore-purified and cultivated again in 125 ml shake flasks in 25 ml of M410 medium containing 0.25 mM CuSO$_4$ for 4 days at 34° C. with shaking at 250 rpm to generate fresh broth for retesting for laccase activity as described in Examples 2, 3, and 4 relative to *A. oryzae* JaL1394 strain expressing the parent *T. villosa* laccase gene. Broths were also analyzed by SDS-PAGE as described in Example 9 for increased expression yield of the *T. villosa* laccase protein product.

Relative improvements in expression yield over the parent laccase in day 4 broths from 48-well deep-well plate and shake flask cultivations for all single site variants at positions L79, F102, V170, V175, S200, A262, V289, T292, Y302, N357, I360, Y393, S397, A485, and D507, are shown in Table III below, and combinatorial variants A262G+I360V, A262G+V289I+T292D+N357D; S37C+A262G+Y939I+A485S; V175T+S200D+A262G+I360V+Y393I; F102A+V175S+A262G+I360V+S397A; F102A+V175T+S200D+A262G+N357D+S397A; and A9R+L79D+L179N are shown in Table IV below. SDS-PAGE analysis of the same broths demonstrated a *T. villosa* laccase band of increased intensity over the parent *T. villosa* laccase for all variants, which correlated well with the relative improvements observed in the activity assays. The SDS-PAGE band for the parent *T. villosa* laccase and variants thereof was 70 kDa, with no obvious changes due to differential glycosylation.

TABLE III

| *Trametes villosa* laccase variant | ABTS Assay |
|---|---|
| Parent (Wild-Type) | 1.0 |
| L79A | 1.3 |
| L79C | <1 |
| L79D | 1.3 |
| L79E | 2.1 |
| L79F | 1.3 |
| L79G | 1.6 |
| L79H | <1 |
| L79I | 1.4 |
| L79K | <1 |
| L79M | 1.2 |
| L79N | 1.2 |
| L79P | <1 |
| L79Q | 1.2 |
| L79R | <1 |
| L79S | 1.6 |
| L79T | <1 |

TABLE III-continued

| Trametes villosa laccase variant | ABTS Assay |
|---|---|
| L79V | <1 |
| L79W | 1.2 |
| L79Y | 1.2 |
| F102A | <1 |
| F102C | <1 |
| F102D | <1 |
| F102E | <1 |
| F102G | <1 |
| F102H | <1 |
| F102I | <1 |
| F102K | <1 |
| F102L | <1 |
| F102M | <1 |
| F102N | <1 |
| F102P | <1 |
| F102Q | <1 |
| F102R | <1 |
| F102S | <1 |
| F102T | <1 |
| F102V | <1 |
| F102W | <1 |
| F102Y | <1 |
| V170A | 1.5 |
| V170C | <1 |
| V170D | <1 |
| V170E | <1 |
| V170F | <1 |
| V170G | <1 |
| V170H | <1 |
| V170I | <1 |
| V170K | <1 |
| V170L | <1 |
| V170M | 1.4 |
| V170N | <1 |
| V170P | <1 |
| V170Q | 1.6 |
| V170R | <1 |
| V170S | 1.7 |
| V170T | 1.8 |
| V170W | <1 |
| V170Y | <1 |
| V175A | <1 |
| V175C | <1 |
| V175D | <1 |
| V175E | <1 |
| V175F | <1 |
| V175G | <1 |
| V175H | <1 |
| V175I | <1 |
| V175K | <1 |
| V175L | <1 |
| V175M | <1 |
| V175N | <1 |
| V175P | <1 |
| V175Q | <1 |
| V175R | <1 |
| V175S | <1 |
| V175T | <1 |
| V175W | <1 |
| V175Y | <1 |
| S200A | <1 |
| S200C | <1 |
| S200D | <1 |
| S200E | <1 |
| S200F | <1 |
| S200G | <1 |
| S200H | <1 |
| S200I | <1 |
| S200K | <1 |
| S200L | <1 |
| S200M | <1 |
| S200N | <1 |
| S200P | <1 |
| S200Q | <1 |
| S200R | <1 |
| S200T | <1 |
| S200V | <1 |
| S200W | <1 |
| S200Y | <1 |
| A262C | <1 |
| A262D | <1 |
| A262E | <1 |
| A262F | <1 |
| A262G | 3.8 |
| A262H | <1 |
| A262I | <1 |
| A262K | <1 |
| A262L | <1 |
| A262M | <1 |
| A262N | <1 |
| A262P | <1 |
| A262Q | <1 |
| A262R | <1 |
| A262S | <1 |
| A262T | <1 |
| A262V | <1 |
| A262W | <1 |
| A262Y | <1 |
| V289A | <1 |
| V289C | <1 |
| V289D | <1 |
| V289E | <1 |
| V289F | <1 |
| V289G | <1 |
| V289H | <1 |
| V289I | <1 |
| V289K | 1.9 |
| V289L | <1 |
| V289M | <1 |
| V289N | <1 |
| V289P | <1 |
| V289Q | 1.3 |
| V289R | 1.8 |
| V289S | <1 |
| V289T | 2.0 |
| V289W | <1 |
| V289Y | <1 |
| T292A | <1 |
| T292C | <1 |
| T292D | 9.0 |
| T292E | <1 |
| T292F | 7.1 |
| T292G | 8.3 |
| T292H | 7.3 |
| T292I | <1 |
| T292K | 9.0 |
| T292L | <1 |
| T292M | <1 |
| T292N | <1 |
| T292P | <1 |
| T292Q | <1 |
| T292R | <1 |
| T292S | <1 |
| T292V | <1 |
| T292W | <1 |
| T292Y | <1 |
| Y302A | <1 |
| Y302C | <1 |
| Y302D | <1 |
| Y302E | <1 |
| Y302F | <1 |
| Y302G | <1 |
| Y302H | <1 |
| Y302I | <1 |
| Y302K | <1 |
| Y302L | <1 |
| Y302M | <1 |
| Y302N | <1 |
| Y302P | <1 |
| Y302Q | <1 |
| Y302R | <1 |
| Y302S | <1 |
| Y302T | <1 |
| Y302V | <1 |

TABLE III-continued

| Trametes villosa laccase variant | ABTS Assay |
|---|---|
| Y302W | <1 |
| N357A | 1.2 |
| N357C | <1 |
| N357D | 2.6 |
| N357E | 1.9 |
| N357F | 1.2 |
| N357G | 2.1 |
| N357H | <1 |
| N357I | <1 |
| N357K | <1 |
| N357L | <1 |
| N357M | 1.6 |
| N357P | <1 |
| N357Q | 1.6 |
| N357R | <1 |
| N357S | 1.5 |
| N357T | 1.4 |
| N357V | 1.4 |
| N357W | <1 |
| N357Y | 1.4 |
| I360A | 3.6 |
| I360C | <1 |
| I360D | <1 |
| I360E | <1 |
| I360F | <1 |
| I360G | <1 |
| I360H | 2.7 |
| I360K | <1 |
| I360L | <1 |
| I360M | 8.3 |
| I360N | <1 |
| I360P | <1 |
| I360Q | <1 |
| I360R | <1 |
| I360S | <1 |
| I360T | <1 |
| I360V | 7.8 |
| I360W | <1 |
| I360Y | <1 |
| Y393A | <1 |
| Y393C | <1 |
| Y393D | <1 |
| Y393E | <1 |
| Y393F | <1 |
| Y393G | <1 |
| Y393H | <1 |
| Y393I | <1 |
| Y393K | <1 |
| Y393L | <1 |
| Y393M | <1 |
| Y393N | <1 |
| Y393P | <1 |
| Y393Q | <1 |
| Y393R | <1 |
| Y393S | <1 |
| Y393T | <1 |
| Y393V | <1 |
| Y393W | <1 |
| S397A | <1 |
| S397C | <1 |
| S397E | <1 |
| S397E | <1 |
| S397F | <1 |
| S397G | <1 |
| S397H | <1 |
| S397I | <1 |
| S397K | <1 |
| S397L | <1 |
| S397M | <1 |
| S397N | <1 |
| S397P | <1 |
| S397Q | <1 |
| S397R | <1 |
| S397T | <1 |
| S397V | <1 |
| S397W | <1 |
| S397Y | <1 |
| A485C | <1 |
| A485D | <1 |
| A485E | <1 |
| A485F | <1 |
| A485G | <1 |
| A485H | <1 |
| A485I | <1 |
| A485K | <1 |
| A485L | <1 |
| A485M | <1 |
| A485N | <1 |
| A485P | <1 |
| A485Q | <1 |
| A485R | <1 |
| A485S | <1 |
| A485T | <1 |
| A485V | <1 |
| A485W | <1 |
| A485Y | <1 |
| D507A | <1 |
| D507C | <1 |
| D507E | <1 |
| D507F | <1 |
| D507G | <1 |
| D507H | <1 |
| D507I | <1 |
| D507K | <1 |
| D507L | <1 |
| D507M | <1 |
| D507N | <1 |
| D507P | <1 |
| D507Q | <1 |
| D507R | <1 |
| D507S | <1 |
| D507T | <1 |
| D507V | <1 |
| D507W | <1 |
| D507Y | <1 |

TABLE IV

| Trametes villosa laccase variant | ABTS Assay |
|---|---|
| Parent (Wild-Type) | 1.0 |
| A262G + I360V | 4.8 |
| A262G + V289I + T292D + N357D | 4.1 |
| S37C + A262G + Y393I + A485S | 3.3 |
| V175T + S200D + A262G + I360V + Y393I | 6.3 |
| F102A + V175S + A262G + I360V + S397A | 3.6 |
| F102A + V175T + S200D + A262G + N357D + S397A | 2.2 |
| A9R + L79D + L179N | 2.3 |

Relative improvements in specific activity over the parent laccase in day 4 broths from 48-well deep-well plate and shake flask cultivations for all single site variants at positions K178, D276, A333, F418, S506, and S518, are shown in Table V below, and combinatorial variants F418I+S506H and A21C+K178S+F418V+S518A are shown in Table VI below.

TABLE V

| Trametes villosa laccase variant | ABTS Assay |
|---|---|
| Parent (Wild-Type) | 1.0 |
| K178A | <1 |
| K178C | <1 |
| K178D | <1 |
| K178E | <1 |

TABLE V-continued

| Trametes villosa laccase variant | ABTS Assay |
|---|---|
| K178F | <1 |
| K178G | <1 |
| K178H | <1 |
| K178I | <1 |
| K178L | <1 |
| K178M | <1 |
| K178N | <1 |
| K178P | <1 |
| K178Q | <1 |
| K178R | <1 |
| K178S | <1 |
| K178T | <1 |
| K178V | <1 |
| K178W | <1 |
| K178Y | <1 |
| D276A | <1 |
| D276C | <1 |
| D276E | <1 |
| D276F | <1 |
| D276G | <1 |
| D276H | <1 |
| D276I | <1 |
| D276K | <1 |
| D276L | <1 |
| D276M | <1 |
| D276N | <1 |
| D276P | <1 |
| D276Q | <1 |
| D276R | <1 |
| D276S | <1 |
| D276T | <1 |
| D276V | <1 |
| D276W | <1 |
| D276Y | <1 |
| A333C | <1 |
| A333D | <1 |
| A333E | 1.3 |
| A333F | <1 |
| A333G | <1 |
| A333H | <1 |
| A333I | <1 |
| A333K | 1.1 |
| A333L | <1 |
| A333M | <1 |
| A333N | <1 |
| A333P | <1 |
| A333Q | <1 |
| A333R | 1.1 |
| A333S | <1 |
| A333T | <1 |
| A333V | <1 |
| A333W | <1 |
| A333Y | <1 |
| F418A | <1 |
| F418C | <1 |
| F418D | <1 |
| F418E | <1 |
| F418G | <1 |
| F418H | <1 |
| F418I | 3.1 |
| F418K | <1 |
| F418L | 2.4 |
| F418M | 2.7 |
| F418N | <1 |
| F418P | <1 |
| F418Q | <1 |
| F418R | <1 |
| F418S | <1 |
| F418T | <1 |
| F418V | 2.6 |
| F418W | <1 |
| F418Y | <1 |
| S506A | <1 |
| S506C | <1 |
| S506D | <1 |
| S506E | <1 |
| S506F | <1 |
| S506G | <1 |
| S506H | <1 |
| S506I | <1 |
| S506K | <1 |
| S506L | <1 |
| S506M | <1 |
| S506N | <1 |
| S506P | <1 |
| S506Q | <1 |
| S506R | <1 |
| S506T | <1 |
| S506V | <1 |
| S506W | <1 |
| S506Y | <1 |
| S518A | <1 |
| S518C | <1 |
| S518D | <1 |
| S518E | <1 |
| S518F | <1 |
| S518G | <1 |
| S518H | <1 |
| S518I | <1 |
| S518K | <1 |
| S518L | <1 |
| S518M | <1 |
| S518N | <1 |
| S518P | <1 |
| S518Q | <1 |
| S518R | <1 |
| S518T | <1 |
| S518V | <1 |
| S518W | <1 |
| S518Y | <1 |

TABLE VI

Relative Improvement of Specific Activity Over Parent

| Trametes villosa laccase variant | ABTS Assay |
|---|---|
| Parent (Wild-Type) | 1.0 |
| F418I + S506H | 3.7 |
| A21C + K178S + F418V + S518A | 4.2 |

Example 11

Fermentation-Scale Confirmation of Improved Expression of *Trametes villosa* Laccase Variant Genes in *Aspergillus oryzae*

A fermentation process was used to express the *Trametes villosa* laccase variants A262G+I360V; A262G+V289I+T292D+N357D; S37C+A262G+Y939I+A485S; V175T+S200D+A262G+I360V+Y393I; F102A+V175S+A262G+I360V+S397A; F102A+V175T+S200D+A262G+N357D+S397A; A9R+L79D+L179N; and A262G relative to the parent *T. villosa* laccase.

Shake flask medium was composed of 50 g of sucrose, 10 g of $KH_2PO_4$, 0.5 g of $CaCl_2$, 2 g of $MgSO_4 \cdot 7H_2O$, 2 g of $K_2SO_4$, 2 g of urea, 10 g of yeast extract, 2 g of citric acid, 0.5 ml of trace metals solution, and deionized water to 1 liter. The trace metals solution was composed of 13.8 g of $FeSO_4 \cdot 7H_2O$, 14.3 g of $ZnSO_4 \cdot 7H_2O$, 8.5 g of $MnSO_4 \cdot H_2O$, 2.5 g of $CuSO_4 \cdot 5H_2O$, 3 g of citric acid, and deionized water to 1 liter.

One hundred ml of shake flask medium were added to a 500 ml shake flask. The shake flask was inoculated with 7 ml of 0.01% TWEEN® 80 with spores scraped from a solid plate culture and incubated at 34° C. on an orbital shaker at 200 rpm for 24 hours. Fifty ml of the shake flask broth were used to inoculate a 3 liter fermentation vessel.

Fermentation batch medium was composed per liter of 10 g of yeast extract, 24 g of sucrose, 5 g of $(NH_4)_2SO_4$, 2 g of $KH_2PO_4$, 0.5 g of $CaCl_2.2H_2O$, 2 g of $MgSO_4.7H_2O$, 1 g of citric acid, 2 g of $K_2SO_4$, 0.25 g $CuSO_4.5H_2O$, 0.5 ml of anti-foam, and 0.5 ml of trace metals solution. The trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. Fermentation feed medium was composed of maltose.

A total of 1.8 liters of the fermentation batch medium was added to a three liter glass jacketed fermentor. Fermentation feed medium was dosed at a rate of 0 to 8.0 g/l/hr. The fermentation vessel was maintained at a temperature of 34° C. and the pH was controlled to a set-point of 6.1+/−0.1. Air was added to the vessel at a rate of 1 vvm and the broth was agitated by Rushton impeller rotating at 1100 rpm. Samples were taken on days 2, 3, 4, 5, 6, and 7 of the fermentation run and centrifuged at 3000×g to remove the biomass. The supernatants were sterile filtered and stored at −20° C.

*T. villosa* laccase variant expression levels were determined relative to the parent gene (cDNA sequence) by the ABTS liquid assay (Example 2) and by SDS-PAGE analysis (Example 9).

Relative improvements in expression yield for day 7 broths of several variants relative to the parent *T. villosa* laccase are shown in Table VII below. Variant A262G+I360V was produced in an amount that was 4.8× greater than the parent *T. villosa* laccase, variant A262G+V289I+T292D+N357D was produced in an amount that was 4.1× greater than the parent *T. villosa* laccase, variant A9R+L79D+L179N was produced in an amount that was 3.3× greater than the parent *T. villosa* laccase, variant V175T+S200D+A262G+I360V+Y393I was produced in an amount that was 6.2× greater than the parent *T. villosa* laccase, variant F102A+V175S+A262G+I360V+S397A was produced in an amount that was 3.6× greater than the parent *T. villosa* laccase, variant F102A+V175T+S200D+A262G+N357D+S397A was produced in an amount that was 2.1× greater than the parent *T. villosa* laccase, variant S37C+A262G+Y939I+A485S was produced in an amount that was 2.2× greater than the parent *T. villosa* laccase, and variant A262G was produced in an amount that was 4.8× greater than the parent *T. villosa* laccase. SDS-PAGE analysis of the same broths showed a *T. villosa* laccase band of increased intensity over the parent *T. villosa* laccase for these variants which correlated well with the relative improvements observed in the activity assay. SDS-PAGE analysis of the samples taken on days 3, 4, 5, 6, and 7 showed increased production of the parent *T. villosa* laccase and each variant day by day with day 7 the strongest.

TABLE VII

| Relative Improvement in Expression Over Parent | |
|---|---|
| Trametes villosa Laccase Variant | ABTS Assay |
| Parent (Wild-Type) | 1.0 |
| A262G + I360V | 4.8 |
| A262G + V289I + T292D + N357D | 4.1 |
| S37C + A262G + Y393I + A485S | 3.3 |
| V175T + S200D + A262G + I360V + Y393I | 6.2 |
| F102A + V175S + A262G + I360V + S397A | 3.6 |
| F102A + V175T + S200D + A262G + N357D + S397A | 2.1 |

TABLE VII-continued

| Relative Improvement in Expression Over Parent | |
|---|---|
| Trametes villosa Laccase Variant | ABTS Assay |
| A9R + L79D + L179N | 2.2 |
| A262G | 4.8 |

Relative improvements in specific activity for day 7 broths of two variants compared to the parent *T. villosa* laccase are shown in Table VIII below. The specific activity was measured by normalizing ABTS activity values (measured as in Example 2) to unit protein amounts by assessing relative laccase production per unit volume by band densitometry values from SDS-PAGE gels loaded with equal volumes of sample broth. The specific activity of variant F418I+S506H was 5.2× higher than the parent *T. villosa* laccase. The specific activity of variant A21C+K178S+F418V+S518A was 4.9× higher than the parent *T. villosa* laccase.

TABLE VIII

| Relative Improvement in Specific Activity Over Parent | |
|---|---|
| Trametes villosa Laccase Variant | ABTS Assay |
| Parent (Wild-Type) | 1.0 |
| F418I + S506H | 5.2 |
| A21C + K178S + F418V + S518A | 4.9 |

Example 12

Construction and Identification of Increased Specific Activity Variants of *Trametes villosa* Laccase Variant V175T+S200D+A262G+I360V+Y393I

*Trametes villosa* laccase gene mutant libraries were constructed by multi-site directed mutagenesis on the improved expression variant V175T+S200D+A262G+I360V+Y393I backbone. Libraries were prepared using mutagenic oligos for positions including K178, D276, A333, F418, S506, and S518. Libraries were transformed into *E. coli* with subsequent isolation of plasmid DNA. PCR was used to lift the laccase ORF using oligos 1206637 and 1206638. Yeast Recombinational cloning was used to assemble plasmids containing a mutant *T. villosa* laccase gene plus *Aspergillus nidulans* orotidine 5'-phosphate decarboxylase pyrG selection marker and the FRT-F and FRT-F3 flippase recognition target sequence. Libraries were transformed into protoplasts of *Aspergillus oryzae* JaL1394 as described in Example 9. After 4 days of protoplast recovery at 34° C. on Minimal medium agar plates overlaid with COVE-N-JP top agarose containing 1 mM ABTS, single colonies with green halos were picked onto individual COVE-N-gly plates and incubated for 3 days at 34° C. Spores from variants were inoculated into 48-well deep-well plates containing 2 ml of M410 medium containing 0.25 mM $CuSO_4$, covered with a breathable seal, and grown for 4 days at 34° C. with no shaking. After 4 days growth the liquid culture medium was assayed for laccase activity as described in Examples 2 and 3 and higher activity variants were scored as hits.

Individual mutant strains were cultivated again in 125 ml shake flasks in 25 ml of M410 medium containing 0.25 mM $CuSO_4$ for 4 days at 34° C. with shaking at 220 rpm to generate fresh broth for retesting relative to *A. oryzae*

JaL1394 strain expressing the *T. villosa* laccase variant V175T+S200D+A262G+I360V+Y393I backbone gene.

Relative improvements in specific activity over the parent in day 4 broths from shake flask cultivations for 2 characterized variants are shown in Table IX below.

TABLE IX

Relative Improvement of Specific Activity Over Parent

| Trametes villosa laccase Variant | ABTS Assay | Syringaldazine Assay |
|---|---|---|
| V175T + S200D + A262G + I360V + Y393I (Parent) | 1.0 | 1.0 |
| V175T + S200D + A262G + D276G + I360V + Y393I + F418I + S506H | 4.1 | 2.6 |
| V175T + S200D + A262G + V275I + D276G + A333S + I360V + Y393I + F418I + S506H | 3.7 | 3.1 |

Example 13

Fermentation-Scale Confirmation of Improved Specific Activity of *Trametes villosa* Laccase Variant Genes in *Aspergillus oryzae*

A fermentation process was used to express the *Trametes villosa* laccase variants V175T+S200D+A262G+D276G+I360V+Y393I+F418I+S506H and V175T+S200D+A262G+V275I+D276G+A333S+I360V+Y393I+F418I+S506H for comparison to the *T. villosa* laccase variant V175T+S200D+A262G+I360V+Y393I, as described in Example 11.

The *T. villosa* laccase variant expression levels were determined relative to the *T. villosa* laccase variant V175T+S200D+A262G+I360V+Y393I by the ABTS liquid assay (Example 2) and by syringaldazine liquid assay (Example 3).

Relative improvements in specific activity for day 7 broths of the two variants relative to the V175T+S200D+A262G+I360V+Y393I improved expression laccase variant are shown in Table X below. Variant V175T+S200D+A262G+D276G+I360V+Y393I+F418I+S506H had a specific activity that was 2.7x greater than the *T. villosa* laccase variant V175T+S200D+A262G+I360V+Y393I, and variant V175T+S200D+A262G+V275I+D276G+A333S+I360V+Y393I+F418I+S506H was produced in an amount that was 2.1x greater than the *T. villosa* laccase variant V175T+S200D+A262G+I360V+Y393I.

The volumetric activity of laccase variant V175T+S200D+A262G+D276G+I360V+Y393I+F418I+S506H was increased 30-fold over the wild-type laccase.

TABLE X

Relative Improvement Over Parent

| Trametes villosa Laccase Variant | ABTS Assay |
|---|---|
| V175T + S200D + A262G + I360V + Y393I (Parent) | 1.0 |
| V175T + S200D + A262G + D276G + I360V + Y393I + F418I + S506H | 2.7 |
| V175T + S200D + A262G + V275I + D276G + A333S + I360V + Y393I + F418I + S506H | 2.1 |

Example 14

*Trichoderma reesei* Protoplast Generation and Transformation

Protoplast preparation and transformation were performed using a modified protocol based on Penttila et al.,
1987, *Gene* 61: 155-164. Briefly, *Trichoderma reesei* strain RutC30 (Montenecourt and Eveleigh, 1979, *Adv. Chem. Ser.* 181: 289-301) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co.) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and re-suspended to a final concentration of $1 \times 10^8$ protoplasts per ml in STC. Excess protoplasts were stored in a Cryo 1° C. Freezing Container (Nalgene) at −80° C.

Approximately 100 µg of a transforming plasmid described in the following examples were digested with Pme I. The digestion reaction was purified by 1% agarose gel electrophoresis using TAE buffer where a DNA band was excised from the gel and extracted using a QIAQUICK® Gel Extraction Kit. The resulting purified DNA was added to 100 µl of the protoplast solution and mixed gently. PEG buffer (250 µl) was added, mixed, and incubated at 34° C. for 30 minutes. STC (3 ml) was then added, mixed, and spread onto COVE plates. The plates were incubated at 28° C. for 4-7 days.

Example 15

Construction of pAMFS200 and pAMFS201 for Expression of *Trametes villosa* Laccase in *Trichoderma reesei*

Figure 7:
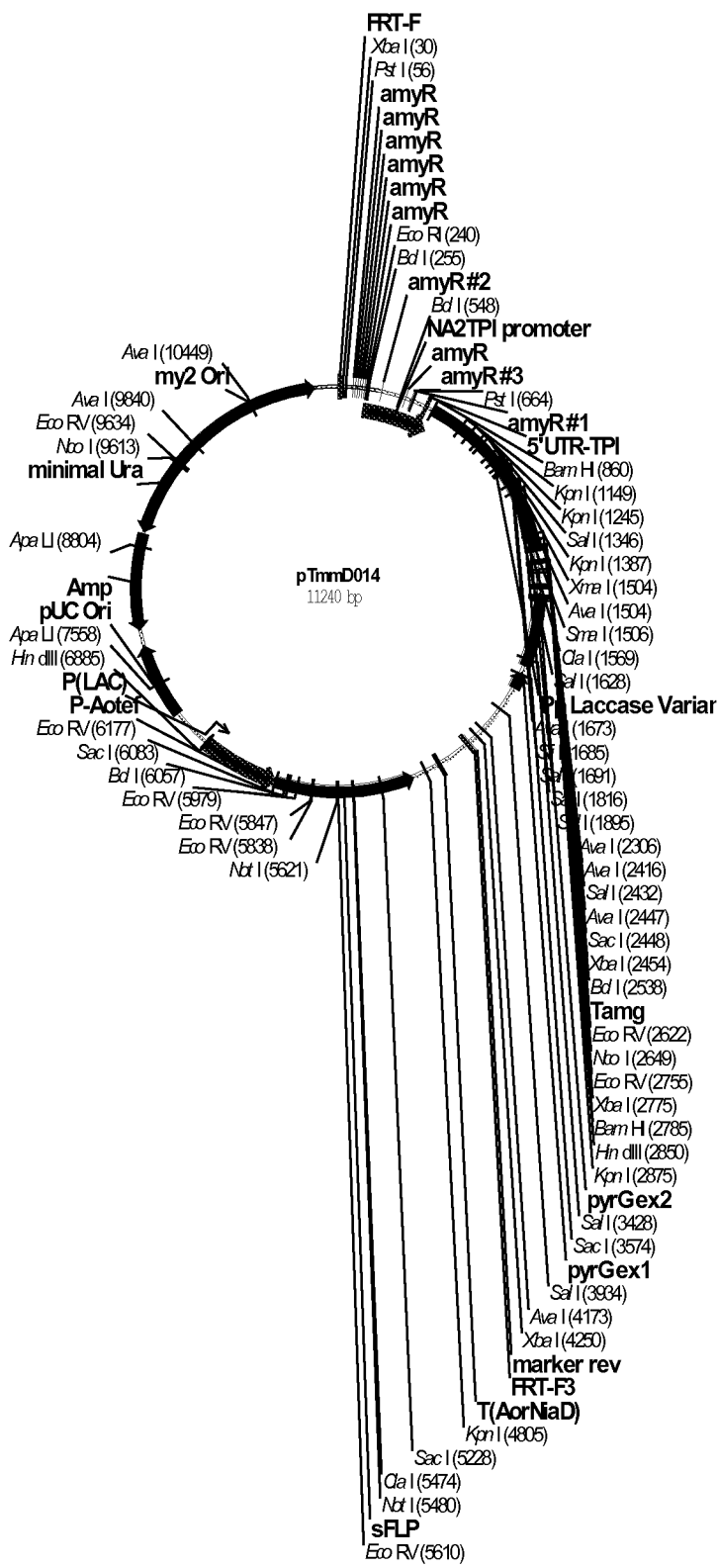
FIG. 7 shows a restriction map of pTmmD014.

The wild-type *Trametes villosa* laccase cDNA (SEQ ID NO; 1 for the cDNA sequence and SEQ ID NO: 2 for the deduced amino acid sequence) and variant V175T+S200D+A262G+I360V+Y393I were amplified by PCR from plasmids pDLHD0140 (Example 8) and pTmmD014 (FIG. 7), respectively, using the same gene-specific forward and reverse primers 1209071 and 1209072. The PCRs were composed of 1 ng of either pDLHD0140 or pTmmD014 DNA, 50 pmoles of each of the primers 1209071 and 1209072, 1 µl of a 10 mM blend of dATP, dTTP, dGTP, and dCTP, 1× PHUSION™ High-Fidelity Hot Start DNA Polymerase Buffer, and 1 unit of PHUSION™ High-Fidelity Hot Start DNA Polymerase in a final volume of 50 µl. The reaction was incubated in an EPPENDORF® MASTERCYCLER® 5333 epgradient S programmed for 1 cycle at 98° C. for 30 seconds; 35 cycles each at 98° C. for 10 seconds, 55° C. for 30 seconds, and 72° C. for 30 seconds; and 1 cycle at 72° C. for 10 minutes. The PCR products were separated by 1% agarose gel electrophoresis using TAE buffer where approximately 1.6 kb fragments were excised from the gel and extracted using a QIAQUICK® Gel Extraction Kit according to the manufacturer's protocol.

Plasmid pMJ09 (WO 2005/047499) was digested with Nco I and Pac I, isolated by 1.0% agarose gel electrophoresis in TBE buffer, excised from the gel, and extracted using a QIAQUICK® Gel Extraction Kit according to the manufacturer's instructions.

Figure 8:
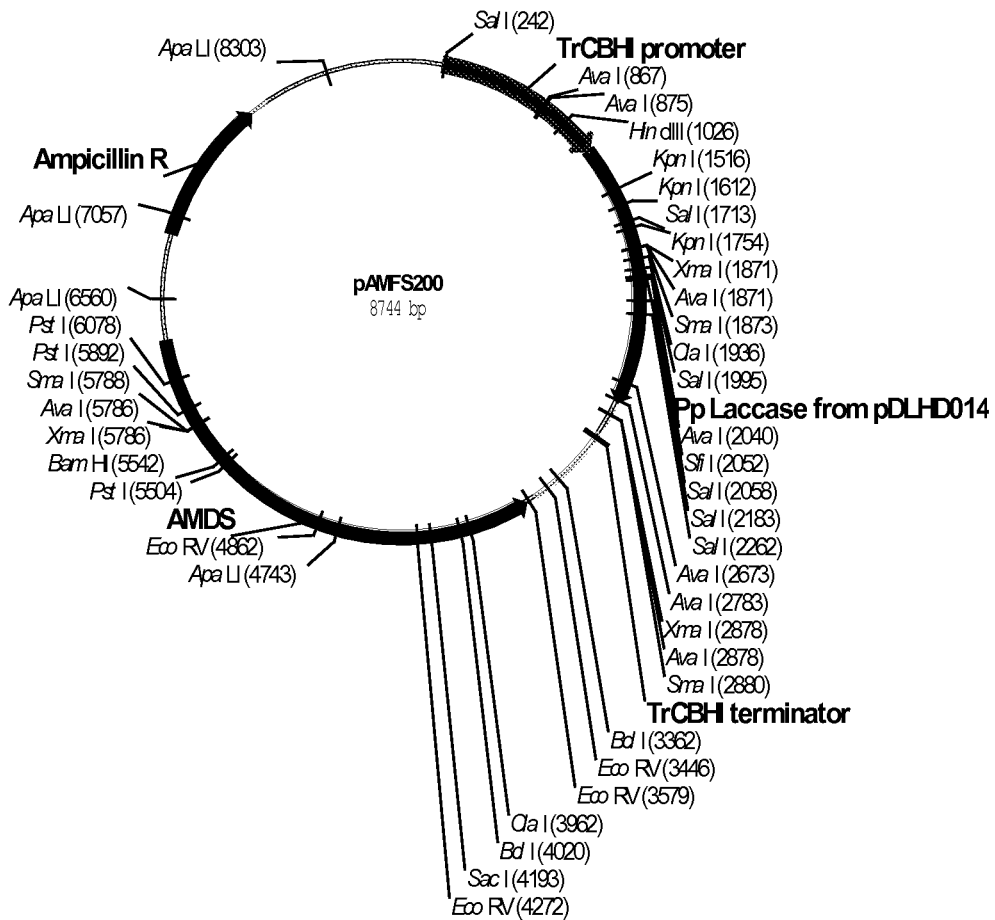
FIG. 8 shows a restriction map of pAMFS200.
Figure 9:
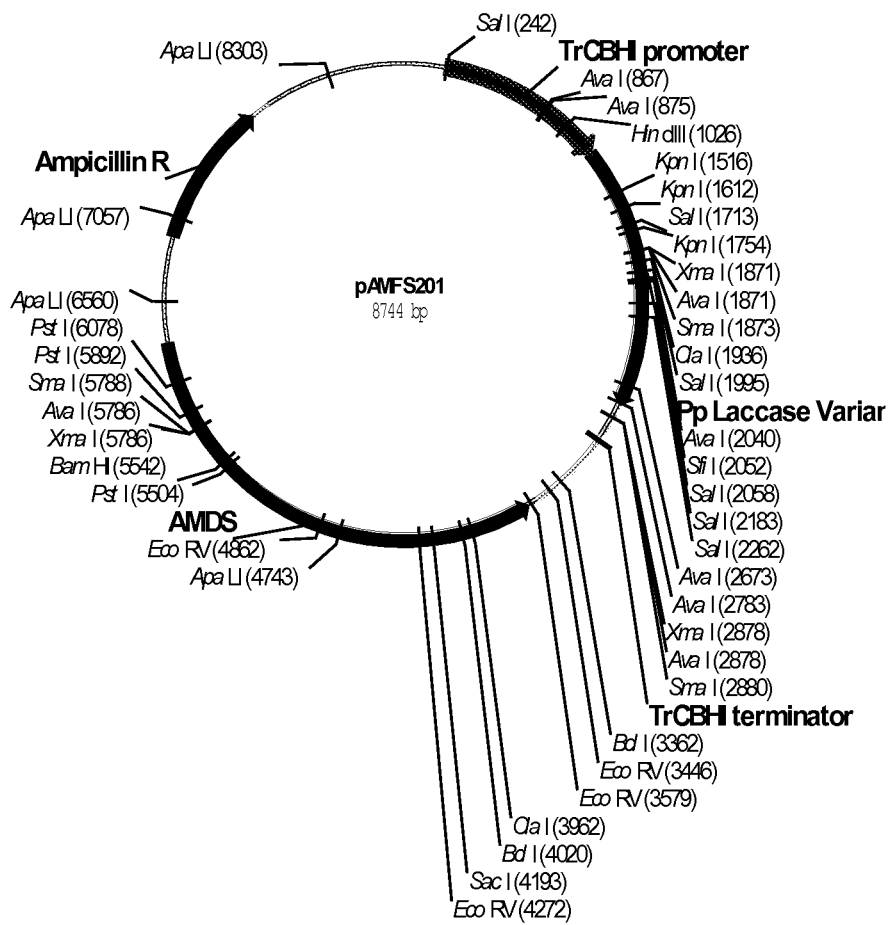
FIG. 9 shows a restriction map of pAMFS201.

The 1.6 kb PCR products were independently inserted into the gel-purified Nco I/Pac I digested pMJ09 using an IN-FUSION™ Advantage PCR Cloning Kit according to the manufacturer's protocol. Each IN-FUSION™ reaction was composed of 1× IN-FUSION™ Reaction Buffer, 200 ng of the gel-purified Nco I/Pac I digested pMJ09, 100 ng of the 1.6 kb PCR product, and 1 µl of IN-FUSION™ Enzyme in a 10 µl reaction volume. The reactions were incubated for 15 minutes at 50° C. After the incubation period 40 µl of TE were added to each reaction. A 2 µl aliquot of each reaction was independently used to transform ONE SHOT® TOP10 competent cells according to the manufacturer's protocol. The E. coli transformation reactions were spread onto 2× YT plus ampicillin plates. The transformants were screened by sequencing and one clone containing the wild-type laccase insert with no PCR errors was identified and designated pAMFS200 (FIG. 8) and one clone containing the laccase variant V175T+S200D+A262G+I360V+Y393I with no PCR errors was identified and designated pAMFS201 (FIG. 9). Both plasmids pAMFS200 and pAMFS201 can be digested with Pme I for T. reesei transformation. The plasmids contain an expression cassette composed of the T. reesei Cel7A cellobiohydrolase I gene promoter, the Trametes villosa laccase polypeptide coding sequence, T. reesei Cel7A cellobiohydrolase I gene terminator and the Aspergillus nidulans acetamidase (amdS) gene.

Example 16

Transformation of pAMFS200 and pAMFS201 into Trichoderma reesei RutC30

Protoplast preparation and transformation of Trichoderma reesei strain RutC30 was performed as described in Example 14.

Approximately 100 µg of pAMFS200 or pAMFS201 were digested with Pme I. Transformation was performed by adding 5-10 µg of Pme I digested pAMFS200 or pAMFS201 to 100 µl of the Trichoderma reesei RutC30 protoplast solution and mixed gently. PEG buffer (250 µl) was added, mixed, and incubated at 34° C. for 30 minutes. STC (3 ml) was then added, mixed, and spread onto two COVE plates. The plates were incubated at 28° C. for 7-10 days. A total of 46 transformants with pAMFS200 and 15 transformants with pAMFS201 were isolated onto COVE2+10 mM uridine plates and grown at 28° C. for 5 days. Fresh spores from these plates were transferred to 48-well deep-well plates containing 2 ml of ClM containing 0.25 mM $CuSO_4$, covered with a breathable seal, and grown for 3 days at 30° C. shaking at 250 rpm. After 3 days of growth the culture medium for each transformant was assayed for laccase activity according to Example 2. A number of transformants showed laccase activity several-fold higher than that of Trichoderma reesei RutC30. The relative improvement in expression yield based on activity measurements for the variant V175T+S200D+A262G+I360V+Y393I over the parent laccase in day 3 broths from 48-well deep-well plate was 5-fold. The top three laccase producing strains were spore-purified once on COVE2+10 mM uridine agar plates and cultivated in liquid using the same conditions described above. Broths were again analyzed for laccase activity according to Example 2 and the top strains were then tested for laccase expression in 2 L fermentation tanks.

Example 17

Fermentation-Scale Confirmation of Improved Expression of Trametes villosa Laccase Variant Gene in Trichoderma reesei A fermentation process was used to express the T. villosa laccase variant V175T+S200D+A262G+I360V+Y393I relative to the parent Trametes villosa laccase.

Shake flask medium was composed of 20 g of glucose, 10 g of corn steep solids, 2.08 g of $KH_2PO_4$, 0.36 g of $CaCl_2$, 0.42 g of $MgSO_4.7H_2O$, 1.45 g of $(NH_4)_2SO_4$, 0.2 ml of T. reesei trace metals solution and deionized water to 1 liter.

One hundred ml of shake flask medium were added to a 500 ml shake flask. The shake flask was inoculated with two plugs from a solid plate culture and incubated at 28° C. on an orbital shaker at 200 rpm for 24 hours. Fifty ml of the shake flask broth were used to inoculate a 3 liter fermentation vessel.

Fermentation batch medium was composed per liter of 10 g of corn steep solids, 30 g of cellulose, 4 g of glucose, 2.6 g of $CaCl_2.2H_2O$, 7.4 g of $(NH_4)_2SO_4$, 2.8 g of $KH_2PO_4$, 1.8 g of $MgSO_4.7H_2O$, 2 g of $K_2SO_4$, 0.25 g of $CuSO_4.5H_2O$, 1.8 ml of anti-foam, and 0.75 ml of T. reesei trace metals solution. The T. reesei trace metals solution was composed of 216 g of $FeSO_4.6H_2O$, 58 g of $ZnSO_4.7H_2O$, 27 g of $MnSO_4.H_2O$, 10 g of $CuSO_4.5H_2O$, 2.4 g $H_3BO_3$, 336 g of citric acid, and deionized water to 1 liter. Fermentation feed medium was composed of glucose and phosphoric acid in water.

A total of 1.8 liters of the fermentation batch medium was added to a three liter glass jacketed fermentor. Fermentation feed medium was dosed at a rate of 0 to 6.4 g/l/hr. The fermentation vessel was maintained at a temperature of 28° C. and the pH was controlled to a set-point of 2.5+/−0.1. Air was added to the vessel at a rate of 1 vvm and the broth was agitated by Rushton impeller rotating at 1100 to 1300 rpm. Samples were taken on days 2, 3, 4, 5, 6, and 7 of the fermentation run and centrifuged at 3000×g to remove the biomass. The supernatants were sterile filtered and stored at −20° C.

Trametes villosa laccase variant expression levels were determined relative to the parent laccase by the ABTS liquid assay (Example 2).

The relative improvement in expression yield based on activity measurements for the variant V175T+S200D+ A262G+I360V+Y393I over the parent laccase in day 7 fermentation broths was 4-fold as shown in Table XI.

TABLE XI

| | Relative Improvement Over Parent | |
|---|---|---|
| Trametes villosa Laccase Variant | ABTS Assay (48 well plates) | ABTS Assay (2 L Tanks) |
| Parent (Wild-Type) | 1.0 | 1.0 |
| V175T + S200D + A262G + I360V + Y393I | 5.5 | 4.4 |

Example 18

Purification of Polyporus pinsitus Laccase Variants

Polyporus pinsitus laccase variants were purified from fermentation broths using the methods previously described in WO 96/000290.

Example 19

Dye Bleaching Assay for Laccase Activity Screening

This assay is used for assessment of laccase activity in the presence or absence of a mediator. Britton-Robinson buffer (0.1 M $H_3BO_3$, 0.04 M $H_3PO_4$ and 0.04 M $CH_3COOH$) was prepared at varied pHs (adjusted to 5.0, 7.0 and 9.0 with NaOH) to obtain an activity profile. Dye solutions were prepared by dissolving indigo carmine and reactive black dyes in water to 0.43 mM and 0.2 mM, respectively. Mediator solutions were prepared by dissolving each of the following mediators to 10 mM in water: syringaldehyde, methylsyringate, hydroxybenzotriazole, 10-phenothiazine-propionic acid, and 2,2,6,6-tetramethylpiperidin-1-yloxy. A laccase standard was diluted using 2-fold steps starting with a 0.06 LAMU/ml concentration and ending with a 0.0075 LAMU/ml concentration in the sample buffer. Reactions were assembled by adding to each well of a 96-well flat bottom plate 20 µl of broth or enzyme standard solution, 100 µl of Britton-Robinson buffer, and 20 µl of mediator solution. Reactions were initiated by adding 100 µl of the dye solution to each well. The plate was then quickly transferred to a SPECTRAMAX® M5 spectrophotometer (Molecular Devices), pre-mixed for 5 seconds, and the decrease in absorbance at the appropriate wavelength for the dye (610 nm for indigo carmine; 600 nm for Reactive black 5) was recorded for 15 minutes with 9 second intervals at 25° C.

Both purified enzyme solutions and crude fermentation broths can be used in this assay. The decolorization of both dyes is visible to the naked eye. The assay can be performed in the absence of mediator. Other mediators and dyes can potentially be used, following the same protocol.

Example 20

Figure 10:
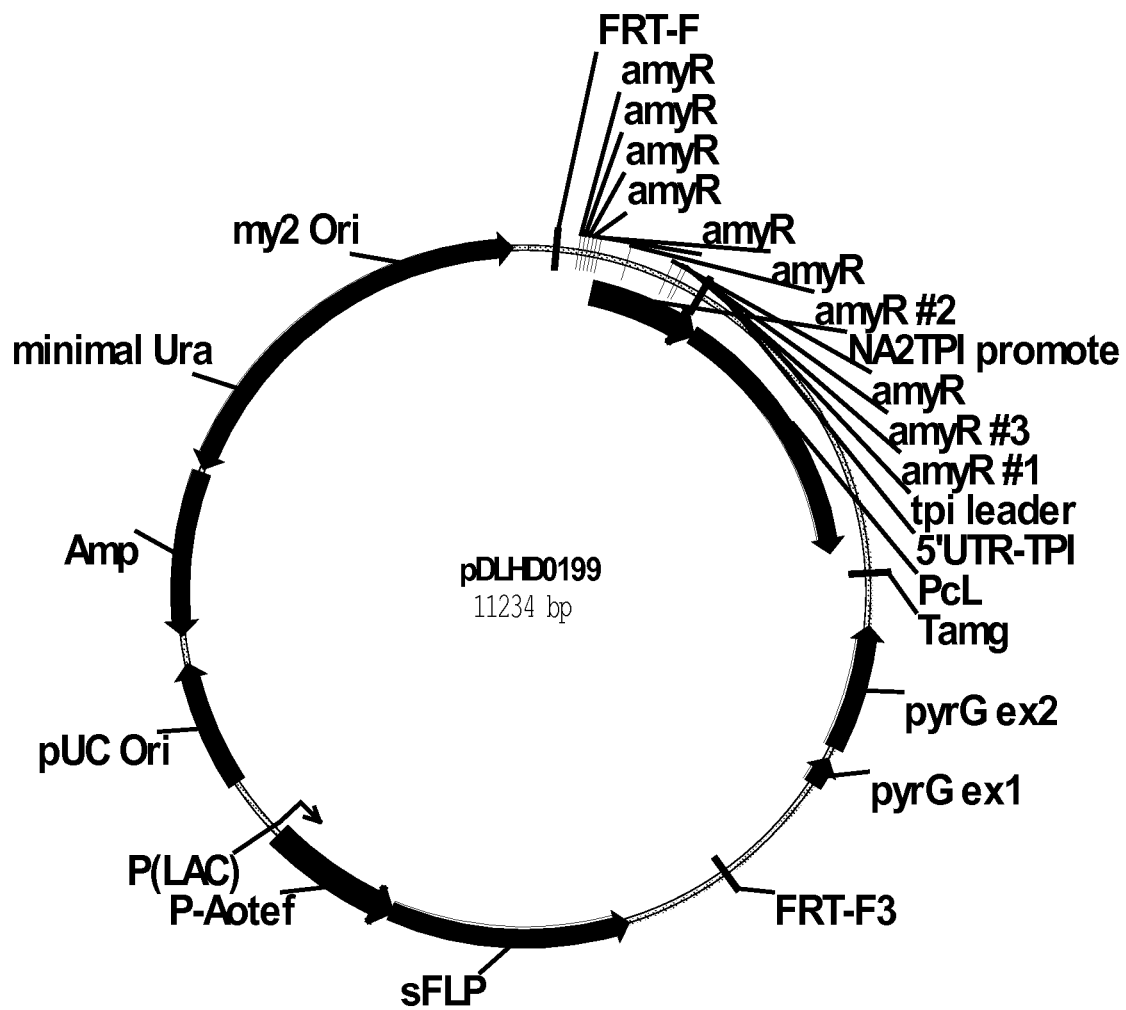
FIG. 10 shows a restriction map of pDLHD0199.

Cloning of the Wild-Type *Pycnoporus cinnabarinus* Laccase for Expression in an *Aspergillus oryzae* Screening Strain The wild-type *Pycnoporus cinnabarinus* laccase cDNA (SEQ ID NO: 92 for the cDNA sequence and SEQ ID NO: 93 for the deduced amino acid sequence) was cloned into a *Saccharomyces cerevisiae/A. oryzae* Flp/FRT shuttle vector by yeast recombinational cloning, resulting in vector pDLHD0199 (FIG. 10).

Expression vector pDLHD0199 was constructed as described in Example 8 for vector pDLHD0140. Fragment 2 was amplified using primer 1217524 (sense) and primer 1217525 (antisense).

Example 21

Figure 11:
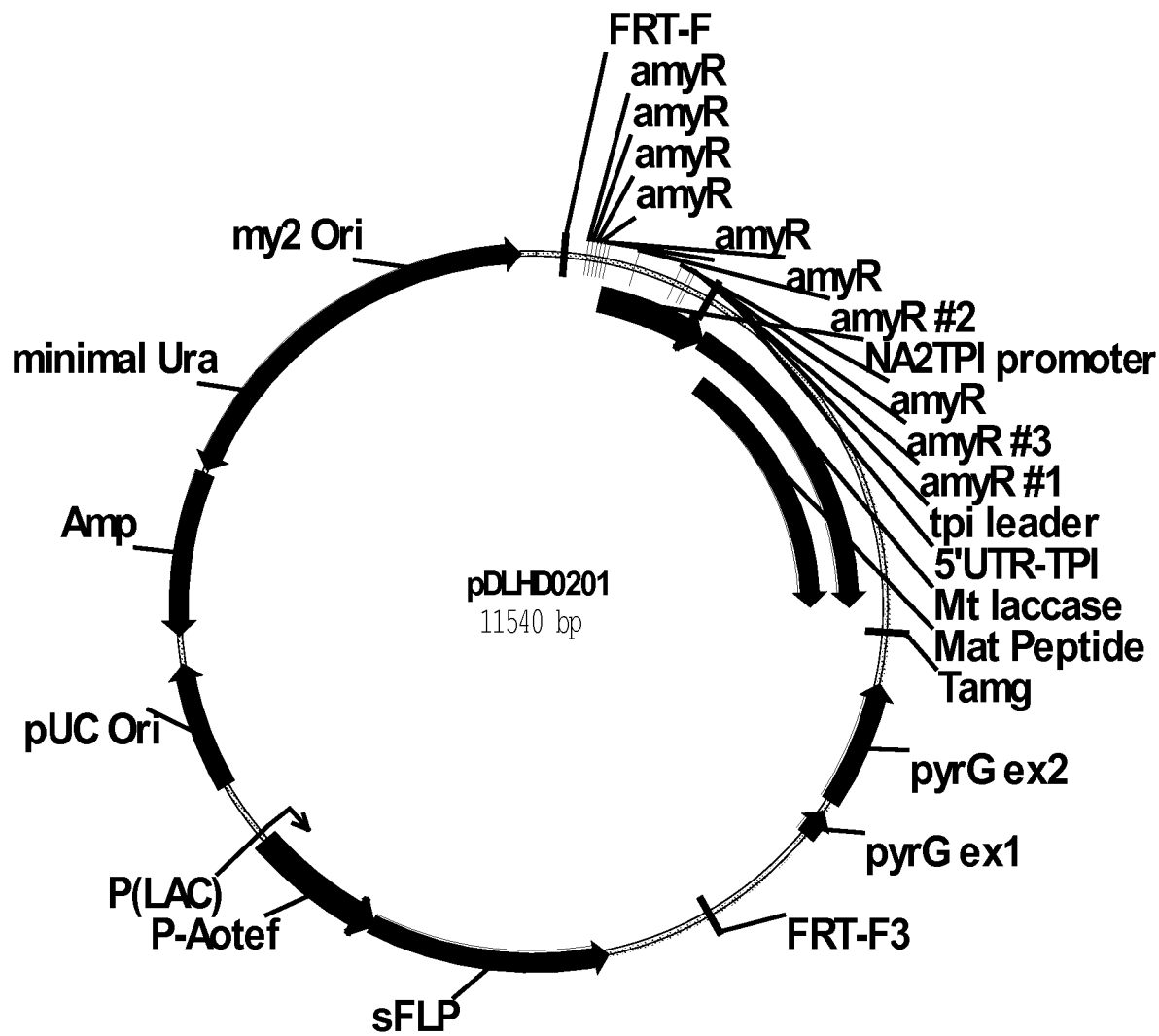
FIG. 11 shows a restriction map of pDLHD0201.

Cloning of the Wild-Type *Myceliophthora thermophila* Laccase for Expression in an *Aspergillus oryzae* Screening Strain The wild-type *Myceliophthora thermophila* laccase cDNA (SEQ ID NO: 94 for the cDNA sequence and SEQ ID NO: 95 for the deduced amino acid sequence) was cloned into a *Saccharomyces cerevisiae/A. oryzae* Flp/FRT shuttle vector by yeast recombinational cloning, resulting in vector pDLHD0201 (FIG. 11).

Expression vector pDLHD0201 was constructed as described in Example 8 for vector pDLHD0140. Fragment 2 was amplified using primer 1217528 (sense) and primer 1217529 (antisense).

Example 22

Confirmation of Wild-Type *Pycnoporus cinnabarinus* Laccase Expression in Single-Copy in *Aspergillus oryzae* Screening Strain JaL1394

As described in Example 9, *Aspergillus oryzae* JaL1394 was transformed with plasmid pDLHD0199 comprising the wild-type *P. cinnabarinus* laccase gene. Transformation plates containing ABTS were incubated at 34° C. until transformants appeared and green ABTS color was observed around each colony. The conversion of ABTS to a visible green color demonstrated that the transformants produced active *P. cinnabarinus* laccase.

Single transformants were subsequently cultivated and assayed for laccase activity according to Examples 2, 3, 4, and 9.

Example 23

Confirmation of Wild-Type *Myceliophthora thermophila* Laccase Expression in Single-Copy in *Aspergillus oryzae* Screening Strain JaL1394

As described in Example 9, *Aspergillus oryzae* JaL1394 was transformed with plasmid pDLHD0201 comprising the wild-type *M. thermophila* laccase gene. Transformation plates containing ABTS were incubated at 34° C. until transformants appeared and green ABTS color was observed around each colony. The conversion of ABTS to a visible green color demonstrated that the transformants produced active *M. thermophila* laccase.

Single transformants were subsequently cultivated and assayed for laccase activity according to Examples 2, 3, 4, and 9.

Example 24

Construction and Identification of Increased Expression and Increased Specific Activity Variants of *Pycnoporus cinnabarinus* Laccase

*Pycnoporus cinnabarinus* laccase gene variants were constructed by site-saturation mutagenesis. The variants of the *P. cinnabarinus* laccase gene were transformed into protoplasts of *Aspergillus oryzae* JaL1394 as described in Example 10. Transformants were cultivated and assayed for laccase activity and expression as described in Examples 2, 3, 4, 9, and 10, and higher activity variants were scored as expression hits.

Relative improvements in expression yield over the parent laccase in day 4 broths from 48-well deep-well plate and shake flask cultivations for variants at positions L79, A170, A262, V289, N292, N357, and I360 are shown in Table XII below. SDS-PAGE analysis of the same broths demonstrated a *P. cinnabarinus* laccase band of increased intensity over wild-type *P. cinnabarinus* laccase for all variants, which correlated well with the relative improvements observed in the activity assays.

TABLE XII

| *Pycnoporus cinnabarinus* laccase variant | ABTS Assay |
| --- | --- |
| Parent (Wild-Type) | 1.0 |
| L79E | <1 |
| L79F | <1 |
| L79G | 2.6 |
| L79S | <1 |
| A170T | <1 |
| A262G | 1.4 |
| T289K | 1.7 |
| A292K | <1 |
| N357D | <1 |
| N357G | 1.3 |
| N357M | 1.1 |

TABLE XII-continued

| Pycnoporus cinnabarinus laccase variant | ABTS Assay |
|---|---|
| N357S | <1 |
| I360M | 1.8 |

Relative improvements in specific activity over the parent laccase in day 4 broths from 48-well deep-well plate and shake flask cultivations for variants at positions P333 and F418 are shown in Table XIII below.

TABLE XIII

Relative Improvement of Specific Activity Over Parent

| Pycnoporus cinnabarinus laccase variant | ABTS Assay |
|---|---|
| Parent (Wild-Type) | 1.0 |
| P333E | <1 |
| F418I | 6.5 |
| F418V | 5.9 |

Example 25

Construction and Identification of Increased Expression and Increased Specific Activity Variants of *Myceliophthora thermophila* Laccase

*Myceliophthora thermophila* laccase gene variants were constructed by site-saturation mutagenesis. The variants of the *M. thermophila* laccase gene were transformed into protoplasts of *Aspergillus oryzae* JaL1394 as described in Example 10. Transformants were cultivated and assayed for laccase activity and expression as described in Examples 2, 3, 4, 9, and 10, and higher activity variants were scored as expression hits.

Relative improvements in expression yield over the parent laccase in day 4 broths from 48-well deep-well plate and shake flask cultivations for variants at positions S220, G317, L344, R349, D437, and L440 are shown in Table XIV below. SDS-PAGE analysis of the same broths demonstrated a *M. thermophila* laccase band of increased intensity over wild-type *M. thermophila* laccase for all variants, which correlated well with the relative improvements observed in the activity assays.

TABLE XIV

| Myceliophthora thermophila laccase variant | ABTS Assay |
|---|---|
| Parent (Wild-Type) | 1.0 |
| S220T | 1.3 |
| G317A | <1 |
| L344K | 1.9 |
| L344T | 1.1 |
| R349K | 1.1 |
| D437G | <1 |
| D437M | <1 |
| D437S | 1.0 |
| L440M | 1.6 |

Relative improvements in specific activity over the parent laccase in day 4 broths from 48-well deep-well plate and shake flask cultivations for variants at position M480 are shown in Table XV below.

TABLE XV

Relative Improvement of Specific Activity Over Parent

| Myceliophthora thermophila laccase variant | ABTS Assay |
|---|---|
| Parent (Wild-Type) | 1.0 |
| M480I | <1 |
| M480V | <1 |

The present invention is further described by the following numbered paragraphs:

[1] A laccase variant, comprising a substitution at one or more positions corresponding to positions 9, 21, 37, 79, 102, 170, 175, 178, 179, 200, 262, 275, 276, 289, 292, 333, 357, 360, 393, 397, 418, 485, 506, and 518 of the full-length polypeptide of SEQ ID NO: 2, wherein the variant has laccase activity and wherein the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the full-length polypeptide of a parent or the mature polypeptide thereof.

[2] The variant of paragraph 1, wherein the parent laccase is selected from the group consisting of: (a) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95; or the mature polypeptide thereof; (b) a polypeptide encoded by a polynucleotide that hybridizes under at least low stringency conditions with (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or the mature polypeptide coding sequence thereof; or (ii) the full-length complement of (i); (c) a polypeptide encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94; or the mature polypeptide coding sequence thereof; and (d) a fragment of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof, which has laccase activity.

[3] The variant of paragraph 1 or 2, wherein the parent laccase has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99% or 100% sequence identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95; or the mature polypeptide thereof.

[4] The variant of any one of paragraphs 1-3, wherein the parent laccase is encoded by a polynucleotide that hybridizes under low stringency conditions, medium stringency conditions, medium-high stringency conditions, high stringency conditions, or very high stringency conditions with (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94, or the mature polypeptide coding sequence thereof; or (ii) the full-length complement of (i).

[5] The variant of any one of paragraphs 1-4, wherein the parent laccase is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 92, or 94; or the mature polypeptide coding sequence thereof.

[6] The variant of any one of paragraphs 1-5, wherein the parent laccase comprises or consists of the full-length polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95; or the mature polypeptide thereof.

[7] The variant of any one of paragraphs 1-6, wherein the parent laccase is a fragment of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 93, or 95, or the mature polypeptide thereof, wherein the fragment has endoglucanase activity.

[8] The variant of any one of paragraphs 1-7, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the full-length polypeptide of the parent laccase, or the mature polypeptide thereof.

[9] The variant of any one of paragraphs 1-8, wherein the variant consists of at least 85%, at least 90%, or at least 95% of the amino acids of the parent.

[10] The variant of any one of paragraphs 1-9, wherein the number of substitutions is 1-24, e.g., 1, 2, 3, 4, 5, 6, 7, 8, 9, 10, 11, 12, 13, 14, 15, 16, 17, 18, 19, 20, 21, 22, 23, or 24 substitutions.

[11] The variant of any one of paragraphs 1-10, which comprises a substitution at a position corresponding to position 9.

[12] The variant of paragraph 11, wherein the substitution is with Arg.

[13] The variant of any one of paragraphs 1-12, which comprises a substitution at a position corresponding to position 21.

[14] The variant of paragraph 13, wherein the substitution is with Cys.

[15] The variant of any one of paragraphs 1-14, which comprises a substitution at a position corresponding to position 37.

[16] The variant of paragraph 15, wherein the substitution is with Cys.

[17] The variant of any one of paragraphs 1-16, which comprises a substitution at a position corresponding to position 79.

[18] The variant of paragraph 17, wherein the substitution is with Ala, Asp, Glu, Phe, Gly, Ile, Met, Asn, Gln, or Ser.

[19] The variant of any one of paragraphs 1-18, which comprises a substitution at a position corresponding to position 102.

[20] The variant of paragraph 19, wherein the substitution is with Ala.

[21] The variant of any one of paragraphs 1-20, which comprises a substitution at a position corresponding to position 170.

[22] The variant of paragraph 21, wherein the substitution is with Ala, Met, Gln, Ser, or Thr.

[23] The variant of any one of paragraphs 1-22, which comprises a substitution at a position corresponding to position 175.

[24] The variant of paragraph 23, wherein the substitution is with Ser or Thr.

[25] The variant of any one of paragraphs 1-24, which comprises a substitution at a position corresponding to position 178.

[26] The variant of paragraph 25, wherein the substitution is with Ser.

[27] The variant of any one of paragraphs 1-26, which comprises a substitution at a position corresponding to position 179.

[28] The variant of paragraph 27, wherein the substitution is with Asn.

[29] The variant of any one of paragraphs 1-28, which comprises a substitution at a position corresponding to position 200.

[30] The variant of paragraph 29, wherein the substitution is with Asp.

[31] The variant of any one of paragraphs 1-30, which comprises a substitution at a position corresponding to position 262.

[32] The variant of paragraph 31, wherein the substitution is with Gly.

[33] The variant of any one of paragraphs 1-32, which comprises a substitution at a position corresponding to position 275.

[34] The variant of paragraph 33, wherein the substitution is with Ile.

[35] The variant of any one of paragraphs 1-34, which comprises a substitution at a position corresponding to position 276.

[36] The variant of paragraph 35, wherein the substitution is with Gly.

[37] The variant of any one of paragraphs 1-36, which comprises a substitution at a position corresponding to position 289.

[38] The variant of paragraph 37, wherein the substitution is with Ile, Lys, Gln, Arg, or Thr.

[39] The variant of any one of paragraphs 1-38, which comprises a substitution at a position corresponding to position 292.

[40] The variant of paragraph 39, wherein the substitution is with Asp, Phe, Gly, His, or Lys.

[41] The variant of any one of paragraphs 1-40, which comprises a substitution at a position corresponding to position 333.

[42] The variant of paragraph 41, wherein the substitution is with Ser, Glu, Lys, or Arg.

[43] The variant of any one of paragraphs 1-42, which comprises a substitution at a position corresponding to position 357.

[44] The variant of paragraph 43, wherein the substitution is with Asp, Ala, Glu, Phe, Gly, Met, Gln, Ser, Thr, Val, or Tyr.

[45] The variant of any one of paragraphs 1-44, which comprises a substitution at a position corresponding to position 360.

[46] The variant of paragraph 45, wherein the substitution is with Val, Ala, His, or Met.

[47] The variant of any one of paragraphs 1-46, which comprises a substitution at a position corresponding to position 393.

[48] The variant of paragraph 47, wherein the substitution is with Ile.

[49] The variant of any one of paragraphs 1-48, which comprises a substitution at a position corresponding to position 397.

[50] The variant of paragraph 49, wherein the substitution is with Ala.

[51] The variant of any one of paragraphs 1-50, which comprises a substitution at a position corresponding to position 418.

[52] The variant of paragraph 51, wherein the substitution is with Ile, Val, Leu, or Met.

[53] The variant of any one of paragraphs 1-52, which comprises a substitution at a position corresponding to position 485.

[54] The variant of paragraph 53, wherein the substitution is with Ser.

[55] The variant of any one of paragraphs 1-54, which comprises a substitution at a position corresponding to position 506.

[56] The variant of paragraph 55, wherein the substitution is with His.

[57] The variant of any one of paragraphs 1-56, which comprises a substitution at a position corresponding to position 518.

[58] The variant of paragraph 57, wherein the substitution is with Ala.

[59] The variant of any one of paragraphs 1-58, which comprises a substitution at two positions corresponding to any of positions 9, 21, 37, 79, 102, 170, 175, 178, 179, 200, 262, 275, 276, 289, 292, 333, 357, 360, 393, 397, 418, 485, 506, and 518.

[60] The variant of any one of paragraphs 1-58, which comprises a substitution at three positions corresponding to any of positions 9, 21, 37, 79, 102, 170, 175, 178, 179, 200, 262, 275, 276, 289, 292, 333, 357, 360, 393, 397, 418, 485, 506, and 518.

[61] The variant of any one of paragraphs 1-58, which comprises a substitution at four positions corresponding to any of positions 9, 21, 37, 79, 102, 170, 175, 178, 179, 200, 262, 275, 276, 289, 292, 333, 357, 360, 393, 397, 418, 485, 506, and 518.

[62] The variant of any one of paragraphs 1-58, which comprises a substitution at five positions corresponding to any of positions 9, 21, 37, 79, 102, 170, 175, 178, 179, 200, 262, 275, 276, 289, 292, 333, 357, 360, 393, 397, 418, 485, 506, and 518.

[63] The variant of any one of paragraphs 1-58, which comprises a substitution at six positions corresponding to any of positions 9, 21, 37, 79, 102, 170, 175, 178, 179, 200, 262, 275, 276, 289, 292, 333, 357, 360, 393, 397, 418, 485, 506, and 518.

[64] The variant of any one of paragraphs 1-58, which comprises a substitution at seven positions corresponding to any of positions 9, 21, 37, 79, 102, 170, 175, 178, 179, 200, 262, 275, 276, 289, 292, 333, 357, 360, 393, 397, 418, 485, 506, and 518.

[65] The variant of any one of paragraphs 1-58, which comprises a substitution at eight positions corresponding to any of positions 9, 21, 37, 79, 102, 170, 175, 178, 179, 200, 262, 275, 276, 289, 292, 333, 357, 360, 393, 397, 418, 485, 506, and 518.

[66] The variant of any one of paragraphs 1-58, which comprises a substitution at nine positions corresponding to any of positions 9, 21, 37, 79, 102, 170, 175, 178, 179, 200, 262, 275, 276, 289, 292, 333, 357, 360, 393, 397, 418, 485, 506, and 518.

[67] The variant of any one of paragraphs 1-58, which comprises a substitution at ten positions corresponding to any of positions 9, 21, 37, 79, 102, 170, 175, 178, 179, 200, 262, 275, 276, 289, 292, 333, 357, 360, 393, 397, 418, 485, 506, and 518.

[68] The variant of any one of paragraphs 1-58, which comprises a substitution at eleven positions corresponding to any of positions 9, 21, 37, 79, 102, 170, 175, 178, 179, 200, 262, 275, 276, 289, 292, 333, 357, 360, 393, 397, 418, 485, 506, and 518.

[69] The variant of any one of paragraphs 1-58, which comprises a substitution at twelve positions corresponding to any of positions 9, 21, 37, 79, 102, 170, 175, 178, 179, 200, 262, 275, 276, 289, 292, 333, 357, 360, 393, 397, 418, 485, 506, and 518.

[70] The variant of any one of paragraphs 1-58, which comprises a substitution at thirteen positions corresponding to any of positions 9, 21, 37, 79, 102, 170, 175, 178, 179, 200, 262, 275, 276, 289, 292, 333, 357, 360, 393, 397, 418, 485, 506, and 518.

[71] The variant of any one of paragraphs 1-58, which comprises a substitution at fourteen positions corresponding to any of positions 9, 21, 37, 79, 102, 170, 175, 178, 179, 200, 262, 275, 276, 289, 292, 333, 357, 360, 393, 397, 418, 485, 506, and 518.

[72] The variant of any one of paragraphs 1-58, which comprises a substitution at fifteen positions corresponding to any of positions 9, 21, 37, 79, 102, 170, 175, 178, 179, 200, 262, 275, 276, 289, 292, 333, 357, 360, 393, 397, 418, 485, 506, and 518.

[73] The variant of any one of paragraphs 1-58, which comprises a substitution at sixteen positions corresponding to any of positions 9, 21, 37, 79, 102, 170, 175, 178, 179, 200, 262, 275, 276, 289, 292, 333, 357, 360, 393, 397, 418, 485, 506, and 518.

[74] The variant of any one of paragraphs 1-58, which comprises a substitution at seventeen positions corresponding to any of positions 9, 21, 37, 79, 102, 170, 175, 178, 179, 200, 262, 275, 276, 289, 292, 333, 357, 360, 393, 397, 418, 485, 506, and 518.

[75] The variant of any one of paragraphs 1-58, which comprises a substitution at eighteen positions corresponding to any of positions 9, 21, 37, 79, 102, 170, 175, 178, 179, 200, 262, 275, 276, 289, 292, 333, 357, 360, 393, 397, 418, 485, 506, and 518.

[76] The variant of any one of paragraphs 1-58, which comprises a substitution at nineteen positions corresponding to any of positions 9, 21, 37, 79, 102, 170, 175, 178, 179, 200, 262, 275, 276, 289, 292, 333, 357, 360, 393, 397, 418, 485, 506, and 518.

[77] The variant of any one of paragraphs 1-58, which comprises a substitution at twenty positions corresponding to any of positions 9, 21, 37, 79, 102, 170, 175, 178, 179, 200, 262, 275, 276, 289, 292, 333, 357, 360, 393, 397, 418, 485, 506, and 518.

[78] The variant of any one of paragraphs 1-58, which comprises a substitution at twenty-one positions corresponding to any of positions 9, 21, 37, 79, 102, 170, 175, 178, 179, 200, 262, 275, 276, 289, 292, 333, 357, 360, 393, 397, 418, 485, 506, and 518.

[79] The variant of any one of paragraphs 1-58, which comprises a substitution at twenty-two positions corresponding to any of positions 9, 21, 37, 79, 102, 170, 175, 178, 179, 200, 262, 275, 276, 289, 292, 333, 357, 360, 393, 397, 418, 485, 506, and 518.

[80] The variant of any one of paragraphs 1-58, which comprises a substitution at twenty-three positions corresponding to any of positions 9, 21, 37, 79, 102, 170, 175, 178, 179, 200, 262, 275, 276, 289, 292, 333, 357, 360, 393, 397, 418, 485, 506, and 518.

[81] The variant of any one of paragraphs 1-58, which comprises a substitution at each position corresponding to positions 9, 21, 37, 79, 102, 170, 175, 178, 179, 200, 262, 275, 276, 289, 292, 333, 357, 360, 393, 397, 418, 485, 506, and 518.

[82] The variant of any one of paragraphs 1-81, which comprises one or more substitutions selected from the group consisting of A9R; A21C; S37C; L79A,D,E,F,G,I,M,N,Q,S; F102A; V170A,M,Q,S,T; V175S,T; K178S; L179N; S200D; A262G; V275I; D276G; V289I,K,Q,R,T; T292D,F,G,H,K; A333S,E,K,R; N357D,A,E,F,G,M,Q,S,T,V,Y; I360V,A,H,M; Y393I; S397A; F418I,V,L,M; A485S; S506H; and S518A.

[83] The variant of paragraph 82, which comprises or consists of the substitutions A262G+I360V.

[84] The variant of paragraph 82, which comprises or consists of the substitutions F418I+S506H.

[85] The variant of paragraph 82, which comprises or consists of the substitutions A9R+L79D+L179N.

[86] The variant of paragraph 82, which comprises or consists of the substitutions A21C+K178S+F418V+S518A.

[87] The variant of paragraph 82, which comprises or consists of the substitutions S37C+A262G+Y393I+A485S.

[88] The variant of paragraph 82, which comprises or consists of the substitutions A262G+V289I+T292D+N357D.

[89] The variant of paragraph 82, which comprises or consists of the substitutions F102A+V175S+A262G+I360V+S397A.

[90] The variant of paragraph 82, which comprises or consists of the substitutions V175T+S200D+A262G+I360V+Y393I.

[91] The variant of paragraph 82, which comprises or consists of the substitutions F102A+V175T+S200D+A262G+N357D+S397A.

[92] The variant of paragraph 82, which comprises or consists of the substitutions V175T+S200D+A262G+D276G+I360V+Y393I+F418I+S506H.

[93] The variant of paragraph 82, which comprises or consists of the substitutions V175T+S200D+A262G+V275I+D276G+A333S+I360V+Y393I+F418I+S506H.

[94] The variant of any one of paragraphs 1-93, which further comprises a substitution at one or more positions corresponding to positions 89, 151, 286, 307, 313, 339, and 355 of the full-length polypeptide of SEQ ID NO: 2, wherein the variant has laccase activity.

[95] The variant of paragraph 94, which further comprises a substitution at a position corresponding to position 89.

[96] The variant of paragraph 95, wherein the substitution is with Ala, Val, Leu, or Ile.

[97] The variant of any one of paragraphs 94-96, which further comprises a substitution at a position corresponding to position 151.

[98] The variant of paragraph 97, wherein the substitution is with Asp, Glu, Arg, or Lys.

[99] The variant of any one of paragraphs 94-98, which further comprises a substitution at a position corresponding to position 286.

[100] The variant of paragraph 99, wherein the substitution is with Arg, His, or Val.

[101] The variant of any one of paragraphs 94-100, which further comprises a substitution at a position corresponding to position 307.

[102] The variant of paragraph 101, wherein the substitution is with Pro, His, or Gly.

[103] The variant of any one of paragraphs 94-102, which further comprises a substitution at a position corresponding to position 313.

[104] The variant of paragraph 103, wherein the substitution is with Asn, Thr, or Ser.

[105] The variant of any one of paragraphs 94-104, which further comprises a substitution at a position corresponding to position 339.

[106] The variant of paragraph 105, wherein the substitution is with Trp, Thr, or Ser.

[107] The variant of any one of paragraphs 94-106, which further comprises a substitution at a position corresponding to position 355.

[108] The variant of paragraph 107, wherein the substitution is with Arg.

[109] The variant of any one of paragraphs 94-108, wherein the one or more substitutions are selected from the group consisting of F89A,V,L,I; N151D,E,R,K; F286R,H,V; A307P,H,G; T313N,T,S; V339W,T,S; and G355R.

[110] The variant of any one of paragraphs 1-109, which has an increased expression yield compared to the parent.

[111] The variant of paragraph 110, wherein the expression yield of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, or at least 40-fold compared to the expression yield of the parent.

[112] The variant of any one of paragraphs 1-111, which has an increased specific activity compared to the parent.

[113] The variant of paragraph 112, wherein the specific activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the specific activity of the parent.

[114] The variant of any one of paragraphs 1-113, which has increased dye bleaching activity compared to the parent.

[115] The variant of paragraph 114, wherein the dye bleaching activity of the variant is increased at least 1.05-fold, at least 1.10-fold, at least 1.20-fold, at least 1.30-fold, at least 1.40-fold, at least 1.50-fold, at least 1.60-fold, at least 1.70-fold, at least 1.80-fold, at least 1.90-fold, at least 2-fold, at least 2.25-fold, at least 2.50-fold, at least 2.75-fold, at least 3.00-fold, at least 3.25-fold, at least 3.50-fold, at least 3.75-fold, at least 4-fold, at least 4.25-fold, at least 4.50-fold, at least 4.75-fold, at least 5-fold, at least 6-fold, at least 7-fold, at least 8-fold, at least 9-fold, at least 10-fold, at least 15-fold, or at least 20-fold compared to the dye bleaching activity of the parent.

[116] An isolated polynucleotide encoding the variant of any one of paragraphs 1-115.

[117] A nucleic acid construct comprising the polynucleotide of paragraph 116.

[118] An expression vector comprising the polynucleotide of paragraph 116.

[119] A recombinant host cell comprising the polynucleotide of paragraph 116.

[120] A method of producing a laccase variant, comprising: (a) cultivating the recombinant host cell of paragraph 119 under conditions suitable for expression of the variant; and optionally (b) recovering the variant.

[121] A method for obtaining a laccase variant, comprising introducing into a parent laccase a substitution at one or more positions corresponding to positions 9, 21, 37, 79, 102, 170, 175, 178, 179, 200, 262, 275, 276, 289, 292, 333, 357, 360, 393, 397, 418, 485, 506, and 518 of the mature polypeptide of SEQ ID NO: 2, wherein the variant has laccase activity.

[122] The method of paragraph 121, wherein the one or more substitutions are selected from the group consisting of A9R; A21C; S37C; L79A,D,E,F,G,I,M,N,Q,S; F102A; V170A,M,Q,S,T; V175S,T; K178S; L179N; S200D; A262G; V275I; D276G; V289I,K,Q,R,T; T292D,F,G,H,K; A333S,E,K,R; N357D,A,E,F,G,M,Q,S,T,V,Y; I360V,A,H,M; Y393I; S397A; F418I,V,L,M; A485S; S506H; and S518A.

[123] The method of paragraph 121 or 122, further comprising introducing into the parent laccase a substitution at one or more positions corresponding to positions 89, 151, 286, 307, 313, 339, and 355 of the mature polypeptide of SEQ ID NO: 2, wherein the variant has laccase activity.

[124] The method of paragraph 123, wherein the one or more substitutions are selected from the group consisting of F89A,V,L,I; N151D,E,R,K; F286R,H,V; A307P,H,G; T313N,T,S; V339W,T,S; and G355R.

[125] The method of any one of paragraphs 121-124, further comprising recovering the variant.

[126] An enzyme composition comprising the variant of any one of paragraphs 1-115.

[127] A whole broth formulation or cell culture composition comprising the variant of any one of paragraphs 1-115.

[128] A method of decolorizing a dye, comprising treating the dye with a laccase variant of any one of paragraphs 1-115.

[129] Use of the variant of any one of paragraphs 1-115.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A synthetic variant polypeptide having laccase activity, comprising a substitution at one or more positions corresponding to positions 9, 21, 37, 102, 175, 200, 262, 275, 276, 289, 292, 333, 357, 360, 393, 397, 418, 506, and 518 of the full-length polypeptide of SEQ ID NO: 2, and wherein the variant has at least 93% sequence identity to SED ID NO: 2.

2. The variant polypeptide of claim 1, which comprises a substitution at one or more positions corresponding to positions 262, 289, 292, 357 and 360 of the full-length polypeptide of SEQ ID NO: 2.

3. The variant polypeptide of claim 1, which comprises one or more substitutions selected from the group consisting of F102A; V175S,T; S200D; A262G; N357D,A,E,F,G,M,Q, S,T,V,Y; I360V,A,H,M; Y393I; and S397A.

4. The variant polypeptide of claim 1, which comprises one or more substitutions selected from the group consisting of F102A; V175T; S200D; A262G; N357D; I360V; Y393I; and S397A.

5. The variant polypeptide of claim 1, which comprises one or more substitutions selected from the group consisting of A262G; N357D; and I360V.

6. The variant polypeptide of claim 1, which comprises the substitution A262G.

7. The variant polypeptide of claim 1, which comprises one or more substitutions selected from the group consisting of N357D,A,E,F,G,M,Q,S,T,V,Y.

8. The variant polypeptide of claim 1, which comprises one or more substitutions selected from the group consisting of I360V,A,H,M.

9. The variant polypeptide of claim 1, which comprises the substitutions A262G+N357D+I360V.

10. The variant polypeptide of claim 1, wherein the variant has at least 94% sequence identity to SED ID NO: 2.

11. The variant polypeptide of claim 1, wherein the variant has at least 95% sequence identity to SED ID NO: 2.

12. The variant polypeptide of claim 1, wherein the variant has at least 96% sequence identity to SED ID NO: 2.

13. The variant polypeptide of claim 1, wherein the variant has at least 97% sequence identity to SED ID NO: 2.

14. The variant polypeptide of claim 1, wherein the variant has at least 98% sequence identity to SED ID NO: 2.

15. The variant polypeptide of claim 1, wherein the variant has at least 99% sequence identity to SED ID NO: 2.

16. An enzyme composition, whole broth formulation, or cell culture composition comprising the variant of claim 1.

17. An isolated polynucleotide encoding the variant of claim 1.

18. A nucleic acid construct comprising the polynucleotide of claim 17.

19. A recombinant host cell comprising the polynucleotide of claim 17.

20. A method of producing a laccase variant, comprising:
(a) cultivating the recombinant host cell of claim 19 under conditions suitable for expression of the variant; and, optionally,
(b) recovering the variant.

* * * * *

SEQUENCE LISTING

```
<160> NUMBER OF SEQ ID NOS: 95

<210> SEQ ID NO 1
<211> LENGTH: 1563
<212> TYPE: DNA
<213> ORGANISM: Polyporus pinsitus

<400> SEQUENCE: 1
atgtcgaggt tcactctct tctcgctttc gtcgttgctt cccttacggc tgtggcccac        60
gctggtatcg gtcccgtcgc cgacctaacc atcaccaacg cagcggtcag ccccgacggg       120
ttttctcgcc aggccgtcgt cgtgaacggc ggcacccctg gccctctcat caccggtaac       180 atggggatc gcttccagct caatgtcatc gacaaccttta ccaaccacac gatgctgaag       240
agcacgagta ttcactggca cggtttcttc cagaagggta ccaactgggc cgacggtccc       300
gccttcatca accagtgccc gatctcatct ggtcactcgt tcctgtacga cttccaggtt       360
cctgaccagg ctggtacctt ctggtatcac agtcacttgt ctacgcagta ctgtgatggt       420
ttgaggggtc cgttcgttgt ttacgacccg aatgacccgg ccgccgacct gtacgacgtc       480
gacaacgacg acactgtcat tacccttgtg gattggtacc acgtcgccgc gaagctgggc       540
cccgcattcc ctctcggcgc cgacgccacc ctcatcaacg gtaagggacg ctcccccagc       600
acgaccaccg cggacctctc agttatcagc gtcacccccg gtaaacgcta ccgtttccgc       660
ctggtgtccc tgtcgtgcga ccccaactac acgttcagca tcgatggtca caacatgacg       720
atcatcgaga ccgactcaat caacacggcg cccctcgtcg tcgactccat tcagatcttc       780
gccgcccagc gttactcctt cgtgctcgag gccaaccagg ccgtcgacaa ctactggatt       840
```

```
cgcgccaacc cgaacttcgg taacgtcggg ttcaccggcg gcattaactc ggctatcctc      900
cgctacgatg gtgccgctgc cgtggagccc accaccacgc aaaccacgtc gactgcgccg      960
ctcaacgagg tcaacctgca cccgctggtt accaccgctg tgcctggctc gcccgtcgct     1020
ggtggtgtcg acctggccat caacatggcg ttcaacttca cggcaccaa cttcttcatc     1080 aacggcgcgt ctttcacgcc cccgaccgtg cctgtcctgc tccagatcat cagcggcgcg     1140
cagaacgcgc aggacctcct gccctccggt agcgtctact cgcttccctc gaacgccgac     1200
atcgagatct ccttccccgc caccgccgcc gccccggtg cgccccaccc cttccacttg     1260
cacgggcacg cgttcgcggt cgtccgcagc gccggcagca cggtttacaa ctacgacaac     1320
cccatcttcc gcgacgtcgt cagcacgggg acgcctgcgg ccggtgacaa cgtcaccatc     1380
cgcttccgca ccgacaaccc cggcccgtgg ttcctccact gccacatcga cttccacctc     1440
gaggccggct cgccgtcgt gttcgcggag gacatccccg acgtcgcgtc ggcgaacccc     1500
gtcccccagg cgtggtccga cctctgcccg acctacgacg cgctcgaccc gagcgaccag     1560
tag                                                                   1563
```

<210> SEQ ID NO 2
<211> LENGTH: 520
<212> TYPE: PRT
<213> ORGANISM: Polyporus pinsitus

<400> SEQUENCE: 2

```
Met Ser Arg Phe His Ser Leu Leu Ala Phe Val Val Ala Ser Leu Thr
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asn His Thr Met Val Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Val Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Ser Val
        195                 200                 205

Ile Ser Val Thr Pro Gly Lys Arg Tyr Arg Phe Arg Leu Val Ser Leu
    210                 215                 220

Ser Cys Asp Pro Asn Tyr Thr Phe Ser Ile Asp Gly His Asn Met Thr
225                 230                 235                 240
```

Ile Ile Glu Thr Asp Ser Ile Asn Thr Ala Pro Leu Val Val Asp Ser
                245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Asn Phe Gly Asn
        275                 280                 285

Val Gly Phe Thr Gly Gly Ile Asn Ser Ala Ile Leu Arg Tyr Asp Gly
    290                 295                 300

Ala Ala Ala Val Glu Pro Thr Thr Thr Gln Thr Thr Ser Thr Ala Pro
305                 310                 315                 320

Leu Asn Glu Val Asn Leu His Pro Leu Val Thr Thr Ala Val Pro Gly
                325                 330                 335

Ser Pro Val Ala Gly Val Asp Leu Ala Ile Asn Met Ala Phe Asn
            340                 345                 350

Phe Asn Gly Thr Asn Phe Phe Ile Asn Gly Thr Ser Phe Thr Pro Pro
        355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
        435                 440                 445

Thr Gly Thr Pro Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
            500                 505                 510

Asp Ala Leu Asp Pro Ser Asp Gln
        515                 520

<210> SEQ ID NO 3
<211> LENGTH: 1563
<212> TYPE: DNA
<213> ORGANISM: Trametes versicolor

<400> SEQUENCE: 3
atgtcgaggt tcactctct tctcgctttc gtcgttgctt cccttacggc tgtggcccac      60
gctggtatcg tcccgtcgc cgacctaacc atcaccaacg cagcggtcag ccccgacggg     120
ttttctcgcc aggccgtcgt cgtgaacggc ggcacccctg ccctctcat caccggtaac     180 atgggggatc gcttccagct caatgtcatc gacaacctca ccaaccacac gatgctgaag     240
agcacgagta ttcactggca cggttttctt cagaagggca ccaactgggc cgacggtccc     300
gccttcatca ccagtgccc gatctcatct ggtcactcgt tcctgtacga cttccaggtt     360
cctgaccagg ctggtacctt ctggtatcac agtcacttgt ctacgcagta ctgtgatggt     420
ttgaggggtc cgttcgttgt ttacgacccg aatgacccgg ccgccgacct gtacgacgtc     480
gacaacgacg acactgtcat taccccttgtg gattggtacc acgtcgccgc gaagctgggc     540

-continued

```
cccgcattcc ctctcggcgc cgacgccacc ctcatcaacg gtaagggacg ctcccccagc      600
acgaccaccg cggacctctc agttatcagc gtcaccccgg gtaaacgcta ccgtttccgc      660
ctggtgtccc tgtcgtgcga ccccaactac acgttcagca tcgatggtca acatgacg       720
atcatcgaga ccgactcaat caacacggcg ccctcgtcg tcgactccat tcagatcttc       780
gccgcccagc gttactcctt cgtgctcgag gccaaccagg ccgtcgacaa ctactggatt      840
cgcgccaacc cgaacttcgg taacgtcggg ttcaccggcg cattaactc ggctatcctc      900
cgctacgatg gtgccgctgc cgtggagccc accaccacgc aaaccacgtc gtctgcgccg      960
ctcaacgagg tcaacctgca cccgctggtt gccaccgctg tgcctggctc gcccgtcgct     1020
ggtggtgtcg acctggccat caacatggcg ttcaacttca acggcaccaa cttcttcatc     1080
aacgcgcgt ctttcacgcc cccgaccgtg cctgtcctcc tccagatcat cagcggcgcg      1140
cagaacgcgc aggacctcct gccctccggc agcgtctact cgcttccctc gaacgccgac     1200
atcgagatct cctccccgc gaccgccgcc gccccggtg cgcccaccc cttccacttg        1260
cacgggcacg cgttcgcggt cgtccgcagc gccggcagca cggtctacaa ctacgacaac     1320
cccatcttcc gcgacgtcgt cagcacgggg acgcctgcgg ccggtgacaa cgtcaccatc     1380
cgcttccgca ccgacaaccc cggcccgtgg ttcctccact gccacatcga cttccacctc     1440
gaggccggct cgccgtcgt gttcgcggag gacatccccg acgtcgcgtc ggcgaaccct     1500
gtcccccagg cgtggtccga cctctgcccg acctacgacg cgctcgaccc gagcgaccag     1560
tag                                                                   1563
```

<210> SEQ ID NO 4
<211> LENGTH: 520
<212> TYPE: PRT
<213> ORGANISM: Trametes versicolor

<400> SEQUENCE: 4

```
Met Ser Arg Phe His Ser Leu Leu Ala Phe Val Val Ala Ser Leu Thr
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Val Asp Trp Tyr His Val Ala
                165                 170                 175

Ala Lys Leu Gly Pro Ala Phe Pro Leu Gly Ala Asp Ala Thr Leu Ile
```

```
                180                 185                 190
Asn Gly Lys Gly Arg Ser Pro Ser Thr Thr Thr Ala Asp Leu Ser Val
                    195                 200                 205

Ile Ser Val Thr Pro Gly Lys Arg Tyr Arg Phe Arg Leu Val Ser Leu
                210                 215                 220

Ser Cys Asp Pro Asn Tyr Thr Phe Ser Ile Asp Gly His Asn Met Thr
225                 230                 235                 240

Ile Ile Glu Thr Asp Ser Ile Asn Thr Ala Pro Leu Val Val Asp Ser
                    245                 250                 255

Ile Gln Ile Phe Ala Ala Gln Arg Tyr Ser Phe Val Leu Glu Ala Asn
                260                 265                 270

Gln Ala Val Asp Asn Tyr Trp Ile Arg Ala Asn Pro Asn Phe Gly Asn
                275                 280                 285

Val Gly Phe Thr Gly Gly Ile Asn Ser Ala Ile Leu Arg Tyr Asp Gly
                290                 295                 300

Ala Ala Ala Val Glu Pro Thr Thr Thr Gln Thr Thr Ser Ser Ala Pro
305                 310                 315                 320

Leu Asn Glu Val Asn Leu His Pro Leu Val Ala Thr Ala Val Pro Gly
                    325                 330                 335

Ser Pro Val Ala Gly Gly Val Asp Leu Ala Ile Asn Met Ala Phe Asn
                340                 345                 350

Phe Asn Gly Thr Asn Phe Phe Ile Asn Gly Ala Ser Phe Thr Pro Pro
                355                 360                 365

Thr Val Pro Val Leu Leu Gln Ile Ile Ser Gly Ala Gln Asn Ala Gln
                370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                    405                 410                 415

Pro Phe His Leu His Gly His Ala Phe Ala Val Val Arg Ser Ala Gly
                420                 425                 430

Ser Thr Val Tyr Asn Tyr Asp Asn Pro Ile Phe Arg Asp Val Val Ser
                435                 440                 445

Thr Gly Thr Pro Ala Ala Gly Asp Asn Val Thr Ile Arg Phe Arg Thr
                450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                    485                 490                 495

Ser Ala Asn Pro Val Pro Gln Ala Trp Ser Asp Leu Cys Pro Thr Tyr
                500                 505                 510

Asp Ala Leu Asp Pro Ser Asp Gln
                515                 520

<210> SEQ ID NO 5
<211> LENGTH: 1563
<212> TYPE: DNA
<213> ORGANISM: Trametes versicolor
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
```

```
<221> NAME/KEY: misc_feature
<222> LOCATION: (1305)..(1305)
<223> OTHER INFORMATION: n is a, c, g, or t

<400> SEQUENCE: 5
atgtcgaggt tcactctct tttcgctttc gtcgttgctt cccttacggc tgtggcccac      60
gctggtatcg gtcccgtcgc cgacctaacc atcaccaacg cagcggtcag ccccgacggg    120
ttttctcgcc aggccgtcgt cgtgaacggg ggcaccctg ccctctcat cacgggtaac     180
atggggatc gcttccagct caatgtcatc gacaaccta ccaccacac gatgctgaag      240
agcacgagta ttcactggca cggtttcttc cagaagggca ccaactgggc cgacggtccc    300
gccttcatca accagtgccc gatctcatct ggtcactcgt tcctgtacga cttccaggtt    360
cctgaccagg ctggtacctt ctggtatcac agtcacttgt ctacgcagta ctgtgatggt    420
ttgaggggtc cgttcgttgt ttacgacccg aacgaccccgg ccgccgacct gtacgacgtc   480
gacaacgacg acactgtcat tacccttgtg gattggtacc acgtcgccgc gaagctgggc    540
cccgcattcc ctctcggcgc cgacgccacc ctcatcaacg gtaagggacg ctcccccagc    600
acgaccaccg cggacctctc agttatcagt gtcaccccgg gtaaacgcta ccgtttccgc    660
ctggtgtccc tgtcgtgcga ccccaactac acgttcagca tcgatggtca acatgacg     720
atcatcgaga ccgactcaat caacacggcg ccctcgtcg tcgactccat tcagattttc     780
gccgcccagc gttactcctt cgtgctcgag gccaaccagg ccgtcgacaa ctactggatt    840
cgcgccaacc caaacttcgg taacgtcggg tttaccggcg gcattaactc ggctatcctc    900
cgctacgatg gtgccgctgc cgtggagccc accaccacgc aaaccacctc gactgcgccg    960
ctcaacgagg tcaacctgca cccgctggtt gccaccgctg tgcctggctc gcccgtcgct   1020
ggtggtgtcg acctggccat caacatggcg ttcaacttca acggcaccaa cttcttcatc   1080
aacggcgcgt cttcacgcc cccgaccgtg cctgtcctnc ttcagatcat cagcggcgcg   1140
cagaacgcgc aggacctcct gccctccggc agcgtctact cgcttccctc gaacgccgac   1200
atcgagatct ccttcccggc gaccgccgcc gccccggtg cgccccaccc nttccacttg   1260
cacgggcacg cgttcgcggt cgtccgcagc gccggcagca cggtntacaa ctacgacaac   1320
cccatcttcc gcgacgtcgt cagcacgggg acgcctgcgg ccggtgacaa tgtcaccatc   1380
cgcttccgca ccgacaaccc cggcccgtgg ttcctccact gccacatcga cttccacctc   1440
gaggccggct cgccgtcgt gttcgcggag gacatccccg acgtcgcgtc ggcgaacccc   1500
gtccccagg cgtggtccga cctctgcccg acctacgacg cgcgcgaccc gagcgaccag   1560
taa                                                                 1563

<210> SEQ ID NO 6
<211> LENGTH: 520
<212> TYPE: PRT
<213> ORGANISM: Trametes versicolor

<400> SEQUENCE: 6

Met Ser Arg Phe His Ser Leu Phe Ala Phe Val Val Ala Ser Leu Thr
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60
```

```
Phe Gln Leu Asn Val Ile Asp Asn Leu Thr Asn His Thr Met Leu Lys
 65                  70                  75                  80

Ser Thr Ser Ile His Trp His Gly Phe Gln Lys Gly Thr Asn Trp
             85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
            115                 120                 125

Tyr His Ser His Leu Ser Thr Gln Tyr Cys Asp Gly Leu Arg Gly Pro
            130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Val Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Ser Val
            195                 200                 205

Ile Ser Val Thr Pro Gly Lys Arg Tyr Arg Phe Arg Leu Val Ser Leu
210                 215                 220

Ser Cys Asp Pro Asn Tyr Thr Phe Ser Ile Asp Gly His Asn Met Thr
225                 230                 235                 240

Ile Ile Glu Thr Asp Ser Ile Asn Thr Ala Pro Leu Val Val Asp Ser
                245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Asn Phe Gly Asn
            275                 280                 285

Val Gly Phe Thr Gly Gly Ile Asn Ser Ala Ile Leu Arg Tyr Asp Gly
            290                 295                 300

Ala Ala Ala Val Glu Pro Thr Thr Thr Gln Thr Thr Ser Thr Ala Pro
305                 310                 315                 320

Leu Asn Glu Val Asn Leu His Pro Leu Val Ala Thr Ala Val Pro Gly
                325                 330                 335

Ser Pro Val Ala Gly Gly Val Asp Leu Ala Ile Asn Met Ala Phe Asn
            340                 345                 350

Phe Asn Gly Thr Asn Phe Phe Ile Asn Gly Ala Ser Phe Thr Pro Pro
            355                 360                 365

Thr Val Pro Val Leu Leu Gln Ile Ile Ser Gly Ala Gln Asn Ala Gln
            370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Ala Pro Gly Ala Pro His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
            435                 440                 445

Thr Gly Thr Pro Ala Ala Gly Asp Asn Val Thr Ile Arg Phe Arg Thr
            450                 455                 460

Asp Asn Pro Gly Pro Trp Phe Leu His Cys His Ile Asp Phe His Leu
465                 470                 475                 480
```

```
        Glu Ala Gly Phe Ala Val Val Phe Ala Glu Asp Ile Pro Asp Val Ala
                        485                 490                 495

Ser Ala Asn Pro Val Pro Gln Ala Trp Ser Asp Leu Cys Pro Thr Tyr
                    500                 505                 510

Asp Ala Arg Asp Pro Ser Asp Gln
                    515             520

<210> SEQ ID NO 7
<211> LENGTH: 1563
<212> TYPE: DNA
<213> ORGANISM: Trametes versicolor

<400> SEQUENCE: 7
atgtcgaggt tcactctct tctcgctttc gtcgttgctt cccttacggc tgtggcccac       60
gctggtatcg tcccgtcgc cgacctcacc atcaccaacg cagcggtcag ccctgatggg      120
ttttctcgcc aggccgtcgt cgtgaacggc ggcacccctg ccctctcat caccggtaac      180 atggggatc gcttccagct caatgtcatc gacaacctca ccaaccacac gatgctgaag      240
agcaccagta ttcactggca cggtttcttc agaagggca cgaactgggc cgacggtccc      300
gccttcatca ccagtgccc gatctcatct ggtcactcgt tcctgtacga cttccaggtt      360
cctgaccagg ctggcacctt ctggtaccac agtcacttgt ccacgcagta ctgtgatggt      420
ctgaggggtc cgttcgttgt ttacgacccg aatgacccgg ccgccgactt gtacgacgtc      480
gacaacgacg acactgtcat taccctcgtg gattggtacc acgtcgccgc gaacgtgggc      540
cctgccttcc ctctcggcgc cgatgcgacc ctcatcaatg gcaagggacg ctcccccagc      600
acgaccaccg cggacctctc tgttatcagc gtcaccccgg gtaaacgcta ccgtttccgc      660
ctggtgtccc tgtcgtgcga ccccaactac acgttcagca tcgatggtca acatgacg      720 atcatcgaga ccgactcgat caacacggcg cccctcgtgg tcgactccat tcagatcttc      780
gccgcccagc gttactcctt cgtgctcgag gccaaccagg ccgtcgacaa ctactggatt      840
cgcgccaacc ccaacttcgg taacgtcggg ttcaccggcg gcatcaactc ggctatcctc      900
cgctacgatg tgccgctgc cgtcgagccc actaccacgc agaccacttc gaccgagccg      960
ctcaatgagg tcaacctgca cccgctggtt gccaccgctg tgcctggctc tcccgttgcg     1020
ggtggtgtcg acctggccat caacatggcg ttcaacttca cggcaccaa cttcttcatc     1080 aacgcgcgt ctttcacgcc cccgaccgtg cctgtcctcc tccagatcat cagcggcgcg     1140
cagaacgcgc aagacctcct gccctctggc agcgtctact cgctccccte gaacgccgac     1200 atcgagatct cgttccccgc caccgccgcc gcccctggtg cgcccacccc cttccacttg     1260
cacgggcacg cgttcgcggt cgtccgcagc gccggcagca cagtctacaa ctacgacaac     1320
cccatcttcc gcgacgtcgt cagcacgggg acgcctgcgg ccggtgacaa cgtcaccatc     1380
cgcttccgca ccgacaaccc cggcccgtgg ttcctccatt gccacatcga cttccacctc     1440
gaggccggtt tcgccgtcgt gttcgcggag gacatccccg acgttgcgtc ggcgaacccc     1500
gtgccccagg cgtggtccga cctctgcccg acctacgatg cgctcgaccc gagcgaccag     1560
taa                                                                  1563

<210> SEQ ID NO 8
<211> LENGTH: 520
<212> TYPE: PRT
<213> ORGANISM: Trametes versicolor

<400> SEQUENCE: 8
```

-continued

```
Met Ser Arg Phe His Ser Leu Leu Ala Phe Val Val Ala Ser Leu Thr
1               5                   10                  15
Ala Val Ala His Ala Gly Ile Gly Pro Val Ala Asp Leu Thr Ile Thr
            20                  25                  30
Asn Ala Ala Val Ser Pro Asp Gly Phe Ser Arg Gln Ala Val Val Val
        35                  40                  45
Asn Gly Gly Thr Pro Gly Pro Leu Ile Thr Gly Asn Met Gly Asp Arg
    50                  55                  60
Phe Gln Leu Asn Val Ile Asp Asn Leu Thr Asn His Thr Met Leu Lys
65                  70                  75                  80
Ser Thr Ser Ile His Trp His Gly Phe Phe Gln Lys Gly Thr Asn Trp
                85                  90                  95
Ala Asp Gly Pro Ala Phe Ile Asn Gln Cys Pro Ile Ser Ser Gly His
            100                 105                 110
Ser Phe Leu Tyr Asp Phe Gln Val Pro Asp Gln Ala Gly Thr Phe Trp
        115                 120                 125
Tyr His Ser His Leu Ser Thr Gln Tyr Cys Asp Gly Leu Arg Gly Pro
    130                 135                 140
Phe Val Val Tyr Asp Pro Asn Asp Pro Ala Ala Asp Leu Tyr Asp Val
145                 150                 155                 160
Asp Asn Asp Asp Thr Val Ile Thr Leu Val Asp Trp Tyr His Val Ala
                165                 170                 175
Ala Asn Val Gly Pro Ala Phe Pro Leu Gly Ala Asp Ala Thr Leu Ile
            180                 185                 190
Asn Gly Lys Gly Arg Ser Pro Ser Thr Thr Thr Ala Asp Leu Ser Val
        195                 200                 205
Ile Ser Val Thr Pro Gly Lys Arg Tyr Arg Phe Arg Leu Val Ser Leu
    210                 215                 220
Ser Cys Asp Pro Asn Tyr Thr Phe Ser Ile Asp Gly His Asn Met Thr
225                 230                 235                 240
Ile Ile Glu Thr Asp Ser Ile Asn Thr Ala Pro Leu Val Val Asp Ser
                245                 250                 255
Ile Gln Ile Phe Ala Ala Gln Arg Tyr Ser Phe Val Leu Glu Ala Asn
            260                 265                 270
Gln Ala Val Asp Asn Tyr Trp Ile Arg Ala Asn Pro Asn Phe Gly Asn
        275                 280                 285
Val Gly Phe Thr Gly Gly Ile Asn Ser Ala Ile Leu Arg Tyr Asp Gly
    290                 295                 300
Ala Ala Ala Val Glu Pro Thr Thr Thr Gln Thr Thr Ser Thr Glu Pro
305                 310                 315                 320
Leu Asn Glu Val Asn Leu His Pro Leu Val Ala Thr Ala Val Pro Gly
                325                 330                 335
Ser Pro Val Ala Gly Gly Val Asp Leu Ala Ile Asn Met Ala Phe Asn
            340                 345                 350
Phe Asn Gly Thr Asn Phe Phe Ile Asn Gly Ala Ser Phe Thr Pro Pro
        355                 360                 365
Thr Val Pro Val Leu Leu Gln Ile Ile Ser Gly Ala Gln Asn Ala Gln
    370                 375                 380
Asp Leu Leu Pro Ser Gly Ser Val Tyr Ser Leu Pro Ser Asn Ala Asp
385                 390                 395                 400
Ile Glu Ile Ser Phe Pro Ala Thr Ala Ala Pro Gly Ala Pro His
                405                 410                 415
Pro Phe His Leu His Gly His Ala Phe Ala Val Val Arg Ser Ala Gly
```

```
                420            425              430
Ser Thr Val Tyr Asn Tyr Asp Asn Pro Ile Phe Arg Asp Val Val Ser
            435                 440                 445

Thr Gly Thr Pro Ala Ala Gly Asp Asn Val Thr Ile Arg Phe Arg Thr
        450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
            500                 505                 510

Asp Ala Leu Asp Pro Ser Asp Gln
            515                 520

<210> SEQ ID NO 9
<211> LENGTH: 1563
<212> TYPE: DNA
<213> ORGANISM: Trametes sp.

<400> SEQUENCE: 9
```

| | | | | | |
|---|---|---|---|---|---|
| atgtcgaggt | ttcactctct | tctcgctttc | gtcgttgctt | cccttacggc | tgtggcccac | 60 |
| gctggtattg | gtcccgtcgc | cgacctcacc | atcaccaacg | cagcggtcag | ccccgacggg | 120 |
| ttttctcgcc | aggccgtcgt | cgtgaacggc | ggcaccctg | ccctctcat | cacgggtaac | 180 |
| atgggggatc | gcttccagct | caatgtcatc | gacaacctta | ccaaccacac | gatgctgaag | 240 |
| agcacgagta | ttcactggca | cggtttcttc | agaagggca | ccaactgggc | cgacggtccc | 300 |
| gccttcatca | accagtgccc | gatctcatct | ggtcactcgt | tcctgtacga | cttccaggtt | 360 |
| cctgaccagg | ctggtacctt | ctggtatcac | agtcacttgt | ccacgcagta | ctgtgatggt | 420 |
| ctgaggggtc | cgttcgttgt | ttacgacccg | aatgatccgg | ccgccgacct | gtacgacgtc | 480 |
| gacaacgacg | acactgtcat | tacccttgtg | gattggtacc | acgtcgccgc | gaagctgggc | 540 |
| cccgcattcc | ctctcggcgc | cgacgccacc | ctcatcaacg | gtaagggacg | ctcccccagc | 600 |
| acgaccaccg | cggacctctc | agttatcagc | gtcaccccgg | gtaaacgcta | ccgtttccgc | 660 |
| ctggtctccc | tgtcgtgcga | ccccaactac | acgttcagca | tcgatggtca | acatgacg | 720 |
| atcatcgaga | ccgactcaat | caacacggcg | ccctcgtcg | tcgactccat | tcagatcttc | 780 |
| gccgcccagc | gttactcctt | cgtgctcgag | gccaaccagg | ccgtcgacaa | ctactggatt | 840 |
| cgtgcaaacc | cgagcttcgg | taatgtcggg | ttcacgggtg | gcatcaactc | ggctatcctc | 900 |
| cgctacgatg | gtgccgctgc | catcgagccc | accaccacgc | agaccacttc | gacggagccg | 960 |
| ctcaacgagg | tgaacctgca | cccgctggtc | gccaccgctg | tgcccggctc | cccgttgcg | 1020 |
| ggtggtgtcg | acctggccat | caacatggcg | ttcaacttca | acggcaccaa | cttcttcatc | 1080 |
| aacggggcgt | ctttcacgcc | cccgactgtg | cctgtcctgc | tccagatcat | cagcggcgca | 1140 |
| cagaacgcgc | aagacctcct | gccctccggc | agcgtctact | cgctcccctc | gaacgctgac | 1200 |
| attgagatct | ccttccccgc | caccaccgcc | gccccggcg | cgccccaccc | cttccacttg | 1260 |
| cacgggcacg | cgttcgcggt | cgtccgcagc | gccggcagca | cggtctacaa | ctacgacaac | 1320 |
| cccatcttcc | gcgacgtcgt | cagcacgggg | acgcctgcgg | ccggtgacaa | cgtcaccatc | 1380 |
| cgcttccgca | ccgacaaccc | cggcccgtgg | ttcctccact | gccacatcga | cttccacctc | 1440 |
| gaggccggct | tcgccgtcgt | gttcgcggag | gacatccccg | acgtcgcgtc | ggcgaacccc | 1500 |
| gtcccccagg | cgtggtccga | cctctgcccg | acctacgacg | cgctcgaccc | gagcgaccag | 1560 |

```
taa                                                              1563
```

<210> SEQ ID NO 10
<211> LENGTH: 520
<212> TYPE: PRT
<213> ORGANISM: Trametes sp.

<400> SEQUENCE: 10

| Met | Ser | Arg | Phe | His | Ser | Leu | Leu | Ala | Phe | Val | Val | Ala | Ser | Leu | Thr |
|---|---|---|---|---|---|---|---|---|---|---|---|---|---|---|---|
| 1 | | | | 5 | | | | | 10 | | | | | 15 | |

| Ala | Val | Ala | His | Ala | Gly | Ile | Gly | Pro | Val | Ala | Asp | Leu | Thr | Ile | Thr |
|---|---|---|---|---|---|---|---|---|---|---|---|---|---|---|---|
| | | | 20 | | | | | 25 | | | | | 30 | | |

| Asn | Ala | Ala | Val | Ser | Pro | Asp | Gly | Phe | Ser | Arg | Gln | Ala | Val | Val | Val |
|---|---|---|---|---|---|---|---|---|---|---|---|---|---|---|---|
| | | 35 | | | | | 40 | | | | | 45 | | | |

| Asn | Gly | Gly | Thr | Pro | Gly | Pro | Leu | Ile | Thr | Gly | Asn | Met | Gly | Asp | Arg |
|---|---|---|---|---|---|---|---|---|---|---|---|---|---|---|---|
| | 50 | | | | | 55 | | | | | 60 | | | | |

| Phe | Gln | Leu | Asn | Val | Ile | Asp | Asn | Leu | Thr | Asn | His | Thr | Met | Leu | Lys |
|---|---|---|---|---|---|---|---|---|---|---|---|---|---|---|---|
| 65 | | | | | 70 | | | | | 75 | | | | | 80 |

| Ser | Thr | Ser | Ile | His | Trp | His | Gly | Phe | Phe | Gln | Lys | Gly | Thr | Asn | Trp |
|---|---|---|---|---|---|---|---|---|---|---|---|---|---|---|---|
| | | | | 85 | | | | | 90 | | | | | 95 | |

| Ala | Asp | Gly | Pro | Ala | Phe | Ile | Asn | Gln | Cys | Pro | Ile | Ser | Ser | Gly | His |
|---|---|---|---|---|---|---|---|---|---|---|---|---|---|---|---|
| | | | 100 | | | | | 105 | | | | | 110 | | |

| Ser | Phe | Leu | Tyr | Asp | Phe | Gln | Val | Pro | Asp | Gln | Ala | Gly | Thr | Phe | Trp |
|---|---|---|---|---|---|---|---|---|---|---|---|---|---|---|---|
| | | | 115 | | | | | 120 | | | | | 125 | | |

| Tyr | His | Ser | His | Leu | Ser | Thr | Gln | Tyr | Cys | Asp | Gly | Leu | Arg | Gly | Pro |
|---|---|---|---|---|---|---|---|---|---|---|---|---|---|---|---|
| | | 130 | | | | | 135 | | | | | 140 | | | |

| Phe | Val | Val | Tyr | Asp | Pro | Asn | Asp | Pro | Ala | Ala | Asp | Leu | Tyr | Asp | Val |
|---|---|---|---|---|---|---|---|---|---|---|---|---|---|---|---|
| 145 | | | | | 150 | | | | | 155 | | | | | 160 |

| Asp | Asn | Asp | Asp | Thr | Val | Ile | Thr | Leu | Val | Asp | Trp | Tyr | His | Val | Ala |
|---|---|---|---|---|---|---|---|---|---|---|---|---|---|---|---|
| | | | | 165 | | | | | 170 | | | | | 175 | |

| Ala | Lys | Leu | Gly | Pro | Ala | Phe | Pro | Leu | Gly | Ala | Asp | Ala | Thr | Leu | Ile |
|---|---|---|---|---|---|---|---|---|---|---|---|---|---|---|---|
| | | | 180 | | | | | 185 | | | | | 190 | | |

| Asn | Gly | Lys | Gly | Arg | Ser | Pro | Ser | Thr | Thr | Thr | Ala | Asp | Leu | Ser | Val |
|---|---|---|---|---|---|---|---|---|---|---|---|---|---|---|---|
| | | 195 | | | | | 200 | | | | | 205 | | | |

| Ile | Ser | Val | Thr | Pro | Gly | Lys | Arg | Tyr | Arg | Phe | Arg | Leu | Val | Ser | Leu |
|---|---|---|---|---|---|---|---|---|---|---|---|---|---|---|---|
| 210 | | | | | 215 | | | | | 220 | | | | | |

| Ser | Cys | Asp | Pro | Asn | Tyr | Thr | Phe | Ser | Ile | Asp | Gly | His | Asn | Met | Thr |
|---|---|---|---|---|---|---|---|---|---|---|---|---|---|---|---|
| 225 | | | | | 230 | | | | | 235 | | | | | 240 |

| Ile | Ile | Glu | Thr | Asp | Ser | Ile | Asn | Thr | Ala | Pro | Leu | Val | Val | Asp | Ser |
|---|---|---|---|---|---|---|---|---|---|---|---|---|---|---|---|
| | | | | 245 | | | | | 250 | | | | | 255 | |

| Ile | Gln | Ile | Phe | Ala | Ala | Gln | Arg | Tyr | Ser | Phe | Val | Leu | Glu | Ala | Asn |
|---|---|---|---|---|---|---|---|---|---|---|---|---|---|---|---|
| | | | 260 | | | | | 265 | | | | | 270 | | |

| Gln | Ala | Val | Asp | Asn | Tyr | Trp | Ile | Arg | Ala | Asn | Pro | Ser | Phe | Gly | Asn |
|---|---|---|---|---|---|---|---|---|---|---|---|---|---|---|---|
| | | 275 | | | | | 280 | | | | | 285 | | | |

| Val | Gly | Phe | Thr | Gly | Gly | Ile | Asn | Ser | Ala | Ile | Leu | Arg | Tyr | Asp | Gly |
|---|---|---|---|---|---|---|---|---|---|---|---|---|---|---|---|
| | 290 | | | | | 295 | | | | | 300 | | | | |

| Ala | Ala | Ala | Ile | Glu | Pro | Thr | Thr | Thr | Gln | Thr | Thr | Ser | Thr | Glu | Pro |
|---|---|---|---|---|---|---|---|---|---|---|---|---|---|---|---|
| 305 | | | | | 310 | | | | | 315 | | | | | 320 |

| Leu | Asn | Glu | Val | Asn | Leu | His | Pro | Leu | Val | Ala | Thr | Ala | Val | Pro | Gly |
|---|---|---|---|---|---|---|---|---|---|---|---|---|---|---|---|
| | | | | 325 | | | | | 330 | | | | | 335 | |

| Ser | Pro | Val | Ala | Gly | Gly | Val | Asp | Leu | Ala | Ile | Asn | Met | Ala | Phe | Asn |
|---|---|---|---|---|---|---|---|---|---|---|---|---|---|---|---|
| | | | 340 | | | | | 345 | | | | | 350 | | |

| Phe | Asn | Gly | Thr | Asn | Phe | Phe | Ile | Asn | Gly | Ala | Ser | Phe | Thr | Pro | Pro |
|---|---|---|---|---|---|---|---|---|---|---|---|---|---|---|---|
| | | 355 | | | | | 360 | | | | | 365 | | | |

```
Thr Val Pro Val Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Thr Ala Ala Pro Gly Ala Pro His
                405                 410                 415

Pro Phe His Leu His Gly His Ala Phe Ala Val Val Arg Ser Ala Gly
                420                 425                 430

Ser Thr Val Tyr Asn Tyr Asp Asn Pro Ile Phe Arg Asp Val Val Ser
                435                 440                 445

Thr Gly Thr Pro Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
                500                 505                 510

Asp Ala Leu Asp Pro Ser Asp Gln
                515                 520

<210> SEQ ID NO 11
<211> LENGTH: 1563
<212> TYPE: DNA
<213> ORGANISM: Trametes versicolor

<400> SEQUENCE: 11
atgtcgaggt tcactctct tctcgctttc gtcgttgctt cccttgcggc tgtggcccac      60
gctggtatcg gtcctgtcgc cgacctcacc atcaccaacg cagcggtcag ccccgacggg     120
ttttctcgcc aggccgtcgt cgtgaacggg ggcacccctg ccctctcat caccggtaac     180 atgggggatc gcttccagct caatgtcatc gacaacctca cgaaccacac gatgctgaag     240
agcaccagta ttcactggca cggtttcttc cagaagggca ccaactgggc cgacggtccc     300
gccttcatca accagtgccc gatctcatct ggccactcgt tcctgtatga cttccaggtt     360
cctgaccagg ctggcacctt ctggtaccac agtcacttgt ccacgcagta ctgtgatggt     420
ctgaggggtc cattcgttgt ttacgacccg aatgacccgg ccgccgacct gtacgacgtc     480
gacaacgacg acacggtcat tacccttgcg gattggtacc acgtcgccgc gaagctgggc     540
cccgcattcc ctctcggcgc cgacgccact ctcatcaacg gtaagggacg ctcccccagc     600
acgaccaccg cggacctcac tgttatcagc gtcactccgg gtaaacgtta ccgtttccgc     660
ctggtgtccc tgtcgtgcga ccccaaccac accttcagca tcgatggcca caacatgacg     720
atcatcgaga ccgactcgat caacacggcg cccctcgtgg tcgactccat tcagatcttc     780
gccgcccagc gttactcctt cgtgctcgag gccaaccagg ccgtcgacaa ctactggatt     840
cgcgccaacc cgagcttcgg taacgtcggg ttcaccggcg gcatcaactc ggctatcctt     900
cgctatgatg gcgccgctgc catcgagccc accaccacgc agaccacttc gaccgagccg     960
ctcaacgagg tcaacctgca cccgctggtt gccaccgctg tccctggctc tcccgttgcg    1020
ggtggtgttg acctggccat caatatggcg ttcaacttca atggcaccaa cttcttcatc    1080
aacggcgcgt ctttcacgcc cccgaccgtg cctgtcctcc tccagatcat cagcggcgcg    1140
cagaacgcgc aggacctcct gccctccggc agcgtatact cgctcccctc gaacgccgac    1200
```

```
atcgagatct ccttccccgc caccgccgct gccccggtg cgccccaccc cttccacttg    1260
catgggcacg cgttcgcggt cgtccgcagc gccggcagca cggtctacaa ctacgacaac    1320
cccatcttcc gcgacgtcgt cagcacgggg acgcctgcgg ccggtgacaa cgtcaccatc    1380
cgcttccgca ccgacaaccc cggcccgtgg ttcctccact gccacatcga cttccacctc    1440
gaggccggct cgccgtcgt gttcgcggag gacatccccg acgtcgcgtc ggcgaaccccc    1500 gtcccccagg cgtggtccga cctctgcccg acctacgacg cgctcgaccc cagcgaccag    1560
taa                                                                  1563
```

<210> SEQ ID NO 12
<211> LENGTH: 520
<212> TYPE: PRT
<213> ORGANISM: Trametes versicolor

<400> SEQUENCE: 12

```
Met Ser Arg Phe His Ser Leu Leu Ala Phe Val Val Ala Ser Leu Ala
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Ala Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Thr Val
        195                 200                 205

Ile Ser Val Thr Pro Gly Lys Arg Tyr Arg Phe Arg Leu Val Ser Leu
    210                 215                 220

Ser Cys Asp Pro Asn His Thr Phe Ser Ile Asp Gly His Asn Met Thr
225                 230                 235                 240

Ile Ile Glu Thr Asp Ser Ile Asn Thr Ala Pro Leu Val Val Asp Ser
                245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Ser Phe Gly Asn
        275                 280                 285

Val Gly Phe Thr Gly Gly Ile Asn Ser Ala Ile Leu Arg Tyr Asp Gly
    290                 295                 300
```

```
Ala Ala Ala Ile Glu Pro Thr Thr Thr Gln Thr Ser Thr Glu Pro
305                 310                 315                 320

Leu Asn Glu Val Asn Leu His Pro Leu Val Ala Thr Ala Val Pro Gly
            325                 330                 335

Ser Pro Val Ala Gly Gly Val Asp Leu Ala Ile Asn Met Ala Phe Asn
            340                 345                 350

Phe Asn Gly Thr Asn Phe Phe Ile Asn Gly Ala Ser Phe Thr Pro Pro
            355                 360                 365

Thr Val Pro Val Leu Leu Gln Ile Ile Ser Gly Ala Gln Asn Ala Gln
            370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
            435                 440                 445

Thr Gly Thr Pro Ala Ala Gly Asp Asn Val Thr Ile Arg Phe Arg Thr
450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
            500                 505                 510

Asp Ala Leu Asp Pro Ser Asp Gln
            515                 520

<210> SEQ ID NO 13
<211> LENGTH: 1563
<212> TYPE: DNA
<213> ORGANISM: Trametes versicolor

<400> SEQUENCE: 13
atgtcgaggt tcactctct tctcgctttc gtcgttgctt cccttgcggc tgtggcccac    60
gctggtatcg tcctgtcgc cgacctcacc atcaccaacg cagcggtcag ccccgacggg   120
ttttctcgcc aggccgtcgt cgtgaacggt ggcacccctg ccctctcat caccggtaac   180 atggggggatc gcttccagct caatgtcatc gacaacctca cggaccacac gatgctgaag   240
agcaccagta ttcactggca cggtttcttc cagaagggca ccaactgggc cgacggtccc   300
gccttcatca ccagtgccc gatctcatct ggccactcgt tcctgtatga cttccaggtt   360
cctgaccagg ctggcacctt ctggtaccac agtcacttgt ccacgcagta ctgtgatggt   420 ctgagggggtc cgttcgttgt ttacgacccg aatgacccgg ccgccgacct gtacgacgtc   480
gacaacgacg acacggtcat tacccttgcg gattggtacc acgtcgccgc gaagctgggc   540
cccgcattcc ctctcggcgc cgacgccact ctcatcaacg gtaagggacg ctcccccagc   600
acgaccaccg cggacctcac tgttatcagc gtcactccgg gtaaacgtta ccgtttccgc   660
ctggtgtccc tgtcgtgcga ccccaaccac accttcagca tcgatggcca caacatgacg   720
atcatcgaga ccgactcgat caacacggcc ccctcgtgg tcgactccat tcagatcttc   780
gctgcccagc gttactcctt cgtgctcgag gccaaccagg ccgtcgacaa ctactggatt   840
cgcgccaacc cgagcttcgg taacgtcggg ttcaccggcg gcatcaactc ggctatcctc   900
```

```
cgctatgatg gcgccgctgc catcgagccc accaccacgc agaccacttc gaccgagccg    960
ctcaacgagg tcaacctgca cccgctggtt gccaccgctg tccctggctc tcccgctgcg   1020
ggtggtgttg acctggccat caatatggcg ttcaacttca atggcaccaa cttcttcatc   1080
aacggcgcgt ctttcacgcc cccgaccgtg cctgtcctcc tccagatcat cagcggcgcg   1140
cagaacgcgc aggacctcct gccctccggc agcgtatact cgctcccctc gaacgccgac   1200
atcgagatct ccttccccgc caccgccgct gccccggtg cgcccacccc cttccacttg    1260
cacgggcacg cgttcgcggt cgtccgcagc gccggcagca cggtctacaa ctacgacaac   1320
cccatcttcc gcgacgtcgt cagcacgggg acgcctgcgg ccggtgacaa cgtcaccatc   1380
cgcttccgca ccgacaaccc cggcccgtgg tttctccact gccacatcga cttccacctc   1440
gaggccggct cgccgtcgt gtttgcggag gacatccccg atgtcgcatc ggcgaacccc    1500
gtcccccagg cgtggtccga cctctgcccg acctacgacg cgcgcgaccc gagcgaccag   1560
taa                                                                1563

<210> SEQ ID NO 14
<211> LENGTH: 520
<212> TYPE: PRT
<213> ORGANISM: Trametes versicolor

<400> SEQUENCE: 14

Met Ser Arg Phe His Ser Leu Leu Ala Phe Val Val Ala Ser Leu Ala
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asp His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Ala Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Thr Val
        195                 200                 205

Ile Ser Val Thr Pro Gly Lys Arg Tyr Arg Phe Arg Leu Val Ser Leu
    210                 215                 220

Ser Cys Asp Pro Asn His Thr Phe Ser Ile Asp Gly His Asn Met Thr
225                 230                 235                 240

Ile Ile Glu Thr Asp Ser Ile Asn Thr Ala Pro Leu Val Val Asp Ser
```

```
            245                 250                 255
Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Ser Phe Gly Asn
            275                 280                 285

Val Gly Phe Thr Gly Gly Ile Asn Ser Ala Ile Leu Arg Tyr Asp Gly
            290                 295                 300

Ala Ala Ala Ile Glu Pro Thr Thr Thr Gln Thr Thr Ser Thr Glu Pro
305                 310                 315                 320

Leu Asn Glu Val Asn Leu His Pro Leu Val Ala Thr Ala Val Pro Gly
                325                 330                 335

Ser Pro Ala Ala Gly Gly Val Asp Leu Ala Ile Asn Met Ala Phe Asn
                340                 345                 350

Phe Asn Gly Thr Asn Phe Phe Ile Asn Gly Ala Ser Phe Thr Pro Pro
                355                 360                 365

Thr Val Pro Val Leu Leu Gln Ile Ile Ser Gly Ala Gln Asn Ala Gln
370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
                420                 425                 430

Ser Thr Val Tyr Asn Tyr Asp Asn Pro Ile Phe Arg Asp Val Val Ser
                435                 440                 445

Thr Gly Thr Pro Ala Ala Gly Asp Asn Val Thr Ile Arg Phe Arg Thr
450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
                500                 505                 510

Asp Ala Arg Asp Pro Ser Asp Gln
                515                 520
```

<210> SEQ ID NO 15
<211> LENGTH: 1563
<212> TYPE: DNA
<213> ORGANISM: Trametes pubescens

<400> SEQUENCE: 15

```
atgtcgaggt tccaatctct tctcgctttc gtcgttgctt ctcttgcggc tgtggcccac    60
gcaggtatcg gtcctgtcgc cgacctcacc atctccaatg ctgccgtcag ccccgacggc   120
ttttctcgcc aggccgttgt ggtgaacggg ggcacccctg tcccctcat accggtaac    180
aaggggaca acttccagct caatgtcatc gacaacctga cgaaccacac gatgctgaag   240
agcaccagta tccactggca cggtttcttc agaagggca cgaactgggc cgacggtccc   300
gccttcatca ccagtgccc tatctcatct ggcaactcgt tcctgtacaa cttccaggtg   360
cctgaccagg ctggcacctt tggtaccac agtcacttgt ccacgcagta ctgtgacggt   420
ctgagggggc cgttcgttgt ctacgaccg aatgaccga cgctgactt gtacgacgtt   480
gacaacgacg acaccgtcat cacgctcgtg gattggtacc acgtcgcggc gaagctaggc   540
```

```
cccgccttcc ctctcggcgc cgacgccacc ctcatcaatg gtaaggggcg ctcccccagt    600
acgacgacgg cggacctcgc tgttatcagc gtcactgcgg gtaaacgcta ccgcttccgc    660
ctggtgtccc tgtcgtgcga ccccaactac gtcttcagca tcgatggtca acatgacg     720
atcatcgaga ccgactcgat caacacgcag ccccttgtgg tcgactccat tcagatcttt    780
gccgcccagc gatactcttt cgtgctggag gctaaccagg cggtcgacaa ctactggatt    840
cgtgccaacc cgaacttcgg aaacgtcggg ttcaccggcg gtatcaactc ggctattctc    900
cgctacgatg gcgccgccgc cattgagccc acgaccacgc agaccacttc gacgcagccc    960
ctcaacgagg tgaacctgca ccctcttgtg gccaccgctg tgcccggctc tcccgttgcg   1020
ggtggcgtcg acctagccat caacatggcg ttcaacttca acggcaccaa cttcttcatc   1080
aacggcgcat ccttcacgcc cccgaccgtg cctgtcctgc tccagatcat cagcggtgcg   1140
cagaacgcgc aggacctcct cccgtccggc agcgtctact cgctcccctc gaacgcggac   1200
atcgaaatct cgttccccgc caccaccgcc gcgcccggtg ctccccaccc cttccacttg   1260
cacgggcacg cgttcgcggt cgtccgcagc gccggcagca ccgtctacaa ctacgacaac   1320
ccgatcttcc gcgacgtcgt cagcacgggg acgcctgcgg ccggtgacaa cgtcacgatc   1380
cgcttccgca ccgacaaccc cggccgtgg ttcctccact gccacatcga cttccacctt    1440
gaggccggct tcgccgtcgt gttcgcggag gatatccctg acgtcgcgtc ggcgaacccg   1500
gtcccccagg cgtggtctga cctctgcccc atctacgacg cgctcgaccc cagcgaccag   1560
tag                                                                1563
```

<210> SEQ ID NO 16
<211> LENGTH: 520
<212> TYPE: PRT
<213> ORGANISM: Trametes pubescens

<400> SEQUENCE: 16

Met Ser Arg Phe Gln Ser Leu Leu Ala Phe Val Val Ala Ser Leu Ala
1               5                   10                  15

Ala Val Ala His Ala Gly Ile Gly Pro Val Ala Asp Leu Thr Ile Ser
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Lys Gly Asp Asn
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly Asn
            100                 105                 110

Ser Phe Leu Tyr Asn Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ser Ala Asp Leu Tyr Asp Val
145                 150                 155                 160

Asp Asn Asp Asp Thr Val Ile Thr Leu Val Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Ala Val
         195                 200                 205

Ile Ser Val Thr Ala Gly Lys Arg Tyr Arg Phe Arg Leu Val Ser Leu
    210                 215                 220

Ser Cys Asp Pro Asn Tyr Val Phe Ser Ile Asp Gly His Asn Met Thr
225                 230                 235                 240

Ile Ile Glu Thr Asp Ser Ile Asn Thr Gln Pro Leu Val Val Asp Ser
            245                 250                 255

Ile Gln Ile Phe Ala Ala Gln Arg Tyr Ser Phe Val Leu Glu Ala Asn
        260                 265                 270

Gln Ala Val Asp Asn Tyr Trp Ile Arg Ala Asn Pro Asn Phe Gly Asn
            275                 280                 285

Val Gly Phe Thr Gly Gly Ile Asn Ser Ala Ile Leu Arg Tyr Asp Gly
    290                 295                 300

Ala Ala Ala Ile Glu Pro Thr Thr Gln Thr Thr Ser Thr Gln Pro
305                 310                 315                 320

Leu Asn Glu Val Asn Leu His Pro Leu Val Ala Thr Ala Val Pro Gly
            325                 330                 335

Ser Pro Val Ala Gly Gly Val Asp Leu Ala Ile Asn Met Ala Phe Asn
        340                 345                 350

Phe Asn Gly Thr Asn Phe Phe Ile Asn Gly Ala Ser Phe Thr Pro Pro
    355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Thr Ala Ala Pro Gly Ala Pro His
            405                 410                 415

Pro Phe His Leu His Gly His Ala Phe Ala Val Val Arg Ser Ala Gly
        420                 425                 430

Ser Thr Val Tyr Asn Tyr Asp Asn Pro Ile Phe Arg Asp Val Val Ser
    435                 440                 445

Thr Gly Thr Pro Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
            485                 490                 495

Ser Ala Asn Pro Val Pro Gln Ala Trp Ser Asp Leu Cys Pro Ile Tyr
        500                 505                 510

Asp Ala Leu Asp Pro Ser Asp Gln
        515                 520

<210> SEQ ID NO 17
<211> LENGTH: 1563
<212> TYPE: DNA
<213> ORGANISM: Trametes hirsuta

<400> SEQUENCE: 17
atgtcgaggt tccagtctct gctcgccttc gtcgtcgcct ctctcgcggc tgtggcccat      60
gccgccattg ggcccaccgc tgacctcacc atctccaatg ccgaggtcag ccccgatggg     120
ttcgctcgtc aggctgtggt tgtcaacaat gttaccccgg gacccctcgt cgcgggcaac     180
aagggtgacc gcttccaact caatgtcatc gacaacctca cgaaccacac tatgctgaag     240

-continued

```
agcacgagta tccactggca tggcttcttc cagaagggga caaactgggc tgatggtccc    300
gcgtttgtga accagtgccc tatttcctct gggcactcgt tcctctacga tttccaggtt    360
cctgaccagg ccggtacctt ctggtaccac agccacttgt ccactcagta ctgtgacggc    420
ctgcggggtc ctttcgtcgt gtacgatccc aatgacccgc acgcgagttt gtatgacgtc    480
gacaatgacg acaccgtgat caccctcgcg gattggtacc acactgccgc gaagctcggc    540
cccgcgttcc cactgggtgc ggatgctacc cttatcaacg ggctcgggcg ttccccagc    600
accacggcgg cggacctcgc agtcatcaac gtcacgaagg caaacgcta ccgtttccgc    660
ctggtctccc tgtcgtgtga ccccaaccac acgttcagca tcgatggtca tgacttgacg    720
atcatcgagg tggactccat caactcgcaa cctctggtgg ttgactccat ccagattttc    780
gctgcgcagc ggtactcctt tgtgttgaat gccgaccagg atgtcggtaa ctactggatt    840
cgcgccaacc ccaacttcgg caacgtcgga tttgcgggtg tatcaactc ggccatcctg    900
cgctacgacg gcgccgaccc ggttgagccc accacgactc agactacgcc gaccaagccc    960
ctgaacgagg tcgacttgca cccgctcgcc accatggctg tgcccggttc cccagtcgcc   1020
ggtggtgttg acacggctat caacatggcc ttcaacttca atggtaccaa cttcttcatc   1080
aacggcgcga gctttgtgcc cccaccgtg ccggtcctgc tccagatcat cagcggcgcc   1140
cagaacgccc aggatctcct cccgtctggc agcgtctact ccctcccgtc aaacgcggat   1200
atcgagatct cgttccctgc tacggcggct gctccgggtg cccctcaccc cttccacttg   1260
cacggtcacg ccttcgccgt cgtccgtagc gctggcagca ccgtctacaa ctacgacaac   1320
cccatcttcc gcgacgtcgt cagcacgggg acgcctgcgg ccggtgacaa cgtcaccatc   1380
cgcttccgca ccgacaaccc tggcccgtgg ttcctccact gccacatcga cttccacctt   1440
gaggccggct ttgcggtcgt gttcgcggag gacatccccg acgtcgcgtc ggcgaacccc   1500
gtccctcagg catggtctga tctgtgcccc atctatgacg cactcgatgt caacgaccag   1560
tag                                                                 1563
```

<210> SEQ ID NO 18
<211> LENGTH: 520
<212> TYPE: PRT
<213> ORGANISM: Trametes hirsuta

<400> SEQUENCE: 18

```
Met Ser Arg Phe Gln Ser Leu Leu Ala Phe Val Val Ala Ser Leu Ala
1               5                   10                  15

Ala Val Ala His Ala Ala Ile Gly Pro Thr Ala Asp Leu Thr Ile Ser
            20                  25                  30

Asn Ala Glu Val Ser Pro Asp Gly Phe Ala Arg Gln Ala Val Val Val
        35                  40                  45

Asn Asn Val Thr Pro Gly Pro Leu Val Ala Gly Asn Lys Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125
```

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Leu Tyr Asp Val
145                 150                 155                 160

Asp Asn Asp Asp Thr Val Ile Thr Leu Ala Asp Trp Tyr His Thr Ala
                165                 170                 175

Ala Lys Leu Gly Pro Ala Phe Pro Leu Gly Ala Asp Ala Thr Leu Ile
            180                 185                 190

Asn Gly Leu Gly Arg Ser Pro Ser Thr Thr Ala Ala Asp Leu Ala Val
        195                 200                 205

Ile Asn Val Thr Lys Gly Lys Arg Tyr Arg Phe Arg Leu Val Ser Leu
    210                 215                 220

Ser Cys Asp Pro Asn His Thr Phe Ser Ile Asp Gly His Asp Leu Thr
225                 230                 235                 240

Ile Ile Glu Val Asp Ser Ile Asn Ser Gln Pro Leu Val Val Asp Ser
                245                 250                 255

Ile Gln Ile Phe Ala Ala Gln Arg Tyr Ser Phe Val Leu Asn Ala Asp
            260                 265                 270

Gln Asp Val Gly Asn Tyr Trp Ile Arg Ala Asn Pro Asn Phe Gly Asn
        275                 280                 285

Val Gly Phe Ala Gly Gly Ile Asn Ser Ala Ile Leu Arg Tyr Asp Gly
    290                 295                 300

Ala Asp Pro Val Glu Pro Thr Thr Thr Gln Thr Thr Pro Thr Lys Pro
305                 310                 315                 320

Leu Asn Glu Val Asp Leu His Pro Leu Ala Thr Met Ala Val Pro Gly
                325                 330                 335

Ser Pro Val Ala Gly Gly Val Asp Thr Ala Ile Asn Met Ala Phe Asn
            340                 345                 350

Phe Asn Gly Thr Asn Phe Phe Ile Asn Gly Ala Ser Phe Val Pro Pro
        355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
        435                 440                 445

Thr Gly Thr Pro Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Ile Tyr
            500                 505                 510

Asp Ala Leu Asp Val Asn Asp Gln
        515                 520

<210> SEQ ID NO 19
<211> LENGTH: 1563
<212> TYPE: DNA

<213> ORGANISM: Trametes hirsuta

<400> SEQUENCE: 19

```
atgtcgaggt tccagtctct gctcgccttc gtcgtcgcct ccctcgcggc tgtggcccat      60
gccgccattg gcccaccgc tgacctcacc atctccaatg ccgaggtcag ccccgatggg     120
ttcgctcgtc aggctgtggt tgtcaacaat gttaccccgg acccctagt cgcgggcaac     180
aagggtgacc gcttccaact caatgtcatc gacaacctca cgaaccacac tatgctgaag     240
agcacgagta tccactggca tggcttcttc cagaagggga caaactgggc tgatggtccc     300
gcgtttgtga accagtgccc tatttcctct gggcactcgt tcctctacga tttccaggtt     360
cctgaccagg ccggtacctt ctggtaccac agccacttgt ccactcagta ctgtgacggc     420
ctgcggggtc ctttcgtcgt gtacgatccc aatgacccgc acgcgagctt gtatgacgtc     480
gacaatgacg acaccgtgat caccctcgcg gattggtacc acactgccgc gaagctcggc     540
cccgccttcc cactgggtgc ggatgctacc cttatcaacg ggctcgggcg ttcccccagc     600
accacggcgg cggacctcgc ggtcatcaac gtcacgaagg gcaaacgcta ccgtttccgc     660
ctggtctccc tgtcgtgtga ccccaaccac acgttcagca tcgatggtca tgacttgacg     720
atcatcgagg tggactccat caactcccaa cctctggtgg ttgactccat ccagattttc     780
gctgcgcagc ggtactcctt tgtgttgaat gccgaccagg acgtcggtaa ctactggatt     840
cgcgccaacc ccaacttcgg caacgtcgga tttgcgggtg gtatcaactc ggccatcctg     900
cgctacgacg gcgccgaccc ggttgagccc accacgactc agactacgcc gaccaagccc     960
ctgaacgagg tcgacttgca cccgctcgcc accatggctg tgcccggttc cccagtcgcc    1020
ggtggtgttg acacggctat caacatggcc ttcaacttca atggtaccaa cttcttcatc    1080
aacgcgcgcga gctttgtgcc ccccaccgtg ccggtcctgc tccagatcat caggcgcgcc    1140
cagaacgccc aggatctcct cccgtctggc agcgtctact ccctcccgtc gaacgcggac    1200
atcgagatct cgttccctgc taccgcggcc cctccgggtg cccctcaccc cttccacttg    1260
catggtcacg ccttcgccgt tgtccgtagc gctggcagca ccgtctacaa ctacgacaac    1320
cccatcttcc gcgacgtcgt cagcacgggg acgcctgcgg ccggtgacaa cgtcaccatc    1380
cgcttccgca ccgacaaccc cggcccgtgg ttcctccact gccacatcga cttccacctt    1440
gaggccggct tgcggtcgt gttcgctgag gacatccccg acgtcgcgtc ggcgaaccct    1500
gtccctcagg cgtggtctga tctgtgcccc atctatgacg cactcgatgt caacgaccag    1560
tag                                                                 1563
```

<210> SEQ ID NO 20
<211> LENGTH: 520
<212> TYPE: PRT
<213> ORGANISM: Trametes hirsuta

<400> SEQUENCE: 20

```
Met Ser Arg Phe Gln Ser Leu Leu Ala Phe Val Val Ala Ser Leu Ala
1               5                   10                  15

Ala Val Ala His Ala Ala Ile Gly Pro Thr Ala Asp Leu Thr Ile Ser
            20                  25                  30

Asn Ala Glu Val Ser Pro Asp Gly Phe Ala Arg Gln Ala Val Val Val
        35                  40                  45

Asn Asn Val Thr Pro Gly Pro Leu Val Ala Gly Asn Lys Gly Asp Arg
    50                  55                  60

Phe Gln Leu Asn Val Ile Asp Asn Leu Thr Asn His Thr Met Leu Lys
```

```
                65                  70                  75                  80
            Ser Thr Ser Ile His Trp His Gly Phe Phe Gln Lys Gly Thr Asn Trp
                            85                  90                  95
            Ala Asp Gly Pro Ala Phe Val Asn Gln Cys Pro Ile Ser Ser Gly His
                            100                 105                 110
            Ser Phe Leu Tyr Asp Phe Gln Val Pro Asp Gln Ala Gly Thr Phe Trp
                            115                 120                 125
            Tyr His Ser His Leu Ser Thr Gln Tyr Cys Asp Gly Leu Arg Gly Pro
                            130                 135                 140
            Phe Val Val Tyr Asp Pro Asn Asp Pro His Ala Ser Leu Tyr Asp Val
            145                 150                 155                 160
            Asp Asn Asp Asp Thr Val Ile Thr Leu Ala Asp Trp Tyr His Thr Ala
                            165                 170                 175
            Ala Lys Leu Gly Pro Ala Phe Pro Leu Gly Ala Asp Ala Thr Leu Ile
                            180                 185                 190
            Asn Gly Leu Gly Arg Ser Pro Ser Thr Thr Ala Ala Asp Leu Ala Val
                            195                 200                 205
            Ile Asn Val Thr Lys Gly Lys Arg Tyr Arg Phe Arg Leu Val Ser Leu
                            210                 215                 220
            Ser Cys Asp Pro Asn His Thr Phe Ser Ile Asp Gly His Asp Leu Thr
            225                 230                 235                 240
            Ile Ile Glu Val Asp Ser Ile Asn Ser Gln Pro Leu Val Val Asp Ser
                            245                 250                 255
            Ile Gln Ile Phe Ala Ala Gln Arg Tyr Ser Phe Val Leu Asn Ala Asp
                            260                 265                 270
            Gln Asp Val Gly Asn Tyr Trp Ile Arg Ala Asn Pro Asn Phe Gly Asn
                            275                 280                 285
            Val Gly Phe Ala Gly Gly Ile Asn Ser Ala Ile Leu Arg Tyr Asp Gly
                            290                 295                 300
            Ala Asp Pro Val Glu Pro Thr Thr Thr Gln Thr Thr Pro Thr Lys Pro
            305                 310                 315                 320
            Leu Asn Glu Val Asp Leu His Pro Leu Ala Thr Met Ala Val Pro Gly
                            325                 330                 335
            Ser Pro Val Ala Gly Gly Val Asp Thr Ala Ile Asn Met Ala Phe Asn
                            340                 345                 350
            Phe Asn Gly Thr Asn Phe Phe Ile Asn Gly Ala Ser Phe Val Pro Pro
                            355                 360                 365
            Thr Val Pro Val Leu Leu Gln Ile Ile Arg Arg Ala Gln Asn Ala Gln
                            370                 375                 380
            Asp Leu Leu Pro Ser Gly Ser Val Tyr Ser Leu Pro Ser Asn Ala Asp
            385                 390                 395                 400
            Ile Glu Ile Ser Phe Pro Ala Thr Ala Ala Pro Gly Ala Pro His
                            405                 410                 415
            Pro Phe His Leu His Gly His Ala Phe Ala Val Val Arg Ser Ala Gly
                            420                 425                 430
            Ser Thr Val Tyr Asn Tyr Asp Asn Pro Ile Phe Arg Asp Val Val Ser
                            435                 440                 445
            Thr Gly Thr Pro Ala Ala Gly Asp Asn Val Thr Ile Arg Phe Arg Thr
                            450                 455                 460
            Asp Asn Pro Gly Pro Trp Phe Leu His Cys His Ile Asp Phe His Leu
            465                 470                 475                 480
            Glu Ala Gly Phe Ala Val Val Phe Ala Glu Asp Ile Pro Asp Val Ala
                            485                 490                 495
```

Ser Ala Asn Pro Val Pro Gln Ala Trp Ser Asp Leu Cys Pro Ile Tyr
            500                 505                 510

Asp Ala Leu Asp Val Asn Asp Gln
            515                 520

<210> SEQ ID NO 21
<211> LENGTH: 1563
<212> TYPE: DNA
<213> ORGANISM: Trametes sp.

<400> SEQUENCE: 21

```
atgtcgaggt tccagtctct gctcgccttc gtcgtcgcct ccctcgcggc tgttgctcat      60
gccgccattg ggcccaccgc tgacctcacc atctctaatg ccgaggtcag ccccgatggg     120
ttcgctcgtc aggccgtggt tgtcaacaac gttaccccgg ggcccctggt cgcgggtaac     180
aagggtgacc gcttccaact caatgtcatc gacaacctca ccaaccacac catgctgaag     240
agcacgagta ttcactggca cggcttcttc agaagggga cgaactgggc tgatggtcct     300
gcgttcgtga accagtgccc tatctcgtct gggcattcgt tcctgtacga cttccaggtt     360
ccggatcagg ccggcacatt ctggtaccac agtcacctgt ccacgcagta ctgcgacggc     420
ctgcgcggtc ccttcgttgt gtacgatccg aatgacacgc acgcgagctt gtatgacgtc     480
gacaacgacg acaccgtgat cacactcgcg gattggtacc acaccgccgc aaagctcgga     540
ccaacatttc cactgggtgc cgacgcaacg ctgatcaacg gcttggccg ctccccgagc     600
accacggctg cggacctcgc agtcatcaac gtcacgaagg ggaaacgcta ccgtttccgc     660
ctcgtctccc tgtcgtgtga tcccaaccac acgttcagca tcgatggtca tgacttgacg     720
atcatcgaag tggactccat caactcccag cctctggtgg ttgactccat ccagatcttc     780
gctgcgcagc ggtactcctt cgtgttgaat gccgaccagg atgtcggcaa ctactggatc     840
cgtgccaacc ctagcttcgg aaacgtcgga tttgcgggcg gtatcaactc ggccatcctg     900
cgctacgacg gcgccgaccc ggtcgagccc accacgacg agactacgcc cactaagccc     960
ctcaacgagg ttgacctgca cccactcgac accatggctg tgcccggctc cccggtcgcc    1020
ggtggtgttg acaaggctat caacatggcc ttcaacttca cggtaccaa cttcttcatc    1080
aacggcgcaa gctttgtgcc ccctaccgtg ccggtcctgc ttcagatcat cagcggcgct    1140
caaaacgccc aggatcttct cccctctggc agtgtctact cgctcccggc gaacgctgac    1200
atcgagatct cgttccctgc taccgcggct gctccgggtg ccctcatcc cttccacttg    1260
cacggtcacg ccttcgccgt cgttcgcagc gctggcagca ccgtgtacaa ctacgacaac    1320
cccatcttcc gcgacgtcgt cagcacgggg acgcctgcgg ccggtgacaa cgtcaccatc    1380
cgcttccgca ccgacaaccc tggcccgtgg ttcctccact gccacatcga cttccacctc    1440
gaggccggtt ttgcggtcgt gatggcggag gacattcctg acgtcgcgtc agcgaaccct    1500
gtcccccagg cgtggtctga cctgtgcccc atctacgacg cgctcgatgt caacgaccag    1560
tag                                                                  1563
```

<210> SEQ ID NO 22
<211> LENGTH: 520
<212> TYPE: PRT
<213> ORGANISM: Trametes sp.

<400> SEQUENCE: 22

Met Ser Arg Phe Gln Ser Leu Leu Ala Phe Val Val Ala Ser Leu Ala
1               5                   10                  15

```
Ala Val Ala His Ala Ala Ile Gly Pro Thr Ala Asp Leu Thr Ile Ser
            20                  25                  30

Asn Ala Glu Val Ser Pro Asp Gly Phe Ala Arg Gln Ala Val Val Val
        35                  40                  45

Asn Asn Val Thr Pro Gly Pro Leu Val Ala Gly Asn Lys Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Thr His Ala Ser Leu Tyr Asp Val
145                 150                 155                 160

Asp Asn Asp Asp Thr Val Ile Thr Leu Ala Asp Trp Tyr His Thr Ala
                165                 170                 175

Ala Lys Leu Gly Pro Thr Phe Pro Leu Gly Ala Asp Ala Thr Leu Ile
            180                 185                 190

Asn Gly Leu Gly Arg Ser Pro Ser Thr Thr Ala Ala Asp Leu Ala Val
        195                 200                 205

Ile Asn Val Thr Lys Gly Lys Arg Tyr Arg Phe Arg Leu Val Ser Leu
            210                 215                 220

Ser Cys Asp Pro Asn His Thr Phe Ser Ile Asp Gly His Asp Leu Thr
225                 230                 235                 240

Ile Ile Glu Val Asp Ser Ile Asn Ser Gln Pro Leu Val Val Asp Ser
                245                 250                 255

Ile Gln Ile Phe Ala Ala Gln Arg Tyr Ser Phe Val Leu Asn Ala Asp
            260                 265                 270

Gln Asp Val Gly Asn Tyr Trp Ile Arg Ala Asn Pro Ser Phe Gly Asn
        275                 280                 285

Val Gly Phe Ala Gly Gly Ile Asn Ser Ala Ile Leu Arg Tyr Asp Gly
    290                 295                 300

Ala Asp Pro Val Glu Pro Thr Thr Gln Thr Thr Pro Thr Lys Pro
305                 310                 315                 320

Leu Asn Glu Val Asp Leu His Pro Leu Asp Thr Met Ala Val Pro Gly
                325                 330                 335

Ser Pro Val Ala Gly Gly Val Asp Lys Ala Ile Asn Met Ala Phe Asn
            340                 345                 350

Phe Asn Gly Thr Asn Phe Phe Ile Asn Gly Ala Ser Phe Val Pro Pro
        355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ala Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
            420                 425                 430
```

```
Ser Thr Val Tyr Asn Tyr Asp Asn Pro Ile Phe Arg Asp Val Val Ser
            435                 440                 445
Thr Gly Thr Pro Ala Ala Gly Asp Asn Val Thr Ile Arg Phe Arg Thr
    450                 455                 460
Asp Asn Pro Gly Pro Trp Phe Leu His Cys His Ile Asp Phe His Leu
465                 470                 475                 480
Glu Ala Gly Phe Ala Val Val Met Ala Glu Asp Ile Pro Asp Val Ala
                485                 490                 495
Ser Ala Asn Pro Val Pro Gln Ala Trp Ser Asp Leu Cys Pro Ile Tyr
            500                 505                 510
Asp Ala Leu Asp Val Asn Asp Gln
            515                 520

<210> SEQ ID NO 23
<211> LENGTH: 1560
<212> TYPE: DNA
<213> ORGANISM: Trametes sp.

<400> SEQUENCE: 23
atgtcgaggt tccagtctct tctcgccttc gtcgtcgcct ccctcgcggc tgttgctcat      60
gccgccattg ggcccaccgc tgacctcacc atctccaatg ccgaggtcag ccccgatggg     120
ttcgctcgtc aggccgtggt tgtcaacaac gttaccccgg acccctggt cgcgggtaac      180 aagggtgacc gcttccaact caatgtcatc gacaacctca ccaaccacac catgctgaag     240
agcacgagta ttcactggca cggcttttc cagaagggga cgaactgggc tgatggtcct      300
gcgttcgtga accagtgccc tatctcgtct gggcattcgt tcctgtacga cttccaggtt     360
ccggatcagg ccggcacatt ctggtaccac agtcacttgt ccacgcagta ttgcgacggc     420
ctgcgcggtc ccttcgttgt gtacgatccg aatgacccgc acgcgagctt gtatgacgtc     480
gacaacgacg acaccgtgat cacgctcgcg gattggtacc acaccgccgc aaagctcgga     540
ccagcattcc cactgggtgc cgacgcaacg ctgatcaacg gcttggccg ctccccaagc      600 accacggctg cggacctcgc agtcatcaac gtcacgaagg ggaaacgcta ccgtttccgc     660
ctcgtctccc tgtcgtgtga tcccaaccac acgttcagta tcgatggtca tgacttgacg     720
atcatcgaag tggactccat caactcccag catctggtgg ttgactccat ccagatcttc     780
gctgcgcagc ggtactcctt cgtgttgaat gccgaccagg atgtcggcaa ctactggatt     840
cgtgccaacc ctagcttcgg aaacgtcgga tttgcgggcg gtatcaactc ggccatcctg     900
cgctacgacg cgccgacccc ggtcgagccc accacgacgc agactacgcc cactaagccc     960
ctcaacgagg ttgacctgca cccgctcgac accatggctc ccggctcccc ggtcgccggt    1020
ggtgttgaca aggctatcaa catggccttc aacttcaacg gtaccaactt cttcatcaac    1080
ggcgcaagct tcgtgccccc taccgtgccg gtcctgcttc agatcatcag cggtgctcaa    1140
aatgcccagg atcttcttcc atctggcagt gtctactcgc tcccggcgaa cgctgacatc    1200
gagatctcgt tccctgctac gcggctgct ccgggtgccc ctcaccccTt ccacttgcac     1260
ggtcacgcct ttgccgtcgt tcgcagcgct ggcagcaccg tgtacaacta cgacaacccc    1320
atcttccgcg acgtcgtcag cacggggacg cctgcggccg tgacaacgt gaccatccgc     1380 ttccgcaccg acaaccctgg cccgtggttc ctccactgcc acatcgactt ccacttggag    1440
gccggttttg ccgtcgtgat ggcggaggac attcctgacg tcgcgtcggc gaacccggtt    1500
ccccaggcgt ggtccgacct ttgccccatc tacgacgcgc tcgatgtcaa cgaccagtag    1560
```

<210> SEQ ID NO 24
<211> LENGTH: 519
<212> TYPE: PRT
<213> ORGANISM: Trametes sp.

<400> SEQUENCE: 24

```
Met Ser Arg Phe Gln Ser Leu Leu Ala Phe Val Val Ala Ser Leu Ala
1               5                   10                  15

Ala Val Ala His Ala Ala Ile Gly Pro Thr Ala Asp Leu Thr Ile Ser
            20                  25                  30

Asn Ala Glu Val Ser Pro Asp Gly Phe Ala Arg Gln Ala Val Val Val
        35                  40                  45

Asn Asn Val Thr Pro Gly Pro Leu Val Ala Gly Asn Lys Gly Asp Arg
50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
130                 135                 140

Phe Val Val Tyr Asp Pro Asn Asp Pro His Ala Ser Leu Tyr Asp Val
145                 150                 155                 160

Asp Asn Asp Asp Thr Val Ile Thr Leu Ala Asp Trp Tyr His Thr Ala
                165                 170                 175

Ala Lys Leu Gly Pro Ala Phe Pro Leu Gly Ala Asp Ala Thr Leu Ile
            180                 185                 190

Asn Gly Leu Gly Arg Ser Pro Ser Thr Thr Ala Ala Asp Leu Ala Val
        195                 200                 205

Ile Asn Val Thr Lys Gly Lys Arg Tyr Arg Phe Arg Leu Val Ser Leu
210                 215                 220

Ser Cys Asp Pro Asn His Thr Phe Ser Ile Asp Gly His Asp Leu Thr
225                 230                 235                 240

Ile Ile Glu Val Asp Ser Ile Asn Ser Gln His Leu Val Val Asp Ser
                245                 250                 255

Ile Gln Ile Phe Ala Ala Gln Arg Tyr Ser Phe Val Leu Asn Ala Asp
            260                 265                 270

Gln Asp Val Gly Asn Tyr Trp Ile Arg Ala Asn Pro Ser Phe Gly Asn
        275                 280                 285

Val Gly Phe Ala Gly Gly Ile Asn Ser Ala Ile Leu Arg Tyr Asp Gly
290                 295                 300

Ala Asp Pro Val Glu Pro Thr Thr Gln Thr Thr Pro Thr Lys Pro
305                 310                 315                 320

Leu Asn Glu Val Asp Leu His Pro Leu Asp Thr Met Ala Pro Gly Ser
                325                 330                 335

Pro Val Ala Gly Gly Val Asp Lys Ala Ile Asn Met Ala Phe Asn Phe
            340                 345                 350

Asn Gly Thr Asn Phe Phe Ile Asn Gly Ala Ser Phe Val Pro Pro Thr
        355                 360                 365

Val Pro Val Leu Leu Gln Ile Ile Ser Gly Ala Gln Asn Ala Gln Asp
370                 375                 380
```

```
Leu Leu Pro Ser Gly Ser Val Tyr Ser Leu Pro Ala Asn Ala Asp Ile
385                 390                 395                 400

Glu Ile Ser Phe Pro Ala Thr Ala Ala Pro Gly Ala Pro His Pro
            405                 410                 415

Phe His Leu His Gly His Ala Phe Ala Val Val Arg Ser Ala Gly Ser
            420                 425                 430

Thr Val Tyr Asn Tyr Asp Asn Pro Ile Phe Arg Asp Val Val Ser Thr
            435                 440                 445

Gly Thr Pro Ala Ala Gly Asp Asn Val Thr Ile Arg Phe Arg Thr Asp
            450                 455                 460

Asn Pro Gly Pro Trp Phe Leu His Cys His Ile Asp Phe His Leu Glu
465                 470                 475                 480

Ala Gly Phe Ala Val Val Met Ala Glu Asp Ile Pro Asp Val Ala Ser
                485                 490                 495

Ala Asn Pro Val Pro Gln Ala Trp Ser Asp Leu Cys Pro Ile Tyr Asp
            500                 505                 510

Ala Leu Asp Val Asn Asp Gln
            515

<210> SEQ ID NO 25
<211> LENGTH: 1563
<212> TYPE: DNA
<213> ORGANISM: Lenzites gibbosa

<400> SEQUENCE: 25
atgtcgaggt tccagactct tctcgctttc gtcgttacct ccctcacagc cgcggcgtat      60
gctgccatcg gacctgtggc cgacctcacc atcactaatg ccgaggtcag tcccgacggg     120
ttcgcccgtc aggctgtcgt tgtcaacggc ggtactcctg gaccgcttgt gacggggaat     180
atgggcgatc gcttccagct taatgtgatc gacaacttga caaaccacac gatgctgaaa     240
agtaccagta ttcactggca tgggttcttc caacacggca ctaactgggc cgatggtcct     300
gctttcgtca accagtgccc aattgcatcg gggcattcgt tcttgtacga cttccaggtc     360
cccgaccaag ccggtacttt ctggtaccac agtcacttgt ccacgcagta ctgcgatggg     420
ctgagaggcc ccttcgttgt ctacgaccca atgaccctc atgcaagcct ctacgacgtt     480
gacaacgacg acactgtgat aacactggcg gattggtacc atgtcgcggc gaagctcggt     540
cctcgtttcc cgctgggcgc ggatgcgact ctgattaacg ggctcggccg ctctccaagt     600
accgtctctg cagacctctc tgtgatcaat gtcacacctg gtaaacgcta ccggttccgc     660
cttgtatcgc tgtcgtgcga cccgaaccac accttcagca ttgatggcca cgatctgacg     720
atcattgaga ccgactccgt caacactcaa cctcttgtgg tggattcaat ccagatcttc     780
gctgctcagc gatactcctt cgtgttgaa gccaaccagc ccgtcgacaa ctattgggtc     840
cgtgcgaacc cctccttcgg aaacgtcggg ttcagcggtg catcaactc tgccatttg      900 cgatacgatg gcgcccctgc agtagagccc acgacgacac agacaacccc aacgaagcct     960
ctcaacgagg ttgacttgca cccgctcacg cctatgcctg tgcctggcga gcccgttgcg    1020
ggaggtgttg acaagccgct caacatggct ttcaacttca acggcaccag cttcttcatc    1080
aacggcgcca gcttcgagcc tcctaccgtt ccagttcttc tccagattct cagtggcgcg    1140
cagacggctc aggagctact ccctccggga agcgtatacg tcctccccag caatgcgtcg    1200
attgagatat ccttcccggc cactgcggcc gcccctggag cacctcaccc cttccacttg    1260
cacggtcaca ccttcgctgt tgtgcgcagc gccggcagta ctgagtacaa ctacgacaac    1320
```

```
cccatcttcc gcgacgtggt cagcacgggc acgcctgcgg ccggcgacaa cgtcaccatc   1380
cgtttccaga cgaacaaccc cgggccgtgg ttcctccact gccacatcga cttccacctc   1440
gacgccggct tcgcggtcgt catggcggag gacatccctg atgtccaggc ggtcaaccct   1500
gttccgcagg cgtggtccga cttgtgcccg atctacgatg cgctcgaccc cagcgaccag   1560
tag                                                                1563
```

<210> SEQ ID NO 26
<211> LENGTH: 520
<212> TYPE: PRT
<213> ORGANISM: Lenzites gibbosa

<400> SEQUENCE: 26

```
Met Ser Arg Phe Gln Thr Leu Leu Ala Phe Val Val Thr Ser Leu Thr
1               5                   10                  15

Ala Ala Ala Tyr Ala Ala Ile Gly Pro Val Ala Asp Leu Thr Ile Thr
            20                  25                  30

Asn Ala Glu Val Ser Pro Asp Gly Phe Ala Arg Gln Ala Val Val
        35                  40                  45

Asn Gly Gly Thr Pro Gly Pro Leu Val Thr Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln His Gly Thr Asn Trp
                85                  90                  95

Ala Asp Gly Pro Ala Phe Val Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Leu Tyr Asp Val
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Ser Thr Val Ser Ala Asp Leu Ser Val
        195                 200                 205

Ile Asn Val Thr Pro Gly Lys Arg Tyr Arg Phe Arg Leu Val Ser Leu
    210                 215                 220

Ser Cys Asp Pro Asn His Thr Phe Ser Ile Asp Gly His Asp Leu Thr
225                 230                 235                 240

Ile Ile Glu Thr Asp Ser Val Asn Thr Gln Pro Leu Val Val Asp Ser
                245                 250                 255

Ile Gln Ile Phe Ala Ala Gln Tyr Ser Phe Val Leu Glu Ala Asn
            260                 265                 270

Gln Pro Val Asp Asn Tyr Trp Val Arg Ala Asn Pro Ser Phe Gly Asn
        275                 280                 285

Val Gly Phe Ser Gly Gly Ile Asn Ser Ala Ile Leu Arg Tyr Asp Gly
    290                 295                 300

Ala Pro Ala Val Glu Pro Thr Thr Gln Thr Thr Pro Thr Lys Pro
305                 310                 315                 320

Leu Asn Glu Val Asp Leu His Pro Leu Thr Pro Met Pro Val Pro Gly
```

|  | 325 |  |  |  | 330 |  |  |  | 335 |  |  |
|---|---|---|---|---|---|---|---|---|---|---|---|

Glu Pro Val Ala Gly Val Asp Lys Pro Leu Asn Met Ala Phe Asn
              340                     345                 350

Phe Asn Gly Thr Ser Phe Phe Ile Asn Gly Ala Ser Phe Glu Pro Pro
        355                     360                 365

Thr Val Pro Val Leu Leu Gln Ile Leu Ser Gly Ala Gln Thr Ala Gln
370                 375                     380

Glu Leu Leu Pro Ser Gly Ser Val Tyr Val Leu Pro Ser Asn Ala Ser
385                 390                     395                 400

Ile Glu Ile Ser Phe Pro Ala Thr Ala Ala Pro Gly Ala Pro His
                405                     410                 415

Pro Phe His Leu His Gly His Thr Phe Ala Val Val Arg Ser Ala Gly
            420                     425                 430

Ser Thr Glu Tyr Asn Tyr Asp Asn Pro Ile Phe Arg Asp Val Val Ser
            435                     440                 445

Thr Gly Thr Pro Ala Ala Gly Asp Asn Val Thr Ile Arg Phe Gln Thr
            450                     455                 460

Asn Asn Pro Gly Pro Trp Phe Leu His Cys His Ile Asp Phe His Leu
465                 470                     475                 480

Asp Ala Gly Phe Ala Val Val Met Ala Glu Asp Ile Pro Asp Val Gln
                485                     490                 495

Ala Val Asn Pro Val Pro Gln Ala Trp Ser Asp Leu Cys Pro Ile Tyr
                500                     505                 510

Asp Ala Leu Asp Pro Ser Asp Gln
            515                     520

<210> SEQ ID NO 27
<211> LENGTH: 1563
<212> TYPE: DNA
<213> ORGANISM: Trametes hirsuta

<400> SEQUENCE: 27

```
atgtcgaggt tcagtctct tctgaccttc atcaatattt cccttgttgc ggttgctcat      60
gcagcggttg ccctgttgc cgacctcacc atcaccgacg cggcggtcag ccctgacggt     120
ttctctcgcc aggctgttgt ggtgaacggc gtcaccctg gaccgctcgt tgcgggcaat     180
attgggggacc gcttccagct caacgtcatt gacaacttga cgaaccatac catgctcaag    240
tcgaccagta ttcactggca cggcttttc cagcatggca cgaactgggc tgatggtccg     300
gcgttcatta accagtgccc tatctctcct gggcactcgt tcttgtacga cttccaggta    360
cctgaccaag ccggtacctt ctggtaccac agtcacttgt cgacccagta ctgtgatggt    420
ttgaggggcc ccttcgttgt ctacgacccg aacgatcccc atgccagccg ctacgacgtc    480
gacaacgacg acacggtcat tactctggcc gactggtacc ataccgctgc caagctcggg    540
ccccggttcc cgggggggcgc ggacgctact ctcattaatg caagggccg cgctcccagt    600
gactctcccg ccgagctgtc ggtgatcaag gtcacgaagg gcaaacgcta ccgtttccgc    660
ttggtctcgc tgtcatgcaa ccccaaccat accttcagca ttgatggtca aacttgact    720
atcatcgagg tcgacagtgt caactcccag ccgctggaag ttgactccat tcagatcttt    780
gcggcgcagc gctactcctt cgtactggac gccaaccagg ccgtcgacaa ctactggatc    840
cgggccaacc caaacttcgg aaatgtcgga ttcgatgggg gtattaactc ggctatcctg    900
cgctatgacg cgcgcccgc tgttgagccc accacgaacc agactacctc ggttaagccg    960
ctgaacgagg tcgacctgca ccctcttgtc tctaccccag tgcccgggag tccttcgtcc   1020
```

-continued

```
ggaggcgtcg acaaggcgat caacatggct ttcaacttca acggctccaa cttcttcatc   1080
aacggcgcca gcttcgtccc gcccaccgtg cctgtcctgc tccagattct cagtggtgcc   1140
cagacggcgc aggacctcct gccctccggc agtgtatacg tccttccgtc gaacgcgtcc   1200
attgagatct cgttccccgc tacggccgcc gcccctggtg ctccccaccc cttccacttg   1260
cacggtcaca ctttcgctgt tgtgcgcagc gccggcagca ccgtgtacaa ctacgacaac   1320
cccatcttcc gtgacgtcgt gagcacgggt acccctgcag cgggtgacaa cgtcaccatc   1380
cgcttcgaca ccaacaaccc aggcccgtgg ttccttcact gccacatcga cttccacttg   1440
gagggtggct ttgcggtcgt catggctgag atactccgg acgtcaaggc tgtcaacccc    1500
gtccctcagg cgtggtccga tctgtgcccg acctacgacg cgctcgaccc caacgaccag   1560
taa                                                                 1563
```

<210> SEQ ID NO 28
<211> LENGTH: 520
<212> TYPE: PRT
<213> ORGANISM: Trametes hirsuta

<400> SEQUENCE: 28

```
Met Ser Arg Phe Gln Ser Leu Leu Thr Phe Ile Asn Ile Ser Leu Val
1               5                   10                  15

Ala Val Ala His Ala Ala Val Gly Pro Val Ala Asp Leu Thr Ile Thr
            20                  25                  30

Asp Ala Ala Val Ser Pro Asp Gly Phe Ser Arg Gln Ala Val Val Val
        35                  40                  45

Asn Gly Val Thr Pro Gly Pro Leu Val Ala Gly Asn Ile Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln His Gly Thr Asn Trp
                85                  90                  95

Ala Asp Gly Pro Ala Phe Ile Asn Gln Cys Pro Ile Ser Pro Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Arg Tyr Asp Val
145                 150                 155                 160

Asp Asn Asp Asp Thr Val Ile Thr Leu Ala Asp Trp Tyr His Thr Ala
                165                 170                 175

Ala Lys Leu Gly Pro Arg Phe Pro Gly Gly Ala Asp Ala Thr Leu Ile
            180                 185                 190

Asn Gly Lys Gly Arg Ala Pro Ser Asp Ser Pro Ala Glu Leu Ser Val
        195                 200                 205

Ile Lys Val Thr Lys Gly Lys Arg Tyr Arg Phe Arg Leu Val Ser Leu
    210                 215                 220

Ser Cys Asn Pro Asn His Thr Phe Ser Ile Asp Gly His Asn Leu Thr
225                 230                 235                 240

Ile Ile Glu Val Asp Ser Val Asn Ser Gln Pro Leu Glu Val Asp Ser
                245                 250                 255

Ile Gln Ile Phe Ala Ala Gln Arg Tyr Ser Phe Val Leu Asp Ala Asn
            260                 265                 270
```

```
Gln Ala Val Asp Asn Tyr Trp Ile Arg Ala Asn Pro Asn Phe Gly Asn
            275                 280                 285

Val Gly Phe Asp Gly Gly Ile Asn Ser Ala Ile Leu Arg Tyr Asp Gly
        290                 295                 300

Ala Pro Ala Val Glu Pro Thr Thr Asn Gln Thr Thr Ser Val Lys Pro
305                 310                 315                 320

Leu Asn Glu Val Asp Leu His Pro Leu Val Ser Thr Pro Val Pro Gly
                325                 330                 335

Ser Pro Ser Ser Gly Gly Val Asp Lys Ala Ile Asn Met Ala Phe Asn
            340                 345                 350

Phe Asn Gly Ser Asn Phe Phe Ile Asn Gly Ala Ser Phe Val Pro Pro
        355                 360                 365

Thr Val Pro Val Leu Leu Gln Ile Leu Ser Gly Ala Gln Thr Ala Gln
370                 375                 380

Asp Leu Leu Pro Ser Gly Ser Val Tyr Val Leu Pro Ser Asn Ala Ser
385                 390                 395                 400

Ile Glu Ile Ser Phe Pro Ala Thr Ala Ala Pro Gly Ala Pro His
                405                 410                 415

Pro Phe His Leu His Gly His Thr Phe Ala Val Val Arg Ser Ala Gly
            420                 425                 430

Ser Thr Val Tyr Asn Tyr Asp Asn Pro Ile Phe Arg Asp Val Val Ser
        435                 440                 445

Thr Gly Thr Pro Ala Ala Gly Asp Asn Val Thr Ile Arg Phe Asp Thr
    450                 455                 460

Asn Asn Pro Gly Pro Trp Phe Leu His Cys His Ile Asp Phe His Leu
465                 470                 475                 480

Glu Gly Gly Phe Ala Val Val Met Ala Glu Asp Thr Pro Asp Val Lys
                485                 490                 495

Ala Val Asn Pro Val Pro Gln Ala Trp Ser Asp Leu Cys Pro Thr Tyr
            500                 505                 510

Asp Ala Leu Asp Pro Asn Asp Gln
            515                 520

<210> SEQ ID NO 29
<211> LENGTH: 1563
<212> TYPE: DNA
<213> ORGANISM: Lenzites gibbosa

<400> SEQUENCE: 29
atgtcgaggt tccagactct tctcgcktts gtcgttacct ccctcacagc cgcggcgtat     60
gctgccatcg gacctgtggc cgacctcacc atcactaatg ccgaggtcag tcccgacggg    120
ttcgcccgtc aggctgtcgt tgtcaacggc ggtactcctg accgcttgt gacggggaat     180 atgggcgatc gcttccagct taatgtgatc gacaacttga caaaccacac gatgccgaaa    240
agtaccagta ttcactggca tgggttcttc aacacggca ctaactgggc cgatggtcct     300
gctttcgtca ccagtgccc aattgcatcg gggcattcgt tcttgtacga cttccaggtc     360
cccgaccaag ccggtacttt ctggtaccac agtcacttgt ccacgcagta ctgcgatggg    420
ctgagaggcc ccttcgttgt ctacgaccca atgaccctc atgcaagcct ctacgacgtt     480
gacaacgacg acactgtgat aacactggcg gattggtacc atgtcgcggc gaagctcggt    540
cctcgtttcc cgctgggcgc ggatgcgact ctgattaacg ggctcggccg ctctccaagt    600
accgtctctg cagacctctc tgtgatcaat gtcacacctg gtaaacgcta ccggttccgc    660
```

```
cttgtatcgc tgtcgtgcga cccgaaccat accttcagca tcgatgggca taacatgact      720
atcatcgaag tcgatggtat caacagcaag cccctcacgg ttgactccat ccagatcttc      780
gcagcgcaac gctactcatt cgtgctgaac gcccatcaaa ctgtgaataa ctactggatc      840
cgtgctaacc ccagctttgg cacgaccggg ttcgccggag gtatcaactc tgccatcctg      900
cgctacgacg gtgcgcccgc cgtcgagccg accacgacgc agactgcctc cgtcatccca      960
ctggtggaga cgaacttgca cccgcttgtg cacatgcctg tgcctggtct gccaacgccc     1020
ggcggtgttg acaagccgct caacttcgcg ttcaacttta acggcaccaa ctccttcatc     1080
aacaatgcat cattcacgcc gccaacagtc cctgtgttgc tgcagatcct gagtggggca     1140
catacggctc aggaactcct gccgcccggg tccgtgtaca cgctcccggg ccactcctct     1200
atcgagatca ccatgcccgc gacctccttg gccccaggcg ctccgcaccc gttccacctg     1260
cacggccacg cgttcgcggt cgtgcgcagc gccggcagca ccgagtacaa ctacgacgat     1320
ccgatcttcc gcgacgtcgt cagcacaggc acgcccgccg cgggcgacaa cgtcaccatc     1380
cgcttccgga cggacaaccc cgggccgtgg ttcctccact gccacatcga cttccacctc     1440
aacgccggct cgcggtcgt catggcggag gacatccctg atgtccaggc ggtcaaccct     1500
gttccgcagg cgtggtccga cttgtgcccg atctacgatg cgctcgaccc cagcgaccag     1560
tag                                                                  1563

<210> SEQ ID NO 30
<211> LENGTH: 520
<212> TYPE: PRT
<213> ORGANISM: Lenzites gibbosa

<400> SEQUENCE: 30

Met Ser Arg Phe Gln Thr Leu Leu Ala Phe Val Val Thr Ser Leu Thr
1               5                   10                  15

Ala Ala Ala Tyr Ala Ala Ile Gly Pro Val Ala Asp Leu Thr Ile Thr
            20                  25                  30

Asn Ala Glu Val Ser Pro Asp Gly Phe Ala Arg Gln Ala Val Val Val
        35                  40                  45

Asn Gly Gly Thr Pro Gly Pro Leu Val Thr Gly Asn Met Gly Asp Arg
    50                  55                  60

Phe Gln Leu Asn Val Ile Asp Asn Leu Thr Asn His Thr Met Pro Lys
65                  70                  75                  80

Ser Thr Ser Ile His Trp His Gly Phe Phe Gln His Gly Thr Asn Trp
                85                  90                  95

Ala Asp Gly Pro Ala Phe Val Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Leu Tyr Asp Val
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Ser Thr Val Ser Ala Asp Leu Ser Val
        195                 200                 205
```

```
Ile Asn Val Thr Pro Gly Lys Arg Tyr Arg Phe Arg Leu Val Ser Leu
210                 215                 220

Ser Cys Asp Pro Asn His Thr Phe Ser Ile Asp Gly His Asn Met Thr
225                 230                 235                 240

Ile Ile Glu Val Asp Gly Ile Asn Ser Lys Pro Leu Thr Val Asp Ser
            245                 250                 255

Ile Gln Ile Phe Ala Ala Gln Arg Tyr Ser Phe Val Leu Asn Ala His
            260                 265                 270

Gln Thr Val Asn Asn Tyr Trp Ile Arg Ala Asn Pro Ser Phe Gly Thr
                275                 280                 285

Thr Gly Phe Ala Gly Gly Ile Asn Ser Ala Ile Leu Arg Tyr Asp Gly
290                 295                 300

Ala Pro Ala Val Glu Pro Thr Thr Thr Gln Thr Ala Ser Val Ile Pro
305                 310                 315                 320

Leu Val Glu Thr Asn Leu His Pro Leu Val His Met Pro Val Pro Gly
            325                 330                 335

Leu Pro Thr Pro Gly Gly Val Asp Lys Pro Leu Asn Phe Ala Phe Asn
            340                 345                 350

Phe Asn Gly Thr Asn Ser Phe Ile Asn Asn Ala Ser Phe Thr Pro Pro
                355                 360                 365

Thr Val Pro Val Leu Leu Gln Ile Leu Ser Gly Ala His Thr Ala Gln
370                 375                 380

Glu Leu Leu Pro Pro Gly Ser Val Tyr Thr Leu Pro Gly His Ser Ser
385                 390                 395                 400

Ile Glu Ile Thr Met Pro Ala Thr Ser Leu Ala Pro Gly Ala Pro His
            405                 410                 415

Pro Phe His Leu His Gly His Ala Phe Ala Val Val Arg Ser Ala Gly
            420                 425                 430

Ser Thr Glu Tyr Asn Tyr Asp Asp Pro Ile Phe Arg Asp Val Val Ser
                435                 440                 445

Thr Gly Thr Pro Ala Ala Gly Asp Asn Val Thr Ile Arg Phe Arg Thr
450                 455                 460

Asp Asn Pro Gly Pro Trp Phe Leu His Cys His Ile Asp Phe His Leu
465                 470                 475                 480

Asn Ala Gly Phe Ala Val Val Met Ala Glu Asp Ile Pro Asp Val Gln
            485                 490                 495

Ala Val Asn Pro Val Pro Gln Ala Trp Ser Asp Leu Cys Pro Ile Tyr
                500                 505                 510

Asp Ala Leu Asp Pro Ser Asp Gln
            515                 520

<210> SEQ ID NO 31
<211> LENGTH: 1563
<212> TYPE: DNA
<213> ORGANISM: Trametes versicolor

<400> SEQUENCE: 31
atgtcgaggt tcactctct tctcgctttc gtcgttgctt cccttgcggc tgtggcccac      60
gctggtatcg tcctgtcgc cgacctcacc atcaccaacg cagcagtcag ccccgacggg     120
ttttctcgcc aggccgtcgt cgtgaacggc ggcacccctg gccctctcat caccggtaac     180 atggggatc gcttccagct caatgtcatc gacaacctca cgaaccacac gatgctgaag     240
agcaccagta ttcactggca cggttttctt cagaagggca ccaactgggc cgacggtccc     300
gccttcatca ccagtgccc gatctcatct ggccactcgt tcctgcatga cttccaggct     360
```

```
cctgaccagg ctggcacctt ctggtatcac agtcacttgt ccacgcagta ctgtgatggt    420 ctgagggtc cgttcgttgt ttacgaaccg aacgacccgg ccgccgacct gtacgacgtc     480
gacaacgacg acacggtcat taccctcgcg gattggtacc acgtcgccgc gaagctgggc    540
cccgcactcc ctctcggcgc cgacgcatct cacaacatcg gtaagggacg ctccccagc    600 acgaccaccg cggatcctat ctgtattacg tgtatccccg ggcaaacgta tccgtttccg    660
cctggtgtcc ctgtcgtgcg accccaacca caccttcagc atcgatggtc acaacaagac    720
gatcatcgat tccgactcaa tcaacacggc gcctcccgtg gttcgaactc aattcgttct    780
gtcgcccagc gtttctcctt cgtgctcgag gccaaccagg ccgtcgacaa ctactggatt    840
cgcgccaacc caaacttcgg taacgtcggg tttaccggcg gcatcaactc ggctatcctc    900
cgctttgatg cgccgctgc catggagccc accaccacgc agaccacttc gaccgagccg     960
ctcaacgggg tcaacctgca cccgctggtt gccaccgctg tccctggctc tccgctgcg    1020 ggtggtgttg acctgccat caatatggcg ttcaacttca atggcaccaa cttcttcatc    1080
aacggcgcgt ctttcacgcc cccgaccgtg cctgtcctcc tccagatcat cagcggcgcg    1140
cagaacgcgc aggacctcct gcactccggc agcgtctact cgctccccc gaacgccgac    1200 attgagatct ccttccccgc caccgctgcc gccccggtg cgctccaccc cttccacttg     1260
cacgggcacg cgttcgcggt cgtccgcagc gccggcagca cggtctacaa ctacgacaac    1320
cccatcttcc gcgacgtcgt cagcacgggg aaccgtgcgg ccggtgacaa cgtcaccatc    1380
cgcttccgca ccgacaaccc cggcccgtgg ttcctccact gccacatcga cttccacctc    1440
gaggccggct tgccgtcgt gttcgcggaa gacatccccg acgtcgcgtc ggcgaacccc    1500
gtcccccagg cgtggtccga cctgtgcccg acctacgacg cgcgcgaccc gagcgaccag    1560
taa                                                                  1563
```

<210> SEQ ID NO 32
<211> LENGTH: 520
<212> TYPE: PRT
<213> ORGANISM: Trametes versicolor

<400> SEQUENCE: 32

```
Met Ser Arg Phe His Ser Leu Leu Ala Phe Val Ala Ser Leu Ala
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu His Asp Phe Gln Ala Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Glu Pro Asn Asp Pro Ala Ala Asp Leu Tyr Asp Val
```

|  |  |  |  | 145 |  |  |  | 150 |  |  |  | 155 |  |  |  | 160 |
|---|---|---|---|---|---|---|---|---|---|---|---|---|---|---|---|---|

Asp Asn Asp Asp Thr Val Ile Thr Leu Ala Asp Trp Tyr His Val Ala
                165                 170                 175

Ala Lys Leu Gly Pro Ala Leu Pro Leu Gly Ala Asp Ala Ser His Asn
            180                 185                 190

Ile Gly Lys Gly Arg Ser Pro Ser Thr Thr Ala Asp Pro Ile Cys
        195                 200                 205

Ile Thr Cys Ile Pro Gly Gln Thr Tyr Pro Phe Pro Pro Gly Val Pro
    210                 215                 220

Val Val Arg Pro Gln Pro His Leu Gln His Arg Trp Ser Gln Gln Asp
225                 230                 235                 240

Asp His Arg Phe Arg Leu Asn Gln His Gly Ala Ser Arg Gly Ser Asn
                245                 250                 255

Ser Ile Arg Ser Val Ala Gln Arg Phe Ser Phe Val Leu Glu Ala Asn
            260                 265                 270

Gln Ala Val Asp Asn Tyr Trp Ile Arg Ala Asn Pro Asn Phe Gly Asn
        275                 280                 285

Val Gly Phe Thr Gly Gly Ile Asn Ser Ala Ile Leu Arg Phe Asp Gly
    290                 295                 300

Ala Ala Ala Met Glu Pro Thr Thr Thr Gln Thr Thr Ser Thr Glu Pro
305                 310                 315                 320

Leu Asn Gly Val Asn Leu His Pro Leu Val Ala Thr Ala Val Pro Gly
                325                 330                 335

Ser Pro Ala Ala Gly Gly Val Asp Leu Ala Ile Asn Met Ala Phe Asn
            340                 345                 350

Phe Asn Gly Thr Asn Phe Phe Ile Asn Gly Ala Ser Phe Thr Pro Pro
        355                 360                 365

Thr Val Pro Val Leu Leu Gln Ile Ile Ser Gly Ala Gln Asn Ala Gln
    370                 375                 380

Asp Leu Leu His Ser Gly Ser Val Tyr Ser Leu Pro Pro Asn Ala Asp
385                 390                 395                 400

Ile Glu Ile Ser Phe Pro Ala Thr Ala Ala Pro Gly Ala Leu His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
        435                 440                 445

Thr Gly Asn Arg Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
            500                 505                 510

Asp Ala Arg Asp Pro Ser Asp Gln
        515                 520

<210> SEQ ID NO 33
<211> LENGTH: 1563
<212> TYPE: DNA
<213> ORGANISM: Trametes sp.

<400> SEQUENCE: 33

```
atgtcgaggt tccactccct tcttactttt atcgtcgcct ctttggcctc ctcggcccttt      60
gcttccattg ggcctgtcgc cgacatgacc atttccaacg cggaagtgag ccctgacggg     120
tttgctcgtc aggctgtcgt tgtcaacggt gtcaccccc gacccctggt aaagggggaac    180
atgggcgacc ggttccagct taatgttatc gacaatttga ccaaccacac catgttgaag     240
agtaccagta ttcactggca cggtcttttc cagcacggca ccaactgggc ggacggaccg     300
gctttcgtga accagtgccc tgtctccgcg ggacactcgt tcctgtacga tttccaggtt     360
ccgggccaag cgggaacttt ctggtaccac agccatctgt ccactcaata ctgtgatggt     420
ttgaggggcc ctctcgttgt ctacgaccct catgaccctc acaagagtcg ttacgacgtc     480
gacaacgatg acacggttat cacgttggcg gactggtacc acgtagcggc gaagcgtcgg     540
tccgcgtttc ccctgggtgc ggacgctact ctcatcaacg gtctcggtcg ctccccgacc     600
acccccagcg ctgacctcgc cgttatcaac gttacccagg caagcggta ccgcttccgt      660
ctggtgtcgc tgtcttgcga ccccaaccac acgttcagca ttgacggtca acatgacc      720
atcatcgagg ttgattcggt caactctcag ccctgtgg tggattcgat ccaaatcttc      780
gctgcccagc gttactcgtt tgtgcttaac gccaaccaag cggtcgacaa ctactgggtc     840
cgcgccaacc cctcgttcgg taacgtcggg ttctctggtg gtatcaactc ggctatcctg     900
cggtacgctg gtgcccctgc tattgagcct accacgaacc aaactacgtc ggtcatccct     960
ctgaatgagg tcaacctgca ccctctggcc cccacgccg tgcccgggaaa ggccgtcgcg   1020
ggtggtgttg acacaccgat caacatggct ttcagcttta acggcaccaa cttcttcatc    1080
aacggcgcga gcttcgtacc ccccactgtc cctgtccttc ttcagatctt gagtggcgcg    1140
cagtcggccc aggacctcct cccgtctggc agcgtctacg ttctccccag caacgcgtcc   1200
attgaaattt ccttccccgc taccgccgcc gctcccggtg ttccccaccc cttccacttg   1260
cacggtcaca cctttgctgt cgtccgcagc gctggcagca ctgagtacaa ctacgacaac    1320
cccatcttcc gcgacgtggt cagcacgggc acgcctgcgg ccggtgacaa cgtcaccatc    1380
cgcttccaga ccaacaaccc tggcccgtgg ttcctccact gccacatcga cttccatctc    1440
gaggccggtt tcgcagtcgt catggctgag gacactcccg acgtcaaggc ggtcaacccc    1500
gttccccagt cgtggtccga cctctgcccc atctacgatg cgcttgacgc cagcgaccag    1560
taa                                                                    1563
```

<210> SEQ ID NO 34
<211> LENGTH: 520
<212> TYPE: PRT
<213> ORGANISM: Trametes sp.

<400> SEQUENCE: 34

Met Ser Arg Phe His Ser Leu Leu Thr Phe Ile Val Ala Ser Leu Ala
1               5                   10                  15

Ser Ser Ala Leu Ala Ser Ile Gly Pro Val Ala Asp Met Thr Ile Ser
            20                  25                  30

Asn Ala Glu Val Ser Pro Asp Gly Phe Ala Arg Gln Ala Val Val Val
        35                  40                  45

Asn Gly Val Thr Pro Gly Pro Leu Val Lys Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Leu Phe Gln His Gly Thr Asn Trp
                85                  90                  95

```
Ala Asp Gly Pro Ala Phe Val Asn Gln Cys Pro Val Ser Ala Gly His
            100                 105                 110

Ser Phe Leu Tyr Asp Phe Gln Val Pro Gly Gln Ala Gly Thr Phe Trp
            115                 120                 125

Tyr His Ser His Leu Ser Thr Gln Tyr Cys Asp Gly Leu Arg Gly Pro
            130                 135                 140

Leu Val Val Tyr Asp Pro His Asp Pro His Lys Ser Arg Tyr Asp Val
145                 150                 155                 160

Asp Asn Asp Asp Thr Val Ile Thr Leu Ala Asp Trp Tyr His Val Ala
                165                 170                 175

Ala Lys Arg Arg Ser Ala Phe Pro Leu Gly Ala Asp Ala Thr Leu Ile
            180                 185                 190

Asn Gly Leu Gly Arg Ser Pro Thr Thr Pro Ser Ala Asp Leu Ala Val
            195                 200                 205

Ile Asn Val Thr Gln Gly Lys Arg Tyr Arg Phe Arg Leu Val Ser Leu
            210                 215                 220

Ser Cys Asp Pro Asn His Thr Phe Ser Ile Asp Gly His Asn Met Thr
225                 230                 235                 240

Ile Ile Glu Val Asp Ser Val Asn Ser Gln Pro Leu Val Val Asp Ser
                245                 250                 255

Ile Gln Ile Phe Ala Ala Gln Arg Tyr Ser Phe Val Leu Asn Ala Asn
            260                 265                 270

Gln Ala Val Asp Asn Tyr Trp Val Arg Ala Asn Pro Ser Phe Gly Asn
            275                 280                 285

Val Gly Phe Ser Gly Gly Ile Asn Ser Ala Ile Leu Arg Tyr Ala Gly
            290                 295                 300

Ala Pro Ala Ile Glu Pro Thr Thr Asn Gln Thr Thr Ser Val Ile Pro
305                 310                 315                 320

Leu Asn Glu Val Asn Leu His Pro Leu Ala Pro Thr Pro Val Pro Gly
            325                 330                 335

Lys Ala Val Ala Gly Gly Val Asp Thr Pro Ile Asn Met Ala Phe Ser
            340                 345                 350

Phe Asn Gly Thr Asn Phe Phe Ile Asn Gly Ala Ser Phe Val Pro Pro
            355                 360                 365

Thr Val Pro Val Leu Leu Gln Ile Leu Ser Gly Ala Gln Ser Ala Gln
            370                 375                 380

Asp Leu Leu Pro Ser Gly Ser Val Tyr Val Leu Pro Ser Asn Ala Ser
385                 390                 395                 400

Ile Glu Ile Ser Phe Pro Ala Thr Ala Ala Pro Gly Val Pro His
            405                 410                 415

Pro Phe His Leu His Gly His Thr Phe Ala Val Val Arg Ser Ala Gly
            420                 425                 430

Ser Thr Glu Tyr Asn Tyr Asp Asn Pro Ile Phe Arg Asp Val Val Ser
            435                 440                 445

Thr Gly Thr Pro Ala Ala Gly Asp Asn Val Thr Ile Arg Phe Gln Thr
            450                 455                 460

Asn Asn Pro Gly Pro Trp Phe Leu His Cys His Ile Asp Phe His Leu
465                 470                 475                 480

Glu Ala Gly Phe Ala Val Val Met Ala Glu Asp Thr Pro Asp Val Lys
                485                 490                 495

Ala Val Asn Pro Val Pro Gln Ser Trp Ser Asp Leu Cys Pro Ile Tyr
            500                 505                 510
```

Asp Ala Leu Asp Ala Ser Asp Gln
        515                 520

<210> SEQ ID NO 35
<211> LENGTH: 1557
<212> TYPE: DNA
<213> ORGANISM: Trametes sanguinea

<400> SEQUENCE: 35

| | | | | |
|---|---|---|---|---|
| atgtcgaggt | tccagtctct | cctctccttc | gtcctcgtct | cccttgccgc cgtggcgaac | 60 |
| gctgccatcg | gccctgtggc | agacctgacc | ctcaccaatg | ccgcggtcag ccctgatggc | 120 |
| ttcagccgtg | aggctgtcgt | ggtcaacggc | caaaccctg | ggcctctcat tgccggtcag | 180 |
| aaaggcgacc | gtttccagct | gaatgtcatt | gacaatctga | cgaaccacac catgttgaag | 240 |
| accaccagta | tccactggca | tggcttcttc | agcatggaa | caaactgggc cgacggccct | 300 |
| gcgttcatta | ccagtgtcc | cattgcatcc | ggtcattcct | tcttatacga ctttcaggtt | 360 |
| cctgaccaag | caggaacctt | ctggtaccac | agccatcttt | ccacgcagta ctgcgatggt | 420 |
| ttgaggggc | cattcgttgt | ctatgatccc | aacgatcccc | aggctagcct ctatgacata | 480 |
| gataatgatg | acacggtcat | cactttggcc | gattggtacc | acgtcgccgc taaactcggg | 540 |
| ccacgcttcc | cgcttggggc | cgacgcgacc | ctcattaatg | gactcggtcg tagccccggt | 600 |
| acgactgcgg | ctgacttggc | tgtgatcaaa | gtcacacagg | gcaagcggta ccgtttccgc | 660 |
| ttggtgtctc | tctcttgcga | cccgaatcat | accttcagca | ttgatggcca cactatgacc | 720 |
| atcatcgaga | cagactcagt | gaacactcag | cctctggagg | tcgactcgat ccagatcttc | 780 |
| gccgcacagc | ggtactcatt | cgtgctggat | gccaaccagc | cggtagacaa ctactggata | 840 |
| cgtgccaacc | cttccttcgg | gaacaccggg | ttcgccggcg | ggattaactc cgccatcctc | 900 |
| cggtatgacg | gcgcgcccga | ggtcgagcct | accacgaacc | agaccactcc tacgaagcct | 960 |
| ctgaacgagg | ttgacttgca | cccgctcacc | cctatggctg | tgcctggcct tcccgagccc | 1020 |
| ggaggtgttg | acaagcctct | gaacatggtc | ttcaacttta | acggcacgaa cttcttcatc | 1080 |
| aacggcgaat | ccttcgtccc | accctctgtt | ccggtcttgc | tccagattct gagcggtgct | 1140 |
| caggcagcac | aagatctggt | tccgtcaggc | agcgtttatg | tgcttcccag caactcgacc | 1200 |
| atcgaaattt | ccttccctgc | gactgccaat | gctcctggcg | caccgcaccc gttccacctg | 1260 |
| cacggtcata | ccttcgctgt | cgtccgaagc | gcaggaagca | gcgagtacaa ctacgataac | 1320 |
| ccgatcttcc | gcgacgttgt | cagcaccggt | acgcccggcg | ataatgtcac catccgcttc | 1380 |
| gagaccaaca | accccggccc | gtggttcctc | cattgccaca | ttgacttcca cctggatgcc | 1440 |
| ggctttgctg | tcgtcatggc | cgaggacact | ccggacacgg | cggcggccaa ccctgtcccc | 1500 |
| cagtcgtggt | cggatttgtg | cccgatctac | gacgcgcttg | accctagcga tctctga | 1557 |

<210> SEQ ID NO 36
<211> LENGTH: 518
<212> TYPE: PRT
<213> ORGANISM: Trametes sanguinea

<400> SEQUENCE: 36

Met Ser Arg Phe Gln Ser Leu Leu Ser Phe Val Leu Val Ser Leu Ala
1               5                   10                  15

Ala Val Ala Asn Ala Ala Ile Gly Pro Val Ala Asp Leu Thr Leu Thr
            20                  25                  30

Asn Ala Ala Val Ser Pro Asp Gly Phe Ser Arg Glu Ala Val Val Val
        35                  40                  45

```
Asn Gly Gln Thr Pro Gly Pro Leu Ile Ala Gly Gln Lys Gly Asp Arg
    50                  55                  60

Phe Gln Leu Asn Val Ile Asp Asn Leu Thr Asn His Thr Met Leu Lys
65                  70                  75                  80

Thr Thr Ser Ile His Trp His Gly Phe Phe Gln His Gly Thr Asn Trp
                85                  90                  95

Ala Asp Gly Pro Ala Phe Ile Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Gly Thr Thr Ala Ala Asp Leu Ala Val
        195                 200                 205

Ile Lys Val Thr Gln Gly Lys Arg Tyr Arg Phe Arg Leu Val Ser Leu
    210                 215                 220

Ser Cys Asp Pro Asn His Thr Phe Ser Ile Asp Gly His Thr Met Thr
225                 230                 235                 240

Ile Ile Glu Thr Asp Ser Val Asn Thr Gln Pro Leu Glu Val Asp Ser
                245                 250                 255

Ile Gln Ile Phe Ala Ala Gln Arg Tyr Ser Phe Val Leu Asp Ala Asn
            260                 265                 270

Gln Pro Val Asp Asn Tyr Trp Ile Arg Ala Asn Pro Ser Phe Gly Asn
        275                 280                 285

Thr Gly Phe Ala Gly Gly Ile Asn Ser Ala Ile Leu Arg Tyr Asp Gly
    290                 295                 300

Ala Pro Glu Val Glu Pro Thr Thr Asn Gln Thr Thr Pro Thr Lys Pro
305                 310                 315                 320

Leu Asn Glu Val Asp Leu His Pro Leu Thr Pro Met Ala Val Pro Gly
                325                 330                 335

Leu Pro Glu Pro Gly Gly Val Asp Lys Pro Leu Asn Met Val Phe Asn
            340                 345                 350

Phe Asn Gly Thr Asn Phe Phe Ile Asn Gly Glu Ser Phe Val Pro Pro
        355                 360                 365

Ser Val Pro Val Leu Leu Gln Ile Leu Ser Gly Ala Gln Ala Ala Gln
    370                 375                 380

Asp Leu Val Pro Ser Gly Ser Val Tyr Val Leu Pro Ser Asn Ser Thr
385                 390                 395                 400

Ile Glu Ile Ser Phe Pro Ala Thr Ala Asn Ala Pro Gly Ala Pro His
                405                 410                 415

Pro Phe His Leu His Gly His Thr Phe Ala Val Val Arg Ser Ala Gly
            420                 425                 430

Ser Ser Glu Tyr Asn Tyr Asp Asn Pro Ile Phe Arg Asp Val Val Ser
        435                 440                 445

Thr Gly Thr Pro Gly Asp Asn Val Thr Ile Arg Phe Glu Thr Asn Asn
    450                 455                 460
```

```
Pro Gly Pro Trp Phe Leu His Cys His Ile Asp Phe His Leu Asp Ala
465                 470                 475                 480

Gly Phe Ala Val Val Met Ala Glu Asp Thr Pro Asp Thr Ala Ala Ala
                485                 490                 495

Asn Pro Val Pro Gln Ser Trp Ser Asp Leu Cys Pro Ile Tyr Asp Ala
            500                 505                 510

Leu Asp Pro Ser Asp Leu
        515
```

<210> SEQ ID NO 37
<211> LENGTH: 1557
<212> TYPE: DNA
<213> ORGANISM: Pycnoporus coccineus

<400> SEQUENCE: 37

```
atgtcgaggt tccagtctct tctctccttc gtcctcgtct cccttgccgc cgtggcgaac      60
gctgccatcg ccctgtggc agacttgacc ctcaccaatg ccgcggtcag ccctgatggc     120
ttcagccgtg aggctgtcgt ggtcaacggc caaacccctg gcctctcat tgccggtcag     180
aaaggcgacc gtttccagct gaatgtcatt gacaatttga cgaaccacac catgttgaag    240
accaccagta tccactggca tggcttcttc agcatggca caaactgggc cgacggcccc     300
gcgttcatca accagtgtcc cattgcatcc ggtcattcct tcttatacga ctttcaggtt    360
cctgaccaag cagggacctt ctggtaccac agccatcttt ccacgcagta ctgcgatggt    420
ttgaggggc cgttcgttgt ctatgatccc aacgatcccc aggctagcct ctatgacata    480
gataatgatg acacggtcat tactttggtt gattggtacc acgtcgccgc taaactgggg    540
ccacgcttcc cgcttggggc cgacgcgacc ctcatcaatg gactcggtcg tagccccggt    600
acgactgcgg ctgacttggc tgtgatcaaa gtcacacagg gcaagcggta ccgtttccgc    660
ttggtgtctc tctcttgcga cccgaatcat accttcagca ttgatggcca caccatgacc    720
atcatcgagg cagactcagt gaacacacaa cctcttgagg ttgactcgat ccagatcttc    780
gccgcgcagc ggtactcctt cgtgctggat gccagccagc ccgtggacaa ctactggatc    840
cgcgccaatc cttccttcgg aaacaccggg ttcgccggtg ggattaactc cgccatcctc    900
cggtatgacg gcgcgcccga ggtcgagcct accacgaccc agaccacttc cacgaagcct    960
ctgaacgagg ttgacttgca cccgctcacc cctatggctg tgcctggccg tcccgagccc   1020
ggaggtgttg acacaccgct gaacatggtc ttcaacttta acggcacgaa tttcttcatc   1080
aacgaccact cctcgtccc accttctgtt ccggtcttgc tccagattct gagcggtgcc    1140
caggcagcac aagatctggc cccgtcaggt agcgtctatg tgcttcccag caactcgtcc   1200
atcgaaatct cctccctgc gactgccaat gctcctggcg cgccgcaccc gttccacctg   1260
cacggtcata ccttcgctgt cgtccgaagc gcaggaagca gcgagtacaa ctacgataac   1320
ccgatcttcc gcgacgttgt cagcaccggt acgcccggcg ataatgtcac catccgcttc   1380
cagaccaaca accctggccc gtggttcctc cattgccaca ttgacttcca cttggatgcc   1440
ggctttgctg tcgtcatggc cgaggacact ccggacacgg cggcggccaa ccctgtcccc   1500
cagtcgtggt cggatttgtg cccgatctac gacgcgcttg accctagcga tctctga      1557
```

<210> SEQ ID NO 38
<211> LENGTH: 518
<212> TYPE: PRT
<213> ORGANISM: Pycnoporus coccineus

<400> SEQUENCE: 38

```
Met Ser Arg Phe Gln Ser Leu Leu Ser Phe Val Leu Val Ser Leu Ala
1               5                   10                  15

Ala Val Ala Asn Ala Ala Ile Gly Pro Val Ala Asp Leu Thr Leu Thr
            20                  25                  30

Asn Ala Ala Val Ser Pro Asp Gly Phe Ser Arg Glu Ala Val Val Val
        35                  40                  45

Asn Gly Gln Thr Pro Gly Pro Leu Ile Ala Gly Gln Lys Gly Asp Arg
50                  55                  60

Phe Gln Leu Asn Val Ile Asp Asn Leu Thr Asn His Thr Met Leu Lys
65                  70                  75                  80

Thr Thr Ser Ile His Trp His Gly Phe Phe Gln His Gly Thr Asn Trp
                85                  90                  95

Ala Asp Gly Pro Ala Phe Ile Asn Gln Cys Pro Ile Ala Ser Gly His
                100                 105                 110

Ser Phe Leu Tyr Asp Phe Gln Val Pro Asp Gln Ala Gly Thr Phe Trp
            115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Val Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Gly Thr Thr Ala Ala Asp Leu Ala Val
        195                 200                 205

Ile Lys Val Thr Gln Gly Lys Arg Tyr Arg Phe Arg Leu Val Ser Leu
    210                 215                 220

Ser Cys Asp Pro Asn His Thr Phe Ser Ile Asp Gly His Thr Met Thr
225                 230                 235                 240

Ile Ile Glu Ala Asp Ser Val Asn Thr Gln Pro Leu Glu Val Asp Ser
                245                 250                 255

Ile Gln Ile Phe Ala Ala Gln Arg Tyr Ser Phe Val Leu Asp Ala Ser
            260                 265                 270

Gln Pro Val Asp Asn Tyr Trp Ile Arg Ala Asn Pro Ser Phe Gly Asn
        275                 280                 285

Thr Gly Phe Ala Gly Gly Ile Asn Ser Ala Ile Leu Arg Tyr Asp Gly
    290                 295                 300

Ala Pro Glu Val Glu Pro Thr Thr Gln Thr Thr Ser Thr Lys Pro
305                 310                 315                 320

Leu Asn Glu Val Asp Leu His Pro Leu Thr Pro Met Ala Val Pro Gly
            325                 330                 335

Arg Pro Glu Pro Gly Gly Val Asp Thr Pro Leu Asn Met Val Phe Asn
        340                 345                 350

Phe Asn Gly Thr Asn Phe Phe Ile Asn Asp His Ser Phe Val Pro Pro
    355                 360                 365

Ser Val Pro Val Leu Leu Gln Ile Leu Ser Gly Ala Gln Ala Ala Gln
370                 375                 380

Asp Leu Ala Pro Ser Gly Ser Val Tyr Val Leu Pro Ser Asn Ser Ser
385                 390                 395                 400

Ile Glu Ile Ser Phe Pro Ala Thr Ala Asn Ala Pro Gly Ala Pro His
                405                 410                 415
```

```
Pro Phe His Leu His Gly His Thr Phe Ala Val Val Arg Ser Ala Gly
            420                 425                 430

Ser Ser Glu Tyr Asn Tyr Asp Asn Pro Ile Phe Arg Asp Val Val Ser
        435                 440                 445

Thr Gly Thr Pro Gly Asp Asn Val Thr Ile Arg Phe Gln Thr Asn Asn
    450                 455                 460

Pro Gly Pro Trp Phe Leu His Cys His Ile Asp Phe His Leu Asp Ala
465                 470                 475                 480

Gly Phe Ala Val Val Met Ala Glu Asp Thr Pro Asp Thr Ala Ala Ala
                485                 490                 495

Asn Pro Val Pro Gln Ser Trp Ser Asp Leu Cys Pro Ile Tyr Asp Ala
            500                 505                 510

Leu Asp Pro Ser Asp Leu
        515

<210> SEQ ID NO 39
<211> LENGTH: 1548
<212> TYPE: DNA
<213> ORGANISM: Trametes hirsuta

<400> SEQUENCE: 39
```

| | | | | |
|---|---|---|---|---|
| atgtcgaggt tccagtcgtt gcttaccttc atcaccatct ccctcgtcgc ggttgctcat | | | | 60 |
| gcggcggttg ccctgtcgc cgacctcacc atcaccgacg cggcggtcag ccctgacggt | | | | 120 |
| ttctctcgcc aggctgttgt ggtgaacggc gtcacccctg accgctcgt tgcgggcaac | | | | 180 |
| attgggacc gcttccagct caacgtcatt gacaacttga cgaaccatac catgctcaag | | | | 240 |
| tcgaccagta tccactggca cggcttcttc cagcatggca cgaactgggc tgatggtccg | | | | 300 |
| gcgttcatta ccagtgccc tatctctcct gggcactcgt tcttgtacga cttccaggta | | | | 360 |
| cctgaccaag ccggtacctt ctggtaccac agtcacttgc gacccagta ctgtgatggt | | | | 420 |
| ttgaggggcc ccttcgttgt ctacgacccg aacgatcccc atgccagccg ctacgacgtc | | | | 480 |
| gacaacgacg acacggtcat tactctggcc gactggtatc ataccgctgc caagctaggt | | | | 540 |
| ccccggttcc cgggtgcggc cgacgccgtc aacatcaacg gcaagggccg cgccccagtg | | | | 600 |
| acactaccgg cgagctgttc ggtgatcaag gtcacgaagg gcaaacgcta ccgtttccgc | | | | 660 |
| ttggtctcgc tgtcatgcaa ccccaaccat accttcagca ttgatggtca aacttgact | | | | 720 |
| atcatcgagg tcgacagtgt caactcccag ccgctggagg ttgactccat ccagatcttc | | | | 780 |
| gcggcgcaac gttactcctt cgtgctggat gccaaccagg ccgtcgacaa ctactggatt | | | | 840 |
| cgggccaacc ccaacttcgg aaatgttgga ttcgacgggg gtatcaactc ggccatcctg | | | | 900 |
| cgctatgacg gcgcgcccgc tgtcgagccc accacgaacc agactacctc cgttaagccg | | | | 960 |
| ctgaacgagg tcgacctgca ccctcttgtc tctaccccgg tgccaggcgc gagcgacaag | | | | 1020 |
| gcgatcaaca tggctttcaa ctttaatggc tccaacttct tcatcaacgg cgccagtttc | | | | 1080 |
| gtcccgccca ccgtgcctgt cctcctccag attctcagtg gtgcccagac ggcgcaggac | | | | 1140 |
| ctcctgcccct ccggcagtgt atacgtcctt ccgtcgaacg cgtccattga gatctcgttc | | | | 1200 |
| cccgctaccg ccgccgcccc tggtgctccc catcccttcc acttgcacgg tcacactttc | | | | 1260 |
| gctgttgtgc gcagcgccgg cagcaccgtg tacaactacg acaatcccat cttccgtggc | | | | 1320 |
| gtcgtgagcc aggtaccccc tgcagcgcga gacaacgtca ccatccgctt cgacaccaac | | | | 1380 |
| caacccggcc cgtggttcct ccactgccac atcgactttc acttggaggg tggctttgcg | | | | 1440 |
| gtcgtcatgg ctgaggatac tccggacgta caggctgtca ccccgttcc tcaggcgtgg | | | | 1500 | tccgacctgt gcccgaccta cgacgcgctc gaccccaacg accagtaa 1548

<210> SEQ ID NO 40
<211> LENGTH: 515
<212> TYPE: PRT
<213> ORGANISM: Trametes hirsuta

<400> SEQUENCE: 40

```
Met Ser Arg Phe Gln Ser Leu Leu Thr Phe Ile Thr Ile Ser Leu Val
1               5                   10                  15

Ala Val Ala His Ala Ala Val Gly Pro Val Ala Asp Leu Thr Ile Thr
            20                  25                  30

Asp Ala Ala Val Ser Pro Asp Gly Phe Ser Arg Gln Ala Val Val Val
        35                  40                  45

Asn Gly Val Thr Pro Gly Pro Leu Val Ala Gly Asn Ile Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Phe Phe Gln His Gly Thr Asn Trp
                85                  90                  95

Ala Asp Gly Pro Ala Phe Ile Asn Gln Cys Pro Ile Ser Pro Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Arg Tyr Asp Val
145                 150                 155                 160

Asp Asn Asp Asp Thr Val Ile Thr Leu Ala Asp Trp Tyr His Thr Ala
                165                 170                 175

Ala Lys Leu Gly Pro Arg Phe Pro Gly Ala Ala Asp Ala Val Asn Ile
            180                 185                 190

Asn Gly Lys Gly Arg Ala Pro Val Thr Leu Pro Ala Ser Cys Ser Val
        195                 200                 205

Ile Lys Val Thr Lys Gly Lys Arg Tyr Arg Phe Arg Leu Val Ser Leu
    210                 215                 220

Ser Cys Asn Pro Asn His Thr Phe Ser Ile Asp Gly His Asn Leu Thr
225                 230                 235                 240

Ile Ile Glu Val Asp Ser Val Asn Ser Gln Pro Leu Glu Val Asp Ser
                245                 250                 255

Ile Gln Ile Phe Ala Ala Gln Arg Tyr Ser Phe Val Leu Asp Ala Asn
            260                 265                 270

Gln Ala Val Asp Asn Tyr Trp Ile Arg Ala Asn Pro Asn Phe Gly Asn
        275                 280                 285

Val Gly Phe Asp Gly Gly Ile Asn Ser Ala Ile Leu Arg Tyr Asp Gly
    290                 295                 300

Ala Pro Ala Val Glu Pro Thr Thr Asn Gln Thr Ser Val Lys Pro
305                 310                 315                 320

Leu Asn Glu Val Asp Leu His Pro Leu Val Ser Thr Val Pro Gly
                325                 330                 335

Ala Ser Asp Lys Ala Ile Asn Met Ala Phe Asn Phe Asn Gly Ser Asn
            340                 345                 350

Phe Phe Ile Asn Gly Ala Ser Phe Val Pro Pro Thr Val Pro Val Leu
        355                 360                 365
```

```
Leu Gln Ile Leu Ser Gly Ala Gln Thr Ala Gln Asp Leu Leu Pro Ser
    370                 375                 380

Gly Ser Val Tyr Val Leu Pro Ser Asn Ala Ser Ile Glu Ile Ser Phe
385                 390                 395                 400

Pro Ala Thr Ala Ala Pro Gly Ala Pro His Pro Phe His Leu His
                405                 410                 415

Gly His Thr Phe Ala Val Val Arg Ser Ala Gly Ser Thr Val Tyr Asn
            420                 425                 430

Tyr Asp Asn Pro Ile Phe Arg Gly Val Val Ser Pro Gly Thr Pro Ala
                435                 440                 445

Ala Arg Asp Asn Val Thr Ile Arg Phe Asp Thr Asn Gln Pro Gly Pro
450                 455                 460

Trp Phe Leu His Cys His Ile Asp Phe His Leu Glu Gly Gly Phe Ala
465                 470                 475                 480

Val Val Met Ala Glu Asp Thr Pro Asp Val Gln Ala Val Asn Pro Val
                485                 490                 495

Pro Gln Ala Trp Ser Asp Leu Cys Pro Thr Tyr Asp Ala Leu Asp Pro
                500                 505                 510

Asn Asp Gln
        515

<210> SEQ ID NO 41
<211> LENGTH: 1563
<212> TYPE: DNA
<213> ORGANISM: Trametes sp.

<400> SEQUENCE: 41
atgtcgaggt tccactccct tcttactttt atcgtcgcct ctttggcctc ctcggccctt      60
gcttccattg ggcctgtcgc cgacatgacc atttccaacg cggaagtgag ccctgacggg     120
tttgctcgtc aggctgtcgt tgtcaacggt gtcaccccg gaccctggt aaagggaac       180 atgggcgacc ggttccagct taatgttatc gacaatttga ccaaccacac catgttgaag    240
agtaccagta ttcactggca cggtctttc cagcacggca ccaactgggc ggacggaccg     300
gctttcgtga accagtgccc tgtctccgcg ggacactcgt tcctgtacga tttccaggtt    360
ccgggccaag cgggaacttt ctggtaccac agccatctgt ccactcaata ctgtgatggt    420
ttgaggggcc ctctcgttgt ctacgaccct catgaccctc acaagagtcg ttacgacgtc    480
gacaacgatg acacggttat cacgttggcg gactggtacc acgtagcggc gaagcgtcgg    540
tccgcgtttc cgctgggtgc ggacgctact ctcatcaacg tctcggtcg ctccccgacc     600 accccagcg ctgacctcgc cgttatcaac gttacccagg gcaagcggta ccgcttccgt     660
ctggtgtcgc tgtcttgcga ccccaaccac acgttcagca ttgacggtca acatgacc     720 atcatcgagg ttgattcggt caactctcag ccctggtgg tggattcgat ccaaatcttc    780
gctgcccagc gttactcgtt tgtgcttaac gccaaccaag cggtcgacaa ctactgggtc    840
cgcgccaacc cctcgttcgg taacgtcggg ttctctggtg gtatcaactc ggctatcctg    900
cggtacgctg gtgcccctgc tattgagcct accacgaacc aaactacgtc ggtcatccct    960
ctgaatgagg tcaacctgca ccctctggcc cccacgcccg tgcccggaaa ggccgtcgcg   1020
ggtggtgttg acacaccgat caacatggct ttcagctta acggcaccaa cttcttcatc    1080
aacggcgcga gcttcgtacc ccccactgtc cctgtcctc ttcagatctt gagtggcgcg   1140
cagtcggccc aggacctcct cccgtctggc agcgtctacg ttctccccag caacgcgtcc   1200
attgaaattt ccttccccgc taccgccgcc gctcccggtg ttccccaccc cttccacttg   1260
```

```
cacggtcaca cctttgctgt cgtccgcagc gctggcagca ctgagtacaa ctacgacaac    1320
cccatcttcc gcgacgtggt cagcacgggc acgcctgcgg ccggtgacaa cgtcaccatc    1380
cgcttccaga ccaacaaccc tggcccgtgg ttcctccact gccacatcga cttccatctc    1440
gaggccgggt cgcagttgt catggctgag gacactcccg acgtcaaggc ggtcaacccc     1500
gttccccagt cgtggtccga cctctgcccc atctacgatg cgcttgacgc cagcgacctc    1560
taa                                                                  1563
```

<210> SEQ ID NO 42
<211> LENGTH: 520
<212> TYPE: PRT
<213> ORGANISM: Trametes sp.

<400> SEQUENCE: 42

```
Met Ser Arg Phe His Ser Leu Leu Thr Phe Ile Val Ala Ser Leu Ala
1               5                   10                  15

Ser Ser Ala Leu Ala Ser Ile Gly Pro Val Ala Asp Met Thr Ile Ser
            20                  25                  30

Asn Ala Glu Val Ser Pro Asp Gly Phe Ala Arg Gln Ala Val Val
        35                  40                  45

Asn Gly Val Thr Pro Gly Pro Leu Val Lys Gly Asn Met Gly Asp Arg
    50                  55                  60

Phe Gln Leu Asn Val Ile Asp Asn Leu Thr Asn His Thr Met Leu Lys
65                  70                  75                  80

Ser Thr Ser Ile His Trp His Gly Leu Phe Gln His Gly Thr Asn Trp
                85                  90                  95

Ala Asp Gly Pro Ala Phe Val Asn Gln Cys Pro Val Ser Ala Gly His
            100                 105                 110

Ser Phe Leu Tyr Asp Phe Gln Val Pro Gly Gln Ala Gly Thr Phe Trp
        115                 120                 125

Tyr His Ser His Leu Ser Thr Gln Tyr Cys Asp Gly Leu Arg Gly Pro
    130                 135                 140

Leu Val Val Tyr Asp Pro His Asp Pro His Lys Ser Arg Tyr Asp Val
145                 150                 155                 160

Asp Asn Asp Asp Thr Val Ile Thr Leu Ala Asp Trp Tyr His Val Ala
                165                 170                 175

Ala Lys Arg Arg Ser Ala Phe Pro Leu Gly Ala Asp Ala Thr Leu Ile
            180                 185                 190

Asn Gly Leu Gly Arg Ser Pro Thr Thr Pro Ser Ala Asp Leu Ala Val
        195                 200                 205

Ile Asn Val Thr Gln Gly Lys Arg Tyr Arg Phe Arg Leu Val Ser Leu
    210                 215                 220

Ser Cys Asp Pro Asn His Thr Phe Ser Ile Asp Gly His Asn Met Thr
225                 230                 235                 240

Ile Ile Glu Val Asp Ser Val Asn Ser Gln Pro Leu Val Asp Ser
                245                 250                 255

Ile Gln Ile Phe Ala Ala Gln Arg Tyr Ser Phe Val Leu Asn Ala Asn
            260                 265                 270

Gln Ala Val Asp Asn Tyr Trp Val Arg Ala Asn Pro Ser Phe Gly Asn
        275                 280                 285

Val Gly Phe Ser Gly Gly Ile Asn Ser Ala Ile Leu Arg Tyr Ala Gly
    290                 295                 300

Ala Pro Ala Ile Glu Pro Thr Thr Asn Gln Thr Thr Ser Val Ile Pro
```

```
                305                 310                 315                 320
Leu Asn Glu Val Asn Leu His Pro Leu Ala Pro Thr Pro Val Pro Gly
                    325                 330                 335

Lys Ala Val Ala Gly Val Asp Thr Pro Ile Asn Met Ala Phe Ser
                340                 345                 350

Phe Asn Gly Thr Asn Phe Phe Ile Asn Gly Ala Ser Phe Val Pro Pro
                    355                 360                 365

Thr Val Pro Val Leu Leu Gln Ile Leu Ser Gly Ala Gln Ser Ala Gln
                370                 375                 380

Asp Leu Leu Pro Ser Gly Ser Val Tyr Val Leu Pro Ser Asn Ala Ser
385                 390                 395                 400

Ile Glu Ile Ser Phe Pro Ala Thr Ala Ala Pro Gly Val Pro His
                        405                 410                 415

Pro Phe His Leu His Gly His Thr Phe Ala Val Val Arg Ser Ala Gly
                    420                 425                 430

Ser Thr Glu Tyr Asn Tyr Asp Asn Pro Ile Phe Arg Asp Val Val Ser
                    435                 440                 445

Thr Gly Thr Pro Ala Ala Gly Asp Asn Val Thr Ile Arg Phe Gln Thr
                450                 455                 460

Asn Asn Pro Gly Pro Trp Phe Leu His Cys His Ile Asp Phe His Leu
465                 470                 475                 480

Glu Ala Gly Phe Ala Val Val Met Ala Glu Asp Thr Pro Asp Val Lys
                    485                 490                 495

Ala Val Asn Pro Val Pro Gln Ser Trp Ser Asp Leu Cys Pro Ile Tyr
                500                 505                 510

Asp Ala Leu Asp Ala Ser Asp Leu
                515                 520

<210> SEQ ID NO 43
<211> LENGTH: 1557
<212> TYPE: DNA
<213> ORGANISM: Pycnoporus coccineus

<400> SEQUENCE: 43
atgtcgaggt tccagtctct tctctccttc gtcctcgtct cccttgccgc cgtggcgaac      60
gctgccatcg gccctatggc agacttgacc ctcaccaatg ccgcggtcag ccctgatggc     120
ttcagccgtg aggctgtcgt ggtcaacggc caaaccctg gcctctcat tgccggtcag      180 aaaggcgacc gtttccagct gaatgtcatt gacaatttga cgaaccacac catgttgaag     240
accaccagta tccactggca tggcttcttc cagcatggca aaactgggc cgacggcccc      300 gcgttcatca accagtgtcc cattgcatcc ggtcattcct tcttatacga ctttcaggtc     360
cctgaccaag cagggacctt ctggtaccac agccatcttt ccacgcagta ctgcgatggt     420 ttgaggggc cgttcgttgt ctatgatccc aacgatcccc aggctagcct ctatgacata     480
gataatgatg acacggtcat tactttggtt gattggtacc acgtcgccgc taaactgggg     540
ccacgcttcc cgcttggggc ggacgcgacc ctcatcaatg gactcggtcg tagccccggt     600
acgactgcgg ctgacttggc tgtgatcaaa gtcacacagg caagcggta ccgtttccgc      660 ttggtgtctc tctcttgcga cccgaatcat accttcagca ttgatggcca caccatgacc     720
atcatcgagg cagactcagt gaacacacaa cctcttgagg ttgactcgat ccagatcttc     780
gccgcgcagc ggtactcctt cgtgctggat gccagccagc ccgtggacaa ctactggatc     840
cgcgccaatc cttccttcgg aaacaccggg ttcgccggtg ggattaactc cgccatcctc     900
```

```
cggtatgacg gcgcgcccga ggtcgagcct accacgaccc agaccacttc cacgaagcct      960
ctgaacgagg ttgacttgca cccgctcacc cctatggctg tgcctggccg tcccgagccc     1020
ggaggtgttg acacaccgct gaacatggtc ttcaacttta acggcacgaa tttcttcatc     1080
aacgaccact ccttcgtccc accttctgtt ccggtcttgc tccagattct gagcggtgcc     1140
caggcagcac aagatctggc cccgtcaggt agcgtctatg tgcttcccag caactcgtcc     1200
atcgaaatct ccttccctgc gactgccaat gctcctggcg cgccgcaccc gttccacctg     1260
cacggtcata ccttcgctgt cgtccgaagc gcaggaagca gcgagtacaa ctacgataac     1320
ccgatcttcc gcgacgttgt cagcaccggt acgcccggcg ataatgtcac catccgcttc     1380
cagaccaaca accctggccc gtggttcctc cattgccaca ttgacttcca cttggatgcc     1440
ggctttgctg tcgtcatggc cgaggacact ccggacacgg cagcggccaa ccctgtcccc     1500
cagtcgtggt cggatttgtg cccgatctac gacgcgcttg accctagcga tctctga       1557
```

<210> SEQ ID NO 44
<211> LENGTH: 518
<212> TYPE: PRT
<213> ORGANISM: Pycnoporus coccineus

<400> SEQUENCE: 44

```
Met Ser Arg Phe Gln Ser Leu Leu Ser Phe Val Leu Val Ser Leu Ala
1               5                   10                  15

Ala Val Ala Asn Ala Ala Ile Gly Pro Met Ala Asp Leu Thr Leu Thr
            20                  25                  30

Asn Ala Ala Val Ser Pro Asp Gly Phe Ser Arg Glu Ala Val Val Val
        35                  40                  45

Asn Gly Gln Thr Pro Gly Pro Leu Ile Ala Gly Gln Lys Gly Asp Arg
    50                  55                  60

Phe Gln Leu Asn Val Ile Asp Asn Leu Thr Asn His Thr Met Leu Lys
65                  70                  75                  80

Thr Thr Ser Ile His Trp His Gly Phe Gln His Gly Thr Asn Trp
                85                  90                  95

Ala Asp Gly Pro Ala Phe Ile Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Val Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Gly Thr Thr Ala Ala Asp Leu Ala Val
        195                 200                 205

Ile Lys Val Thr Gln Gly Lys Arg Tyr Arg Phe Arg Leu Val Ser Leu
    210                 215                 220

Ser Cys Asp Pro Asn His Thr Phe Ser Ile Asp Gly His Thr Met Thr
225                 230                 235                 240

Ile Ile Glu Ala Asp Ser Val Asn Thr Gln Pro Leu Glu Val Asp Ser
                245                 250                 255

Ile Gln Ile Phe Ala Ala Gln Arg Tyr Ser Phe Val Leu Asp Ala Ser
```

```
                        260                 265                 270
        Gln Pro Val Asp Asn Tyr Trp Ile Arg Ala Asn Pro Ser Phe Gly Asn
                    275                 280                 285

Thr Gly Phe Ala Gly Gly Ile Asn Ser Ala Ile Leu Arg Tyr Asp Gly
                    290                 295                 300

Ala Pro Glu Val Glu Pro Thr Thr Thr Gln Thr Thr Ser Thr Lys Pro
        305                 310                 315                 320

Leu Asn Glu Val Asp Leu His Pro Leu Thr Pro Met Ala Val Pro Gly
                        325                 330                 335

Arg Pro Glu Pro Gly Gly Val Asp Thr Pro Leu Asn Met Val Phe Asn
                    340                 345                 350

Phe Asn Gly Thr Asn Phe Phe Ile Asn Asp His Ser Phe Val Pro Pro
                    355                 360                 365

Ser Val Pro Val Leu Leu Gln Ile Leu Ser Gly Ala Gln Ala Ala Gln
                    370                 375                 380

Asp Leu Ala Pro Ser Gly Ser Val Tyr Val Leu Pro Ser Asn Ser Ser
        385                 390                 395                 400

Ile Glu Ile Ser Phe Pro Ala Thr Ala Asn Ala Pro Gly Ala Pro His
                        405                 410                 415

Pro Phe His Leu His Gly His Thr Phe Ala Val Val Arg Ser Ala Gly
                    420                 425                 430

Ser Ser Glu Tyr Asn Tyr Asp Asn Pro Ile Phe Arg Asp Val Val Ser
                    435                 440                 445

Thr Gly Thr Pro Gly Asp Asn Val Thr Ile Arg Phe Gln Thr Asn Asn
                    450                 455                 460

Pro Gly Pro Trp Phe Leu His Cys His Ile Asp Phe His Leu Asp Ala
        465                 470                 475                 480

Gly Phe Ala Val Val Met Ala Glu Asp Thr Pro Asp Thr Ala Ala Ala
                        485                 490                 495

Asn Pro Val Pro Gln Ser Trp Ser Asp Leu Cys Pro Ile Tyr Asp Ala
                    500                 505                 510

Leu Asp Pro Ser Asp Leu
                515

<210> SEQ ID NO 45
<211> LENGTH: 1557
<212> TYPE: DNA
<213> ORGANISM: Cinnabarina coccineus

<400> SEQUENCE: 45
atgtcgagat ccaatctctc cctctccttt gtcctcgtct ctcttgccgc tgtgccaac      60 gctgccatcg gtcctgtggc agacttgacc ctcaccaacg ccgcggtcag ccccgatggc    120
ttcagccgcg aggctgttgt ggtcaatggg atcacccccg ctcctctcat tgctggacaa    180
aaaggcgacc gtttccagct gaatgtcatc gacaatctga cgaaccatac catgctgaag    240
actactagta tccactggca tggcttcttc agcacggta cgaattgggc cgacggtgtg     300
tcgttcgtca accagtgccc catcgcttcg ggccattcgt tcttgtacga cttccaggtt    360
cccgaccaag cagggacgtt ctggtatcac agccatcttt ccacccagta ctgtgatggt    420 ttgcggggc ccttcgtcgt ctacgacccc aatgatcctc aggctagcct gtatgacatt     480
gacaacgatg acactgtcat tacattggcc gactggtacc acgtcgccgc taagcttggc    540
ccacgcttcc cgcttggcgc ggatgcaact ctcatcaacg gctgggtcg aagcccggt     600 actaccactg ctgatctggc agttatcaag gtcacgcagg gcaagcggta ccgattccgt    660
```

```
ttggtgtccc tttcttgcga cccgaaccac acctttagca tcgatggcca cactatgact    720
gtgatcgagg cggactcagt gaatactcag cccctcgaag ttgactcgat tcagatcttc    780
gccgcccagc ggtactcctt cgtgctggat gctagccagc ccgtcgacaa ctactggatc    840
cgtgctaacc ctgctttcgg aaacgtcgga ttcgccggtg aatcaactc tgctattctg     900
cggtatgacg gcgcacccga ggtggagcct accacgaccc aaaccacttc gacgaagcct    960
ctcaacgagg ctgacttgca tcccctcacc cctatgcctg tgcctggtcg tcccgaggcc   1020
ggtggtgttg acaagcctct gaacatggtc ttcaacttca acggcaccaa cttcttcatc   1080
aacaatcact cctttgtccc accctccgtc ccggttctgc tccagattct cagcggtgct   1140
caggccgcgc aggacctcgt tccggacggc agcgtctacg ttctcccgag caactcgtct   1200
attgagatct ccttccccgc aactgccaat gctcctggca cccctcaccc cttccacctg   1260
cacggtcaca ccttcgctgt cgtccgaagc gccggaagca gcgagtacaa ctacgataac   1320
ccgatcttcc gcgacgtcgt gagcaccggc cagcccggag acaacgtcac catccggttc   1380
cagaccaaca accccggccc ctggttcctc cactgccaca tcgacttcca cttggaagcc   1440
ggttttgctg tcgtcctggc cgaggacact ccagacacgg cggcggtcaa ccctgtcccc   1500
cagtcgtggt cggatctgtg ccccatctac gacgcacttg accccagcga tctctga      1557
```

<210> SEQ ID NO 46
<211> LENGTH: 518
<212> TYPE: PRT
<213> ORGANISM: Cinnabarina coccineus

<400> SEQUENCE: 46

| Met | Ser | Arg | Phe | Gln | Ser | Leu | Leu | Ser | Phe | Val | Leu | Val | Ser | Leu | Ala |
|---|---|---|---|---|---|---|---|---|---|---|---|---|---|---|---|
| 1 | | | | 5 | | | | | 10 | | | | | 15 | |

Ala Val Ala Asn Ala Ala Ile Gly Pro Val Ala Asp Leu Thr Leu Thr
            20                  25                  30

Asn Ala Ala Val Ser Pro Asp Gly Phe Ser Arg Glu Ala Val Val Val
        35                  40                  45

Asn Gly Ile Thr Pro Ala Pro Leu Ile Ala Gly Gln Lys Gly Asp Arg
    50                  55                  60

Phe Gln Leu Asn Val Ile Asp Asn Leu Thr Asn His Thr Met Leu Lys
65                  70                  75                  80

Thr Thr Ser Ile His Trp His Gly Phe Phe Gln His Gly Thr Asn Trp
                85                  90                  95

Ala Asp Gly Val Ser Phe Val Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Leu Gly Arg Ser Pro Gly Thr Thr Thr Ala Asp Leu Ala Val
        195                 200                 205

Ile Lys Val Thr Gln Gly Lys Arg Tyr Arg Phe Arg Leu Val Ser Leu

```
                    210                 215                 220
Ser Cys Asp Pro Asn His Thr Phe Ser Ile Asp Gly His Thr Met Thr
225                 230                 235                 240

Val Ile Glu Ala Asp Ser Val Asn Thr Gln Pro Leu Glu Val Asp Ser
                    245                 250                 255

Ile Gln Ile Phe Ala Ala Gln Arg Tyr Ser Phe Val Leu Asp Ala Ser
                260                 265                 270

Gln Pro Val Asp Asn Tyr Trp Ile Arg Ala Asn Pro Ala Phe Gly Asn
            275                 280                 285

Val Gly Phe Ala Gly Gly Ile Asn Ser Ala Ile Leu Arg Tyr Asp Gly
290                 295                 300

Ala Pro Glu Val Glu Pro Thr Thr Thr Gln Thr Thr Ser Thr Lys Pro
305                 310                 315                 320

Leu Asn Glu Ala Asp Leu His Pro Leu Thr Pro Met Pro Val Pro Gly
                    325                 330                 335

Arg Pro Glu Ala Gly Gly Val Asp Lys Pro Leu Asn Met Val Phe Asn
                340                 345                 350

Phe Asn Gly Thr Asn Phe Phe Ile Asn Asn His Ser Phe Val Pro Pro
            355                 360                 365

Ser Val Pro Val Leu Leu Gln Ile Leu Ser Gly Ala Gln Ala Ala Gln
370                 375                 380

Asp Leu Val Pro Asp Gly Ser Val Tyr Val Leu Pro Ser Asn Ser Ser
385                 390                 395                 400

Ile Glu Ile Ser Phe Pro Ala Thr Ala Asn Ala Pro Gly Thr Pro His
                    405                 410                 415

Pro Phe His Leu His Gly His Thr Phe Ala Val Val Arg Ser Ala Gly
                420                 425                 430

Ser Ser Glu Tyr Asn Tyr Asp Asn Pro Ile Phe Arg Asp Val Val Ser
            435                 440                 445

Thr Gly Gln Pro Gly Asp Asn Val Thr Ile Arg Phe Gln Thr Asn Asn
450                 455                 460

Pro Gly Pro Trp Phe Leu His Cys His Ile Asp Phe His Leu Glu Ala
465                 470                 475                 480

Gly Phe Ala Val Val Leu Ala Glu Asp Thr Pro Asp Thr Ala Ala Val
                    485                 490                 495

Asn Pro Val Pro Gln Ser Trp Ser Asp Leu Cys Pro Ile Tyr Asp Ala
                500                 505                 510

Leu Asp Pro Ser Asp Leu
            515

<210> SEQ ID NO 47
<211> LENGTH: 1557
<212> TYPE: DNA
<213> ORGANISM: Trametes cinnabarina

<400> SEQUENCE: 47
atgtccagat ccaatctctc cctctccttt gtcctcgtct ctcttgccgc tgtggccaac     60
gctgccatcg gtcctgtggc agacttgacc ctcaccaacg ccgcggtcag ccccgatggc    120
ttcagccgcg aggctgttgt ggtcaatggg atcacccccg ctcctctcat tgctggacaa    180
aaaggcgacc gtttccagct gaatgtcatc gacaatctga cgaaccatac catgctgaag    240
actactagta tccactggca tggcttcttc agcacggta  cgaattgggc cgacggtgtg    300
tcgttcgtca accagtgccc catcgcttcg ggccattcgt tcttgtacga cttccaggtt    360
```

```
cccgaccaag cagggacgtt ctggtatcac agccatcttt ccacccagta ctgtgatggt    420
ttgcggggc ccttcgtcgt ctacgacccc aatgatcctc aggctagcct gtatgacatt    480
gacaacgatg acactgtcat tacattggcc gactggtacc acgtcgccgc taagcttggc    540
ccacgcttcc cgcttggcgc ggatgcaact ctcatcaacg ggctgggtcg aagcccggt     600
actaccactg ctgatctggc agtcatcaag gtcacgcagg gcaagcggta ccgattccgt    660
ttggtgtccc tttcttgcga cccgaaccac acctttagca tcgatggcca cactatgact    720
gtgatcgagg cggactcagt gaatactcag cccctcgaag ttgactcgat tcagatcttc    780
gccgcccagc ggtactcctt cgtgctggat gctagccagc ccgtcgacaa ctactggatc    840
cgtgctaacc ctgctttcgg aaacgtcgga ttcgccggtg aatcaactc tgctattctg     900
cggtatgacg cgcacccga ggtggagcct accacgaccc aaaccacttc gacgaagcct     960
ctcaacgagg ctgacttgca tccctcacc cctatgcctg tgcctggtcg tcccgaggcc    1020
ggtggtgttg acaagcctct gagcatggtc ttcaacttca cggcaccaa cttcttcatc    1080
aacaatcact cctttgtccc accctccgtc ccggttctgc tccagattct cagcggtgct    1140
caggccgcgc aggacctcgt tccggacggc agcgtctacg ttctcccgag caactcgtct    1200
attgagatct ccttccccgc aactgccaat gctcctggca cccctcaccc cttccacctg    1260
cacggtcaca ccttcgctgt cgtccgaagc gccggaagca gcgagtacaa ctacgataac    1320
ccgatcttcc gcgacgtcgt gagcaccggc cagcccggag acaacgtcac catccggttc    1380
cagaccaaca accccggccc ctggttcctc cactgccaca tcgacttcca cttggaagcc    1440
cagttttgctg tcgtcctggc cgaggacact ccagacacgg cggcggtcaa ccctgtcccc    1500
cagtcgtggt cggatctgtg ccccatctac gacgcacttg accccagcga tctctga       1557
```

<210> SEQ ID NO 48
<211> LENGTH: 518
<212> TYPE: PRT
<213> ORGANISM: Trametes cinnabarina

<400> SEQUENCE: 48

```
Met Ser Arg Phe Gln Ser Leu Leu Ser Phe Val Leu Val Ser Leu Ala
1               5                   10                  15

Ala Val Ala Asn Ala Ala Ile Gly Pro Val Ala Asp Leu Thr Leu Thr
            20                  25                  30

Asn Ala Ala Val Ser Pro Asp Gly Phe Ser Arg Glu Ala Val Val Val
        35                  40                  45

Asn Gly Ile Thr Pro Ala Pro Leu Ile Ala Gly Gln Lys Gly Asp Arg
    50                  55                  60

Phe Gln Leu Asn Val Ile Asp Asn Leu Thr Asn His Thr Met Leu Lys
65                  70                  75                  80

Thr Thr Ser Ile His Trp His Gly Phe Phe Gln His Gly Thr Asn Trp
                85                  90                  95

Ala Asp Gly Val Ser Phe Val Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Ala Asp Trp Tyr His Val Ala
```

```
                        165                 170                 175
Ala Lys Leu Gly Pro Arg Phe Pro Leu Gly Asp Ala Thr Leu Ile
            180                 185                 190

Asn Gly Leu Gly Arg Ser Pro Gly Thr Thr Ala Asp Leu Ala Val
            195                 200                 205

Ile Lys Val Thr Gln Gly Lys Arg Tyr Arg Phe Arg Leu Val Ser Leu
            210                 215                 220

Ser Cys Asp Pro Asn His Thr Phe Ser Ile Asp Gly His Thr Met Thr
225                 230                 235                 240

Val Ile Glu Ala Asp Ser Val Asn Thr Gln Pro Leu Glu Val Asp Ser
                245                 250                 255

Ile Gln Ile Phe Ala Ala Gln Arg Tyr Ser Phe Val Leu Asp Ala Ser
                260                 265                 270

Gln Pro Val Asp Asn Tyr Trp Ile Arg Ala Asn Pro Ala Phe Gly Asn
                275                 280                 285

Val Gly Phe Ala Gly Gly Ile Asn Ser Ala Ile Leu Arg Tyr Asp Gly
            290                 295                 300

Ala Pro Glu Val Glu Pro Thr Thr Gln Thr Thr Ser Thr Lys Pro
305                 310                 315                 320

Leu Asn Glu Ala Asp Leu His Pro Leu Thr Pro Met Pro Val Pro Gly
                325                 330                 335

Arg Pro Glu Ala Gly Gly Val Asp Lys Pro Leu Ser Met Val Phe Asn
                340                 345                 350

Phe Asn Gly Thr Asn Phe Phe Ile Asn Asn His Ser Phe Val Pro Pro
            355                 360                 365

Ser Val Pro Val Leu Leu Gln Ile Leu Ser Gly Ala Gln Ala Ala Gln
370                 375                 380

Asp Leu Val Pro Asp Gly Ser Val Tyr Val Leu Pro Ser Asn Ser Ser
385                 390                 395                 400

Ile Glu Ile Ser Phe Pro Ala Thr Ala Asn Ala Pro Gly Thr Pro His
                405                 410                 415

Pro Phe His Leu His Gly His Thr Phe Ala Val Val Arg Ser Ala Gly
                420                 425                 430

Ser Ser Glu Tyr Asn Tyr Asp Asn Pro Ile Phe Arg Asp Val Val Ser
            435                 440                 445

Thr Gly Gln Pro Gly Asp Asn Val Thr Ile Arg Phe Gln Thr Asn Asn
            450                 455                 460

Pro Gly Pro Trp Phe Leu His Cys His Ile Asp Phe His Leu Glu Ala
465                 470                 475                 480

Gly Phe Ala Val Val Leu Ala Glu Asp Thr Pro Asp Thr Ala Ala Val
                485                 490                 495

Asn Pro Val Pro Gln Ser Trp Ser Asp Leu Cys Pro Ile Tyr Asp Ala
                500                 505                 510

Leu Asp Pro Ser Asp Leu
            515

<210> SEQ ID NO 49
<211> LENGTH: 1557
<212> TYPE: DNA
<213> ORGANISM: Trametes sanguinea

<400> SEQUENCE: 49
atgtcgaggt tccagtccct cttcttcttc gtcctcgctt ccctcgccgc tgtggccaac    60
gctgccatcg gtcctgtggc agacttgacc ctcaccaacg ccgcagtcag ccctgatggc   120
```

```
ttcacccgcg aggctgttgt tgtcaacggc atcactcctg ctcctctcat tgccgggaag    180
aaaggcgacc gcttccagct gaatgtcatc gacaatttga caaaccatac catgctgaag    240
accaccagta ttcactggca tggcttcttc caacacggca cgaactgggc agacggcgtg    300
tcgttcgtca accagtgccc catcgcttcg ggcattcgt tcttgtacga cttccaggtc     360
cccgaccaag caggaacttt ctggtatcac agtcatcttt ccacccagta ttgtgatgga    420
ttgagaggcc ccttcgtcgt ctacgacccg aatgatcccc aggccagctt gtatgacatt    480
gacaacgacg acactgtgat tactttggcc gactggtacc atcttgccgc caaagttgga    540
cagcgcttcc cagttggcgc ggatgcgact ctgattaacg gcttggtcg aaccccggc      600
acgacctctg ctgatctggc ggttatcaag gtcacacagg caagcggta ccgattccgt     660
ttggtgtccc tgtcttgcga cccgaaccat accttcagca tcgatggtca ccatgacc     720
gtcattgaag cggattcggt gaacacccag cccctcgaag ttgactcaat tcagatcttc    780
gccgcacagc ggtactcctt cgtgctggat gctagtcagc cggtggacaa ctactggatc    840
cgtgccaacc ctcccttcgg aaacgtcgga ttcgccggtg aatcaactc tgctattctg     900
cgatacgatg cgctcccga ggtcgagccc accgacccc agaccactcc cacgaagcct     960
ctgaatgagg ctgacttgca tcctcttact cccatgcctg tgcctggacg ccccgagccc   1020
ggaggtgtcg acaagccgct caacatggtc ttcaacttca cggcacgaa cttcttcatc   1080
aacaaccatt ctttcgtccc accctccgtg ccggtcctgc tccagattct cagcggcgct   1140
caggccgcac aggacctggt cccggaaggc agcgtctacg ttctcccgag caacgcctct   1200
attgagatct ccttccccgc aactgccaat gctcctggca gccctcaccc cttccacctg   1260
cacggtcaca ccttcgctgt cgtccgaagc gccggaagca gcgagtacaa ctacgacaac   1320
ccggtcttcc gcgacgtcgt gagcaccggt acgcccggcg acaacgtcac catccggttc   1380
cagaccaaca ccccggccc ttggttcctc cactgccaca tcgacttcca cttggatgcc   1440
ggctttgctg tcgtcatggc cgaggacact ccagacaccg cctcggtcaa ccaggtccct   1500
cagtcatggt cggatttgtg cccgatctac gacgcgcttg acctcagcga cctctga      1557
```

<210> SEQ ID NO 50
<211> LENGTH: 518
<212> TYPE: PRT
<213> ORGANISM: Trametes sanguinea

<400> SEQUENCE: 50

Met Ser Arg Phe Gln Ser Leu Phe Phe Phe Val Leu Ala Ser Leu Ala
1               5                   10                  15

Ala Val Ala Asn Ala Ala Ile Gly Pro Val Ala Asp Leu Thr Leu Thr
            20                  25                  30

Asn Ala Ala Val Ser Pro Asp Gly Phe Thr Arg Glu Ala Val Val Val
        35                  40                  45

Asn Gly Ile Thr Pro Ala Pro Leu Ile Ala Gly Lys Lys Gly Asp Arg
    50                  55                  60

Phe Gln Leu Asn Val Ile Asp Asn Leu Thr Asn His Thr Met Leu Lys
65                  70                  75                  80

Thr Thr Ser Ile His Trp His Gly Phe Phe Gln His Gly Thr Asn Trp
                85                  90                  95

Ala Asp Gly Val Ser Phe Val Asn Gln Cys Pro Ile Ala Ser Gly His
            100                 105                 110

Ser Phe Leu Tyr Asp Phe Gln Val Pro Asp Gln Ala Gly Thr Phe Trp 115                 120                 125
Tyr His Ser His Leu Ser Thr Gln Tyr Cys Asp Gly Leu Arg Gly Pro
            130                 135                 140

Phe Val Val Tyr Asp Pro Asn Asp Pro Gln Ala Ser Leu Tyr Asp Ile
145                 150                 155                 160

Asp Asn Asp Asp Thr Val Ile Thr Leu Ala Asp Trp Tyr His Leu Ala
                165                 170                 175

Ala Lys Val Gly Gln Arg Phe Pro Val Gly Ala Asp Ala Thr Leu Ile
            180                 185                 190

Asn Gly Leu Gly Arg Thr Pro Gly Thr Thr Ser Ala Asp Leu Ala Val
            195                 200                 205

Ile Lys Val Thr Gln Gly Lys Arg Tyr Arg Phe Arg Leu Val Ser Leu
            210                 215                 220

Ser Cys Asp Pro Asn His Thr Phe Ser Ile Asp Gly His Thr Met Thr
225                 230                 235                 240

Val Ile Glu Ala Asp Ser Val Asn Thr Gln Pro Leu Glu Val Asp Ser
                245                 250                 255

Ile Gln Ile Phe Ala Ala Gln Arg Tyr Ser Phe Val Leu Asp Ala Ser
            260                 265                 270

Gln Pro Val Asp Asn Tyr Trp Ile Arg Ala Asn Pro Pro Phe Gly Asn
            275                 280                 285

Val Gly Phe Ala Gly Gly Ile Asn Ser Ala Ile Leu Arg Tyr Asp Gly
            290                 295                 300

Ala Pro Glu Val Glu Pro Thr Thr Gln Thr Thr Pro Thr Lys Pro
305                 310                 315                 320

Leu Asn Glu Ala Asp Leu His Pro Leu Thr Pro Met Pro Val Pro Gly
                325                 330                 335

Arg Pro Glu Pro Gly Gly Val Asp Lys Pro Leu Asn Met Val Phe Asn
            340                 345                 350

Phe Asn Gly Thr Asn Phe Phe Ile Asn Asn His Ser Phe Val Pro Pro
            355                 360                 365

Ser Val Pro Val Leu Leu Gln Ile Leu Ser Gly Ala Gln Ala Ala Gln
            370                 375                 380

Asp Leu Val Pro Glu Gly Ser Val Tyr Val Leu Pro Ser Asn Ala Ser
385                 390                 395                 400

Ile Glu Ile Ser Phe Pro Ala Thr Ala Asn Ala Pro Gly Ser Pro His
                405                 410                 415

Pro Phe His Leu His Gly His Thr Phe Ala Val Val Arg Ser Ala Gly
            420                 425                 430

Ser Ser Glu Tyr Asn Tyr Asp Asn Pro Val Phe Arg Asp Val Val Ser
            435                 440                 445

Thr Gly Thr Pro Gly Asp Asn Val Thr Ile Arg Phe Gln Thr Asn Asn
            450                 455                 460

Pro Gly Pro Trp Phe Leu His Cys His Ile Asp Phe His Leu Asp Ala
465                 470                 475                 480

Gly Phe Ala Val Val Met Ala Glu Asp Thr Pro Asp Thr Ala Ser Val
                485                 490                 495

Asn Gln Val Pro Gln Ser Trp Ser Asp Leu Cys Pro Ile Tyr Asp Ala
            500                 505                 510

Leu Asp Leu Ser Asp Leu
            515

<210> SEQ ID NO 51

```
<211> LENGTH: 1557
<212> TYPE: DNA
<213> ORGANISM: Trametes cinnabarina

<400> SEQUENCE: 51
atgtcgaggt tccagtccct cttcttcttc gtcctcgtct ccctcaccgc tgtggccaac      60
gcagccatag ggcctgtggc ggacctgacc cttaccaatg cccaggtcag ccccgatggc     120
ttcgctcgcg aggccgtcgt ggtgaacggt atcaccgctg ccctctcat acaggcaat      180
aagggcgatc gattccagct caatgtcatc gaccagttga caaatcatac catgttgaaa     240
acatctagta ttcattggca cggcttcttc cagcaaggca cgaactgggc cgatggtccc     300
gcgttcgtga accagtgtcc catcgcttcg ggccactcgt tcttgtatga ctttcaagtt     360
cccgaccaag cagggacttt ctggtaccat agccatctct ccacgcaata ctgcgatggt     420
ttgaggggc ctttcgtcgt ctacgacccc aacgatcctc acgctagcct gtatgacatt     480
gataacgacg acactgtcat tacgctggct gattggtatc acgttgctgc caagctcgga     540
cctcgcttcc catttggctc cgattcaacc cttatcaatg acttggtcg aaccactggc     600
atagcaccgt ccgacttggc agttatcaag gtcacgcagg gcaagcgcta ccgcttccgc     660
ttggtgtcgc tttcttgcga tccgaaccat acattcagca ttgataatca cacaatgact     720
ataattgagg cggactcgat caacactcaa cccctagagg ttgattcaat ccagattttt     780
gccgcgcagc gctactcctt cgtgctggat gctagccagc cggtggataa ctactggatc     840
cgcgcaaacc ctgccttcgg aaacacaggt tttgctggtg aatcaattc tgccatcctg     900
cgttatgatg gcgcacccga gatcgagcct acgtctgtcc agactactcc tacgaagcct     960
ctgaacgagg tcgacttgca tcctctctcg cctatgcctg tgcctggcag ccccgagccc    1020
ggaggtgtcg acaagcctct gaacttggtc ttcaacttca acggcaccaa cttcttcatc    1080
aacgaccaca cctttgtccc gccgtctgtc ccagtcttgc tacaaatcct cagtggggcg    1140
caggcggctc aggacctggt cccggagggc agcgtgttcg ttcttcccag caactcgtcc    1200
attgagatat ccttccctgc cactgccaat gcccctggat tccccatcc gttccacttg    1260
cacggtcacg ccttcgctgt cgtccggagc gccgggagca gcgtctacaa ctacgacaac    1320
ccgatcttcc gcgacgtcgt cagcaccggc cagcccggcg acaacgtcac gattcgcttc    1380
gagaccaata acccaggccc gtggttcctc cactgccaca ttgacttcca cctcgacgca    1440
ggctttgctg tagtcatggc cgaggacact ccggacacca aggccgcgaa ccctgttcct    1500
caggcgtggt cggacttgtg ccccatctat gatgcacttg accccagcga cctctga      1557

<210> SEQ ID NO 52
<211> LENGTH: 518
<212> TYPE: PRT
<213> ORGANISM: Trametes cinnabarina

<400> SEQUENCE: 52

Met Ser Arg Phe Gln Ser Leu Phe Phe Phe Val Leu Val Ser Leu Thr
1               5                   10                  15

Ala Val Ala Asn Ala Ala Ile Gly Pro Val Ala Asp Leu Thr Leu Thr
            20                  25                  30

Asn Ala Gln Val Ser Pro Asp Gly Phe Ala Arg Glu Ala Val Val Val
        35                  40                  45

Asn Gly Ile Thr Pro Ala Pro Leu Ile Thr Gly Asn Lys Gly Asp Arg
    50                  55                  60

Phe Gln Leu Asn Val Ile Asp Gln Leu Thr Asn His Thr Met Leu Lys
```

```
                65                  70                  75                  80
Thr Ser Ser Ile His Trp His Gly Phe Phe Gln Gln Gly Thr Asn Trp
                        85                  90                  95
Ala Asp Gly Pro Ala Phe Val Asn Gln Cys Pro Ile Ala Ser Gly His
                        100                 105                 110
Ser Phe Leu Tyr Asp Phe Gln Val Pro Asp Gln Ala Gly Thr Phe Trp
                        115                 120                 125
Tyr His Ser His Leu Ser Thr Gln Tyr Cys Asp Gly Leu Arg Gly Pro
                        130                 135                 140
Phe Val Val Tyr Asp Pro Asn Asp Pro His Ala Ser Leu Tyr Asp Ile
145                 150                 155                 160
Asp Asn Asp Asp Thr Val Ile Thr Leu Ala Asp Trp Tyr His Val Ala
                        165                 170                 175
Ala Lys Leu Gly Pro Arg Phe Pro Phe Gly Ser Asp Ser Thr Leu Ile
                        180                 185                 190
Asn Gly Leu Gly Arg Thr Thr Gly Ile Ala Pro Ser Asp Leu Ala Val
                        195                 200                 205
Ile Lys Val Thr Gln Gly Lys Arg Tyr Arg Phe Arg Leu Val Ser Leu
                        210                 215                 220
Ser Cys Asp Pro Asn His Thr Phe Ser Ile Asp Asn His Thr Met Thr
225                 230                 235                 240
Ile Ile Glu Ala Asp Ser Ile Asn Thr Gln Pro Leu Glu Val Asp Ser
                        245                 250                 255
Ile Gln Ile Phe Ala Ala Gln Arg Tyr Ser Phe Val Leu Asp Ala Ser
                        260                 265                 270
Gln Pro Val Asp Asn Tyr Trp Ile Arg Ala Asn Pro Ala Phe Gly Asn
                        275                 280                 285
Thr Gly Phe Ala Gly Gly Ile Asn Ser Ala Ile Leu Arg Tyr Asp Gly
                        290                 295                 300
Ala Pro Glu Ile Glu Pro Thr Ser Val Gln Thr Thr Pro Thr Lys Pro
305                 310                 315                 320
Leu Asn Glu Val Asp Leu His Pro Leu Ser Pro Met Pro Val Pro Gly
                        325                 330                 335
Ser Pro Glu Pro Gly Gly Val Asp Lys Pro Leu Asn Leu Val Phe Asn
                        340                 345                 350
Phe Asn Gly Thr Asn Phe Phe Ile Asn Asp His Thr Phe Val Pro Pro
                        355                 360                 365
Ser Val Pro Val Leu Leu Gln Ile Leu Ser Gly Ala Gln Ala Ala Gln
                        370                 375                 380
Asp Leu Val Pro Glu Gly Ser Val Phe Val Leu Pro Ser Asn Ser Ser
385                 390                 395                 400
Ile Glu Ile Ser Phe Pro Ala Thr Ala Asn Ala Pro Gly Phe Pro His
                        405                 410                 415
Pro Phe His Leu His Gly His Ala Phe Ala Val Val Arg Ser Ala Gly
                        420                 425                 430
Ser Ser Val Tyr Asn Tyr Asp Asn Pro Ile Phe Arg Asp Val Val Ser
                        435                 440                 445
Thr Gly Gln Pro Gly Asp Asn Val Thr Ile Arg Phe Glu Thr Asn Asn
                        450                 455                 460
Pro Gly Pro Trp Phe Leu His Cys His Ile Asp Phe His Leu Asp Ala
465                 470                 475                 480
Gly Phe Ala Val Val Met Ala Glu Asp Thr Pro Asp Thr Lys Ala Ala
                        485                 490                 495
```

Asn Pro Val Pro Gln Ala Trp Ser Asp Leu Cys Pro Ile Tyr Asp Ala
                500                 505                 510

Leu Asp Pro Ser Asp Leu
        515

<210> SEQ ID NO 53
<211> LENGTH: 1575
<212> TYPE: DNA
<213> ORGANISM: Trametes sp.

<400> SEQUENCE: 53

```
atgtcgggct tccgtctcct tccttcattc gcgtcacttg ctgtgatcgt gtcgctcgcg      60
ctcaacacgt tcgcggcggt cggtcccgtg accgacctga ccatctccaa cgcgaacgtc     120
tcccccgacg gtttccagcg tgcggcggtc gtcgcgaacg gcggggtccc tggcccgctc     180
attaacggcc agaagggtga ccatttccag atcaatgtgg tcaaccagct tacgaaccac     240
accatgctca gtccaccagt atccactgga cacggtttct tccagaaggg cacgaactgg     300
gcggacggtc ctgccttcgt gaaccagtgt cctattgcaa ccggccattc gttcctgtat     360
gacttccagg tccccgatca ggctggtact ttctggtatc acagccactt gtcgacgcag     420
tactgtgatg gtctgcgcgg accgttcgtc gtctacgacc cgaatgatcc tcatgccagc     480
ctttacgatg tggacaacga ggacaccgtc atcactctcg ccgactggta tcatgttgcg     540
gcaaagcttg gccggcgtt cctccccgc gccgatgcca ccttgatcaa tggcctcggt     600
cgctcaacgg atactccgac gcggacttg gccgtcatca aggtcacgtc gggcaagcgg     660
taccgtttcc gtctggcatc gctttcttgc gaccccgcgt tcactttcag cattgacaac     720
catgatatga ctatcatcga ggccgatgct gtcaacactc agccgcttga ggtcgactcg     780
ctccagatct ttgctggtca gcgttactcg ttcgtcctcg aggcgaacca ggctgtcgac     840
aactactggg ttcgtgcgaa cccattcttt ggtacgacgg gctttgcggg cgggatcaac     900
tctgccatcc tccgctacga tggcgccgcc gaggtcgagc cgactaccac gcaaagcacg     960
tcgacgaagc cgctcgctga aaccgacctt gtgcccctgg cgtcgatgcc ggttccgggt    1020
tccccgtgt ctggtggagt cgacaaggcg atcaactttg cgttcacctt caacggcacc    1080
aacttcttcg tgaacggcgc gaccttcacg cctcccagca ctcctgttct gctgcagatc    1140
atgagcggtg cgcaggatgc ctcggctctt ctcccgtctg gcgatgtcta ctccctgccc    1200
tcgaacgcca cgattgagct caccttcccg gccacgactg gcgcacccgg tgctcctcat    1260
cccttccact gcacggtca caccttcgcc gttgttcgca gcgcaggcag caccaagtac    1320
aactacgata cccgatctg gcgcgatgtt gttagcactg gaactcctgc gcgggtgac    1380
aacgttacta tccgcttcag gaccgacaac cccgggccat ggttcctcca ctgccacatc    1440
gacttccacc tcgaggccgg gttcgccgtt gtcatggccg aagacattcc tgacactaag    1500
cttgccaacc ctgttcctca ggcgtggtcg gacctgtgcc cgatctacga tgcgctcgac    1560
cccagcgacc agtga                                                    1575
```

<210> SEQ ID NO 54
<211> LENGTH: 524
<212> TYPE: PRT
<213> ORGANISM: Trametes sp.

<400> SEQUENCE: 54

Met Ser Gly Phe Arg Leu Leu Pro Ser Phe Ala Ser Leu Ala Val Ile
1               5                   10                  15

```
Val Ser Leu Ala Leu Asn Thr Phe Ala Ala Val Gly Pro Val Thr Asp
             20                  25                  30

Leu Thr Ile Ser Asn Ala Asn Val Ser Pro Asp Gly Phe Gln Arg Ala
         35                  40                  45

Ala Val Val Ala Asn Gly Gly Val Pro Gly Pro Leu Ile Asn Gly Gln
50                  55                  60

Lys Gly Asp His Phe Gln Ile Asn Val Val Asn Gln Leu Thr Asn His
65                  70                  75                  80

Thr Met Leu Lys Ser Thr Ser Ile His Trp His Gly Phe Phe Gln Lys
                 85                  90                  95

Gly Thr Asn Trp Ala Asp Gly Pro Ala Phe Val Asn Gln Cys Pro Ile
             100                 105                 110

Ala Thr Gly His Ser Phe Leu Tyr Asp Phe Gln Val Pro Asp Gln Ala
         115                 120                 125

Gly Thr Phe Trp Tyr His Ser His Leu Ser Thr Gln Tyr Cys Asp Gly
     130                 135                 140

Leu Arg Gly Pro Phe Val Val Tyr Asp Pro Asn Asp Pro His Ala Ser
145                 150                 155                 160

Leu Tyr Asp Val Asp Asn Glu Asp Thr Val Ile Thr Leu Ala Asp Trp
                 165                 170                 175

Tyr His Val Ala Ala Lys Leu Gly Pro Ala Phe Pro Pro Arg Ala Asp
             180                 185                 190

Ala Thr Leu Ile Asn Gly Leu Gly Arg Ser Thr Asp Thr Pro Thr Ala
         195                 200                 205

Asp Leu Ala Val Ile Lys Val Thr Ser Gly Lys Arg Tyr Arg Phe Arg
     210                 215                 220

Leu Ala Ser Leu Ser Cys Asp Pro Ala Phe Thr Phe Ser Ile Asp Asn
225                 230                 235                 240

His Asp Met Thr Ile Ile Glu Ala Asp Ala Val Asn Thr Gln Pro Leu
                 245                 250                 255

Glu Val Asp Ser Leu Gln Ile Phe Ala Gly Gln Arg Tyr Ser Phe Val
             260                 265                 270

Leu Glu Ala Asn Gln Ala Val Asp Asn Tyr Trp Val Arg Ala Asn Pro
         275                 280                 285

Phe Phe Gly Thr Thr Gly Phe Ala Gly Gly Ile Asn Ser Ala Ile Leu
     290                 295                 300

Arg Tyr Asp Gly Ala Ala Glu Val Glu Pro Thr Thr Gln Ser Thr
305                 310                 315                 320

Ser Thr Lys Pro Leu Ala Glu Thr Asp Leu Val Pro Leu Ala Ser Met
                 325                 330                 335

Pro Val Pro Gly Ser Pro Val Ser Gly Gly Val Asp Lys Ala Ile Asn
             340                 345                 350

Phe Ala Phe Thr Phe Asn Gly Thr Asn Phe Phe Val Asn Gly Ala Thr
         355                 360                 365

Phe Thr Pro Pro Ser Thr Pro Val Leu Leu Gln Ile Met Ser Gly Ala
     370                 375                 380

Gln Asp Ala Ser Ala Leu Leu Pro Ser Gly Asp Val Tyr Ser Leu Pro
385                 390                 395                 400

Ser Asn Ala Thr Ile Glu Leu Thr Phe Pro Ala Thr Gly Ala Pro
                 405                 410                 415

Gly Ala Pro His Pro Phe His Leu His Gly His Thr Phe Ala Val Val
             420                 425                 430
```

```
Arg Ser Ala Gly Ser Thr Lys Tyr Asn Tyr Asp Asn Pro Ile Trp Arg
            435                 440                 445

Asp Val Val Ser Thr Gly Thr Pro Ala Ala Gly Asp Asn Val Thr Ile
    450                 455                 460

Arg Phe Arg Thr Asp Asn Pro Gly Pro Trp Phe Leu His Cys His Ile
465             470                 475                 480

Asp Phe His Leu Glu Ala Gly Phe Ala Val Val Met Ala Glu Asp Ile
                485                 490                 495

Pro Asp Thr Lys Leu Ala Asn Pro Val Pro Gln Ala Trp Ser Asp Leu
            500                 505                 510

Cys Pro Ile Tyr Asp Ala Leu Asp Pro Ser Asp Gln
            515                 520
```

<210> SEQ ID NO 55
<211> LENGTH: 1575
<212> TYPE: DNA
<213> ORGANISM: Trametes sp.

<400> SEQUENCE: 55

```
atgtcgggct tccgtctcct tccttcattc gcgtcacttg ctgtgatcgt gtcgctcgcg    60
ctcaacacgt tcgcggcggt cggtcccgtg accgacctga ccatctccaa cgcgaacgtc   120
tcccccgacg gtttccagcg tgcggcggtc gtcgcgaacg cggggtcccc tggcccgctc   180
attaacggca agaagggtga ccatttccag atcaatgtgg tcaaccagct tacgaaccac   240
accatgctca gtccaccag tatccactgg cacggtttct tccagaaggg cacgaactgg   300
gcggacggtc ctgccttcgt gaaccagtgt cctattgcaa ccggccattc gttcctgtat   360
gacttccagg tccccgatca ggctggtact ttctggtatc acagccactt gtcgacgcag   420
tactgtgatg gtctgcgcgg accgttcgtc gtctacgacc cgaatgatcc tcatgccagc   480
ctttacgatg tggacaacga ggacaccgtc atcactctcg ccgactggta tcatgttgcg   540
gcaaagcttg gccggcgtt ccctcccgc gccgatgcca ccttgatcaa tggcctcggt   600
cgctcaacgg atactccgac cgcggacttg gccgtcatca aggtcacgtc gggcaagcgg   660
taccgtttcc gtctggcatc gctttcttgc gaccccgcgt tcactttcag cattgacaac   720
catgatatga ctatcatcga ggccgatgct gtcaacactc agccgcttga ggtcgactcg   780
ctccagatct tgctggtca gcgttactcg ttcgtcctcg aggcgaacca ggctgtcgac   840
aactactggg ttcgtgcgaa cccattcttt ggtacgacgg gctttgcggg cgggatcaac   900
tctgccatcc tccgctacga tggcgccgcc gaggtcgagc cgactaccac gcaaagcacg   960
tcgacgaagc cgctcgctga aaccgacctt gtgcccctgg cgtcgatgcc ggttccgggt  1020
tccccgtgt ctggtggagt cgacaagggg atcaactttg cgttcacctt caacggcacc  1080
aacttcttcg tgaacggcgc gaccttcacg cctcccagca ctcctgttct gctgcagatc  1140
atgagcggtg cgcaggatgc ctcggctctt ctcccgtctg cgatgtcta ctccctgccc  1200
tcgaacgcca cgattgagct caccttcccg gccacgactg gcgcacccgg tgctcctcat  1260
cccttccact gcacggtca caccttcgcc gttgttcgca gcgcaggcag caccaagtac  1320
aactacgata cccgatctg gcgcgatgtt gttagcactg gaactcctgc cgcgggtgac  1380
aacgttacta tccgcttcag gaccgacaac cccggcccat ggttcctcca ctgccacatc  1440
gacttccacc tcgaggccgg tttcgccgtt gtcatggccg aggacattcc tgacactaag  1500
cttgccaacc ctgttcctca ggcgtggtcg gacctgtgcc cgatctacga tgcgctcgac  1560
cccagcgacc agtga                                                    1575
```

```
<210> SEQ ID NO 56
<211> LENGTH: 524
<212> TYPE: PRT
<213> ORGANISM: Trametes sp.

<400> SEQUENCE: 56

Met Ser Gly Phe Arg Leu Leu Pro Ser Phe Ala Ser Leu Ala Val Ile
1               5                   10                  15

Val Ser Leu Ala Leu Asn Thr Phe Ala Val Gly Pro Val Thr Asp
                20                  25                  30

Leu Thr Ile Ser Asn Ala Asn Val Ser Pro Asp Gly Phe Gln Arg Ala
                35                  40                  45

Ala Val Ala Asn Gly Gly Val Pro Gly Pro Leu Ile Asn Gly Gln
        50                  55                  60

Lys Gly Asp His Phe Gln Ile Asn Val Val Asn Gln Leu Thr Asn His
65                  70                  75                  80

Thr Met Leu Lys Ser Thr Ser Ile His Trp His Gly Phe Phe Gln Lys
                85                  90                  95

Gly Thr Asn Trp Ala Asp Gly Pro Ala Phe Val Asn Gln Cys Pro Ile
            100                 105                 110

Ala Thr Gly His Ser Phe Leu Tyr Asp Phe Gln Val Pro Asp Gln Ala
        115                 120                 125

Gly Thr Phe Trp Tyr His Ser His Leu Ser Thr Gln Tyr Cys Asp Gly
    130                 135                 140

Leu Arg Gly Pro Phe Val Val Tyr Asp Pro Asn Asp Pro His Ala Ser
145                 150                 155                 160

Leu Tyr Asp Val Asp Asn Glu Asp Thr Val Ile Thr Leu Ala Asp Trp
                165                 170                 175

Tyr His Val Ala Ala Lys Leu Gly Pro Ala Phe Pro Pro Arg Ala Asp
            180                 185                 190

Ala Thr Leu Ile Asn Gly Leu Gly Arg Ser Thr Asp Thr Pro Thr Ala
        195                 200                 205

Asp Leu Ala Val Ile Lys Val Thr Ser Gly Lys Arg Tyr Arg Phe Arg
210                 215                 220

Leu Ala Ser Leu Ser Cys Asp Pro Ala Phe Thr Phe Ser Ile Asp Asn
225                 230                 235                 240

His Asp Met Thr Ile Ile Glu Ala Asp Ala Val Asn Thr Gln Pro Leu
                245                 250                 255

Glu Val Asp Ser Leu Gln Ile Phe Ala Gly Gln Arg Tyr Ser Phe Val
            260                 265                 270

Leu Glu Ala Asn Gln Ala Val Asp Asn Tyr Trp Val Arg Ala Asn Pro
        275                 280                 285

Phe Phe Gly Thr Thr Gly Phe Ala Gly Gly Ile Asn Ser Ala Ile Leu
    290                 295                 300

Arg Tyr Asp Gly Ala Ala Glu Val Glu Pro Thr Thr Thr Gln Ser Thr
305                 310                 315                 320

Ser Thr Lys Pro Leu Ala Glu Thr Asp Leu Val Pro Leu Ala Ser Met
                325                 330                 335

Pro Val Pro Gly Ser Pro Val Ser Gly Val Asp Lys Gly Ile Asn
            340                 345                 350

Phe Ala Phe Thr Phe Asn Gly Thr Asn Phe Val Asn Gly Ala Thr
        355                 360                 365

Phe Thr Pro Pro Ser Thr Pro Val Leu Leu Gln Ile Met Ser Gly Ala
```

```
                370               375               380
Gln Asp Ala Ser Ala Leu Leu Pro Ser Gly Asp Val Tyr Ser Leu Pro
385                 390                 395                 400

Ser Asn Ala Thr Ile Glu Leu Thr Phe Pro Ala Thr Thr Gly Ala Pro
                405                 410                 415

Gly Ala Pro His Pro Phe His Leu His Gly His Thr Phe Ala Val Val
                420                 425                 430

Arg Ser Ala Gly Ser Thr Lys Tyr Asn Tyr Asp Asn Pro Ile Trp Arg
            435                 440                 445

Asp Val Val Ser Thr Gly Thr Pro Ala Ala Gly Asp Asn Val Thr Ile
        450                 455                 460

Arg Phe Arg Thr Asp Asn Pro Gly Pro Trp Phe Leu His Cys His Ile
465                 470                 475                 480

Asp Phe His Leu Glu Ala Gly Phe Ala Val Val Met Ala Glu Asp Ile
                485                 490                 495

Pro Asp Thr Lys Leu Ala Asn Pro Val Pro Gln Ala Trp Ser Asp Leu
                500                 505                 510

Cys Pro Ile Tyr Asp Ala Leu Asp Pro Ser Asp Gln
            515                 520
```

<210> SEQ ID NO 57
<211> LENGTH: 1566
<212> TYPE: DNA
<213> ORGANISM: Lentinus sp.

<400> SEQUENCE: 57

| | |
|---|---:|
| atggccaagt tccagtcgtt gctttcttac actgtcctct ccttcgtcgc ggctgcctat | 60 |
| gctgccatcg gcccagtcgc tgaccttacc atcagcaatg cccaagtcag ccccgacggc | 120 |
| ttcctccgcg atgccgtcgt gaccaacggc ctggtccctg ggcccctcat cacgggcaac | 180 |
| aagggcgatc gcttccagtt gaatgtcatt gatcaaatga ccaaccacac gatgttgaag | 240 |
| actacgagca ttcactggca cggcttcttc cagaagggca ccaactgggc tgatggacct | 300 |
| gcgtttgtga accagtgccc cattgccagc ggcaactcct tcctctacga cttccaggtc | 360 |
| cctgaccagg ctggcacctt ctggtatcac agccaccttt cgacccagta ctgcgacggt | 420 |
| ctccgggggc ctctcgttgt gtacgacccc aatgacccac acgctgccct ctatgatatc | 480 |
| gacgatgata acaccgttat tactttgact gactggtacc atactgcggc caggctcgga | 540 |
| cctcgtttcc cgctgggagc agatgccact ctcatcaacg gcctgggccg cagcccagcc | 600 |
| acgccgaccg ccaacctaac tgtcatcaac gttactcagg caagcgcta ccgcttccgc | 660 |
| ctcgtgtcga tctcttgcga cccgaactat gtgttcagca tcgacaacca cacgatgagc | 720 |
| gtcattgaga cggacactgt caacactcaa ccgctcacgg tcgatagcat tcagatctac | 780 |
| gccgcccagc gctactcctt tgtgctcacc gccaaccagt ccgtggataa ctactggatc | 840 |
| cgggcaaacc ccaacttcgg taacgtcggc ttcacggatg ctatcaactc ggccatcctc | 900 |
| cgctatgacg gtgctcccga cgctgagccc tccgctacca ctgcaccgac gttgaccaac | 960 |
| ccgctggttg aggcgaacct tcacccgctt gcttcgatgc ccgtgcccgg atccctgtg | 1020 |
| tctggcggtg tggacaaggc cattaacttc gtcttcaact tcaacggcac gaacttctcc | 1080 |
| atcaacaacg cgactttcgt tccgcccacc gttccggtgc tgctccagat catgagcggc | 1140 |
| gccaacaccg cccaagacct cctgccctct ggcagcgtgt acacactccc gtccaacgct | 1200 |
| accattgagc tgtccttccc tgcgacgagc aacgcccccg cgctcctca cccttccac | 1260 |

```
ttgcacggtc acgtcttcgc cgttgtccgc agcgctggca gcaccgtcta caactacgac      1320
aaccccatct ggcgcgacgt cgtcagcacc ggcacccctg cagcgggcga caacgtcacc      1380
atccgcttcc agaccaacaa ccctggtccc tggttcctcc actgtcacat cgacttccac      1440
ctcgacgccg gctttgccgt ggtcatggct gaggaccctg ttgacactcc gacggcggat      1500
cccgttcccc aggcgtggtc cgatctctgc ccgacatacg acgcgctttc cgtcgacgac      1560
cagtga                                                                 1566
```

<210> SEQ ID NO 58
<211> LENGTH: 521
<212> TYPE: PRT
<213> ORGANISM: Lentinus sp.

<400> SEQUENCE: 58

```
Met Ala Lys Phe Gln Ser Leu Leu Ser Tyr Thr Val Leu Ser Phe Val
1               5                   10                  15

Ala Ala Ala Tyr Ala Ala Ile Gly Pro Val Ala Asp Leu Thr Ile Ser
            20                  25                  30

Asn Ala Gln Val Ser Pro Asp Gly Phe Leu Arg Asp Ala Val Val Thr
        35                  40                  45

Asn Gly Leu Val Pro Gly Pro Leu Ile Thr Gly Asn Lys Gly Asp Arg
    50                  55                  60

Phe Gln Leu Asn Val Ile Asp Gln Met Thr Asn His Thr Met Leu Lys
65                  70                  75                  80

Thr Thr Ser Ile His Trp His Gly Phe Phe Gln Lys Gly Thr Asn Trp
                85                  90                  95

Ala Asp Gly Pro Ala Phe Val Asn Gln Cys Pro Ile Ala Ser Gly Asn
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Leu Val Val Tyr Asp Pro Asn Asp Pro His Ala Ala Leu Tyr Asp Ile
145                 150                 155                 160

Asp Asp Asp Asn Thr Val Ile Thr Leu Thr Asp Trp Tyr His Thr Ala
                165                 170                 175

Ala Arg Leu Gly Pro Arg Phe Pro Leu Gly Ala Asp Ala Thr Leu Ile
            180                 185                 190

Asn Gly Leu Gly Arg Ser Pro Ala Thr Pro Thr Ala Asn Leu Thr Val
        195                 200                 205

Ile Asn Val Thr Gln Gly Lys Arg Tyr Arg Phe Arg Leu Val Ser Ile
    210                 215                 220

Ser Cys Asp Pro Asn Tyr Val Phe Ser Ile Asp Asn His Thr Met Ser
225                 230                 235                 240

Val Ile Glu Thr Asp Thr Val Asn Thr Gln Pro Leu Thr Val Asp Ser
                245                 250                 255

Ile Gln Ile Tyr Ala Ala Gln Arg Tyr Ser Phe Val Leu Thr Ala Asn
            260                 265                 270

Gln Ser Val Asp Asn Tyr Trp Ile Arg Ala Asn Pro Asn Phe Gly Asn
        275                 280                 285

Val Gly Phe Thr Asp Ala Ile Asn Ser Ala Ile Leu Arg Tyr Asp Gly
    290                 295                 300

Ala Pro Asp Ala Glu Pro Ser Ala Thr Thr Ala Pro Thr Leu Thr Asn
305                 310                 315                 320
```

```
Pro Leu Val Glu Ala Asn Leu His Pro Leu Ala Ser Met Pro Val Pro
            325                 330                 335

Gly Ser Pro Val Ser Gly Gly Val Asp Lys Ala Ile Asn Phe Val Phe
            340                 345                 350

Asn Phe Asn Gly Thr Asn Phe Ser Ile Asn Asn Ala Thr Phe Val Pro
            355                 360                 365

Pro Thr Val Pro Val Leu Leu Gln Ile Met Ser Gly Ala Asn Thr Ala
            370                 375                 380

Gln Asp Leu Leu Pro Ser Gly Ser Val Tyr Thr Leu Pro Ser Asn Ala
385                 390                 395                 400

Thr Ile Glu Leu Ser Phe Pro Ala Thr Ser Asn Ala Pro Gly Ala Pro
                405                 410                 415

His Pro Phe His Leu His Gly His Val Phe Ala Val Val Arg Ser Ala
                420                 425                 430

Gly Ser Thr Val Tyr Asn Tyr Asp Asn Pro Ile Trp Arg Asp Val Val
                435                 440                 445

Ser Thr Gly Thr Pro Ala Ala Gly Asp Asn Val Thr Ile Arg Phe Gln
            450                 455                 460

Thr Asn Asn Pro Gly Pro Trp Phe Leu His Cys His Ile Asp Phe His
465                 470                 475                 480

Leu Asp Ala Gly Phe Ala Val Val Met Ala Glu Asp Pro Val Asp Thr
                485                 490                 495

Pro Thr Ala Asp Pro Val Pro Gln Ala Trp Ser Asp Leu Cys Pro Thr
                500                 505                 510

Tyr Asp Ala Leu Ser Val Asp Asp Gln
                515                 520

<210> SEQ ID NO 59
<211> LENGTH: 1575
<212> TYPE: DNA
<213> ORGANISM: Trametes sp.

<400> SEQUENCE: 59
atgggcagac ttcagcgttt ttcagccttc gttcccctca cactctcctt catatctcaa      60
gcgtccgctg caataggacc tgtcacggac ttgaccatct ccgatgctga catctccccc     120
gatggtttca ctcgtgccgc cgtggtgatg aatgaccaat ccccggaccc ttgatcgct     180 ggaaacaagg gagacaactt ccaaatcaat gtcatcgaca atctctccaa tagtacaatg     240
ctcacttcca ccactatcca ctggcacggc ttcttccaga aaggcactaa ttgggcggac     300
ggtgcggcat tcgtcaatca atgtccgatc tcggccggca attcgttctt gtacgacttc     360
acggcgacgg accaagccgg cacattctgg tatcacagtc acttgtcgac gcagtactgt     420
gatggcctgc gtggtcccat ggttgtctat gatcccgacg atccacatgc ctccctgtac     480
gatgtggacg acgattcaac tgtcattacg ctctcggact ggtaccacac tgccgcgcgt     540
ctcggcgctc gtttccctgc tggggccgac tcaactctca ttaacggttt gggccgtgcg     600
gcaggcggcg atgcggacgc cgctctcgca gtattcaacg ttacccaagg ctcgcgttac     660
cgcttccgcc tggtttccct gtcatgcgac ccgaacttca acttcaccat ccaagatcac     720
aacatgacga tcatcgaggt tgatggggtc aacgtcgagc ccgtcactgt cgactcgatc     780
cagatttccg ccgggcagag atactccttc gtgctcaccg cggatcaaga tatcggtaac     840
tactggatca aggccgttcc taacaccggt acagtcacca ccgatggcgg cgttaactct     900
gccattctgc gttacgacac ggcggacccg atcgaacccg acgccgcaga ccccaccagc     960
```

```
agtatcccgc tcgtggagac agacctcgtc ccgctggaga acctcgcagc gcccggagat   1020
cccaccgtcg gtggtgttga cctggcgatg aacctggagt tcgactttaa tggcacgtgg   1080
ttctttatca acggcgagcc attcgttcct cctagtgtcc ctgttttgct gcaaatcatg   1140
agtggcgcgc agtctgctgc ggaccttctc ccgagcggaa gcgtatacac gctccccgcc   1200
aactctacca tcgagatttc cttccctatg aacactacag cagcgcccgg tgcgccgcat   1260
ccgttccacc ttcacgggca cacgttctac gtcgtgcgca gcgcgggcag caccgaatac   1320
aactacgtga acccacccca gcgcgacacc gtcagcacgg gcaccgacgg agacaatgtc   1380
accatccggt tcacgacgaa caaccccggc ccgtggttcc tccactgcca catcgacttt   1440
cacctcgacg ccggcttcgc catcgtgctc agcgaggaca ctccggacgc tgcttcggcc   1500
aacacgccct cctctgcgtg ggatgatctt tgccccactt ataacaccga ctatcccgac   1560
ggtctcgggc gctga                                                     1575
```

<210> SEQ ID NO 60
<211> LENGTH: 524
<212> TYPE: PRT
<213> ORGANISM: Trametes sp.

<400> SEQUENCE: 60

```
Met Gly Arg Leu Gln Arg Phe Ser Ala Phe Val Pro Leu Thr Leu Ser
1               5                   10                  15

Phe Ile Ser Gln Ala Ser Ala Ala Ile Gly Pro Val Thr Asp Leu Thr
                20                  25                  30

Ile Ser Asp Ala Asp Ile Ser Pro Asp Gly Phe Thr Arg Ala Ala Val
            35                  40                  45

Val Met Asn Asp Gln Phe Pro Gly Pro Leu Ile Ala Gly Asn Lys Gly
        50                  55                  60

Asp Asn Phe Gln Ile Asn Val Ile Asp Asn Leu Ser Asn Ser Thr Met
65                  70                  75                  80

Leu Thr Ser Thr Thr Ile His Trp His Gly Phe Phe Gln Lys Gly Thr
                85                  90                  95

Asn Trp Ala Asp Gly Ala Ala Phe Val Asn Gln Cys Pro Ile Ser Ala
                100                 105                 110

Gly Asn Ser Phe Leu Tyr Asp Phe Thr Ala Thr Asp Gln Ala Gly Thr
            115                 120                 125

Phe Trp Tyr His Ser His Leu Ser Thr Gln Tyr Cys Asp Gly Leu Arg
        130                 135                 140

Gly Pro Met Val Val Tyr Asp Pro Asp Pro His Ala Ser Leu Tyr
145                 150                 155                 160

Asp Val Asp Asp Ser Thr Val Ile Thr Leu Ser Asp Trp Tyr His
                165                 170                 175

Thr Ala Ala Arg Leu Gly Ala Arg Phe Pro Ala Gly Ala Asp Ser Thr
            180                 185                 190

Leu Ile Asn Gly Leu Gly Arg Ala Gly Gly Asp Ala Asp Ala Ala
        195                 200                 205

Leu Ala Val Phe Asn Val Thr Gln Gly Ser Arg Tyr Arg Phe Arg Leu
        210                 215                 220

Val Ser Leu Ser Cys Asp Pro Asn Phe Asn Phe Thr Ile Gln Asp His
225                 230                 235                 240

Asn Met Thr Ile Ile Glu Val Asp Gly Val Asn Val Glu Pro Val Thr
                245                 250                 255
```

```
Val Asp Ser Ile Gln Ile Phe Ala Gly Gln Arg Tyr Ser Phe Val Leu
            260                 265                 270

Thr Ala Asp Gln Asp Ile Gly Asn Tyr Trp Ile Gln Ala Val Pro Asn
            275                 280                 285

Thr Gly Thr Val Thr Thr Asp Gly Gly Val Asn Ser Ala Ile Leu Arg
            290                 295                 300

Tyr Asp Thr Ala Asp Pro Ile Glu Pro Asp Ala Ala Asp Pro Thr Ser
305                 310                 315                 320

Ser Ile Pro Leu Val Glu Thr Asp Leu Val Pro Leu Glu Asn Leu Ala
            325                 330                 335

Ala Pro Gly Asp Pro Thr Val Gly Gly Val Asp Leu Ala Met Asn Leu
            340                 345                 350

Glu Phe Asp Phe Asn Gly Thr Trp Phe Phe Ile Asn Gly Glu Pro Phe
            355                 360                 365

Val Pro Pro Ser Val Pro Val Leu Leu Gln Ile Met Ser Gly Ala Gln
            370                 375                 380

Ser Ala Ala Asp Leu Leu Pro Ser Gly Ser Val Tyr Thr Leu Pro Ala
385                 390                 395                 400

Asn Ser Thr Ile Glu Ile Ser Phe Pro Met Asn Thr Thr Ala Ala Pro
            405                 410                 415

Gly Ala Pro His Pro Phe His Leu His Gly His Thr Phe Tyr Val Val
            420                 425                 430

Arg Ser Ala Gly Ser Thr Glu Tyr Asn Tyr Val Asn Pro Pro Gln Arg
            435                 440                 445

Asp Thr Val Ser Thr Gly Thr Asp Gly Asp Asn Val Thr Ile Arg Phe
            450                 455                 460

Thr Thr Asn Asn Pro Gly Pro Trp Phe Leu His Cys His Ile Asp Phe
465                 470                 475                 480

His Leu Asp Ala Gly Phe Ala Ile Val Leu Ser Glu Asp Thr Pro Asp
            485                 490                 495

Ala Ala Ser Ala Asn Thr Pro Ser Ser Ala Trp Asp Asp Leu Cys Pro
            500                 505                 510

Thr Tyr Asn Thr Asp Tyr Pro Asp Gly Leu Gly Arg
            515                 520

<210> SEQ ID NO 61
<211> LENGTH: 1554
<212> TYPE: DNA
<213> ORGANISM: Basidiomycete PM1

<400> SEQUENCE: 61
atggccaagt ccaatctctc cctcaccttc atcaccctct cgctcgttgc ctcagtgtac      60
gctagcattg ggccagtcgc agacctcacc atctccaacg gtgctgtcag tcccgatggt     120
ttctctcggc aggccatcct ggtcaacgac gtcttcccca gtcccctcat tacggggaac     180
aagggtgatc gtttccaact caatgtcatc gacaacatga ccaaccacac catgttgaag     240
tccaccagta tccattggca cggcttcttc aacacggca ccaactgggc cgacggcccc      300
gccttcgtga accagtgccc gatttctacc gggcatgcgt tcctttacga cttccaggtc     360
cctgaccaag ctggtacttt ctggtaccac agtcacttgt ccactcaata ctgtgacggt     420
ctcaggggtc cgattgttgt ctatgaccct caagatcccc acaagagcct ttacgatgtt     480
gatgacgact ccactgtaat cactctcgcg gattggtacc acttggctgc caaagtcggc     540
ccggcggtcc cgactgccga tgcgactctt atcaacggcc tcggtcgcag catcaacacg     600
```

```
ctcaacgccg atttggctgt catcacggtc acgaagggca agcgctatcg cttccgcctg    660
gtgtcgctgt catgcgaccc gaatcacacg ttcagcattg atggtcactc tctgaccgtc    720
atcgaggcgg acagcgtgaa tctcaagccc agactgtcg actccatcca gatcttcgct     780
gcccagcggt actcgtttgt gctcaacgca gatcaggatg tggacaacta ctggatccgt    840
gcccttccca actccgggac caggaacttc gacggcggcg ttaactccgc catccttcgc    900
tacgacggtg ctgcgcccgt tgagcccacc acgacccaga cgccgtcgac gcagcctttg    960
gtggagtccg ccctgaccac tctcgaaggc accgctgcgc ccggcaaccc gacccctggc   1020
ggtgtcgacc tggctctcaa catggctttc ggctttgccg gcggcaggtt caccatcaac   1080
ggcgcgagct tcaccccgcc caccgtcccc gtcctcctgc agatcctgag cggcgcgcag   1140
tcggcgcagg acctcctccc ctctggaagt gtatactcgc tccctgcgaa cgcggacatt   1200
gagatctccc tccccgccac ctccgccgcc cccggcttcc cgcacccctt ccacttgcac   1260
gggcacacct tcgccgtcgt gcgcagcgcc ggctcgtcga cgtacaacta cgcgaacccg   1320
gtctaccgcg acgtcgtcag cacgggctcg cccggggaca acgtcacgat ccggttcagg   1380
acggacaacc ccggcccgtg gttcctccac tgccacatcg acttccacct cgaggctggg   1440
ttcgcggtcg tcatggccga ggacattccc gacgtcgccg ctacgaaccc ggtcccgcaa   1500
gcatggtcgg atctgtgccc gacctatgat gcgctctcgc ctgacgacca gtga         1554
```

<210> SEQ ID NO 62
<211> LENGTH: 517
<212> TYPE: PRT
<213> ORGANISM: Basidiomycete PM1

<400> SEQUENCE: 62

Met Ala Lys Phe Gln Ser Leu Leu Thr Phe Ile Thr Leu Ser Leu Val
1               5                   10                  15

Ala Ser Val Tyr Ala Ser Ile Gly Pro Val Ala Asp Leu Thr Ile Ser
            20                  25                  30

Asn Gly Ala Val Ser Pro Asp Gly Phe Ser Arg Gln Ala Ile Leu Val
        35                  40                  45

Asn Asp Val Phe Pro Ser Pro Leu Ile Thr Gly Asn Lys Gly Asp Arg
    50                  55                  60

Phe Gln Leu Asn Val Ile Asp Asn Met Thr Asn His Thr Met Leu Lys
65                  70                  75                  80

Ser Thr Ser Ile His Trp His Gly Phe Phe Gln His Gly Thr Asn Trp
                85                  90                  95

Ala Asp Gly Pro Ala Phe Val Asn Gln Cys Pro Ile Ser Thr Gly His
            100                 105                 110

Ala Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Ile Val Val Tyr Asp Pro Gln Asp Pro His Lys Ser Leu Tyr Asp Val
145                 150                 155                 160

Asp Asp Asp Ser Thr Val Ile Thr Leu Ala Asp Trp Tyr His Leu Ala
                165                 170                 175

Ala Lys Val Gly Pro Ala Val Pro Thr Ala Asp Ala Thr Leu Ile Asn
            180                 185                 190

Gly Leu Gly Arg Ser Ile Asn Thr Leu Asn Ala Asp Leu Ala Val Ile
        195                 200                 205

```
Thr Val Thr Lys Gly Lys Arg Tyr Arg Phe Arg Leu Val Ser Leu Ser
            210                 215                 220

Cys Asp Pro Asn His Thr Phe Ser Ile Asp Gly His Ser Leu Thr Val
225                 230                 235                 240

Ile Glu Ala Asp Ser Val Asn Leu Lys Pro Gln Thr Val Asp Ser Ile
                245                 250                 255

Gln Ile Phe Ala Ala Gln Arg Tyr Ser Phe Val Leu Asn Ala Asp Gln
                260                 265                 270

Asp Val Asp Asn Tyr Trp Ile Arg Ala Leu Pro Asn Ser Gly Thr Arg
            275                 280                 285

Asn Phe Asp Gly Gly Val Asn Ser Ala Ile Leu Arg Tyr Asp Gly Ala
290                 295                 300

Ala Pro Val Glu Pro Thr Thr Thr Gln Thr Pro Ser Thr Gln Pro Leu
305                 310                 315                 320

Val Glu Ser Ala Leu Thr Thr Leu Glu Gly Thr Ala Ala Pro Gly Asn
                325                 330                 335

Pro Thr Pro Gly Gly Val Asp Leu Ala Leu Asn Met Ala Phe Gly Phe
            340                 345                 350

Ala Gly Gly Arg Phe Thr Ile Asn Gly Ala Ser Phe Thr Pro Pro Thr
            355                 360                 365

Val Pro Val Leu Leu Gln Ile Leu Ser Gly Ala Gln Ser Ala Gln Asp
370                 375                 380

Leu Leu Pro Ser Gly Ser Val Tyr Ser Leu Pro Ala Asn Ala Asp Ile
385                 390                 395                 400

Glu Ile Ser Leu Pro Ala Thr Ser Ala Ala Pro Gly Phe Pro His Pro
                405                 410                 415

Phe His Leu His Gly His Thr Phe Ala Val Val Arg Ser Ala Gly Ser
            420                 425                 430

Ser Thr Tyr Asn Tyr Ala Asn Pro Val Tyr Arg Asp Val Val Ser Thr
            435                 440                 445

Gly Ser Pro Gly Asp Asn Val Thr Ile Arg Phe Arg Thr Asp Asn Pro
450                 455                 460

Gly Pro Trp Phe Leu His Cys His Ile Asp Phe His Leu Glu Ala Gly
465                 470                 475                 480

Phe Ala Val Val Met Ala Glu Asp Ile Pro Asp Val Ala Ala Thr Asn
                485                 490                 495

Pro Val Pro Gln Ala Trp Ser Asp Leu Cys Pro Thr Tyr Asp Ala Leu
            500                 505                 510

Ser Pro Asp Asp Gln
            515

<210> SEQ ID NO 63
<211> LENGTH: 1620
<212> TYPE: DNA
<213> ORGANISM: Coprinopsis cinerea

<400> SEQUENCE: 63
atggtcaaga acctcctctc gttcgcccct ctggcgatta gcgttgccaa cgctcagatc      60
gtcaattcgg tcgataccat gaccctcacc aacgcgaacg tcagtcccga cggtttcact     120
cgagctggta tcctcgtcaa tggagttcat ggacctctta ttcgaggtgg aaagaacgac     180
aactttgagc tcaacgtcgt taacgacttg gacaacccca ctatgcttcg gcctaccagt     240
atccattggc acggtctctt ccaacgaggg accaactggg ctgatggtgc agatggtgtc     300
aaccagtgcc cgatctctcc aggccatgct ttcctctaca agttcactcc agctggccac     360
```

```
gctggtactt tctggtacca ttcccacttt ggcacccaat actgcgatgg tctccgtggt      420
ccaatggtca tttacgacga caatgaccca cacgctgccc tctacgacga ggatgacgag      480
aacaccatca ttaccctcgc cgattggtac catatccccg ctccctccat tcagggtgct      540
gcccagcctg acgctacgct catcaacggt aagggtcgct acgtgggcgg cccagctgcc      600
gagctttcga tcgtcaatgt cgagcaaggg aagaagtacc gaatgcgttt gatctcgctg      660
tcctgcgacc ccaactggca gttctccatt gacggacatg agttgacgat cattgaagtc      720
gatggtcagc ttactgagcc gcatacggtt gatcgtctcc agatcttcac tggtcaaagg      780
tactccttcg ttctcgacgc caaccagccg gtggacaact actggatccg tgctcaaccc      840
aacaagggtc gaaacggact tgctggtacc ttcgccaacg tgtcaactc ggccatcctt       900 cgctatgccg cgctgccaa cgctgatcca accacctccg ccaacccaa ccccgcccaa        960 ctcaacgaag ccgacctcca tgctctcatc gaccccgctg ctcccggtat ccccactccg     1020
ggcgctgcag acgtcaacct ccgattccaa ttgggcttca gcggcggtcg attcacgatt     1080
aacggaaccg catacgagag tccaagcgtt cctacgctct tgcagattat gagtggtgcg     1140
cagagtgcga acgacttgct ccctgctgga tcggtgtatg agttgcccag gaaccaagtt     1200
gttgagcttg ttgttcctgc tggtgtcctc ggtggtcctc atccttttcca tctccacggt    1260 catgcgttca gtgtcgtcag gagtgcaggc agcagcacct acaactttgt caaccccgtc     1320
aagcgcgatg ttgttagtct tggtgttact ggagacgaag ttaccattcg attcgtcacc     1380
gataacccag gcccgtggtt cttccactgc cacattgaat ccatctcat gaacggcttg      1440 gcgatcgtct ttgctgaaga catggcgaac acggttgatg ctaacaaccc acctgtcgag     1500
tgggcccagc tttgcgagat ttacgatgac ctgccgcctg aggcgacctc gattcaaacc     1560
gttgtgcgtc gcgctgagcc caccggcttt tcggccaagt ccgcaggga gggcttgtag      1620
```

<210> SEQ ID NO 64
<211> LENGTH: 539
<212> TYPE: PRT
<213> ORGANISM: Coprinopsis cinerea

<400> SEQUENCE: 64

```
Met Val Lys Asn Leu Leu Ser Phe Ala Leu Leu Ala Ile Ser Val Ala
1               5                   10                  15

Asn Ala Gln Ile Val Asn Ser Val Asp Thr Met Thr Leu Thr Asn Ala
            20                  25                  30

Asn Val Ser Pro Asp Gly Phe Thr Arg Ala Gly Ile Leu Val Asn Gly
        35                  40                  45

Val His Gly Pro Leu Ile Arg Gly Gly Lys Asn Asp Asn Phe Glu Leu
    50                  55                  60

Asn Val Val Asn Asp Leu Asp Asn Pro Thr Met Leu Arg Pro Thr Ser
65                  70                  75                  80

Ile His Trp His Gly Leu Phe Gln Arg Gly Thr Asn Trp Ala Asp Gly
                85                  90                  95

Ala Asp Gly Val Asn Gln Cys Pro Ile Ser Pro Gly His Ala Phe Leu
            100                 105                 110

Tyr Lys Phe Thr Pro Ala Gly His Ala Gly Thr Phe Trp Tyr His Ser
        115                 120                 125

His Phe Gly Thr Gln Tyr Cys Asp Gly Leu Arg Gly Pro Met Val Ile
    130                 135                 140

Tyr Asp Asp Asn Asp Pro His Ala Ala Leu Tyr Asp Glu Asp Asp Glu
```

| | | 145 | | | 150 | | | | 155 | | | 160 |
|---|---|---|---|---|---|---|---|---|---|---|---|---|

Asn Thr Ile Ile Thr Leu Ala Asp Trp Tyr His Ile Pro Ala Pro Ser
                  165                  170                  175

Ile Gln Gly Ala Ala Gln Pro Asp Ala Thr Leu Ile Asn Gly Lys Gly
                180                185              190

Arg Tyr Val Gly Gly Pro Ala Ala Glu Leu Ser Ile Val Asn Val Glu
        195                200              205

Gln Gly Lys Lys Tyr Arg Met Arg Leu Ile Ser Leu Ser Cys Asp Pro
210                215                220

Asn Trp Gln Phe Ser Ile Asp Gly His Glu Leu Thr Ile Ile Glu Val
225                230              235              240

Asp Gly Gln Leu Thr Glu Pro His Thr Val Asp Arg Leu Gln Ile Phe
            245              250              255

Thr Gly Gln Arg Tyr Ser Phe Val Leu Asp Ala Asn Gln Pro Val Asp
        260              265              270

Asn Tyr Trp Ile Arg Ala Gln Pro Asn Lys Gly Arg Asn Gly Leu Ala
    275              280              285

Gly Thr Phe Ala Asn Gly Val Asn Ser Ala Ile Leu Arg Tyr Ala Gly
        290              295              300

Ala Ala Asn Ala Asp Pro Thr Thr Ser Ala Asn Pro Asn Pro Ala Gln
305                310              315              320

Leu Asn Glu Ala Asp Leu His Ala Leu Ile Asp Pro Ala Ala Pro Gly
            325              330              335

Ile Pro Thr Pro Gly Ala Ala Asp Val Asn Leu Arg Phe Gln Leu Gly
        340              345              350

Phe Ser Gly Gly Arg Phe Thr Ile Asn Gly Thr Ala Tyr Glu Ser Pro
    355              360              365

Ser Val Pro Thr Leu Leu Gln Ile Met Ser Gly Ala Gln Ser Ala Asn
        370              375              380

Asp Leu Leu Pro Ala Gly Ser Val Tyr Glu Leu Pro Arg Asn Gln Val
385                390              395              400

Val Glu Leu Val Val Pro Ala Gly Val Leu Gly Gly Pro His Pro Phe
            405              410              415

His Leu His Gly His Ala Phe Ser Val Val Arg Ser Ala Gly Ser Ser
        420              425              430

Thr Tyr Asn Phe Val Asn Pro Val Lys Arg Asp Val Val Ser Leu Gly
            435              440              445

Val Thr Gly Asp Glu Val Thr Ile Arg Phe Val Thr Asp Asn Pro Gly
450                455              460

Pro Trp Phe Phe His Cys His Ile Glu Phe His Leu Met Asn Gly Leu
465                470              475              480

Ala Ile Val Phe Ala Glu Asp Met Ala Asn Thr Val Asp Ala Asn Asn
            485              490              495

Pro Pro Val Glu Trp Ala Gln Leu Cys Glu Ile Tyr Asp Asp Leu Pro
        500              505              510

Pro Glu Ala Thr Ser Ile Gln Thr Val Val Arg Arg Ala Glu Pro Thr
    515              520              525

Gly Phe Ser Ala Lys Phe Arg Arg Glu Gly Leu
        530              535

<210> SEQ ID NO 65
<211> LENGTH: 1602
<212> TYPE: DNA
<213> ORGANISM: Pleurotus ostreatus

<400> SEQUENCE: 65

```
atgtttccag gcgcacggat tcttgctacg cttaccttgg ctcttcatct tttacatggg      60
actcatgctg ccatcgggcc cactggcaac atgtacatcg tcaacgagga cgtctctcct    120
gatggattcg ctcgttcggc ggttgtcgct cgctcggtgc ccgctacaga tccgacgcct    180
gcgacagtat ccattcctgg cgttctcgtt caaggaaaca agggcgataa cttccagctg    240
aacgtcgtca atcaattgtc ggacacgacc atgttgaaga cgaccagtat ccattggcac    300
ggtttcttcc aagccggatc ttcgtgggct gatggtcccg ctttcgtgac ccaatgcccc    360
gtcgcctctg ggatagttt cctgtacaat ttcaatgtcc cagaccaagc tggaacgttt    420
tggtatcact cgcatctttc acccaatat tgtgacggcc tcagaggacc attcgtggta    480
tacgaccct cggatccgca cttgagttta cgatattg acaacgccga cacggtcatt    540
acgcttgagg attggtatca tatcgtggct ccccaaaacg cggcaatccc aactccggat    600
agtaccctca tcaatggtaa aggtcgttat gccgggggcc ctacctctcc tttgtccatc    660
atcaacgtcg aaagcaacaa gcgctatcgt ttcagacttg tctcaatgtc ttgtgacccc    720
aatttcacgt tctcgatcga cggtcactct ttgctcgtca ttgaagcaga tgctgtcaac    780
attgttccca tcaccgtgga tagtattcag atcttcgctg ccaacgcta ctccttcgtc    840
ttgactgctg atcaaaccgt tggcaactac tggattcgcg cgaatcctaa cttgggatcg    900
actggcttcg atggtggtat caattccgct attcttcggt atgctggtgc cactgaggat    960
gaccccacca caacctcgtc gacgagcacc ccattgctgg agaccaacct tgttccgctt   1020
gagaatcctg gtgctcctgg cccagccgtg cctggtggag cagacatcaa catcaatctc   1080
gctatggcct tcgacttcac taacttcgaa ttgactatca acggcgttcc tttcatccca   1140
cccactgccc ctgtccttct tcaaattctc tcaggagcct cctctgctgc ctcgctgctt   1200
ccttctggta gtatttacgc gctggagcct aataaggttg ttgaaatctc gatgcctgcg   1260
ctggctgtcg ggggaccca tccattccat ctccacggcc acaccttcga cgttattagg   1320
agtgcgggtt ccactacata caactttgac actcctgcgc ccgcgacgt agtcaacact   1380
ggcactggcg cgaacgacaa cgtcactatt cgcttcgtga ccgacaaccc agggccgtgg   1440
ttcctccact gtcacattga ttggcatctc gaaattggtc tcgctgtcgt tttcgccgaa   1500
gacgtgacat ccatttcggc cccacctgcc gcgtgggacg acttgtgccc catctatgac   1560
gcattgagcg acaacgacaa aggaggcatc gttccgtcct aa                     1602
```

<210> SEQ ID NO 66
<211> LENGTH: 533
<212> TYPE: PRT
<213> ORGANISM: Pleurotus ostreatus

<400> SEQUENCE: 66

Met Phe Pro Gly Ala Arg Ile Leu Ala Thr Leu Thr Leu Ala Leu His
1               5                   10                  15

Leu Leu His Gly Thr His Ala Ala Ile Gly Pro Thr Gly Asn Met Tyr
            20                  25                  30

Ile Val Asn Glu Asp Val Ser Pro Asp Gly Phe Ala Arg Ser Ala Val
        35                  40                  45

Val Ala Arg Ser Val Pro Ala Thr Asp Pro Thr Pro Ala Thr Val Ser
    50                  55                  60

Ile Pro Gly Val Leu Val Gln Gly Asn Lys Gly Asp Asn Phe Gln Leu
65                  70                  75                  80

```
Asn Val Val Asn Gln Leu Ser Asp Thr Thr Met Leu Lys Thr Thr Ser
            85                  90                  95
Ile His Trp His Gly Phe Phe Gln Ala Gly Ser Ser Trp Ala Asp Gly
                100                 105                 110
Pro Ala Phe Val Thr Gln Cys Pro Val Ala Ser Gly Asp Ser Phe Leu
                115                 120                 125
Tyr Asn Phe Asn Val Pro Asp Gln Ala Gly Thr Phe Trp Tyr His Ser
        130                 135                 140
His Leu Ser Thr Gln Tyr Cys Asp Gly Leu Arg Gly Pro Phe Val Val
145                 150                 155                 160
Tyr Asp Pro Ser Asp Pro His Leu Ser Leu Tyr Asp Ile Asp Asn Ala
                165                 170                 175
Asp Thr Val Ile Thr Leu Glu Asp Trp Tyr His Ile Val Ala Pro Gln
                180                 185                 190
Asn Ala Ala Ile Pro Thr Pro Asp Ser Thr Leu Ile Asn Gly Lys Gly
                195                 200                 205
Arg Tyr Ala Gly Gly Pro Thr Ser Pro Leu Ser Ile Asn Val Glu
        210                 215                 220
Ser Asn Lys Arg Tyr Arg Phe Arg Leu Val Ser Met Ser Cys Asp Pro
225                 230                 235                 240
Asn Phe Thr Phe Ser Ile Asp Gly His Ser Leu Leu Val Ile Glu Ala
                245                 250                 255
Asp Ala Val Asn Ile Val Pro Ile Thr Val Asp Ser Ile Gln Ile Phe
                260                 265                 270
Ala Gly Gln Arg Tyr Ser Phe Val Leu Thr Ala Asp Gln Thr Val Gly
                275                 280                 285
Asn Tyr Trp Ile Arg Ala Asn Pro Asn Leu Gly Ser Thr Gly Phe Asp
        290                 295                 300
Gly Gly Ile Asn Ser Ala Ile Leu Arg Tyr Ala Gly Ala Thr Glu Asp
305                 310                 315                 320
Asp Pro Thr Thr Thr Ser Ser Thr Ser Thr Pro Leu Leu Glu Thr Asn
                325                 330                 335
Leu Val Pro Leu Glu Asn Pro Gly Ala Pro Gly Pro Ala Val Pro Gly
                340                 345                 350
Gly Ala Asp Ile Asn Ile Asn Leu Ala Met Ala Phe Asp Phe Thr Asn
        355                 360                 365
Phe Glu Leu Thr Ile Asn Gly Val Pro Phe Ile Pro Pro Thr Ala Pro
        370                 375                 380
Val Leu Leu Gln Ile Leu Ser Gly Ala Ser Ala Ala Ser Leu Leu
385                 390                 395                 400
Pro Ser Gly Ser Ile Tyr Ala Leu Glu Pro Asn Lys Val Val Glu Ile
                405                 410                 415
Ser Met Pro Ala Leu Ala Val Gly Gly Pro His Pro Phe His Leu His
                420                 425                 430
Gly His Thr Phe Asp Val Ile Arg Ser Ala Gly Ser Thr Thr Tyr Asn
        435                 440                 445
Phe Asp Thr Pro Ala Arg Arg Asp Val Val Asn Thr Gly Thr Gly Ala
        450                 455                 460
Asn Asp Asn Val Thr Ile Arg Phe Val Thr Asp Asn Pro Gly Pro Trp
465                 470                 475                 480
Phe Leu His Cys His Ile Asp Trp His Leu Glu Ile Gly Leu Ala Val
                485                 490                 495
```

Val Phe Ala Glu Asp Val Thr Ser Ile Ser Ala Pro Ala Ala Trp
            500                 505                 510

Asp Asp Leu Cys Pro Ile Tyr Asp Ala Leu Ser Asp Asn Asp Lys Gly
        515                 520                 525

Gly Ile Val Pro Ser
        530

<210> SEQ ID NO 67
<211> LENGTH: 1596
<212> TYPE: DNA
<213> ORGANISM: Thanatephorus cucumeris

<400> SEQUENCE: 67

| | | | | | |
|---|---|---|---|---|---|
| atgctttcta | gcattaccct | cctacctttg | cttgctgcgg | tttcaacccc | cgcctttgct | 60 |
| gccgtccgca | actacaagtt | cgacatcaag | aacgtcaatg | tcgctcccga | tggctttcag | 120 |
| cgtcctatcg | tctccgtcaa | cggtctagtt | cctggcacgt | tgatcacggc | caacaagggc | 180 |
| gacaccttgc | gcattaatgt | cacgaatcaa | ctcacggacc | ctagtatgcg | tcgtgccaca | 240 |
| acgattcatt | ggcatggatt | gttccaagct | actaccgccg | acgaggatgg | ccccgcattc | 300 |
| gtcacgcaat | gccctattgc | gcaaaatttg | tcctatacat | acgagatccc | gttgcacggc | 360 |
| caaacaggaa | ccatgtggta | tcacgcccat | cttgcgagtc | aatatgtcga | tggattgcga | 420 |
| ggccctttgg | tcatctatga | tccaaacgac | ccacacaagt | cgcgctacga | cgtggatgat | 480 |
| gcgagcacag | tagtcatgct | tgaggactgg | taccatactc | cggcacccgt | tctagaaaag | 540 |
| caaatgttct | cgactaataa | caccgctctg | ctctctcctg | ttccggactc | gggtcttatc | 600 |
| aatggcaaag | gcgctatgt | gggcggtccc | gcagttcccc | ggtcagtaat | caacgtaaaa | 660 |
| cgtgggaaac | gatatcgctt | gcgcgtaatc | aacgcttctg | ctatcgggtc | gtttaccttt | 720 |
| tcgatcgaag | gacatcgtct | gactgtcatt | gaggccgatg | ggatcccgca | ccagcccttg | 780 |
| cctgttgata | gcttccagat | ttacgctgga | caacgctact | ctgtcatcgt | tgaagccaac | 840 |
| caaaccgctg | ccaattactg | gattcgcgca | ccaatgaccg | ttgcaggagc | aggaaccaac | 900 |
| gcaaacttgg | accccaccaa | tgtctttgcc | gtgttgcact | acgagggagc | acccaacgcc | 960 |
| gaacccacga | cggaacaagg | cagtgctatc | ggtactgcac | tcgttgaaga | gaacctccat | 1020 |
| gcgctcatca | accctggcgc | tccgggcggc | tccgctcccg | cagacgtttc | cctcaatctc | 1080 |
| gcaattgggc | gcagtacagt | tgatgggatt | cttaggttca | catttaataa | catcaagtac | 1140 |
| gaggctcctt | cgttgcccac | gctcttgaag | attttggcaa | ataatgcgag | caatgacgcc | 1200 |
| gatttcacgc | caaatgagca | cactatcgta | ttgccacaca | ataaagttat | cggagctcaa | 1260 |
| catcaccgag | gtgcagacca | ccctatccat | ctccacggcc | atgtgtttga | cattgtcaaa | 1320 |
| tcgctcggtg | gtaccccgaa | ctatgtcaac | ccgcctcgca | gggatgtagt | tcgtgtcgga | 1380 |
| ggcaccggtg | tggtactccg | attcaaggcc | gataacccag | gcccatggtt | tgttcactgc | 1440 |
| cacattgact | gcacttggag | gctgggctcg | cacttgtctt | tgccgaggcc | cccagccaga | 1500 |
| ttcgccaggg | tgtccagtcg | gtccagccca | acaatgcctg | gaaccagctc | tgccccaagt | 1560 |
| acgcggctct | tcctcccgat | tgcagtaaa | tggtga | | | 1596 |

<210> SEQ ID NO 68
<211> LENGTH: 531
<212> TYPE: PRT
<213> ORGANISM: Thanatephorus cucumeris

<400> SEQUENCE: 68

```
Met Leu Ser Ser Ile Thr Leu Leu Pro Leu Ala Ala Val Ser Thr
1               5                   10                  15

Pro Ala Phe Ala Ala Val Arg Asn Tyr Lys Phe Asp Ile Lys Asn Val
            20                  25                  30

Asn Val Ala Pro Asp Gly Phe Gln Arg Pro Ile Val Ser Val Asn Gly
            35                  40                  45

Leu Val Pro Gly Thr Leu Ile Thr Ala Asn Lys Gly Asp Thr Leu Arg
50                  55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
            100                 105                 110

Thr Tyr Glu Ile Pro Leu His Gly Gln Thr Gly Thr Met Trp Tyr His
            115                 120                 125

Ala His Leu Ala Ser Gln Tyr Val Asp Gly Leu Arg Gly Pro Leu Val
            130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
            165                 170                 175

Val Leu Glu Lys Gln Met Phe Ser Thr Asn Asn Thr Ala Leu Leu Ser
            180                 185                 190

Pro Val Pro Asp Ser Gly Leu Ile Asn Gly Lys Gly Arg Tyr Val Gly
            195                 200                 205

Gly Pro Ala Val Pro Arg Ser Val Ile Asn Val Lys Arg Gly Lys Arg
210                 215                 220

Tyr Arg Leu Arg Val Ile Asn Ala Ser Ala Ile Gly Ser Phe Thr Phe
225                 230                 235                 240

Ser Ile Glu Gly His Arg Leu Thr Val Ile Glu Ala Asp Gly Ile Pro
            245                 250                 255

His Gln Pro Leu Pro Val Asp Ser Phe Gln Ile Tyr Ala Gly Gln Arg
            260                 265                 270

Tyr Ser Val Ile Val Glu Ala Asn Gln Thr Ala Ala Asn Tyr Trp Ile
            275                 280                 285

Arg Ala Pro Met Thr Val Ala Gly Ala Gly Thr Asn Ala Asn Leu Asp
            290                 295                 300

Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
            325                 330                 335

Glu Asn Leu His Ala Leu Ile Asn Pro Gly Ala Pro Gly Gly Ser Ala
            340                 345                 350

Pro Ala Asp Val Ser Leu Asn Leu Ala Ile Gly Arg Ser Thr Val Asp
            355                 360                 365

Gly Ile Leu Arg Phe Thr Phe Asn Asn Ile Lys Tyr Glu Ala Pro Ser
370                 375                 380

Leu Pro Thr Leu Leu Lys Ile Leu Ala Asn Ala Ser Asn Asp Ala
385                 390                 395                 400

Asp Phe Thr Pro Asn Glu His Thr Ile Val Leu Pro His Asn Lys Val
            405                 410                 415

Ile Gly Ala Gln His His Arg Gly Ala Asp His Pro Ile His Leu His
```

```
            420             425             430
Gly His Val Phe Asp Ile Val Lys Ser Leu Gly Gly Thr Pro Asn Tyr
            435             440             445
Val Asn Pro Pro Arg Arg Asp Val Val Arg Val Gly Gly Thr Gly Val
        450             455             460
Val Leu Arg Phe Lys Ala Asp Asn Pro Gly Pro Trp Phe Val His Cys
465             470             475             480
His Ile Asp Cys Thr Trp Arg Leu Gly Ser His Leu Ser Leu Pro Arg
                485             490             495
Pro Pro Ala Arg Phe Ala Arg Val Ser Ser Arg Ser Ser Pro Thr Met
            500             505             510
Pro Gly Thr Ser Ser Ala Pro Ser Thr Arg Leu Phe Leu Pro Ile Cys
        515             520             525
Ser Lys Trp
    530

<210> SEQ ID NO 69
<211> LENGTH: 1557
<212> TYPE: DNA
<213> ORGANISM: Volvariella volvacea

<400> SEQUENCE: 69
atgcaatctt tgctcaacac actcaccgcc atggtgaccg tggtgggatg gggtgctaac      60
tttgctgcag ccgcattgag ctcgcatacg ttgacactta ccaatggctt cgcctcccccc    120 gatggccact ctcgcgaagt ggttctggtc aatgggggggc tgttccaagc tgtcatcgcg    180
ggtaacaagg gcgatgactt cgagatcgaa gtagacaacc aattgaccgt tgagatttta    240
cgcaagagta cctctattca ctggcacgga ctgttccaac gcggaagtgc atgggcagat    300
ggtcctgcct tcgtcactca gtgcccaatt gctcctggaa ataccttcac ctacgagttc    360
acgcccaccg atgaagttgg gacattctgg tatcattccc atctcgatgc gcaatattgt    420
gatggactca gaggacccctt tgtcatctat gaccccaacg accctcatct cgccctctac    480
gatgttgacg atgaggatac catcattact ctggctgatt ggtaccacac tgcggctgag    540
ttactcaccg gtgtagttat tcctgactcg gctcttatca atggtttggg tcgcacatcc    600
acgacaacta cttcacctct cgctgtgata aacgttgtac aaggaaccaa gtatcgcatg    660
aggctgattt cgatctcttg cgatccaaac aactatatat tctccattga agatcatgag    720 atgcacagtaa ttgaagcgga tggtattagt gtggatcctg ttactgtgac atcattgcag    780
attttcgttg gccaacgata ctcctttatc cttcacgcaa accaacccgt tgataactac    840
tggatccgtg caaaccccaa cctaggacca accggatttt ctggtggcat caatagtgca    900
attttgcgct accaaggagc accagttgca gaccccaccg gtccaggact tcaggatgca    960
ctcaaccgtc tggcagaaac tgacttgcac cccatcgtca accctggtgc tcctgaccca   1020
gtagacattg acttggttat caatattgga ttttctgctg gtttattcaa catcgatggt   1080
acttcatacg tatctcccga tgttccatct ctccttcaga tccttaacgg tgttcccgtt   1140
agctcgctct tgcctagtgg ttcatacatc gaattgccac taataaggt agtgcagctt   1200 tcattcccag tgattgctgg ccaaggttcc gccattggtg ctcctcatcc catccatctt   1260
cacggccacg ccttcgacgt cattcgtagc gccggatctt caacctataa ccttgtcgat   1320
cctgtccgtc gggatgtcgt ttctataggt acacctggcg ataacgttac aatccgcttc   1380
gtcaccgata atgcaggccc ttggtacttg cactgccata ttgagtggca cctccgcgct   1440
```

```
gggctgggtg tcattttttgc tgaagatgct gcaggaagtc tacttcaacc tgcacctcca    1500
acggcttggg gtgatctttg cgatatttac gatctcttgc ccctgagga tcagtaa       1557
```

<210> SEQ ID NO 70
<211> LENGTH: 518
<212> TYPE: PRT
<213> ORGANISM: Volvariella volvacea

<400> SEQUENCE: 70

```
Met Gln Ser Leu Leu Asn Thr Leu Thr Ala Met Val Thr Val Val Gly
1               5                   10                  15

Trp Gly Ala Asn Phe Ala Ala Ala Ala Leu Ser Ser His Thr Leu Thr
            20                  25                  30

Leu Thr Asn Gly Phe Ala Ser Pro Asp Gly His Ser Arg Glu Val Val
        35                  40                  45

Leu Val Asn Gly Gly Leu Phe Gln Ala Val Ile Ala Gly Asn Lys Gly
    50                  55                  60

Asp Asp Phe Glu Ile Glu Val Asp Asn Gln Leu Thr Val Glu Ile Leu
65                  70                  75                  80

Arg Lys Ser Thr Ser Ile His Trp His Gly Leu Phe Gln Arg Gly Ser
                85                  90                  95

Ala Trp Ala Asp Gly Pro Ala Phe Val Thr Gln Cys Pro Ile Ala Pro
            100                 105                 110

Gly Asn Thr Phe Thr Tyr Glu Phe Thr Pro Thr Asp Glu Val Gly Thr
        115                 120                 125

Phe Trp Tyr His Ser His Leu Asp Ala Gln Tyr Cys Asp Gly Leu Arg
    130                 135                 140

Gly Pro Phe Val Ile Tyr Asp Pro Asn Asp Pro His Leu Ala Leu Tyr
145                 150                 155                 160

Asp Val Asp Asp Glu Asp Thr Ile Ile Thr Leu Ala Asp Trp Tyr His
                165                 170                 175

Thr Ala Ala Glu Leu Leu Thr Gly Val Val Ile Pro Asp Ser Ala Leu
            180                 185                 190

Ile Asn Gly Leu Gly Arg Thr Ser Thr Thr Thr Ser Pro Leu Ala
        195                 200                 205

Val Ile Asn Val Val Gln Gly Thr Lys Tyr Arg Met Arg Leu Ile Ser
    210                 215                 220

Ile Ser Cys Asp Pro Asn Asn Tyr Ile Phe Ser Ile Glu Asp His Glu
225                 230                 235                 240

Met Thr Val Ile Glu Ala Asp Gly Ile Ser Val Asp Pro Val Thr Val
                245                 250                 255

Thr Ser Leu Gln Ile Phe Val Gly Gln Arg Tyr Ser Phe Ile Leu His
            260                 265                 270

Ala Asn Gln Pro Val Asp Asn Tyr Trp Ile Arg Ala Asn Pro Asn Leu
        275                 280                 285

Gly Pro Thr Gly Phe Ser Gly Gly Ile Asn Ser Ala Ile Leu Arg Tyr
    290                 295                 300

Gln Gly Ala Pro Val Ala Asp Pro Thr Gly Pro Gly Leu Gln Asp Ala
305                 310                 315                 320

Leu Asn Arg Leu Ala Glu Thr Asp Leu His Pro Ile Val Asn Pro Gly
                325                 330                 335

Ala Pro Asp Pro Val Asp Ile Asp Leu Val Ile Asn Ile Gly Phe Ser
            340                 345                 350

Ala Gly Leu Phe Asn Ile Asp Gly Thr Ser Tyr Val Ser Pro Asp Val
```

```
            355                 360                 365
Pro Ser Leu Leu Gln Ile Leu Asn Gly Val Pro Val Ser Ser Leu Leu
    370                 375                 380

Pro Ser Gly Ser Tyr Ile Glu Leu Pro Pro Asn Lys Val Val Gln Leu
385                 390                 395                 400

Ser Phe Pro Val Ile Ala Gly Gln Gly Ser Ala Ile Gly Ala Pro His
                405                 410                 415

Pro Ile His Leu His Gly His Ala Phe Asp Val Ile Arg Ser Ala Gly
            420                 425                 430

Ser Ser Thr Tyr Asn Leu Val Asp Pro Val Arg Arg Asp Val Val Ser
        435                 440                 445

Ile Gly Thr Pro Gly Asp Asn Val Thr Ile Arg Phe Val Thr Asp Asn
    450                 455                 460

Ala Gly Pro Trp Tyr Leu His Cys His Ile Glu Trp His Leu Arg Ala
465                 470                 475                 480

Gly Leu Gly Val Ile Phe Ala Glu Asp Ala Ala Gly Ser Leu Leu Gln
                485                 490                 495

Pro Ala Pro Pro Thr Ala Trp Gly Asp Leu Cys Asp Ile Tyr Asp Leu
            500                 505                 510

Leu Pro Pro Glu Asp Gln
        515

<210> SEQ ID NO 71
<211> LENGTH: 59
<212> TYPE: DNA
<213> ORGANISM: Artificial Sequence
<220> FEATURE:
<223> OTHER INFORMATION: Artificial DNA Primer

<400> SEQUENCE: 71
tcctctatat acacaactgg ggatccacca tgtcgaggtt tcactctctt ctcgctttc      59

<210> SEQ ID NO 72
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 72
tctagatctc gagctcgcta gagtcgacct actggtcgct cgggtcgag                 49

<210> SEQ ID NO 73
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 73
catggtggat ccccagttgt gtatatagag g                                    31

<210> SEQ ID NO 74
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 74
taggtcgact ctagcgagct cgagatc                                         27
```

<210> SEQ ID NO 75
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 75
acatgtcttt gataagctag cgggccgcat catgta                        36

<210> SEQ ID NO 76
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 76
tacatgatgc ggcccgctag cttatcaaag acatgt                        36

<210> SEQ ID NO 77
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 77
ttaatcgcct tgcagcacac cgcttcctcg ctcactgact c                  41

<210> SEQ ID NO 78
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 78
acaataaccc tgataaatgc ggaacaaac tcaaccctat ctcggtc             47

<210> SEQ ID NO 79
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 79
agatagggtt gagtgttgtt ccgcatttat cagggttatt gtctcatgag cgg     53

<210> SEQ ID NO 80
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 80
ttctacacga aggaaagagg aggagagagt tgaacctgga cg                 42

<210> SEQ ID NO 81
<211> LENGTH: 47
<212> TYPE: DNA
<213> ORGANISM: Artificial Sequence
<220> FEATURE:

<223> OTHER INFORMATION: Artificial DNA Primer

<400> SEQUENCE: 81
aggttcaact ctctcctcct ctttccttcg tgtagaagac cagacag   47

<210> SEQ ID NO 82
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 82
tcagtgagcg aggaagcggt gtgctgcaag gcgattaagt tgg   43

<210> SEQ ID NO 83
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 83
tcaaccgcgg actgcgcacc atgtcgaggt ttcactctct   40

<210> SEQ ID NO 84
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 84
ggctttcgcc acggagctta ctactggtcg ctcgggtcga   40

<210> SEQ ID NO 85
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 85
ctggccgtag agcttaaagt atgtccc   27

<210> SEQ ID NO 86
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 86
cggtcgatta caatcacatg acttggcttc   30

<210> SEQ ID NO 87
<211> LENGTH: 11101
<212> TYPE: DNA
<213> ORGANISM: Artificial Sequence
<220> FEATURE:
<223> OTHER INFORMATION: Artificial DNA Sequence

<400> SEQUENCE: 87
ttgaagttcc tattccgagt tcctattctc tagaaagtat aggaacttca gtacccgggt   60
ataagctagc ttccgttaaa ttgccgtcgt cagccgttaa attaccgatt aatcccgata   120

```
aatttccgag atctccgtta aattgccgtt cgcagccgtt aaattaccgg ggacgaccga    180
taaatttccg cgatgaattc atggtgtttt gatcatttta aatttttata tggcgggtgg    240
tgggcaactc gcttgcgcgg gcaactcgct taccgattac gttagggctg atatttacgt    300
aaaaatcgtc aagggatgca agaccaaacc gttaaatttc cggagtcaac agcatccaag    360
cccaagtcct tcacggagaa accccagcgt ccacatcacg agcgaaggac cacctctagg    420
catcggacgc accatccaat tagaagcagc aaagcgaaac agcccaagaa aaaggtcggc    480
ccgtcggcct tttctgcaac gctgatcacg ggcagcgatc caaccaacac cctccagagt    540
gactaggggc ggaaatttat cgggattaat ttccactcaa ccacaaatca cagtcgtccc    600
cggtaattta acggctgcag acggcaattt aacggcttct gcgaatcgct tggattcccc    660
gcccctggcc gtagagctta aagtatgtcc cttgtcgatg cgatgtatca caacatataa    720
atactggcaa gggatgccat gcttggagtt ccaactcaa tttacctcta tccacacttc      780
tcttccttcc tcaatcctct atatacacaa ctggggatcc accatgttct cggcaggcca    840
caagattaag ggtacagtcg tcctcatgcc taaaaacgag ttggaagtga accccgatgg    900
ctccgcagtc gataacctca acgcattcct cggacgttcg gtgtcgctcc agctcatctc    960
cgcgaccaaa gccgacgccc acggtaaggg aaaggtgggc aaggacacgt tcttggaagg   1020
tatcaacact tcgctcccta ccttgggagc aggagagtcc gcattcaaca ttcacttcga   1080
gtgggacggt tcgatgggca ttcccggagc gttctatatc aagaactata tgcaggtgga   1140
gttcttcttg aagtccttga ccttggaggc aatctcgaac cagggtacca tccgtttcgt   1200
gtgtaactcg tgggtctaca acaccaagct ctacaaatcc gtgcggatct tcttcgcgaa   1260
ccacacttac gtcccttcgg agacacctgc ccctttggtg tcgtaccgcg aggaggaatt   1320
gaagtccctc cgtggtaacg gtactggaga aaggaaggag tatgatagga tctacgacta   1380
cgacgtctat aacgatttgg gtaaccccga caaatcggaa aagttggcac gtcctgtgtt   1440
gggaggctcc tccaccttcc cctaccctcg acgcggccgc acgggacgcg gtcccactgt   1500
caccgatccg aacacagaga agcagggcga agtcttctac gtgccagggg acgaaaacct   1560
cggccacttg aagtcgaagg atgcattgga gattggaacc aagtccctct cccagatcgt   1620
ccagcctgca ttcgaatcgg cgttcgattt gaaatcgacg cccatcgagt tccactcgtt   1680
ccaggacgtc catgacttgt atgaaggtgg tatcaaattg cctcgggacg tcatctccac   1740
cattatcccc ctccccgtga tcaaggaatt gtaccgcacc gacggccagc atattctcaa   1800 attccccag ccgcacgtcg tccaggtctc gcagtccgca tggatgacag atgaggaatt    1860
cgcgagggaa atgattgcag gtgtcaaccc gtgtgtcatc cgaggcttgg aggagttccc   1920
tcctaagtcc aacctcgatc ctgccatcta tggagaccag tcctccaaga ttacagccga   1980
ttccctcgat ctcgacggtt atactatgga tgaagcactc ggttccaggc gattgttcat   2040
gctcgattat catgatatct tcatgcccta tgtgcgccag atcaaccagt tgaactcggc   2100
aaaaacatat gcaacgagga cgatcctctt cctccgagaa gacggcacac tcaagcctgt   2160
ggcaatcgag ctctcgctcc cccattccgc aggcgatctc tccgcagccg tgtcgcaggt   2220
ggtgttgcct gcaaaagaag gagtggagtc gaccatctgg ctcttggcca aagcatatgt   2280
gattgtgaac gattcctgtt atcaccagct catgtcgcat ggctcaaca ctcacgcggc     2340 aatggaaccc ttcgtgatcg ccacgcaccg gcacctctcg gtgctccacc cgatctacaa   2400
gctcctcact ccccactacc gtaacaacat gaacattaac gccttggcac ggcagtcgtt   2460
```

-continued

```
gatcaacgcg aacggcatca ttgagacaac gttcctcccc tccaagtact ccgtcgaaat   2520
gtcgtccgca gtctacaaaa actgggtctt caccgaccag gcgttgcctg ccgacttgat   2580
caaacgaggc gtcgcaatca aagatccctc cactcctcat ggcgtccgcc tcttgatcga   2640
ggactacccc tacgcagcgg acggattgga aatctgggca gccatcaaga cctgggtgca   2700
ggaatacgtc cctttgtact atgcgaggga cgatgatgtc aaaaacgact cggaactcca   2760
gcattggtgg aaggaggcag tggaaaaggg ccatggagat ctcaaggata aaccctggtg   2820
gcctaagctc cagaccttgg aggacctcgt cgaagtgtgt ttgatcatta tctggatcgc   2880
atccgcgttg catgcagccg tgaacttcgg acagtatccc tatggaggcc tcatcatgaa   2940
ccgtcccacc gcatccagga ggctcctccc cgaaaaagga cacccgaat acgaagaaat    3000 gatcaacaac cacgaaaagg catacctccg gaccatcact tccaaactcc cgaccttgat   3060
ctcgctctcc gtgatcgaga ttttgtcgac acatgcgtcg gacgaggtct atttgggtca   3120
gcgggataac ccgcactgga catccgattc caaggccctc caggcgttcc agaagttcgg   3180
caacaagctc aaggagatcg aggagaaact cgtgaggcgg aacaacgacc cttccctcca   3240
gggaaaccgg ttgggacctg tccagctccc gtatacgttg ctctacccct cctcggaaga   3300
aggcctcact ttcaggggta tccccaactc gatttccatc tgactcgaga tctagagggt   3360
gactgacacc tggcggtaga caatcaatcc atttcgctat agttaaagga tggggatgag   3420
ggcaattggt tatatgatca tgtatgtagt gggtgtgcat aatagtagtg aaatggaagc   3480
caagtcatgt gattgtaatc gaccgacgga attgaggata tccggaaata cagacaccgt   3540
gaaagccatg gtctttcctt cgtgtagaag accagacaga cagtccctga tttacccttg   3600
cacaaagcac tagaaaatta gcattccatc cttctctgct tgctctgctg atatcactgt   3660
cattcaatgc atagccatga gctcatctta gatccaagca cgtaattcca tagccgaggt   3720
ccacagtgga gcagcaacat tccccatcat tgctttcccc aggggcctcc caacgactaa   3780
atcaagagta tatctctacc gtccaataga tcgtcttcgc ttcaaaatct ttgacaattc   3840
caagagggtc cccatccatc aaacccagtt caataatagc cgagatgcat ggtggagtca   3900
attaggcagt attgctggaa tgtcggggcc agttggccgg tggtcattg gccgcctgtg    3960 atgccatctg ccactaaatc cgatcattga tccaccgccc acgaggcgcg tctttgcttt   4020
ttgcgcggcg tccaggttca actctctctt aattaaatag cgacaagccg aacggcaccg   4080
gcaggtacaa tggttcgctg tacttgcttg cgcaagcggg tctttgggga ttgagcgcat   4140
ttggtgttgc aaaggatttg atgtaaatgt agtcgacatc ttagcacaga ggggagagtt   4200
gataaaatgt ggtctgtttg aatgatagtc gggttcgtga cctatattcg tgatagtgga   4260
gataggtctg cgcctatctt atcgggccgg agcaaaaatt ccaccgcagc ggggtgagtt   4320 tcgttatac agccatccca cttccagctt caaattgtca gtttaatcca gcccaattca    4380
atcattggag aaccggtttt atgtcttcga agtcccacct cccctacgca attcgcgcaa   4440
ccaaccatcc caacccttta acatctaaac tcttctccat cgccgaggag aagaaaacca   4500
acgtcaccgt ctccgcagac gttactactt ccgccgagct cctcgatctt gctgaccgcc   4560
taggccccta tcgcagtt ctgaaaaccc acatcgacat cctcaccgat ctcacccgt      4620 cgacccttc ctcgctccaa tccctcgcga caaagcacaa cttcctcatc tttgaggacc    4680
gcaagttcat cgacatcggc aacaccgtgc aaaagcagta ccacggtggc gctctccgca   4740
tctccgaatg gcacacatc atcaactgcg ccatcctgcc gggcgaaggg atcgtcgagg    4800
ccctcgcaca gacaaccaag tctcctgact ttaaagacgc gaatcaacga ggtctcctga   4860
```

```
ttcttgccga gatgacgagt aagggatctc ttgcgacagg ggagtacacg gcacgctcgg   4920
ttgagtacgc gcggaagtat aaggggtttg tgatgggatt cgtgagtaca agggcgttga   4980
gtgaggtgct gcccgaacag aaagaggaga gcgaggattt tgtcgtcttt acgactgggg   5040
tgaatctgtc ggataagggg gataagctgg ggcagcagta tcagacacct gggtcggcgg   5100
ttgggcgagg tgcggacttt atcattgcgg gtaggggcat ctataaggcg gacgatccag   5160
tcgaggcggt tcagaggtac cgggaggaag gctggaaagc ttacgagaaa agagttggac   5220
tttgagggtg actgacacct ggcggtagac aatcaatcca tttcgctata gttaaaggat   5280
ggggatgagg gcaattggtt atatgatcat gtatgtagtg ggtgtgcata atagtagtga   5340
aatggaagcc aagtcatgtg attgtaatcg accgacggaa ttgaggatat ccggaaatac   5400
agacaccgtg aaagccatgg tctttccttc gtgtagaaga ccagacagac agtccctgat   5460
ttacccttgc acaaagcact agaaaattag cattccatcc ttctctgctt gctctgctga   5520
tatcactgtc attcaatgca tagccatgag ctcatcttag atccaagcac gtaattccat   5580
agccgaggtc cacagtggag cagcaacatt ccccatcatt gctttcccca ggggcctccc   5640
aacgactaaa tcaagagtat atctctaccg tccaatagat cgtcttcgct tcaaaatctt   5700
tgacaattcc aagagggtcc ccatccatca aacccagttc aataatagcc gagatgcatg   5760
gtggagtcaa ttaggcagta ttgctggaat gtcggggcca gttggccggg tggtcattgg   5820
ccgcctgtga tgccatctgc cactaaatcc gatcattgat ccaccgccca cgaggcgcgt   5880
ctttgctttt tgcgcggcgt ccaggttcaa ctctctcctc taggttgaag ttcctattcc   5940
gagttcctat tcttcaaata gtataggaac ttcaactagc tagtgcatgc gtacgatttt   6000
gacatttgct ccattgtcga ggatggatgg aacgagcggc gtgcgccacg aaagtgaggc   6060
tattgcctat cagctctttg ctacattccg gaaacaaaca tccctttttg tgaattatct   6120
acgcaactta gatggcgtga acgcatcttc aaagtctttc ggcaggtccg gcacgacttt   6180
tgcatccaga gaagcgccta catgtgtatt cgaccacctc ctagcgcgct tggatatgag   6240
gaaatattac tgagagtcga aaacaagctc caccgcacca gctcttcttg gagttttata   6300
ttaaagaata ttcccagctc gttgtattat tctttttcta ccgtgctaat gtatcaagga   6360
ctttggtacc tattaacgtt attattcgtg tgctattccc aaacataacc ctgtatatgt   6420
ttcgaacgcc gttatgaccc atgtcttaca tactcattaa gtcattccct tggataatct   6480
cgactcagat gcggcggttg atgtaggagg agaggtaatc gaggacctcc tgggagatga   6540
tgccgttcca ggcggggtag cggatggagc cctcggcgga gcccttgagc tgctcgatat   6600
gctgccactc ctcgatgggg ttggtctcat ccttgagggc gatcatctcc ttggagatgg   6660
gatcgtaggc gtagtagcgg gagactagtg cgaagtaatg atcggggatg gcggtgatct   6720
gatgggtgta ggtggtgcgg gcgacggcgg aggcgcgctt atcggaccag ttgccgacga   6780
cgttggtgag ctcggtgagg cccttcatgg agaggaagga ggtcatgaga tggcggccga   6840
tatgggactt ggggccgttc ttgatggcga agatggagta ggggcgttc ttcttgaggg   6900
ccttgttgta ggagcggacg aggttatcct tgaggagctg gtactcctgc ttgttggagg   6960
aggagttgcc ggtgcggttg acgcgcttga ggacgggctc ggagttgcgg aggaactcat   7020
cgaggtagac gaggggatcg atgcggccgc gggcggagaa gaagtagata tggcgggaga   7080
cggaggtctt ggtctcggtg acgaggcact ggatgatgac gccgaggtac ttgttctgga   7140
cgagcttgaa ggacttggga tcgacgttct tgatatcgga gaagcggccg cagttgatga   7200
```

```
aggtggcgag gaagaggaac tggtagaggg tcttggtctt ggtgaagcgg gaggtgtact   7260
cgaaggagtt gaggatcttc tcggtgatct cccagatgga ctcgccctcg agaggaggg    7320 ccttgagcat cttcttggaa tgggagttgc ccttatcggc ctcctcggag gactcgaact   7380
ggagctggag ggaggagacg atatcggtga tatcggactg atgcttctgg ccgtagtagg   7440
ggatgatggt gaactcccag gcggggatga gcttcttgag ggaggcctcc aggatggtgg   7500
ccttctgggg cttgtacttg aactggaggg acttgttgac gatatcgaag agagggagt    7560 tggagatgat ggtgttgtag gacatgaagg tggcgcgctt gatggcggtg ccgttatggg   7620
tgatcatcca gcagaggtag gtgagctcgg cggcgcagag ggcgatcttc tcgccggagg   7680
ggcgctcgaa gcgctcgacg aactggcgga cgaggacctt ggggggggtc ttgcagagga   7740
tatcgaactg gggcatggtg ctcagatact acggctgatc gcgtagaggt actgagcaaa   7800
acagatgtca gtaaggagaa gagttgaatg aatggaagaa gagtaggaaa ggaggtatgg   7860
gggaaagata tacgtactga tgcggacgaa gagagaaaga aggaaaaaag ttgtgggagg   7920
ggaaggaggg ggaatcctta tatggagggg caagcgagaa ggcgaattag tgggcgggct   7980
taagccctcg accgccgccc ttatcattgg acatggaggg gtaatgcccc caccacgcat   8040
gtgcgggacc gacgcagaat ctgcacggcg gagtctcttc cagactgttg acttttgggc   8100
gatgactctt gttgctgcgg ccttttgggt acaccaacct cgttgatctt gtttccttgg   8160 ttctcttttcg ctcggagacc cgaccatgac cccaccatca gtcactatcc tgcctcgtcg   8220
ataaaaattt tttcttccct ctgattgtta catagtatgt ttccaccttt ccggtggatt   8280
tcggacagtc aaactgggca tcaacgcagt ggtgggctgc ttcgtttgct gcgtgttgta   8340
cttgtttgca tttgaacccc gcggtcgttc gagtccttaa ttggtccgct cccggtcaac   8400
acccaagcag ctgtggcccg gccgagtggc gcctgtctgg tccacagtaa gcttggcgta   8460
atcatggtca tagctgtttc ctgtgtgaaa ttgttatccg ctcacaattc cacacaacat   8520
acgagccgga agcataaagt gtaaagcctg gggtgcctaa tgagtgagct aactcacatt   8580
aattgcgttg cgctcactgc ccgctttcca gtcgggaaac ctgtcgtgcc agctgcatta   8640
atgaatcggc caacgcgcgg ggagaggcgg tttgcgtatt gggcgctctt ccgcttcctc   8700
gctcactgac tcgctgcgct cggtcgttcg gctgcggcga gcggtatcag ctcactcaaa   8760
ggcggtaata cggttatcca cagaatcagg ggataacgca ggaaagaaca tgtgagcaaa   8820
aggccagcaa aaggccagga accgtaaaaa ggccgcgttg ctggcgtttt tccataggct   8880
ccgcccccct gacgagcatc acaaaaatcg acgctcaagt cagaggtggc gaaacccgac   8940
aggactataa agataccagg cgtttccccc tggaagctcc ctcgtgcgct ctcctgttcc   9000
gaccctgccg cttaccggat acctgtccgc ctttttccct tcgggaagcg tggcgctttc   9060
tcatagctca cgctgtaggt atctcagttc ggtgtaggtc gttcgctcca agctgggctg   9120
tgtgcacgaa ccccccgttc agcccgaccg ctgcgcctta tccggtaact atcgtcttga   9180
gtccaacccg gtaagacacg acttatcgcc actggcagca gccactggta acaggattag   9240
cagagcgagg tatgtaggcg gtgctacaga gttcttgaag tggtggccta actacggcta   9300
cactagaaga acagtatttg gtatctgcgc tctgctgaag ccagttacct tcggaaaaag   9360
agttggtagc tcttgatccg gcaaacaaac caccgctggt agcggtggtt tttttgtttg   9420
caagcagcag attacgcgca gaaaaaaagg atctcaagaa gatcctttga tcttttctac   9480
ggggtctgac gctcagtgga acgaaaactc acgttaaggg attttggtca tgagattatc   9540
aaaaaggatc ttcacctaga tccttttaaa ttaaaaatga agttttaaat caatctaaag   9600
```

-continued

```
tatatatgag taaacttggt ctgacagtta ccaatgctta atcagtgagg cacctatctc      9660
agcgatctgt ctatttcgtt catccatagt tgcctgactc cccgtcgtgt agataactac      9720
gatacgggag ggcttaccat ctggccccag tgctgcaatg ataccgcgag acccacgctc      9780
accggctcca gatttatcag caataaacca gccagccgga agggccgagc gcagaagtgg      9840
tcctgcaact ttatccgcct ccatccagtc tattaattgt tgccgggaag ctagagtaag      9900
tagttcgcca gttaatagtt tgcgcaacgt tgttgccatt gctacaggca tcgtggtgtc      9960
acgctcgtcg tttggtatgg cttcattcag ctccggttcc caacgatcaa ggcgagttac     10020
atgatccccc atgttgtgca aaaaagcggt tagctccttc ggtcctccga tcgttgtcag     10080
aagtaagttg gccgcagtgt tatcactcat ggttatggca gcactgcata attctcttac     10140
tgtcatgcca tccgtaagat gcttttctgt gactggtgag tactcaacca agtcattctg     10200
agaatagtgt atgcggcgac cgagttgctc ttgcccggcg tcaatacggg ataataccgc     10260
gccacatagc agaactttaa aagtgctcat cattggaaaa cgttcttcgg ggcgaaaact     10320
ctcaaggatc ttaccgctgt tgagatccag ttcgatgtaa cccactcgtg cacccaactg     10380
atcttcagca tcttttactt tcaccagcgt ttctgggtga gcaaaaacag gaaggcaaaa     10440
tgccgcaaaa aagggaataa gggcgacacg gaaatgttga atactcatac tcttcctttt     10500
tcaatattat tgaagcattt atcagggtta ttgtctcatg agcggataca tatttgaatg     10560
tatttagaaa aataaacaaa tagggggttcc gcgcacattt ccccgaaaag tgccacctga     10620
cgtctaagaa accattatta tcatgacatt aacctataaa aataggcgta tcacgaggcc     10680
ctttcgtctc gcgcgtttcg gtgatgacgg tgaaaacctc tgacacatgc agctcccgga     10740
gacggtcaca gcttgtctgt aagcggatgc cgggagcaga caagcccgtc agggcgcgtc     10800
agcgggtgtt ggcgggtgtc ggggctggct taactatgcg gcatcagagc agattgtact     10860
gagagtgcac catatgcggt gtgaaatacc gcacagatgc gtaaggagaa aataccgcat     10920
caggcgccat tcgccattca ggctgcgcaa ctgttgggaa gggcgatcgg tgcgggcctc     10980
ttcgctatta cgccagctgg cgaaaggggg atgtgctgca aggcgattaa gttgggtaac     11040
gccagggttt tcccagtcac gacgttgtaa aacgacggcc agtgaattcg agctcggtac     11100
c                                                                     11101
```

<210> SEQ ID NO 88
<211> LENGTH: 60
<212> TYPE: DNA
<213> ORGANISM: Artificial
<220> FEATURE:
<223> OTHER INFORMATION: Artificial DNA Sequence

<400> SEQUENCE: 88

```
tcctctatat acacaactgg ggatccacca tgtcgaggtt ccagtctctt ttcttcttcg        60
```

<210> SEQ ID NO 89
<211> LENGTH: 53
<212> TYPE: DNA
<213> ORGANISM: Artificial
<220> FEATURE:
<223> OTHER INFORMATION: Artificial DNA Sequence

<400> SEQUENCE: 89

```
tctagatctc gagctcgcta gagtcgacct agaggtcgct cgggtcgagc gcg              53
```

<210> SEQ ID NO 90

```
<211> LENGTH: 55
<212> TYPE: DNA
<213> ORGANISM: Artificial
<220> FEATURE:
<223> OTHER INFORMATION: Artificial DNA Sequence

<400> SEQUENCE: 90
tcctctatat acacaactgg ggatccacca tgaggtcctt catcagcgcc gcgac          55

<210> SEQ ID NO 91
<211> LENGTH: 53
<212> TYPE: DNA
<213> ORGANISM: Artificial
<220> FEATURE:
<223> OTHER INFORMATION: Artificial DNA Sequence

<400> SEQUENCE: 91
tctagatctc gagctcgcta gagtcgacct acgccttgac cagccactcg ccc            53

<210> SEQ ID NO 92
<211> LENGTH: 1557
<212> TYPE: DNA
<213> ORGANISM: Pycnoporus cinnabarinus

<400> SEQUENCE: 92
atgtcgaggt tccagtccct cttcttcttc gtcctcgtct ccctcaccgc tgtggccaac      60
gcagccatag ggcctgtggc ggacctgacc cttaccaatg cccaggtcag ccccgatggc     120
ttcgctcgcg aggccgtcgt ggtgaacggt atcaccctg  cccctctcat cacaggcaat     180
aagggcgatc gattccagct caatgtcatc gaccagttga caaatcatac catgttgaaa     240
acatctagta ttcattggca cggcttcttc cagcaaggca cgaactgggc cgatggtccc     300
gcgttcgtga accagtgtcc catcgcttcg ggccactcgt tcttgtatga ctttcaagtt     360
cccgaccaag cagggacttt ctggtaccat agccatctct ccacgcaata ctgcgatggt     420
ttgagggggc ctttcgtcgt ctacgacccc aacgatcctc acgctagcct gtatgacatt     480
gataacgacg acactgtcat tacgctggct gattggtatc acgttgctgc caagctcgga     540
cctcgcttcc catttggctc cgattcaacc cttatcaatg acttggtcg  aaccactggc     600
atagcaccgt ccgacttggc agttatcaag gtcacgcagg gcaagcgcta ccgcttccgc     660
ttggtgtcgc tttcttgcga tccgaaccat acattcagca ttgataatca cacaatgact     720
ataattgagg cggactcgat caacactcaa cccctagagg ttgattcaat ccagattttt     780
gccgcgcagc gctactcctt cgtgctggat gctagccagc cggtggataa ctactggatc     840
cgcgcaaacc ctgccttcgg aaacacaggt tttgctggtg aatcaattc  tgccatcctg     900
cgttatgatg gcgcacccga gatcgagcct acgtctgtcc agactactcc tacgaagcct     960
ctgaacgagg tcgacttgca tcctctctcg cctatgcctg tgcctggcag ccccgagccc    1020
ggaggtgtcg acaagcctct gaacttggtc ttcaacttca acggcaccaa cttcttcatc    1080
aacgaccaca cctttgtccc gccgtctgtc ccagtcttgc tacaaatcct cagtggggcg    1140
caggcggctc aggacctggt cccggagggc agcgtgttcg ttcttcccag caactcgtcc    1200
attgagatat ccttccctgc cactgccaat gcccctggat ccccccatcc gttccacttg    1260
cacggtcacg ccttcgctgt cgtccggagc gccgggagca gcgtctacaa ctacgacaac    1320
ccgatcttcc gcgacgtcgt cagcaccggc cagcccggcg acaacgtcac gattcgcttc    1380
gagaccaata acccaggccc gtggttcctc cactgccaca ttgacttcca cctcgacgca    1440
ggctttgctg tagtcatggc cgaggacact ccggacacca aggccgcgaa ccctgttcct    1500
```
caggcgtggt cggacttgtg ccccatctat gatgcacttg accccagcga cctctag      1557

<210> SEQ ID NO 93
<211> LENGTH: 518
<212> TYPE: PRT
<213> ORGANISM: Pycnoporus cinnabarinus

<400> SEQUENCE: 93

```
Met Ser Arg Phe Gln Ser Leu Phe Phe Phe Val Leu Val Ser Leu Thr
1               5                   10                  15

Ala Val Ala Asn Ala Ala Ile Gly Pro Val Ala Asp Leu Thr Leu Thr
            20                  25                  30

Asn Ala Gln Val Ser Pro Asp Gly Phe Ala Arg Glu Ala Val Val Val
        35                  40                  45

Asn Gly Ile Thr Pro Ala Pro Leu Ile Thr Gly Asn Lys Gly Asp Arg
    50                  55                  60

Phe Gln Leu Asn Val Ile Asp Gln Leu Thr Asn His Thr Met Leu Lys
65                  70                  75                  80

Thr Ser Ser Ile His Trp His Gly Phe Gln Gln Gly Thr Asn Trp
                85                  90                  95

Ala Asp Gly Pro Ala Phe Val Asn Gln Cys Pro Ile Ala Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro His Ala Ser Leu Tyr Asp Ile
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Phe Gly Ser Asp Ser Thr Leu Ile
            180                 185                 190

Asn Gly Leu Gly Arg Thr Thr Gly Ile Ala Pro Ser Asp Leu Ala Val
        195                 200                 205

Ile Lys Val Thr Gln Gly Lys Arg Tyr Arg Phe Arg Leu Val Ser Leu
    210                 215                 220

Ser Cys Asp Pro Asn His Thr Phe Ser Ile Asp Asn His Thr Met Thr
225                 230                 235                 240

Ile Ile Glu Ala Asp Ser Ile Asn Thr Gln Pro Leu Glu Val Asp Ser
                245                 250                 255

Ile Gln Ile Phe Ala Ala Gln Arg Tyr Ser Phe Val Leu Asp Ala Ser
            260                 265                 270

Gln Pro Val Asp Asn Tyr Trp Ile Arg Ala Asn Pro Ala Phe Gly Asn
        275                 280                 285

Thr Gly Phe Ala Gly Gly Ile Asn Ser Ala Ile Leu Arg Tyr Asp Gly
    290                 295                 300

Ala Pro Glu Ile Glu Pro Thr Ser Val Gln Thr Thr Pro Thr Lys Pro
305                 310                 315                 320

Leu Asn Glu Val Asp Leu His Pro Leu Ser Pro Met Pro Val Pro Gly
                325                 330                 335

Ser Pro Glu Pro Gly Gly Val Asp Lys Pro Leu Asn Leu Val Phe Asn
            340                 345                 350

Phe Asn Gly Thr Asn Phe Phe Ile Asn Asp His Thr Phe Val Pro Pro
        355                 360                 365
```

```
Ser Val Pro Val Leu Leu Gln Ile Leu Ser Gly Ala Gln Ala Gln
        370                 375                 380

Asp Leu Val Pro Glu Gly Ser Val Phe Val Leu Pro Ser Asn Ser Ser
385                 390                 395                 400

Ile Glu Ile Ser Phe Pro Ala Thr Ala Asn Ala Pro Gly Phe Pro His
                405                 410                 415

Pro Phe His Leu His Gly His Ala Phe Ala Val Val Arg Ser Ala Gly
            420                 425                 430

Ser Ser Val Tyr Asn Tyr Asp Asn Pro Ile Phe Arg Asp Val Val Ser
        435                 440                 445

Thr Gly Gln Pro Gly Asp Asn Val Thr Ile Arg Phe Glu Thr Asn Asn
    450                 455                 460

Pro Gly Pro Trp Phe Leu His Cys His Ile Asp Phe His Leu Asp Ala
465                 470                 475                 480

Gly Phe Ala Val Val Met Ala Glu Asp Thr Pro Asp Thr Lys Ala Ala
                485                 490                 495

Asn Pro Val Pro Gln Ala Trp Ser Asp Leu Cys Pro Ile Tyr Asp Ala
                500                 505                 510

Leu Asp Pro Ser Asp Leu
            515

<210> SEQ ID NO 94
<211> LENGTH: 1863
<212> TYPE: DNA
<213> ORGANISM: Myceliophthora thermophila

<400> SEQUENCE: 94
atgaggtcct tcatcagcgc cgcgacgctt ttggtgggca ttctcacccc tagcgttgct      60
gctgcccctc catccacccc tgagcagcgc gacctgctcg tcccgatcac ggagagggag     120
gaggcagccg tgaaggctcg ccagcagagc tgcaacaccc ccagcaaccg ggcgtgctgg     180
actgacggat acgacatcaa caccgactac gaagtggaca gcccggacac gggtgttgtt     240 cggcccttata ctctgactct caccgaagtc gacaactgga ccggacctga tggcgtcgtc     300
aaggagaagg tcatgctggt taacaatagt ataatcggac aacaatcttt gcggactgg     360 ggcgacacga tccaggtaac ggtcatcaac aacctcgaga ccaacggcac gtcgatccac     420
tggcacggac tgcaccagaa gggcaccaac ctgcacgacg cgccaacgg tatcaccgag     480 tgcccgatcc cgcccaaggg agggaggaag gtgtaccggt tcaaggctca gcagtacggg     540
acgagctggt accactcgca cttctcggcc cagtacggca acggcgtggt cggggccatt     600
cagatcaacg ggccggcctc gctgccgtac gacaccgacc tgggcgtgtt ccccatcagc     660
gactactact caagctcggc cgacgagctg gtggaactca ccaagaactc gggcgcgccc     720
ttcagcgaca acgtcctgtt caacggcacg gccaagcacc cggagacggg cgagggcgag     780
tacgccaacg tgacgctcac cccggggccgg cggcaccgcc tgcgcctgat caacacgtcg     840
gtcgagaacc acttccaggt ctcgctcgtc aaccacacca tgaccatcat cgccgccgac     900
atggtgcccg tcaacgccat gacggtcgac agcctcttcc tcggcgtcgg ccagcgctac     960
gatgtcgtca tcgaagccag ccgaacgccc ggaactact ggtttaacgt cacatttggc    1020
ggcggcctgc tctgcggcgg ctccaggaat ccctacccgg ccgccatctt ccactacgcc    1080 ggcgccccg cgccccgcc cacggacgag ggcaaggccc cggtcgacca caactgcctg    1140
gacctcccca acctcaagcc cgtcgtggcc cgcgacgtgc ccctgagcgg cttcgccaag    1200
```

-continued

```
cggcccgaca acacgctcga cgtcaccctc gacaccacgg gcacgcccct gttcgtctgg    1260
aaggtcaacg gcagcgccat caacatcgac tggggcaggc ccgtcgtcga ctacgtcctc    1320
acgcagaaca ccagcttccc acccgggtac aacattgtcg aggtgaacgg agctgatcag    1380
tggtcgtact ggttgatcga gaacgatccc ggcgcacctt tcaccctacc gcatccgatg    1440
cacctgcacg ccacgactt ttacgtgctg gccgctcgc ccgacgagtc gccggcatcc      1500
aacgagcggc acgtgttcga tccggcgcgg gacgcgggcc tgctgagcgg ggccaaccct    1560
gtgcggcggg acgtgacgat gctgccggcg ttcgggtggg tggtgctggc cttccgggcc    1620 gacaaccccgg gcgcctggct gttccactgc cacatcgcct ggcacgtctc gggcggcctg    1680
ggcgtcgtct acctcgagcg cgccgacgac ctgcgcgggg ccgtctcgga cgccgacgcc    1740
gacgacctcg accgctctg cgccgactgg cgccgctact ggcctaccaa ccccctacccc    1800 aagtccgact cgggcctcaa gcaccgctgg gtcgaggagg cgagtggct ggtcaaggcg     1860 tag                                                                   1863
```

<210> SEQ ID NO 95
<211> LENGTH: 620
<212> TYPE: PRT
<213> ORGANISM: Myceliophthora thermophila

<400> SEQUENCE: 95

```
Met Arg Ser Phe Ile Ser Ala Ala Thr Leu Leu Val Gly Ile Leu Thr
1               5                   10                  15

Pro Ser Val Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
        35                  40                  45

Gln Ser Cys Asn Thr Pro Ser Asn Arg Ala Cys Trp Thr Asp Gly Tyr
    50                  55                  60

Asp Ile Asn Thr Asp Tyr Glu Val Asp Ser Pro Asp Thr Gly Val Val
65                  70                  75                  80

Arg Pro Tyr Thr Leu Thr Leu Thr Glu Val Asp Asn Trp Thr Gly Pro
                85                  90                  95

Asp Gly Val Val Lys Glu Lys Val Met Leu Val Asn Asn Ser Ile Ile
            100                 105                 110

Gly Pro Thr Ile Phe Ala Asp Trp Gly Asp Thr Ile Gln Val Thr Val
        115                 120                 125

Ile Asn Asn Leu Glu Thr Asn Gly Thr Ser Ile His Trp His Gly Leu
    130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
            180                 185                 190

Gly Asn Gly Val Val Gly Ala Ile Gln Ile Asn Gly Pro Ala Ser Leu
        195                 200                 205

Pro Tyr Asp Thr Asp Leu Gly Val Phe Pro Ile Ser Tyr Tyr Tyr
    210                 215                 220

Ser Ser Ala Asp Glu Leu Val Glu Leu Thr Lys Asn Ser Gly Ala Pro
225                 230                 235                 240

Phe Ser Asp Asn Val Leu Phe Asn Gly Thr Ala Lys His Pro Glu Thr
                245                 250                 255
```

```
Gly Glu Gly Glu Tyr Ala Asn Val Thr Leu Thr Pro Gly Arg Arg His
            260                 265                 270

Arg Leu Arg Leu Ile Asn Thr Ser Val Glu Asn His Phe Gln Val Ser
            275                 280                 285

Leu Val Asn His Thr Met Thr Ile Ile Ala Ala Asp Met Val Pro Val
            290                 295                 300

Asn Ala Met Thr Val Asp Ser Leu Phe Leu Gly Val Gly Gln Arg Tyr
305                 310                 315                 320

Asp Val Val Ile Glu Ala Ser Arg Thr Pro Gly Asn Tyr Trp Phe Asn
            325                 330                 335

Val Thr Phe Gly Gly Leu Leu Cys Gly Gly Ser Arg Asn Pro Tyr
            340                 345                 350

Pro Ala Ala Ile Phe His Tyr Ala Gly Ala Pro Gly Gly Pro Pro Thr
            355                 360                 365

Asp Glu Gly Lys Ala Pro Val Asp His Asn Cys Leu Asp Leu Pro Asn
    370                 375                 380

Leu Lys Pro Val Val Ala Arg Asp Val Pro Leu Ser Gly Phe Ala Lys
385                 390                 395                 400

Arg Pro Asp Asn Thr Leu Asp Val Thr Leu Asp Thr Thr Gly Thr Pro
            405                 410                 415

Leu Phe Val Trp Lys Val Asn Gly Ser Ala Ile Asn Ile Asp Trp Gly
            420                 425                 430

Arg Pro Val Val Asp Tyr Val Leu Thr Gln Asn Thr Ser Phe Pro Pro
            435                 440                 445

Gly Tyr Asn Ile Val Glu Val Asn Gly Ala Asp Gln Trp Ser Tyr Trp
    450                 455                 460

Leu Ile Glu Asn Asp Pro Gly Ala Pro Phe Thr Leu Pro His Pro Met
465                 470                 475                 480

His Leu His Gly His Asp Phe Tyr Val Leu Gly Arg Ser Pro Asp Glu
            485                 490                 495

Ser Pro Ala Ser Asn Glu Arg His Val Phe Asp Pro Ala Arg Asp Ala
            500                 505                 510

Gly Leu Leu Ser Gly Ala Asn Pro Val Arg Arg Asp Val Thr Met Leu
            515                 520                 525

Pro Ala Phe Gly Trp Val Val Leu Ala Phe Arg Ala Asp Asn Pro Gly
    530                 535                 540

Ala Trp Leu Phe His Cys His Ile Ala Trp His Val Ser Gly Gly Leu
545                 550                 555                 560

Gly Val Val Tyr Leu Glu Arg Ala Asp Asp Leu Arg Gly Ala Val Ser
            565                 570                 575

Asp Ala Asp Ala Asp Asp Leu Asp Arg Leu Cys Ala Asp Trp Arg Arg
            580                 585                 590

Tyr Trp Pro Thr Asn Pro Tyr Pro Lys Ser Asp Ser Gly Leu Lys His
            595                 600                 605

Arg Trp Val Glu Glu Gly Glu Trp Leu Val Lys Ala
            610                 615                 620
```